(12) United States Patent
Abrams et al.

(10) Patent No.: US 12,344,675 B2
(45) Date of Patent: Jul. 1, 2025

(54) POLYPEPTIDE COMPRISING A SINGLE-DOMAIN ANTIBODY VARIABLE REGION THAT BINDS DELTA-LIKE LIGAND 3 (DLL3) AND METHOD OF USE THEREOF TO MAKE A RADIONUCLIDE COMPLEX

(71) Applicant: ABDERA THERAPEUTICS INC., Vancouver (CA)

(72) Inventors: Michael J. Abrams, Custer, WA (US); Emma Jane Cummins, Vancouver (CA); Adam Daniel Judge, Bainbridge Island, WA (US); Alexander Laurence Mandel, Vancouver (CA); Raja Solomon Viswas, Vancouver (CA)

(73) Assignee: ABDERA THERAPEUTICS INC., South San Francisco, CA (US)

( * ) Notice: Subject to any disclaimer, the term of this patent is extended or adjusted under 35 U.S.C. 154(b) by 0 days.

(21) Appl. No.: 18/927,497

(22) Filed: Oct. 25, 2024

(65) Prior Publication Data

US 2025/0051476 A1    Feb. 13, 2025

Related U.S. Application Data

(63) Continuation of application No. PCT/US2023/072586, filed on Aug. 21, 2023.

(60) Provisional application No. 63/477,261, filed on Dec. 27, 2022, provisional application No. 63/373,184, filed on Aug. 22, 2022.

(51) Int. Cl.
| | |
|---|---|
| *C07K 16/30* | (2006.01) |
| *A61K 35/00* | (2006.01) |
| *A61K 47/68* | (2017.01) |
| *A61K 51/10* | (2006.01) |

(52) U.S. Cl.
CPC .......... *C07K 16/3023* (2013.01); *A61K 35/00* (2013.01); *A61K 47/68035* (2023.08); *A61K 47/6851* (2017.08); *A61K 51/1054* (2013.01); *A61K 51/1096* (2013.01); *A61K 2121/00* (2013.01); *C07K 2317/24* (2013.01); *C07K 2317/569* (2013.01); *C07K 2317/92* (2013.01)

(58) Field of Classification Search
CPC ............ A61K 47/6851; A61K 51/1096; C07K 2317/569; C07K 2317/92
See application file for complete search history.

(56) References Cited

U.S. PATENT DOCUMENTS

| | | |
|---|---|---|
| 3,940,475 A | 2/1976 | Gross |
| RE30,985 E | 6/1982 | Cartaya |
| 4,399,216 A | 8/1983 | Axel et al. |
| 4,485,045 A | 11/1984 | Regen |
| 4,544,545 A | 10/1985 | Ryan et al. |
| 4,560,655 A | 12/1985 | Baker |
| 4,657,866 A | 4/1987 | Kumar |
| 4,767,704 A | 8/1988 | Cleveland et al. |
| 4,816,567 A | 3/1989 | Cabilly et al. |
| 4,927,762 A | 5/1990 | Darfler |
| 4,943,529 A | 7/1990 | Van et al. |
| 4,946,783 A | 8/1990 | Beckwith et al. |
| 5,010,182 A | 4/1991 | Brake et al. |
| 5,013,556 A | 5/1991 | Woodle et al. |
| 5,122,469 A | 6/1992 | Mather et al. |
| 5,208,020 A | 5/1993 | Chari et al. |
| 5,264,365 A | 11/1993 | Georgiou et al. |
| 5,364,934 A | 11/1994 | Drayna et al. |
| 5,500,362 A | 3/1996 | Robinson et al. |
| 5,508,192 A | 4/1996 | Georgiou et al. |
| 5,624,821 A | 4/1997 | Winter et al. |
| 5,639,635 A | 6/1997 | Joly et al. |
| 5,648,237 A | 7/1997 | Carter |
| 5,648,260 A | 7/1997 | Winter et al. |
| 5,739,277 A | 4/1998 | Presta et al. |
| 5,789,199 A | 8/1998 | Joly et al. |
| 5,821,337 A | 10/1998 | Carter et al. |
| 5,840,523 A | 11/1998 | Simmons et al. |
| 5,959,177 A | 9/1999 | Hein et al. |
| 6,027,888 A | 2/2000 | Georgiou et al. |
| 6,040,498 A | 3/2000 | Stomp et al. |
| 6,083,715 A | 7/2000 | Georgiou et al. |
| 6,165,745 A | 12/2000 | Ward et al. |
| 6,171,586 B1 | 1/2001 | Lam et al. |
| 6,194,551 B1 | 2/2001 | Idusogie et al. |
| 6,267,958 B1 | 7/2001 | Andya et al. |
| 6,277,375 B1 | 8/2001 | Ward |
| 6,329,507 B1 | 12/2001 | Mezes et al. |
| 6,403,771 B1 | 6/2002 | Geerlings |
| 6,417,429 B1 | 7/2002 | Hein et al. |
| 6,420,548 B1 | 7/2002 | Vezina et al. |

(Continued)

FOREIGN PATENT DOCUMENTS

| | | |
|---|---|---|
| CA | 2431600 A1 | 8/2002 |
| CA | 2768658 A1 | 1/2011 |

(Continued)

OTHER PUBLICATIONS

Adams, Gregory P. et al. Highly specific in vivo tumor targeting by monovalent and divalent forms of 741F8 anti-c-erbB-2 single-chain Fv. Cancer Research 53(17):4026-4034 (1993).

Alfthan, Kaija. et al. Properties of a single-chain antibody containing different linker peptides. Protein Eng. 8:725-731 (1995).

Al-Lazikani, Bissan. et al. Standard Conformations for the Canonical Structures of Immunoglobulins. Journal of Molecular Biology 273(4):927-948 (1997).

(Continued)

*Primary Examiner* — Robert S Landsman

(74) *Attorney, Agent, or Firm* — WILSON SONSINI GOODRICH & ROSATI

(57) ABSTRACT

Described herein are heavy chain antibodies that bind to DLL3 and immunoconjugates of DLL3 heavy chain antibodies useful for cancer therapy.

30 Claims, 43 Drawing Sheets

Specification includes a Sequence Listing.

(56) References Cited

U.S. PATENT DOCUMENTS

| | | |
|---|---|---|
| 6,528,624 B1 | 3/2003 | Idusogie et al. |
| 6,602,677 B1 | 8/2003 | Wood et al. |
| 6,602,684 B1 | 8/2003 | Umana et al. |
| 6,737,056 B1 | 5/2004 | Presta |
| 7,083,784 B2 | 8/2006 | Dall'Acqua et al. |
| 7,125,978 B1 | 10/2006 | Vezina et al. |
| 7,332,581 B2 | 2/2008 | Presta |
| 7,371,826 B2 | 5/2008 | Presta |
| 7,374,936 B2 | 5/2008 | Geerlings |
| 7,416,727 B2 | 8/2008 | Presta |
| 7,521,541 B2 | 4/2009 | Eigenbrot et al. |
| 8,067,548 B2 | 11/2011 | Wang et al. |
| 8,088,376 B2 | 1/2012 | Chamberlain et al. |
| 8,318,907 B2 | 11/2012 | Chamberlain et al. |
| 8,324,351 B2 | 12/2012 | Chamberlain et al. |
| 8,338,574 B2 | 12/2012 | Chamberlain et al. |
| 8,367,805 B2 | 2/2013 | Chamberlain et al. |
| 8,394,925 B2 | 3/2013 | Chamberlain et al. |
| 8,613,926 B2 | 12/2013 | Kjaergaard et al. |
| 8,852,586 B2 | 10/2014 | Chamberlain et al. |
| 8,883,973 B2 | 11/2014 | Chamberlain et al. |
| 9,603,954 B2 | 3/2017 | Simon et al. |
| 9,855,348 B2 | 1/2018 | Devoogdt et al. |
| 10,336,818 B2 | 7/2019 | Chamberlain et al. |
| 11,061,841 B2 | 7/2021 | Trojanowski et al. |
| 11,419,821 B2 | 8/2022 | Fallon et al. |
| 2002/0164328 A1 | 11/2002 | Shinkawa et al. |
| 2003/0115614 A1 | 6/2003 | Kanda et al. |
| 2003/0157108 A1 | 8/2003 | Presta |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2005/0014934 A1 | 1/2005 | Hinton et al. |
| 2005/0123546 A1 | 6/2005 | Umana et al. |
| 2005/0238649 A1 | 10/2005 | Doronina et al. |
| 2005/0256030 A1 | 11/2005 | Feng |
| 2006/0122377 A1 | 6/2006 | Dennis |
| 2015/0368355 A1 | 12/2015 | Yoshida et al. |
| 2016/0030606 A1 | 2/2016 | Devoogdt et al. |
| 2021/0380679 A1 | 12/2021 | Eckelman et al. |
| 2024/0207462 A1 | 6/2024 | Judge et al. |

FOREIGN PATENT DOCUMENTS

| | | |
|---|---|---|
| CA | 2954359 A1 | 2/2016 |
| CA | 2991398 A1 | 1/2017 |
| CN | 116262786 A | 6/2023 |
| DE | 266710 A3 | 4/1989 |
| EP | 0139383 A1 | 5/1985 |
| EP | 0183070 A2 | 6/1986 |
| EP | 0244234 A2 | 11/1987 |
| EP | 0362179 A2 | 4/1990 |
| EP | 0394538 A1 | 10/1990 |
| EP | 0402226 A1 | 12/1990 |
| EP | 2203180 A1 | 7/2010 |
| EP | 2341060 A1 | 7/2011 |
| EP | 2354149 A1 | 8/2011 |
| JP | 5985392 B2 | 9/2016 |
| JP | 6268127 B2 | 1/2018 |
| JP | 6289733 B2 | 3/2018 |
| WO | WO-8700195 A1 | 1/1987 |
| WO | WO-8705330 A1 | 9/1987 |
| WO | WO-8905859 A1 | 6/1989 |
| WO | WO-9003430 A1 | 4/1990 |
| WO | WO-9013646 A1 | 11/1990 |
| WO | WO-9015625 A1 | 12/1990 |
| WO | WO-9100357 A1 | 1/1991 |
| WO | WO-9209690 A2 | 6/1992 |
| WO | WO-9404678 A1 | 3/1994 |
| WO | WO-9411026 A2 | 5/1994 |
| WO | WO-9429351 A2 | 12/1994 |
| WO | WO-9730087 A1 | 8/1997 |
| WO | WO-9738731 A1 | 10/1997 |
| WO | WO-9858964 A1 | 12/1998 |
| WO | WO-9922764 A1 | 5/1999 |
| WO | WO-9938884 A2 | 8/1999 |
| WO | WO-9951642 A1 | 10/1999 |
| WO | WO-0061739 A1 | 10/2000 |
| WO | WO-0129246 A1 | 4/2001 |
| WO | WO-0231140 A1 | 4/2002 |
| WO | WO-02060919 A2 | 8/2002 |
| WO | WO-03011878 A2 | 2/2003 |
| WO | WO-03084570 A1 | 10/2003 |
| WO | WO-03085107 A1 | 10/2003 |
| WO | WO-03085119 A1 | 10/2003 |
| WO | WO-2004056312 A2 | 7/2004 |
| WO | WO-2005035586 A1 | 4/2005 |
| WO | WO-2005035778 A1 | 4/2005 |
| WO | WO-2004056312 A3 | 5/2005 |
| WO | WO-2005053742 A1 | 6/2005 |
| WO | WO-2005100402 A1 | 10/2005 |
| WO | WO-2006029879 A2 | 3/2006 |
| WO | WO-2006044908 A2 | 4/2006 |
| WO | WO-2006044908 A3 | 8/2006 |
| WO | WO-2007084181 A2 | 7/2007 |
| WO | WO-2008020079 A1 | 2/2008 |
| WO | WO-2008077546 A1 | 7/2008 |
| WO | WO-2011011592 A1 | 1/2011 |
| WO | WO-2011093097 A1 | 8/2011 |
| WO | WO-2013126746 A2 | 8/2013 |
| WO | WO-2013126746 A3 | 3/2014 |
| WO | WO-2014130879 A2 | 8/2014 |
| WO | WO-2014130879 A3 | 10/2014 |
| WO | WO-2015095953 A1 | 7/2015 |
| WO | WO-2016016021 A1 | 2/2016 |
| WO | WO-2017031458 A2 | 2/2017 |
| WO | WO-2017155937 A1 | 9/2017 |
| WO | WO-2017202776 A1 | 11/2017 |
| WO | WO-2018232152 A1 | 12/2018 |
| WO | WO-2020007967 A1 | 1/2020 |
| WO | WO-2020069028 A1 | 4/2020 |
| WO | WO-2020076977 A2 | 4/2020 |
| WO | WO-2020181140 A1 | 9/2020 |
| WO | WO-2020186328 A1 | 9/2020 |
| WO | WO-2020247873 A1 | 12/2020 |
| WO | WO-2021000017 A1 | 1/2021 |
| WO | WO-2021000018 A1 | 1/2021 |
| WO | WO-2021226204 A2 | 11/2021 |
| WO | WO-2022051647 A2 | 3/2022 |
| WO | WO-2022084915 A1 | 4/2022 |
| WO | WO-2022098979 A1 | 5/2022 |
| WO | WO-2022175750 A1 | 8/2022 |
| WO | WO-2023034566 A1 | 3/2023 |
| WO | WO-2024044547 A1 | 2/2024 |
| WO | WO-2024044550 A1 | 2/2024 |
| WO | WO-2024044551 A1 | 2/2024 |

OTHER PUBLICATIONS

Altschul, Stephen F. et al. Basic Local Alignment Search Tool. Journal of Molecular Biology 215(3):403-410 (1990).

Altunay et al.: HER2-directed antibodies, affibodies and nanobodies as drug-delivery vehicles in breast cancer with a specific focus on radioimmunotherapy and radioimmunoimaging. Eur J Nucl Med Mol Imaging. 48(5):1371-1389 (2021).

Amsberry, Kent L, and Ronald T. Borchardt. The lactonization of 2'-hydroxyhydrocinnamic acid amides: A potential prodrug for amines. The Journal of Organic Chemistry 55(23):5867-5877 (1990).

Andersen et al.: Anti-carcinoembryonic antigen single-chain variable fragment antibody variants bind mouse and human neonatal Fc receptor with different affinities that reveal distinct cross-species differences in serum half-life. J Biol Chem. 287(27):22927-22937 (2012).

Andersson, C. et al. Rapid-Onset Clinical And Mechanistic Effects Of Anti-C5aR Treatment In The Mouse Collagen-Induced Arthritis Model. Clinical and Experimental Immunology 177(1):219-233 (2014).

Andrini, Elisa. et al. Large Cell Neuroendocrine Carcinoma Of The Lung: Current Understanding And Challenges. Journal Of Clinical Medicine 11(5):1461, 1-18 (2022).

(56) References Cited

OTHER PUBLICATIONS

Anthony. Chapter 10: Metabolism in the methylotrophic yeasts. The Biochemistry of Methylotrophs (124 pgs) (1982).

Aplin, John D. et al. Preparation, Properties, and Applications of Carbohydrate Conjugates of Proteins and Lipids. CRC Critical Reviews in Biochemistry 10(4):259-306 (1981).

Arie, Jean-Philippe. et al. Chaperone function of FkpA, a heat shock prolyl isomerase, in the periplasm of Escherichia coli. Molecular Microbiology 39(1):199-210 (2001).

Asano, Ryutaro. et al. Multimerization of Anti-(Epidermal Growth Factor Receptor) IgG Fragments Induces an Antitumor Effect: the Case for Humanized 528 scFv Multimers. FEBS journal 280(19):4816-4826 (2013).

Ausubel, Frederick. et al. Current Protocols in Molecular Biology. Greene Publishing Associates and Wiley-Interscience (1987).

Avery, Lindsay B. et al. Establishing in Vitro in Vivo Correlations to Screen Monoclonal Antibodies for Physicochemical Properties Related to Favorable Human Pharmacokinetics. mAbs 10(2):244-255 (2018).

Avery, Lindsay B. et al. Utility of a Human FcRn Transgenic Mouse Model in Drug Discovery for Early Assessment and Prediction of Human Pharmacokinetics of Monoclonal Antibodies. mAbs 8(6):1064-1078 (2016).

Baillie, George S. et al. Compartmentalisation of Phosphodiesterases and Protein Kinase a: Opposites Attract. FEBS letters 579(15):3264-3270 (2005).

Ballance, D. J. et al. Transformation of Aspergillus nidulans by the orotidine-5'-phosphate decarboxylase gene of Neurospora crassa. Biochemical and biophysical research communications 112(1):284-289 (1983).

Banerjee. Lutetium-177 therapeutic radiopharmaceuticals:linking chemistry, radiochemistry, and practical applications. Chem. Rev. 115:2934-2974 (2015).

Barbas, Carlos F. Phage Display: A Laboratory Manual. Cold Spring Harbor Laboratory Press (2001).

Barnes, David, and Gordon Sato. Methods for growth of cultured cells in serum-free medium. Analytical biochemistry 102(2):255-270 (1980).

Bass, Steven. et al. Hormone Phage: an Enrichment Method for Variant Proteins With Altered Binding Properties. Proteins 8(4):309-314 (1990).

Bates, Adam. et al. David vs. Goliath: The Structure, Function, and Clinical Prospects of Antibody Fragments. Antibodies (Basel) 8(2):28, 1-31 (2019).

Beach, David, and Paul Nurse. High-frequency transformation of the fission yeast Schizosaccharomyces pombe. Nature 290(5802):140-142 (1981).

Behrens, Christopher R. et al. Antibody-Drug Conjugates (ADCs) Derived from Interchain Cysteine Cross-Linking Demonstrate Improved Homogeneity and Other Pharmacological Properties over Conventional Heterogeneous ADCs. Mol Pharmaceutics 12(11):3986-3998 (2015).

Bell, Andrea. et al. Differential Tumor-targeting Abilities of Three Single-domain Antibody Formats. Cancer Letters 289(1):81-90 (2010).

Berge, Stephen M. et al. Pharmaceutical Salts. Journal of Pharmaceutical Sciences 66(1):1-19 (1977).

Bird, Matthew. et al. Chapter 8: Bridged cysteine conjugations. Antibody-Drug Conjugates: Methods and Protocols:113-129 (2020).

Borrok et al.: pH-dependent binding engineering reveals an FcRn affinity threshold that governs IgG recycling. J Biol Chem. 290(7):4282-4290 (2015).

Borsi, Laura. et al. Selective Targeting of Tumoral Vasculature: Comparison of Different Formats of an Antibody (L19) to the ED-B Domain of Fibronectin. International Journal of Cancer 102(1):75-85 (2002).

Bothmann, Hendrick, and Andreas Pluckthun. The periplasmic Escherichia coli peptidylprolyl cis,trans-isomerase FkpA. I. Increased functional expression of antibody fragments with and without cis-prolines. Journal of Biological Chemistry 275(22):17100-17105 (2000).

Bowie, James U. et al. Deciphering the message in protein sequences: tolerance to amino acid substitutions. Science 247(4948):1306-1310 (1990).

Braren, Ingke. et al. Comparative Expression of Different Antibody Formats in Mammalian Cells and Pichia Pastoris. Biotechnology and Applied Biochemistry 47(Pt 4):205-214 (2007).

Brechbiel, Martin W. Bifunctional Chelates for Metal Nuclides. The quarterly journal of nuclear medicine and molecular imaging 52(2):166-173 (2008). Published Online Nov. 28, 2007.

Brüggemann, Marianne. et al. Comparison of the Effector Functions of Human Immunoglobulins Using a Matched Set of Chimeric Antibodies. The Journal of Experimental Medicine 166(5):1351-1361 (1987).

Burvenich et al.: Engineering anti-Lewis-Y hu3S193 antibodies with improved therapeutic ratio for radioimmunotherapy of epithelial cancers. EJNMMI Res. 6(1):26:1-13 (2016).

Burvenich, Ingrid J G. et al. Cross-species analysis of Fc engineered anti-Lewis-Y human IgG1 vari-ants in human neonatal receptor transgenic mice reveal importance of S254 and Y436 in bind-ing human neonatal Fc receptor. MAbs 8(4):775-786 (2016).

Cao et al., A single-domain i-body, AD-114, attenuates renal fibrosis through blockade of CXCR4. JCI Insight 7(4):e143018 (Feb. 2022).

Caron, Philip C. et al. Engineered humanized dimeric forms of IgG are more effective antibodies. The Journal of experimental medicine 176(4):1191-1195 (1992).

Carter, Paul. et al. High Level Escherichia coli Expression and Production of a Bivalent Humanized Antibody Fragment. Bio/Technology 10(2):163-167 (1992).

Carter, Paul. et al. Improved Oligonucleotide Site-directed Mutagenesis using M13 Vectors. Nucleic Acids Research 13:4331-4343 (1985).

Case, Mary E. et al. Efficient transformation of Neurospora crassa by utilizing hybrid plasmid DNA.Proceedings of the National Academy of Sciences 76(10):5259-5263 (1979).

Chabrol et al., Biochemistry, structure, and cellular internalization of a four nanobody-bearing Fc dimer. Protein Science 30:1946-1957 (2021).

Chang, Chien-hsing. et al. The Dock and Lock Method: a Novel Platform Technology for Building Multivalent, Multifunctional Structures of Defined Composition With Retained Bioactivity. Clinical Cancer Research 13(18 Pt 2):5586s-5591s (2007).

Chappell, L L. et al. Synthesis and Evaluation of Novel Bifunctional Chelating Agents Based on 1, 4, 7, 10-tetraazacyclododecane-N, N', N ", N'''-tetraacetic Acid for Radiolabeling Proteins. Nuclear Medicine and Biology 30(6):581-595 (2003).

Chappell, Lara L. et al. Synthesis, Conjugation, and Radiolabeling of a Novel Bifunctional Chelating Agent for 225ac Radioimmunotherapy Applications. Bioconjugate Chemistry 11(4):510-519 (2000).

Chari, Ravi V.J. et al. Immunoconjugates Containing Novel Maytansinoids: Promising Anticancer Drugs. Cancer Research 52(1):127-131 (1992).

Charlton, Keith A. Expression and Isolation of Recombinant Antibody Fragments in E. coli. Chapter 14. Methods in Molecular Biology 248:245-254 (2003).

Chen, Jun. et al. Chaperone activity of DsbC. Journal of Biological Chemistry 274(28):19601-19605 (1999).

Chen, Xiaoyuan. et al. MicroPET and Autoradiographic Imaging of Breast Cancer αv-Integrin Expression Using 18F- and 64Cu-Labeled RGD Peptide. Bioconjugate chemistry 15(1):41-49 (2004).

Chothia, Cyrus. et al. Canonical Structures for the Hypervariable Regions of Immunoglobulins. Journal of Molecular Biology 196(4):901-917 (1987).

Chowdhury, Partha S. Engineering Hot Spots for Affinity Enhancement of Antibodies. Methods in Molecular Biology 207:179-196 (2003).

Clackson, Tim. et al. Making Antibody Fragments using Phage Display Libraries. Nature 352(6336):624-628 (1991).

(56) References Cited

OTHER PUBLICATIONS

Cloutier, S M. et al. Streptabody, a High Avidity Molecule Made by Tetramerization of in Vivo Biotinylated, Phage Display-selected scFv Fragments on Streptavidin. Molecular Immunology 37(17):1067-1077 (2000).

Clynes, Raphael. et al. Fc Receptors Are Required in Passive and Active Immunity to Melanoma. Proceedings of the National Academy of Sciences of the United States of America 95(2):652-656 (1998).

Comba, Peter. et al. Synthesis and Coordination Chemistry of Hexadentate Picolinic Acid Based Bispidine Ligands. Inorganic Chemistry 55(24):12531-12543 (2016).

Cortinovis, Diego Luigi. et al. Harnessing DLL3 inhibition: From old promises to new therapeutic horizons. Frontiers in Medicine 9:989405, 1-9 (2022).

Cragg, Mark S, and Martin J Glennie. et al. Antibody Specificity Controls in Vivo Effector Mechanisms of anti-CD20 Reagents. Blood 103(7):2738-2743 (2004).

Cragg, Mark S. et al. Complement-mediated Lysis by Anti-CD20 mAb Correlates with Segregation into Lipid Rafts. Blood 101(3):1045-1052 (2003).

Cree et al. Individualizing chemotherapy for solid tumors—is there any alternative? Anti-Cancer Drugs 6:398-404 (1995).

Creighton, Thomas E. Proteins: Structures and Molecular Properties. W.H. Freeman and Company :79-86 (1983).

Crouch et al. The use of ATP bioluminescence as a measure of cell proliferation and cytotoxicity. J Immunol Methods. 160(1):81-8 (1993).

Cunningham, Brian C, and James A. Wells. High-resolution Epitope Mapping of hGH-receptor Interactions by Alanine-scanning Mutagenesis. Science 244(4908):1081-1085 (1989).

Datta-Mannan, Amita. et al. FcRn Affinity-pharmacokinetic Relationship of Five Human IgG4 Antibodies Engineered for Improved in Vitro FcRn Binding Properties in Cynomolgus Monkeys. Drug Metabolism and Disposition 40(8):1545-1555 (2012).

David, Gary S, and Ralph A. Reisfeld. Protein iodination with solid state lactoperoxidase. Biochemistry 13(5):1014-1021 (1974).

Davis, I A. et al. Comparison of 225actinium Chelates: Tissue Distribution and Radiotoxicity. Nuclear Medicine and Biology 26(5):581-589 (1999).

Davis, Patricia M. et al. Abatacept Binds To The Fc Receptor CD64 But Does Not Mediate Complement-Dependent Cytotoxicity Or Antibody-Dependent Cellular Cytotoxicity. The Journal of Rheumatology 34(11):2204-2210 (2007).

De Genst, Erwin. et al. Antibody Repertoire Development in Camelids. Developmental and Comparative Immunology 30(1-2):187-198 (2006).

De Kruif, J, and T Logtenberg. Leucine Zipper Dimerized Bivalent and Bispecific scFv Antibodies From a Semi-synthetic Antibody Phage Display Library. Journal of Biological Chemistry 271(13):7630-7634 (1996).

De Louvencourt, Laurence. et al. Transformation of Kluyveromyces lactis by killer plasmid DNA. Journal of Bacteriology 154(2):737-742 (1983).

Delsuc, Nicolas. et al. Proteomorphous Objects From Abiotic Backbones. Angewandte Chemie 46(1-2):214-217 (2007).

Desplancq, Dominique. et al. Multimerization Behaviour Of Single Chain Fv Variants For The Tumour-Binding Antibody B72.3. Protein Engineering 7(8):1027-1033 (1994).

Deyev, Sergey M. et al. Design of Multivalent Complexes Using the Barnase*barstar Module. Nature Biotechnology 21(12):1486-1492 (2003).

D'Huyvetter et al.: Targeted radionuclide therapy with A 177Lu-labeled anti-HER2 nanobody. Theranostics. 4(7):708-720 (2014).

D'Huyvetter, Matthias, et al. Radiolabeled nanobodies as theranostic tools in targeted radionuclide therapy of cancer. Expert Opin. Drug Deliv. 11(12):1939-1954 (2014).

Dieffenbach, Carl W, and Gabriela S Dveksler. PCR Primer: A Laboratory Manual. Cold Spring Harbor Laboratory Press (1995).

Dolezal, Olan. et al. Single-chain Fv Multimers of the Anti-neuraminidase Antibody Nc10: the Residue at Position 15 in the V(L) Domain of the Scfv-0 (V(L)-v(H)) Molecule is Primarily Responsible for Formation of a Tetramer-trimer Equilibrium. Protein Engineering 16(1):47-56 (2003).

Doronina, Svetlana O. et al. Development of Potent Monoclonal Antibody Auristatin Conjugates for Cancer Therapy. Nature Biotechnology 21(7):778-784 (2003).

Dumet et al.: Insights into the IgG heavy chain engineering patent landscape as applied to IgG4 antibody development. MAbs 11(8):1341-1350 (2019).

Duncan, Alexander R, and Greg Winter. The Binding Site for C1q on IgG. Nature 332(6166):738-740 (1988).

Edge, Albert S.B. et al. Deglycosylation of Glycoproteins by Trifluoromethanesulfonic Acid. Analytical Biochemistry 118: 131-137 (1981).

Eppstein, Deborah A. et al. Biological activity of liposome-encapsulated murine interferon gamma is mediated by a cell membrane receptor. Proceedings of the National Academy of Sciences 82(11):3688-3692 (1985).

Flatman, Stephen. et al. Process Analytics for Purification of Monoclonal Antibodies. Journal of Chromatography 848:79-87 (2007). Published Online on Dec. 11, 2006.

Fleer, R. et al. Stable Multicopy Vectors for High-Level Secretion of Recombinant Human Serum Albumin by Kluyveromyces Yeasts. Bio/technology 9(10):968-975 (1991).

Fraker, Pamela J. and John C. Speck Jr. Protein and cell membrane iodinations with a sparingly soluble chloroamide, 1, 3, 4, 6-tetrachloro-3a, 6a-diphenylglycoluril. Biochemical and biophysical research communications 80(4):849-857 (1978).

Freshney, R Ian. Culture of Animal Cells: A Manual of Basic Technique, 2nd Edition. Alan R. Liss (1987).

Gabizon, Alberto. et al. Pharmacokinetics and tissue distribution of doxorubicin encapsulated in stable liposomes with long circulation times. Journal of the National Cancer Institute 81(19):1484-1488 (1989).

Gait, M J. Oligonucleotide Synthesis: A Practical Approach. IRL Press Limited (1984).

Gazzano-Santoro, Helene. et al. A Non-radioactive Complement-dependent Cytotoxicity Assay for Anti-CD20 Monoclonal Antibody. Journal of Immunological Methods 202(2):163-171 (1997).

GenBank Accession No. NC_000017. Version No. NC_000017.11. *Homo sapiens* chromosome 17, GRCh38.p13 Primary Assembly. Record created Aug. 29, 2002. 2 pages. Retrieved Feb. 10, 2021 at URL: https://www.ncbi.nlm.nih.gov/nuccore/NC_000017.

George, A. J. et al. Radiometal labeling of recombinant proteins by a genetically engineered minimal chelation site: technetium-99m coordination by single-chain Fv antibody fusion proteins through a C-terminal cysteinyl peptide. Proceedings of the national Academy of Sciences 92(18):8358-8362 (1995).

Gerngross, Tillman U. Advances In The Production Of Human Therapeutic Proteins In Yeasts and Filamentous Fungi. Nature Biotechnology 22(11):1409-1414 (2004).

Ghahroudi, M Arbabi. et al. Selection and Identification of Single Domain Antibody Fragments From Camel Heavy-chain Antibodies. FEBS letters 414(3):521-526 (1997).

Giffin, Michael J. et al. AMG 757, a half-life extended, DLL3-targeted bispecific T-cell engager, shows high potency and sensitivity in preclinical models of small-cell lung cancer. Clinical Cancer Research 27(5):1526-1537 (2021).

Gil, Diana. et al. Strategies to Stabilize Compact Folding and Minimize Aggregation of Antibody-based Fragments. Advances in Bioscience and Biotechnology 4(4a):73-84 (2013).

Glockshuber, Rudi. et al. A comparison of strategies to stabilize immunoglobulin Fv-fragments. Biochemistry 29(6):1362-1367 (1990).

Günaydin, Gökçe, et al. Fusion of the mouse IgG1 Fc domain to the VHH fragment (ARP1) enhances protection in a mouse model of rotavirus. Scientific Reports 6:30171 (2016). DOI: 10.1038/srep30171.

Gong, Jun, and Ravi Salgia. Managing patients with relapsed small-cell lung cancer. Journal of oncology practice 14(6):359-366 (2018).

(56) References Cited

OTHER PUBLICATIONS

Gouin, Sebastien G. et al. Synthesis and Metal Complexation Properties of Ph-DTPA and Ph-TTHA: Novel Radionuclide Chelating Agents for Use in Nuclear Medicine. Organic & Biomolecular Chemistry 3(3):454-461 (2005).
Graham, Frank L. et al. A new technique for the assay of infectivity of human adenovirus 5 DNA. Virology 52(2):456-467 (1973).
Graham, Frank L. et al. Characteristics of a Human Cell line Transformed by DNA from Human Adenovirus type 5. Journal of General Virology 36(1):59-72 (1977).
Griffiths, Andrew D. et al. Human anti-self antibodies with high specificity from phage display libraries. The EMBO Journal 12(2):725-734 (1993).
Grimwood, J. et al. GenBank Accession No. NC_000019. Version No. NC_000019.10. *Homo sapiens* chromosome 19, GRCh38 Primary Assembly: pp. 1-2. Record Created Feb. 3, 2014. Retrieved Oct. 10, 2024. Retrieved from: https://www.ncbi.nlm.nih.gov/nuccore/NC_000019.10/.
Guss, Bengt. et al. Structure of the IgG-binding regions of streptococcal protein G. The EMBO journal 5(7):1567-1575 (1986).
Guyer, Ruth L. et al. Immunoglobulin Binding by Mouse Intestinal Epithelial Cell Receptors. Journal of Immunology 117(2):587-593 (1976).
Ham, Richard G, and Wallace L. McKeehan. Media and growth requirements. Methods Enzymol 58:44-93 (1979).
Hamann, Philip R. Monoclonal antibody-drug conjugates. Expert Opinion on Therapeutic Patents 15(9):1087-1103 (2005).
Hamblett et al.: Altering Antibody-Drug Conjugate Binding to the Neonatal Fc Receptor Impacts Efficacy and Tolerability. Molecular Pharmaceutics 13(7):2387-2396 (2016).
Hamers-Casterman, C. et al. Naturally Occurring Antibodies Devoid of Light Chains. Nature 363(6428):446-448 (1993).
Hara, Hiroshi et al. Overproduction of penicillin-binding protein 7 suppresses thermosensitive growth defect at low osmolarity due to an spr mutation of *Escherichia coli*. Microbial Drug Resistance 2(1):63-72 (1996).
Harlow, Ed, and Lane D. Antibodies, a Laboratory Manual, 1st Edition. Cold Spring Harbor Laboratory (1988).
Hartimath et al., Preclinical Evaluation of 111In-Labeled PEGylated Maytansine Nimotuzumab Drug Conjugates in EGFR-Positive Cancer Models. J Nucl Med 60:1103-1110 (2019).
Hay, Michael P. et al. A2-nitroimidazole carbamate prodrug of 5-amino-1-(chloromethyl)-3-[(5, 6, 7-trimethoxyindol-2-yl) carbonyl]-1, 2-dihydro-3H-benz [e] indole (amino-seco-CBI-TMI) for use with ADEPT and GDEPT. Bioorganic & medicinal chemistry letters 9(15):2237-2242 (1999).
Hellstrom, Ingegerd. et al. Strong Antitumor Activities of IgG3 Antibodies to a Human Melanoma-associated Ganglioside. Proceedings of the National Academy of Sciences of the United States of America 82(5):1499-1502 (1985).
Hellstrom, Ingegerd. et al. Antitumor Effects of L6, and IgG2a Antibody that Reacts with Most Human Carcinomas. Proceedings of the National Academy of Sciences 83(18):7059-7063 (1986).
Higgins, Desmond G. et al. Using CLUSTAL for Multiple Sequence Alignments. Methods in Enzymology 266:383-402 (1996).
Ho, Joanne M. et al. Efficient Reassignment of a Frequent Serine Codon in Wild-type *Escherichia coli*. ACS Synthetic Biology 5(2):163-171 (2016).
Holliger, Philipp. et al. "Diabodies": Small Bivalent and Bispecific Antibody Fragments. Proceedings of the National Academy of Sciences of the United States of America 90(14):6444-6448 (1993).
Honegger, Annemarie et al. Yet another numbering scheme for immunoglobulin variable domains: an automatic modeling and analysis tool. Journal of Molecular Biology 309(3):657-670 (2001).
Hoogenboom, Hennie R, and Greg Winter. By-Passing Immunisation: Human Antibodies From Synthetic Repertoires Of Germline VH Gene Segments Rearranged In Vitro. Journal of Molecular Biology 227(2):381-388 (1992).

Hoogenboom, Hennie R. Overview Of Antibody Phage-display Technology And Its Applications. Methods In Molecular Biology 178:1-37 (2002).
Hornick et al.: Single amino acid substitution in the Fc region of chimeric TNT-3 antibody accelerates clearance and improves immunoscintigraphy of solid tumors. J Nucl Med. 41(2):355-362 (2000).
Howard. Chapter 9: Antibody-Drug Conjugates (ADCs) in Protein Therapeutics (ed. Vaughan, Osbourn and Jallal) pp. 278-309 (2017).
Howard, Philip W. First Edition, Chapter 9: Antibody-drug Conjugates (ADCs). Protein Therapeutics 1: 278-279 (2017).
Hsiao, Chu-Lai, and John Carbon. High-frequency transformation of yeast by plasmids containing the cloned yeast ARG4 gene. Proceedings of the National Academy of Sciences 76(8):3829-3833 (1979).
Hu, S. et al. Minibody: a Novel Engineered Anti-carcinoembryonic Antigen Antibody Fragment (Single-chain Fv-CH3) Which Exhibits Rapid, High-level Targeting of Xenografts. Cancer Research 56(13):3055-3061 (1996).
Hunter et al., Preparation of iodine-131 labelled human growth hormone of high specific activity. Nature 194:495-6 (1962).
Hwang, Karl J. et al. Hepatic uptake and degradation of unilamellar sphingomyelin/cholesterol liposomes: A kinetic study. PNAS USA 77(7):4030-4034 (1980).
Idusogie, Esohe E. et al. Mapping of the C1q Binding Site on Rituxan, a Chimeric Antibody with a Human IgG1 Fc. Journal of Immunology 164(8):4178-4184 (2000).
Iqbal, U. et al. Kinetic Analysis of Novel Mono- and Multivalent Vhh-fragments and Their Application for Molecular Imaging of Brain Tumours. British Journal of Pharmacology 160(4):1016-1028 (2010).
Jackman, David M, and Bruce E. Johnson. Small-cell lung cancer. The Lancet 366(9494):1385-1396 (2005).
Jaggi, Jaspreet Singh. et al. Efforts To Control The Errant Products Of A Targeted In Vivo Generator. Cancer Research 65(11):4888-4895 (2005).
Jawa, Vibha. et al. T-cell Dependent Immunogenicity of Protein Therapeutics: Preclinical Assessment and Mitigation. Clinical Immunology 149(3):534-555 (2013).
Jefferis, Roy, and Marie-Paule Lefranc. Human Immunoglobulin Allotypes: Possible Implications for Immunogenicity. MAbs 1(4):332-338 (2009).
Jones, Andrew J S. Analysis of Polypeptides and Proteins. Advanced Drug Delivery Review 10:29-90 (1993).
Jones, Peter T. et al. Replacing The Complementarity-determining Regions In A Human Antibody With Those From A Mouse. Nature 321(6069):522-525 (1986).
Kabat, Elvin A. et al. Sequences of Proteins of Immunological Interest, 5th Edition. U.S. Department of Health and Human Services NIH Publication No. 91-3242 (1991).
Kanda, Yutaka. et al. Comparison of Cell Lines for Stable Production of Fucose-negative Antibodies With Enhanced ADCC. Biotechnology and Bioengineering 94(4):680-688 (2006).
Karlin, Samuel, and Stephen F. Altschul. Applications and Statistics for Multiple High-scoring Segments in Molecular Sequences. Proceedings of the National Academy of Sciences of the United States of America 90(12):5873-5877 (1993).
Karlin, Samuel. et al. Methods for Assessing the Statistical Significance of Molecular Sequence Features by Using General Scoring Schemes. PNAS USA 87(6):2264-2268 (1990).
Kelly, Joan M, and Michael J. Hynes. Transformation of Aspergillus niger by the amdS gene of Aspergillus nidulans. The EMBO journal 4(2):475-479 (1985).
Kenanova et al.: Radioiodinated versus radiometal-labeled anti-carcinoembryonic antigen single-chain Fv-Fc antibody fragments: optimal pharmacokinetics for therapy. Cancer Res. 67(2):718-726 (2007).
Kenanova et al.: Tailoring the pharmacokinetics and positron emission tomography imaging properties of anti-carcinoembryonic antigen single-chain Fv-Fc antibody fragments. Cancer Res. 65(2):622-631 (2005).
Keown, Wayne A. et al. Methods for introducing DNA into mammalian cells 185:527-537 (1990).

(56) References Cited

OTHER PUBLICATIONS

Kim et al.: Mapping the site on human IgG for binding of the MHC class I-related receptor, FcRn. Eur J Immunol. 29(9):2819-2825 (1999).
Kindt et al. Kuby Immunology, Sixth Edition. W.H. Freeman and Co, p. 91 (2007).
Kingsbury, William D. et al. A novel peptide delivery system involving peptidase activated prodrugs as antimicrobial agents. Synthesis and biological activity of peptidyl derivatives of 5-fluorouracil. Journal of Medicinal Chemistry 27(11):1447-1451 (1984).
Kipriyanov, S M. et al. Affinity Enhancement of a Recombinant Antibody: Formation of Complexes With Multiple Valency by a Single-chain Fv Fragment-core Streptavidin Fusion. Protein Engineering 9(2):203-211 (1996).
Kipriyanov, S M. et al. Single-chain Antibody Streptavidin Fusions: Tetrameric Bifunctional scFv-complexes With Biotin Binding Activity and Enhanced Affinity to Antigen. Human Antibodies and Hybridomas 6(3):93-101 (1995).
Korsen, et al. Delta-like Ligand 3 (DLL3) is a novel target for molecular imaging of Neuroendocrine Prostate Cancer. Journal of Nuclear Medicine. vol. 61, Supplement 1, Abstract No. 133 (2020): 1 page.
Kunz, Patrick. et al. Exploiting Sequence and Stability Information for Directing Nanobody Stability Engineering. Biochimica Biophysica Acta. General Subjects 1861(9):2196-2205 (2017).
Kunz, Patrick. et al. The Structural Basis of Nanobody Unfolding Reversibility and Thermoresistance. Scientific Reports 8(1):7934, 1-10 (2018).
Larsen, Roy H. et al. Radiolysis Of Radioimmunoconjugates. Reduction In Antigen-Binding Ability By α-Particle Radiation. Journal of Labelled Compounds and Radiopharmaceuticals 36(10):1009-1018 (1995).
Lefranc, Marie-Paule. et al. IMGT Unique Numbering for Immunoglobulins and T-Cell Receptor Variable Domains and Ig Superfamily V-Like Domains. Developmental and Comparative Immunology 27(1):55-77 (2003).
Li, Feng. et al. Cell Culture Processes for Monoclonal Antibody Production. MAbs. 2(5):466-477 (2010).
Li, Huijuan. et al. Optimization of humanized IgGs in glycoengineered Pichia pastoris. Nature biotechnology 24(2):210-215 (2006).
Li, Lily. et al. 225Ac-H4py4pa for Targeted Alpha Therapy. Bioconjugate Chemistry 32(7):1348-1363 (2021).
Li, S L. et al. Single-chain Antibodies Against Human Insulin-like Growth Factor I Receptor: Expression, Purification, and Effect on Tumor Growth. Cancer Immunology, Immunotherapy 49(4-5):243-252 (2000).
Lindmark, Roger. et al. Binding of immunoglobulins to protein A and immunoglobulin levels in mammalian sera. Journal of immunological methods 62(1):1-13 (1983).
Liu, Mengyuan. et al. Targeting TNF-alpha with a Tetravalent Mini-antibody TNF-TeAb. Biochemical Journal 406(2):237-246 (2007).
Liu, Yuqi. et al. High-throughput Screening for Developability During Early-stage Antibody Discovery Using Self-interaction Nanoparticle Spectroscopy. mAbs 6(2):483-492 (2014).
Maccallum, Robert M. et al. Antibody-Antigen Interactions: Contact Analysis And Binding Site Topography. Journal of Molecular Biology 262(5):732-745 (1996).
Mansour, Suzanne L. et al. Disruption of the proto-oncogene int-2 in mouse embryo-derived stem cells: a general strategy for targeting mutations to non-selectable genes. Nature 336(6197):348-352 (1988).
Mardirossian, G. et al. Radiation absorbed dose from indium-111-CYT-356. The Journal of Nuclear Medicine 37(9):1583-1588 (1996).
Marks, James D. et al. By-passing immunization: building high affinity human antibodies by chain shuffling. Bio/technology 10(7):779-783 (1992).
Marks, James D. et al. By-passing immunization: human antibodies from V-gene libraries displayed on phage. Journal of molecular biology 222(3):581-597 (1991).

Martin, Andrew CR. Protein Sequence and Structure Analysis of Antibody Variable Domains. Antibody Engineering 2:33-51 (2010).
Mather, Jennie P. Establishment and characterization of two distinct mouse testicular epithelial cell lines. Biology of reproduction 23(1):243-252 (1980).
Mather, Jennie P. et al. Culture of testicular cells in hormone-supplemented serum-free medium. Annals of the New York Academy of Sciences 383(1):44-68 (1982).
Mccafferty, John. et al. Phage Antibodies: Filamentous Phage Displaying Antibody Variable Domains. Nature 348(6301):552-554 (1990).
Mccartney, John E. et al. Engineering disulfide-linked single-chain Fv dimers [(sFv') 2] with improved solution and targeting properties: anti-digoxin 26-10 (sFv') 2 and anti-c-erbB-2 741F8 (sFv') 2 made by protein folding and bonded through C-terminal cysteinyl peptides. Protein Engineering, Design and Selection 8(3):301-314 (1995).
McDevitt, Michael R. et al. Design and Synthesis of 225Ac Radioimmunopharmaceuticals. Applied Radiation and Isotopes 57(6):841-847 (2002).
Mcmahon, Conor. et al. Yeast Surface Display Platform for Rapid Discovery of Conformationally Selective Nanobodies. Nature Structural & Molecular Biology 25(3):289-296 (2018).
Merrifield, Robert B. Solid Phase Peptide Synthesis. I. The Synthesis of a Tetrapeptide. Journal of the American Chemical Society 85(14):2149-2154 (1963).
Miranda, Ana Claudia Camargo. et al. Anti-hER2 Monoclonal Antibody Based-radioimmunoconjugates: Assessment of the Chelating Agent Influence. Bioorganic & Medicinal Chemistry 33:115996, 1-9 (2021).
Miranda, Ana Claudia Camargo. et al. Radioimmunotheranostic Pair Based on the Anti-HER2 Monoclonal Antibody: Influence of Chelating Agents and Radionuclides on Biological Properties. Pharmaceutics 13(7):971, 1-16 (2021).
Moore et al. Apoptosis in CHO cell batch cultures: examination by flow cytometr. Cytotechnology 17:1-11 (1995).
Morris, Glenn E. Epitope Mapping Protocols. Methods in Molecular Biology 66:1-22 (1996).
Morrison, Sherie L. et al. Chimeric Human Antibody Molecules: Mouse Antigen-Binding Domains With Human Constant Region Domains. PNAS USA 81(21):6851-6855 (1984).
Mosmann. Rapid colorimetric assays for cellular growth and survival: application to proliferation and cytotoxicity assays. Journal of Immunological Methods. 65:55-63 (1983).
Moutel, Sandrine. et al. NaLi-H1: a Universal Synthetic Library of Humanized Nanobodies Providing Highly Functional Antibodies and Intrabodies. Elife 5:e16228, 1-31 (2016).
Muller, K M. et al. The First Constant Domain (C(H)1 and C(L)) of an Antibody Used as Heterodimerization Domain for Bispecific Miniantibodies. FEBS letters 422(2):259-264 (1998).
Mullis, Kary B. et al. The Polymerase Chain Reaction. Springer Science+Business Media (1994).
Munson, Peter, and Rodbard, David. Ligand: a Versatile Computerized Approach for Characterization of Ligand-binding Systems. Analytical Biochemistry 107(1):220-239 (1980).
Muyldermans, Serge. Single Domain Camel Antibodies: Current Status. Reviews in Molecular Biotechnology 74(4):277-302 (2001).
Nelson et al., Targeted Alpha Therapy:Progress in Radio-nuclide Production, Radiochemistry, and Applications. Pharmaceutics 13(1):49 (2021).
Nygren, H. et al. Conjugation of Horseradish Peroxidase to Fab Fragments With Different Homobifunctional and Heterobifunctional Cross-linking Reagents. A Comparative Study. The Journal of Histochemistry and Cytochemistry 30(5):407-412 (1982).
Okazaki, Akira. et al. Fucose Depletion From Human IgG1 Oligosaccharide Enhances Binding Enthalpy and Association Rate Between IgG1 and FcgammaRIIIa. Journal of Molecular Biology 336(5):1239-1249 (2004).
Olafsen et al.: Optimizing radiolabeled engineered anti-p185HER2 antibody fragments for in vivo imaging. Cancer Res. 65(13):5907-5916 (2005).
Olafsen et al.: Recombinant anti-CD20 antibody fragments for small-animal PET imaging of B-cell lymphomas. Recombinant

(56) References Cited

OTHER PUBLICATIONS anti-CD20 antibody fragments for small-animal PET imaging of B-cell lymphomas. J Nucl Med. 50(9):1500-1508 (2009).
Olafsen, Tove. et al. Covalent Disulfide-linked Anti-CEA Diabody Allows Site-specific Conjugation and Radiolabeling for Tumor Targeting Applications. Protein Engineering, Design & Selection 17(1):21-27 (2004).
Osol, Arthur. Remington's Pharmaceutical Sciences, 16th Edition. Mack Publishing Company (1980).
O'Sullivan, M J, and V Marks. Methods for the Preparation of Enzyme-antibody Conjugates for Use in Enzyme Immunoassay. Methods in Enzymology 73(Pt B):147-166 (1981).
Pack, P, and A Pluckthun. Miniantibodies: Use of Amphipathic Helices to Produce Functional, Flexibly Linked Dimeric Fv Fragments With High Avidity in *Escherichia coli*. Biochemistry 31(6):1579-1584 (1992).
Pain, D, and A Surolia. Preparation of Protein a-peroxidase Monoconjugate Using a Heterobifunctional Reagent, and Its Use in Enzyme Immunoassays. Journal of Immunological Methods 40(2):219-230 (1981).
PCT/IB2022/000077 International Search Report and Written Opinion dated Jun. 29, 2022.
PCT/US2023/072583 International Search Report and Written Opinion dated Nov. 20, 2023.
PCT/US2023/072586 International Search Report and Written Opinion mailed Dec. 5, 2023.
PCT/US2023/072588 International Search Report and Written Opinion dated Jan. 17, 2024.
Pearson, William R, and David J. Lipman. Improved Tools for Biological Sequence Comparison. Proceedings of the National Academy of Sciences 85(8):2444-2448 (1988).
Perisic, Olga. et al. Crystal Struction of a diabody, a bivalen antibody fragment. Structure 2(12):1217-1226 (1994).
Petkova, Stefka B. et al. Enhanced Half-life of Genetically Engineered Human IgG1 Antibodies in a Humanized FcRn Mouse Model: Potential Application in Humorally Mediated Autoimmune Disease. International Immunology 18(12):1759-1769 (2006).
Pluckthun, Andreas. Mono- and bivalent antibody fragments produced in *Escherichia coli*: engineering, folding and antigen binding. Immunological Reviews 130(1):151-188 (1992).
Portolano, Stefano. et al. Lack of Promiscuity In Autoantigen-specific H and L Chain Combinations as Revealed By Human H And L Chain "roulette". Journal of Immunology 150(3):880-887 (1993).
Pothin, Elodie, et al. Brain Delivery of Single-Domain Antibodies: A Focus on VHH and VNAR. Pharmaceutics 12, 937 (2020). doi:10.3390/pharmaceutics12100937.
Poty, S. et al. The inverse electron-demand Diels-Alder reaction as a new methodology for the synthesis of 225Ac-labelled radioimmunoconjugates. Chemical Communications 54(21):2599-2602 (2018).
Presta, Leonard G. Antibody Engineering. Current Opinion in Structural Biology 2:593-596 (1992).
Price, Eric W, and Chris Orvig. Matching Chelators to Radiometals for Radiopharmaceuticals. Chemical Society Reviews 43(1):260-290 (2014). Published Online Oct. 30, 2013.
Puttemans, Janik, et al. Preclinical Targeted alpha- and beta-Radionuclide Therapy in HER2-Positive Brain Metastasis Using Camelid Single-Domain Antibodies. Cancers 12, 1017 (2020). doi:10.3390/cancers12041017.
Ramm, Kathrin, and Andreas Pluckthun. The periplasmic *Escherichia coli* peptidylprolyl cis, trans-isomerase FkpA: II. Isomerase-independent chaperone activity in vitro. Journal of Biological Chemistry 275(22):17106-17113 (2000).
Ravetch, J V. et al. Fc Receptors. Annual Review of Immunology 9:457-492 (1991).
Rheinnecker, M. et al. Multivalent Antibody Fragments With High Functional Affinity for a Tumor-associated Carbohydrate Antigen. Journal of Immunology 157(7):2989-2997 (1996).
Riechmann, Lutz. et al. Reshaping Human Antibodies for Therapy. Nature 332(6162):323-327 (1988).

Ripka, James. et al. Two Chinese Hamster Ovary Glycosylation Mutants Affected in the Conversion of GDP-mannose to GDP-fucose. Archives of Biochemistry and Biophysics 249(2):533-545 (1986).
Robertson, Andrew Kyle Henderson. et al. Development of 225Ac Radiopharmaceuticals: TRIUMF Perspectives and Experiences. Current Radiopharmaceuticals 11(3):156-172 (2018).
Rodrigues, Maria L. et al. Synthesis and β-lactamase-mediated activation of a cephalosporin-taxol prodrug. Chemistry & biology 2(4):223-227 (1995).
Rossi, Edmund A. et al. Stably Tethered Multifunctional Structures of Defined Composition Made by the Dock and Lock Method for Use in Cancer Targeting. Proceedings of the National Academy of Sciences of the United States of America 103(18):6841-6846 (2006).
Rotman et al.: Fusion of hIgG1-Fc to 111In-anti-amyloid single domain antibody fragment VHH-pa2H prolongs blood residential time in APP/PS1 mice but does not increase brain uptake. Nucl Med Biol. 42(8):695-702 (2015).
Rudin, Charles M. et al. Emerging therapies targeting the delta-like ligand 3 (DLL3) in small cell lung cancer. Journal of Hematology & Oncology 16(1):66, 1-21 (2023).
Sadiki, Amissi. et al. Site-specific Conjugation of Native Antibody. Antibody Therapeutics 3(4):271-284 (2020).
Salako, Q A. et al. Effects of Radiolysis on Yttrium-90-Labeled Lym-1 Antibody Preparations. Journal of Nuclear Medicine 39(4):667-670 (1998).
Sathekge et al.: 225Ac-PSMA-617 in chemotherapy-naive patients with advanced prostate cancer: a pilot study. Eur J Nucl Med Mol Imaging. 46(1):129-138 (2019).
Saunders, Kevin O. Conceptual Approaches to Modulating Antibody Effector Functions and Circulation Half-Life. Frontiers in Immunology 10:1296, 1-20 (2019).
Saunders, Laura R. et al. A DLL3-targeted antibody-drug conjugate eradicates high-grade pulmonary neuroendocrine tumor-initiating cells in vivo. Science translational medicine 7(302):302ra136, 1-14 (2015).
Scheinberg, David A, and Michael R McDevitt. Actinium-225 in Targeted Alpha-particle Therapeutic Applications. Current Radiopharmaceuticals 4(4):306-320 (2011).
Schmiedl, A. et al. Expression of a Bispecific dsFv-dsFv' Antibody Fragment in *Escherichia coli*. Protein Engineering 13(10):725-734 (2000).
Schoonjans, R. et al. Fab Chains as an Efficient Heterodimerization Scaffold for the Production of Recombinant Bispecific and Trispecific Antibody Derivatives. Journal of Immunology 165(12):7050-7057 (2000).
Scopes, Robert K. Protein Purification: Principles and Practice. Springer Science & Business Media (1982).
Sgouros, George, and Robert F Hobbs. Dosimetry for Radiopharmaceutical Therapy. Seminars in Nuclear Medicine 44(3):172-178 (2014).
Sgouros, George. et al. MIRD pamphlet No. 22 (abridged): radiobiology and dosimetry of α-particle emitters for targeted radionuclide therapy. Journal of nuclear medicine 51(2):311-328 (2010).
Shan, Lu. et al. Developability Assessment of Engineered Monoclonal Antibody Variants With a Complex Self-association Behavior Using Complementary Analytical and in Silico Tools. Molecular Pharmaceutics 15(12):5697-5710 (2018).
Sharma, Rohit. et al. Dose-dependent cell cycle arrest and apoptosis in HER2 breast cancer cells by177Lu-CHX-A"-DTPA-Trastuzumab. Journal of Cancer Research and Therapeutics 16(6):1426-1434 (2020).
Sharma, Sai Kiran. et al. A Rapid Bead-based Radioligand Binding Assay for the Determination of Target-binding Fraction and Quality Control of Radiopharmaceuticals. Nuclear Medicine and Biology 71:32-38 (2019).
Shaw, Charles H. et al. A general method for the transfer of cloned genes to plant cells. Gene 23(3):315-330 (1983).
Shields, Robert L. et al. High Resolution Mapping of the Binding Site on Human IgG1 for Fc Gamma RI, Fc Gamma RII, Fc Gamma RIII, and FcRn and design of IgG1 Variants with Improved Binding to the Fc Gamma R. Journal of Biological Chemistry 276(9):6591-6604 (2001).

(56) References Cited

OTHER PUBLICATIONS

Shopes, Bob. A genetically engineered human IgG mutant with enhanced cytolytic activity. Journal of immunology 148(9):2918-2922 (1992).

Shu, L. et al. Secretion Of A Single-Gene-Encoded Immunoglobulin From Myeloma Cells. Proceedings of the National Academy of Sciences of the United States of America 90(17):7995-7999 (1993).

Siegel, Rebecca L. et al. Cancer statistics, 2023. CA: a cancer journal for clinicians 73(1):17-48 (2023).

Simmons, David P, et al. Dimerisation Strategies for Shark IgNAR Single Domain Antibody Fragments. Journal of Immunological Methods 315(1-2):171-184 (2006).

Simmons, Laura C. et al. Expression of full-length immunoglobulins in *Escherichia coli*: rapid and efficient production of aglycosylated antibodies. Journal of immunological methods 263(1-2):133-147 (2002).

Skerra, Arne. Bacterial Expression of Immunoglobulin Fragments. Current Opinion in Immunology 5(2):256-262 (1993).

Sojar, Hakimuddin T, and Om P. Bahl. A chemical method for the deglycosylation of proteins. Archives of biochemistry and biophysics 259(1):52-57 (1987).

Solomon et al. $^{111}$In- and $_{225}$Ac-Labeled Cixutumumab for Imaging and α-Particle Radiotherapy of IGF-1R Positive Triple-Negative Breast Cancer. Mol. Pharmaceutics 12:4807-4816 (2019).

Sreekrishna, K. et al. High level expression of heterologous proteins in methylotrophic yeast *Pichia pastoris*. Journal of basic microbiology 28(4):265-278 (1988).

Stabin, Michael G. OLINDA/EXM: the second-generation personal computer software for internal dose assessment in nuclear medicine. J Nucl Med 46(6):1023-1027 (2005).

Stevenson et al. A chimeric antibody with dual Fc regions (bisFabFc) prepared by manipulations at the IgG hinge. Anti-Cancer Drug Design 3:219-230 (1989).

Storm, Dan R, and D. E. Koshland Jr. Effect of small changes in orientation on reaction rate. Journal of the American Chemical Society 94(16):5815-5825 (1972).

Sun, Chengzao. et al. Enabling ScFvs as multi-drug carriers: a dendritic approach. Bioorganic & medicinal chemistry 11(8):1761-1768 (2003).

Sun, Chengzao. et al. Syntheses of dendritic linkers containing chlorambucil residues for the preparation of antibody-multidrug immunoconjugates. Bioorganic & medicinal chemistry letters 12(16):2213-2215 (2002).

Tai, Mei Sheng. et al. A bifunctional fusion protein containing Fc-binding fragment B of staphylococcal protein A amino-terminal to antidigoxin single-chain Fv. Biochemistry 29(35):8024-8030 (1990).

Taylor, T. et al. GenBank Accession No. NC_000011. Version No. NC_000011.10. *Homo sapiens* chromosome 11, GRCh38.p14 Primary Assembly Record Created Feb. 3, 2014. Retrieved from: https://www.ncbi.nlm.nih.gov/nuccore/NC_000011.10.

Terskikh, A V. et al. "Peptabody": a New Type of High Avidity Binding Protein. Proceedings of the National Academy of Sciences of the United States of America 94(5):1663-1668 (1997).

Thiele, Nikki A. et al. An Eighteen-membered Macrocyclic Ligand for Actinium-225 Targeted Alpha Therapy. Angewandte Chemie International Edition 56(46):14712-14717 (2017).

Thotakura, Nageswara R. et al. Chapter 28: Enzymatic deglycosylation of glycoproteins. Methods in Enzymology 138:350-359 (1987).

Tilburn, Joan. et al. Transformation by integration in Aspergillus nidulans. Gene 26(2-3):205-221 (1983).

Torelli, Alberto, and Carlo A. Robotti. ADVANCE and ADAM: Two Algorithms for the Analysis of Global Similarity Between Homologous Informational Sequences. Bioinformatics 10(1): 3-5 (1994).

Tully, Kathryn M. et al. Radioimmunotherapy targeting delta-like ligand 3 in small cell lung cancer exhibits antitumor efficacy with low toxicity. Clinical Cancer Research 28(7):1391-1401 (2022).

UniProtKB Accession No. P01857. Immunoglobulin heavy constant gamma 1. Record created Nov. 1, 1988. pp. 1-16. Retrieved Oct. 11, 2024 at URL: https://www.uniprot.org/uniprotkb/P01857/entry.

UniProtKB Accession No. P01859. Immunoglobulin heavy constant gamma 2. Record created Nov. 1, 1988. pp. 1-9. Retrieved Oct. 11, 2024 at URL: https://www.uniprot.org/uniprotkb/P01859/entry.

UniProtKB Accession No. P01860. Immunoglobulin heavy constant gamma 3. Record created Nov. 1, 1988. pp. 1-14. Retrieved Oct. 11, 2024 at URL: https://www.uniprot.org/uniprotkb/P01860/entry.

UniProtKB Accession No. P01861. Immunoglobulin heavy constant gamma 4. Record created Nov. 1, 1988. pp. 1-13. Retrieved Oct. 11, 2024 at URL: https://www.uniprot.org/uniprotkb/P01861/entry.

UniProtKB Accession No. P15328. Folate receptor alpha. Record created Apr. 1, 1990. pp. 1-8. Retrieved Oct. 10, 2024 at URL: https://www.uniprot.org/uniprotkb/P15328/entry.

UniProtKB Accession No. Q9NYJ7. Delta-like protein 3. Record created Oct. 1, 2000. pp. 1-9. Retrieved Oct. 10, 2024 at URL: https://www.uniprot.org/uniprotkb/Q9NYJ7/entry.

Urlaub, Gail, and Lawrence A. Isolation of Chinese hamster cell mutants deficient in dihydrofolate reductase activity. Proceedings of the National Academy of Sciences 77(7):4216-4220 (1980).

Vallabhajosula, Shankar. et al. Pharmacokinetics and biodistribution of 111In- and 177Lu-labeled J591 antibody specific for prostate-specific membrane antigen: prediction of 90Y-J591 radiation dosimetry based on 111In or 177Lu ?. J Nucl Med 46(4):634-641 (2005).

Van Den Berg, Johan A. et al. Kluyveromyces as a host for heterologous gene expression: expression and secretion of prochymosin. Bio/technology 8(2):135-139 (1990).

Van Solingen, Pieter, and Johannes B. Van Der Plaat. Fusion of yeast spheroplasts Journal of Bacteriology 130(2):946-947 (1977).

Verhoeyen, Martine. et al. Reshaping Human Antibodies: Grafting an Antilysozyme Activity. Science 239(4847):1534-1536 (1988).

Vincke, Cecile. et al. General Strategy to Humanize a Camelid Single-domain Antibody and Identification of a Universal Humanized Nanobody Scaffold. Journal of Biological Chemistry 284(5):3273-3284 (2009).

Vincke, Cecile. et al. Generation of Single Domain Antibody Fragments Derived From Camelids and Generation of Manifold Constructs. Methods in Molecular Biology 907:145-176 (2012).

Vitetta, Ellen S. et al. Redesigning Nature's Poisons to Create Anti-tumor Reagents. Science 238(4830):1098-1104 (1987).

Wakankar, Aditya. et al. Analytical Methods for Physicochemical Characterization of Antibody Drug Conjugates. mAbs 3(2):161-172 (2011).

Wang, Yiyan. et al. Reassigning Sense Codon AGA to Encode Noncanonical Amino Acids in *Escherichia coli*. Chembiochem 17(23):2234-2239 (2016).

Wanner et al., Nanobodies: new avenue to treat kidney disease, Cell and Tissue Research 385:445 (2021).

Waterhouse, Peter. et al. Combinatorial infection and in vivo recombination: a strategy for making large phage antibody repertoires. Nucleic Acids Research 21(9):2265-2266 (1993).

Wells, James A. et al. Cassette mutagenesis: An Efficient Method for Generation of Multiple Mutations at Defined Sites. Gene 34:315-323 (1985).

Whitelegg, Nicholas R. et al. WAM: an improved algorithm for modelling antibodies on the WEB. Protein engineering 13(12):819-824 (2000).

Whitlow, M. et al. An Improved Linker for Single-chain Fv With Reduced Aggregation and Enhanced Proteolytic Stability. Protein Engineering 6(8):989-995 (1993).

Whitlow, Marc. et al. Multivalent Fvs: Characterization Of Single-Chain Fv Oligomers And Preparation Of A Bispecific Fv. Protein Engineering 7(8):1017-1026 (1994).

Wickstroem, Katrine. et al. Preclinical Combination Studies of an FGFR2 Targeted Thorium-227 Conjugate and the ATR Inhibitor Bay 1895344. International Journal of Radiation Oncology* Biology* Physics 105(2):410-422 (2019).

Winter, Greg. et al. Making Antibodies by Phage Display Technology. Annual Review of Immunology 12(1):433-455 (1994).

(56) References Cited

OTHER PUBLICATIONS

Wolff et al., Monoclonal antibody homodimers: enhanced antitumor activity in nude mice. Cancer Research 53:2560-5 (1993).

Wong, Wei, and John D Scott. AKAP Signalling Complexes: Focal Points in Space and Time. Nature Reviews. Molecular Cell Biology 5(12):959-970 (2004).

Wright, Ann, and Sherie L. Morrison. et al. Effect of Glycosylation on Antibody Function: Implications for Genetic Engineering. Trends in Biotechnology 15(1):26-32 (1997).

Wu, Anna M. et al. Multimerization Of A Chimeric Anti-CD20 Single-chain Fv-Fc Fusion Protein Is Mediated Through Variable Domain Exchange. Protein Engineering 14(12):1025-1033 (2001).

Wu, Yanling, et al. Single-domain antibodies as therapeutics against human viral diseases. Frontiers in Immunology 8(1802):1-13 (2017).

Yamane-Ohnuki, Naoko. et al. Establishment of FUT8 Knockout Chinese Hamster Ovary Cells: an Ideal Host Cell Line for Producing Completely Defucosylated Antibodies With Enhanced Antibody-dependent Cellular Cytotoxicity. Biotechnology and Bioengineering 87(5):614-622 (2004).

Yang, Hua. et al. Harnessing α-emitting radionuclides for therapy: radiolabeling method review. Journal of Nuclear Medicine 63(1):5-13 (2022).

Yang, Hua. et al. Synthesis and Evaluation of a Macrocyclic Actinium-225 Chelator, Quality Control and in Vivo Evaluation of 225ac-crown-amsh Peptide. Chemistry—a European Journal 26(50):11435-11440 (2020).

Yazaki, Paul J, and Anna M Wu. Expression of Recombinant Antibodies in Mammalian Cell Lines. Methods in Molecular Biology 248:255-268 (2004).

Yelton, M Melanie. et al. Transformation of Aspergillus nidulans by using a trpC plasmid. Proceedings of the National Academy of Sciences 81(5):1470-1474 (1984).

Yu et al.: Humanized CD7 nanobody-based immunotoxins exhibit promising anti-T-cell acute lymphoblastic leukemia potential. Int J Nanomedicine. 12:1969-1983 (2017).

Zalutsky, Michael R. et al. High-Level Production of α-Particle-Emitting 211At and Preparation of 211At-Labeled Antibodies for Clinical Use. Journal of Nuclear Medicine 42(10):1508-1515 (2001).

Zhang et al. Epidermal growth factor receptor-related protein inhibits cell growth and induces apoptosis of BxPC3 pancreatic cancer cells. Cancer Res. 65:3877-82 (2005).

Zhang, Jianbing. et al. Pentamerization of Single-domain Antibodies From Phage Libraries: a Novel Strategy for the Rapid Generation of High-avidity Antibody Reagents. Journal of Molecular Biology 335(1):49-56 (2004).

Zhang, Jianbing. et al. Transient Expression and Purification of Chimeric Heavy Chain Antibodies. Protein Expression and Purification 65(1):77-82 (2009).

Zoller, Mark J, and Michael Smith. Oligonucleotide-directed mutagenesis using M13-derived vectors: an efficient and general procedure for the production of point mutations in any fragment of DNA. Nucleic Acids Research 10(20):6487-6500 (1982).

Co-pending U.S. Appl. No. 19/104,553, inventors Abrams; Michael J. et al., filed Feb. 18, 2025.

Co-pending U.S. Appl. No. 19/104,559, inventors Abrams; Michael J. et al., filed Feb. 18, 2025.

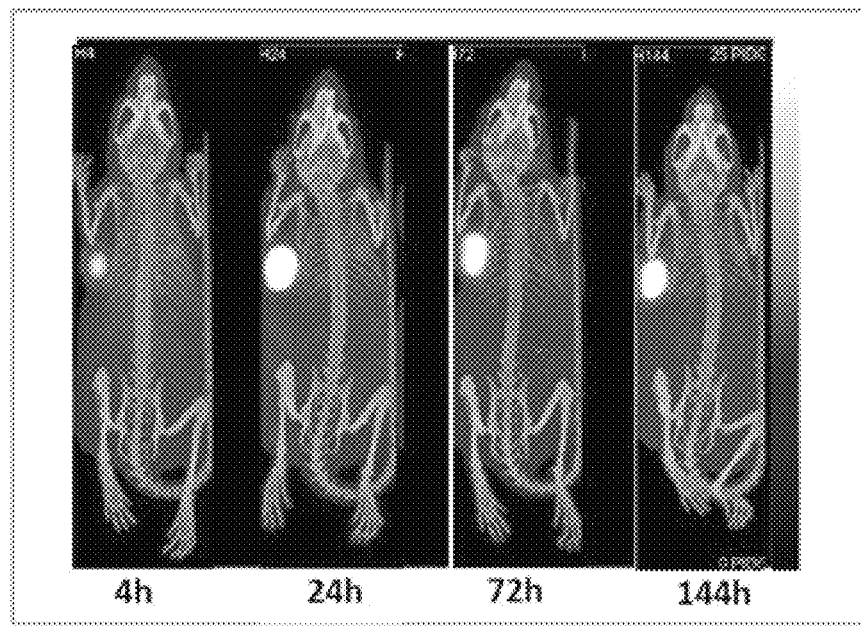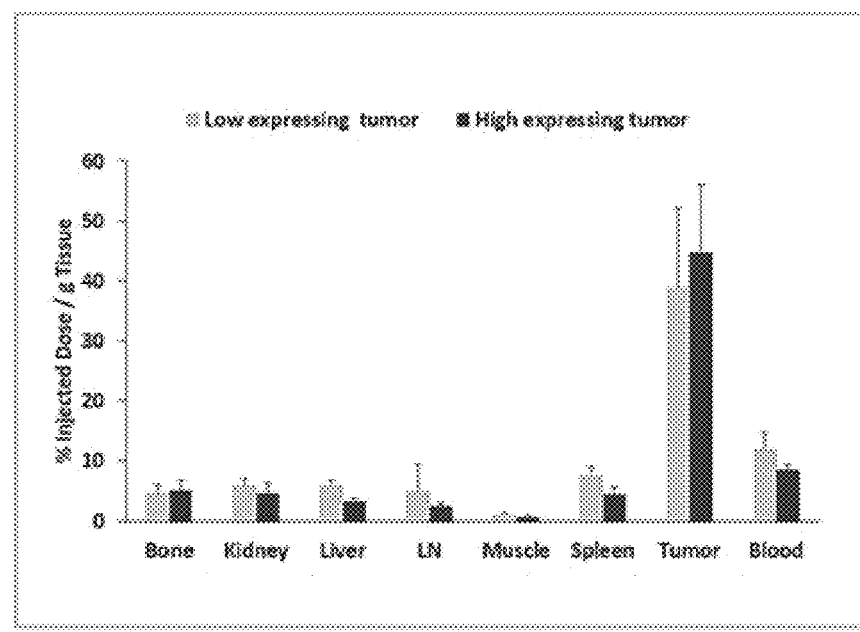
FIG. 8

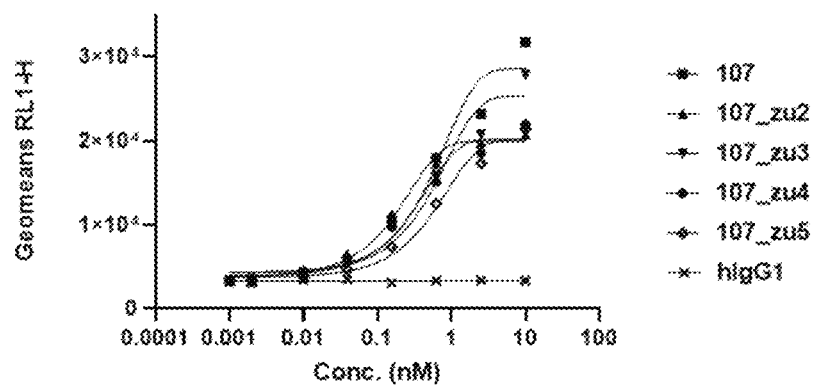
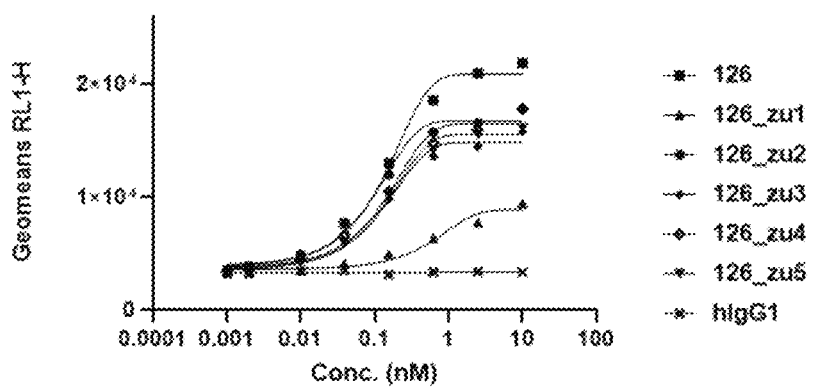
FIG. 20A
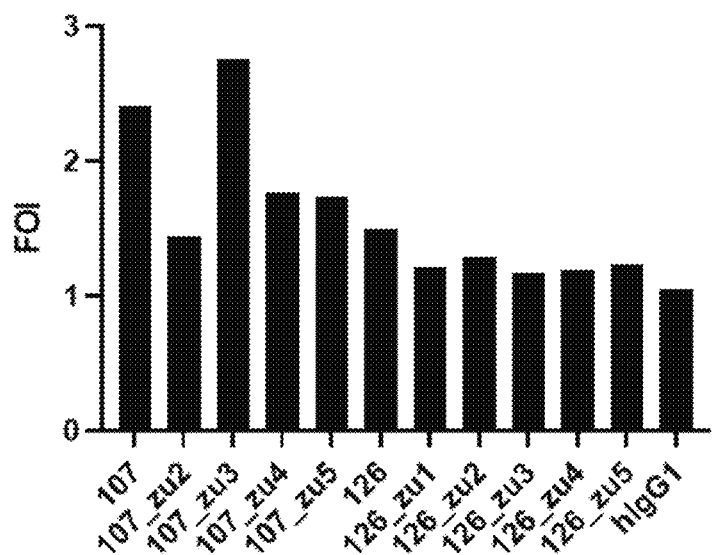
FIG. 20B

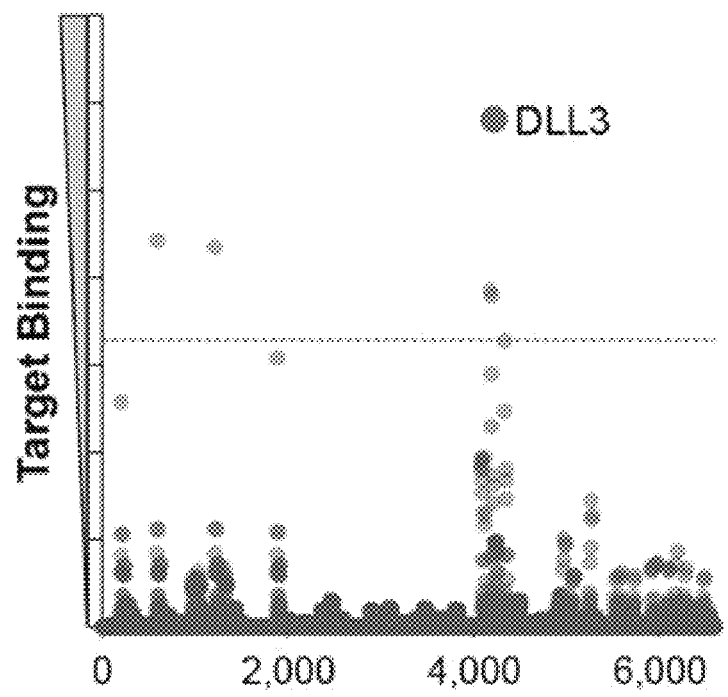
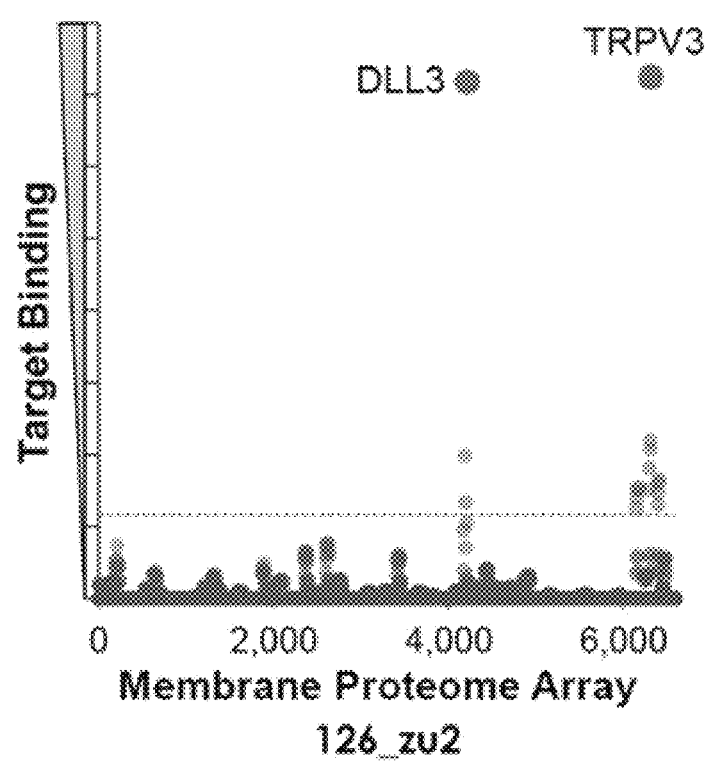
FIG. 23

SEQ ID NO. 532

```
1   APLVCRAGCSPEHGFCEQPGCECRCLEGWTGPLCTVPVSTSSCLSPRGPSSATTGCLVPGPGPCDSMPCANGGSCSETPRSFECTCPRGFYGLRCEVSGVT  100
101 CARGPCFNGGLQVGGADPDSAYICHCPPGFQGSNCEKRVDRCSLQPQRNGGLCLDLGHALRCRCRAGPAGPRCEHQLDDCAGRACANGGTCVEGGGAHRC  200
201 SCALGFGGRDCREFADPCAARPCAHGGRCYAHFSGLVCACAPGYMGARCEFPVHPDGASALPAAPPGLRAPGDPQRYLARGPTIKPCPPCKCPAPAILGG  300
301 PSVFIFPPKIKDVLMISLSPIVTCVVVDVSEDDPDVCISMFVNNVEVHTAQTQTHREDYNSTLRVVSALPIQHQDWMSGKEFKCAVNKDLPAPIERTISK  400
401 PKGSVRAPQVYVLPPPEEEMTKKQVTLTCMVTGFMPEDIYVEWTNNGKTELNYKNTEPVLDSDGSYFMYSKLRVEKKNWVERNSYSCSVVHEGLHNHH    500
501 TTNSFSRTPGK
```

FIG. 31

```
                              SEQUENCE LISTING

Sequence total quantity: 539
SEQ ID NO: 1             moltype = AA  length = 216
FEATURE                  Location/Qualifiers
source                   1..216
                         mol_type = protein
                         organism = synthetic construct
SEQUENCE: 1
APELLGGPSV FLFPPKPKDT LMASRTPEVT CVVVDVSHED PEVKFNWYVD GVEVHNAKTK   60
PREEQYNSTY RVVSVLTVLH QDWLNGKEYK CKVSNKALPA PIEKTISKAK GQPREPQVYT  120
LPPSREEMTK NQVSLTCLVK GFYPSDIAVE WESNGQPENN YKTTPPVLDS DGSFFLYSKL  180
TVDKSRWQQG NVFSCSVMHE ALHNHYTQKS LSLSPG                            216

SEQ ID NO: 2             moltype = AA  length = 216
FEATURE                  Location/Qualifiers
source                   1..216
                         mol_type = protein
                         organism = synthetic construct
SEQUENCE: 2
APELLGGPSV FLFPPKPKDT LMIARTPEVT CVVVDVSHED PEVKFNWYVD GVEVHNAKTK   60
PREEQYNSTY RVVSVLTVLH QDWLNGKEYK CKVSNKALPA PIEKTISKAK GQPREPQVYT  120
LPPSREEMTK NQVSLTCLVK GFYPSDIAVE WESNGQPENN YKTTPPVLDS DGSFFLYSKL  180
TVDKSRWQQG NVFSCSVMHE ALHNHYTQKS LSLSPG                            216

SEQ ID NO: 3             moltype = AA  length = 216
FEATURE                  Location/Qualifiers
source                   1..216
                         mol_type = protein
                         organism = synthetic construct
SEQUENCE: 3
APELLGGPSV FLFPPKPKDT LMISRTPEVT CVVVDVSHED PEVKFNWYVD GVEVHNAKTK   60
PREEQYNSTY RVVSVLTVLA QDWLNGKEYK CKVSNKALPA PIEKTISKAK GQPREPQVYT  120
LPPSREEMTK NQVSLTCLVK GFYPSDIAVE WESNGQPENN YKTTPPVLDS DGSFFLYSKL  180
TVDKSRWQQG NVFSCSVMHE ALHNHYTQKS LSLSPG                            216

SEQ ID NO: 4             moltype = AA  length = 216
FEATURE                  Location/Qualifiers
source                   1..216
                         mol_type = protein
                         organism = synthetic construct
SEQUENCE: 4
APELLGGPSV FLFPPKPKDT LMISRTPEVT CVVVDVSHED PEVKFNWYVD GVEVHNAKTK   60
PREEQYNSTY RVVSVLTVLH QDWLNGKEYK CKVSNKALPA PIEKTISKAK GQPREPQVYT  120
LPPSREEMTK NQVSLTCLVK GFYPSDIAVE WESNGQPENN YKTTPPVLDS DGSFFLYSKL  180
TVDKSRWQQG NVFSCSVMHE ALHNQYTQKS LSLSPG                            216

SEQ ID NO: 5             moltype = AA  length = 216
FEATURE                  Location/Qualifiers
source                   1..216
                         mol_type = protein
                         organism = synthetic construct
SEQUENCE: 5
APELLGGPSV FLFPPKPKDT LMISRTPEVT CVVVDVSHED PEVKFNWYVD GVEVHNAKTK   60
PREEQYNSTY RVVSVLTVLH QDWLNGKEYK CKVSNKALPA PIEKTISKAK GQPREPQVYT  120
LPPSREEMTK NQVSLTCLVK GFYPSDIAVE WESNGQPENN YKTTPPVLDS DGSFFLYSKL  180
TVDKSRWQQG NVFSCSVMHE ALHNHATQKS LSLSPG                            216

SEQ ID NO: 6             moltype = AA  length = 216
```

```
FEATURE                 Location/Qualifiers
source                  1..216
                        mol_type = protein
                        organism = synthetic construct
SEQUENCE: 6
APELLGGPSV FLFPPKPKDT LMISRTPEVT CVVVDVSHED PEVKFNWYVD GVEVHNAKTK    60
PREEQYNSTY RVVSVLTVLA QDWLNGKEYK CKVSNKALPA PIEKTISKAK GQPREPQVYT   120
LPPSREEMTK NQVSLTCLVK GFYPSDIAVE WESNGQPENN YKTTPPVLDS DGSFFLYSKL   180
TVDKSRWQQG NVFSCSVMHE ALHNQYTQKS LSLSPG                             216

SEQ ID NO: 7            moltype = AA  length = 216
FEATURE                 Location/Qualifiers
source                  1..216
                        mol_type = protein
                        organism = synthetic construct
SEQUENCE: 7
APEAEGAPSV FLFPPKPKDT LMISRTPEVT CVVVDVSHED PEVKFNWYVD GVEVHNAKTK    60
PREEQYNSTY RVVSVLTVLH QDWLNGKEYK CKVSNKALPS SIEKTISKAK GQPREPQVYT   120
LPPSREEMTK NQVSLTCLVK GFYPSDIAVE WESNGQPENN YKTTPPVLDS DGSFFLYSKL   180
TVDKSRWQQG NVFSCSVMHE ALHNHYTQKS LSLSPG                             216

SEQ ID NO: 8            moltype = AA  length = 216
FEATURE                 Location/Qualifiers
source                  1..216
                        mol_type = protein
                        organism = synthetic construct
SEQUENCE: 8
APEAEGAPSV FLFPPKPKDT LMISRTPEVT CVVVDVSHED PEVKFNWYVD GVEVHNAKTK    60
PREEQYNSTY RVVSVLTVLA QDWLNGKEYK CKVSNKALPS SIEKTISKAK GQPREPQVYT   120
LPPSREEMTK NQVSLTCLVK GFYPSDIAVE WESNGQPENN YKTTPPVLDS DGSFFLYSKL   180
TVDKSRWQQG NVFSCSVMHE ALHNHYTQKS LSLSPG                             216

SEQ ID NO: 9            moltype = AA  length = 216
FEATURE                 Location/Qualifiers
source                  1..216
                        mol_type = protein
                        organism = synthetic construct
SEQUENCE: 9
APEAEGAPSV FLFPPKPKDT LMISRTPEVT CVVVDVSHED PEVKFNWYVD GVEVHNAKTK    60
PREEQYNSTY RVVSVLTVLH QDWLNGKEYK CKVSNKALPS SIEKTISKAK GQPREPQVYT   120
LPPSREEMTK NQVSLTCLVK GFYPSDIAVE WESNGQPENN YKTTPPVLDS DGSFFLYSKL   180
TVDKSRWQQG NVFSCSVMHE ALHNQYTQKS LSLSPG                             216

SEQ ID NO: 10           moltype = AA  length = 216
FEATURE                 Location/Qualifiers
source                  1..216
                        mol_type = protein
                        organism = unidentified
SEQUENCE: 10
APELLGGPSV FLFPPKPKDT LMISRTPEVT CVVVDVSHED PEVKFNWYVD GVEVHNAKTK    60
PREEQYNSTY RVVSVLTVLH QDWLNGKEYK CKVSNKALPA PIEKTISKAK GQPREPQVYT   120
LPPSREEMTK NQVSLTCLVK GFYPSDIAVE WESNGQPENN YKTTPPVLDS DGSFFLYSKL   180
TVDKSRWQQG NVFSCSVMHE ALHNHYTQKS LSLSPG                             216

SEQ ID NO: 11           moltype =     length =
SEQUENCE: 11
000

SEQ ID NO: 12           moltype =     length =
SEQUENCE: 12
000

SEQ ID NO: 13           moltype =     length =
SEQUENCE: 13
000

SEQ ID NO: 14           moltype =     length =
SEQUENCE: 14
000

SEQ ID NO: 15           moltype =     length =
SEQUENCE: 15
000

SEQ ID NO: 16           moltype =     length =
SEQUENCE: 16
000

SEQ ID NO: 17           moltype =     length =
```

```
SEQUENCE: 17
000

SEQ ID NO: 18           moltype =    length =
SEQUENCE: 18
000

SEQ ID NO: 19           moltype =    length =
SEQUENCE: 19
000

SEQ ID NO: 20           moltype = AA   length = 115
FEATURE                 Location/Qualifiers
source                  1..115
                        mol_type = protein
                        organism = synthetic construct
SEQUENCE: 20
QVQLQESGGG SVQAGGSLKL TCAASGYIFN SCGMGWYRQS PGRERELVSR ISGDGDTWHK    60
ESVKGRFTIS QDNVKKTLYL QMNSLKPEDT AVYFCAVCYN LETYWGQGTQ VTVSS        115

SEQ ID NO: 21           moltype = AA   length = 8
FEATURE                 Location/Qualifiers
source                  1..8
                        mol_type = protein
                        organism = synthetic construct
SEQUENCE: 21
GYIFNSCG                                                             8

SEQ ID NO: 22           moltype = AA   length = 7
FEATURE                 Location/Qualifiers
source                  1..7
                        mol_type = protein
                        organism = synthetic construct
SEQUENCE: 22
ISGDGDT                                                              7

SEQ ID NO: 23           moltype = AA   length = 9
FEATURE                 Location/Qualifiers
source                  1..9
                        mol_type = protein
                        organism = synthetic construct
SEQUENCE: 23
AVCYNLETY                                                            9

SEQ ID NO: 24           moltype =    length =
SEQUENCE: 24
000

SEQ ID NO: 25           moltype =    length =
SEQUENCE: 25
000

SEQ ID NO: 26           moltype =    length =
SEQUENCE: 26
000

SEQ ID NO: 27           moltype =    length =
SEQUENCE: 27
000

SEQ ID NO: 28           moltype =    length =
SEQUENCE: 28
000

SEQ ID NO: 29           moltype =    length =
SEQUENCE: 29
000

SEQ ID NO: 30           moltype = AA   length = 120
FEATURE                 Location/Qualifiers
source                  1..120
                        mol_type = protein
                        organism = synthetic construct
SEQUENCE: 30
EVQLVESGGG EVQPGGSLRL SCAASGSIFS INAMGWYRQA PGKQRELVAG FTGDTNTIYA    60
ESVKGRFTIS RDNAKNTVYL QMSSLRAEDT AVYYCAADVQ LFSRDYEFYW GQGTLVTVKP   120

SEQ ID NO: 31           moltype = AA   length = 8
FEATURE                 Location/Qualifiers
```

```
source                  1..8
                        mol_type = protein
                        organism = synthetic construct
SEQUENCE: 31
GSIFSINA                                                                8

SEQ ID NO: 32           moltype = AA   length = 7
FEATURE                 Location/Qualifiers
source                  1..7
                        mol_type = protein
                        organism = synthetic construct
SEQUENCE: 32
FTGDTNT                                                                 7

SEQ ID NO: 33           moltype = AA   length = 14
FEATURE                 Location/Qualifiers
source                  1..14
                        mol_type = protein
                        organism = synthetic construct
SEQUENCE: 33
AADVQLFSRD YEFY                                                        14

SEQ ID NO: 34           moltype =   length =
SEQUENCE: 34
000

SEQ ID NO: 35           moltype =   length =
SEQUENCE: 35
000

SEQ ID NO: 36           moltype =   length =
SEQUENCE: 36
000

SEQ ID NO: 37           moltype =   length =
SEQUENCE: 37
000

SEQ ID NO: 38           moltype =   length =
SEQUENCE: 38
000

SEQ ID NO: 39           moltype =   length =
SEQUENCE: 39
000

SEQ ID NO: 40           moltype = AA   length = 15
FEATURE                 Location/Qualifiers
source                  1..15
                        mol_type = protein
                        organism = Homo sapiens
SEQUENCE: 40
EPKSCDKTHT CPPCP                                                       15

SEQ ID NO: 41           moltype = AA   length = 15
FEATURE                 Location/Qualifiers
source                  1..15
                        mol_type = protein
                        organism = Homo sapiens
SEQUENCE: 41
EPKSSDKTHT CPPCP                                                       15

SEQ ID NO: 42           moltype = AA   length = 231
FEATURE                 Location/Qualifiers
source                  1..231
                        mol_type = protein
                        organism = synthetic construct
SEQUENCE: 42
EPKSSDKTHT CPPCPAPELL GGPSVFLFPP KPKDTLMISR TPEVTCVVVD VSHEDPEVKF       60
NWYVDGVEVH NAKTKPREEQ YNSTYRVVSV LTVLHQDWLN GKEYKCKVSN KALPAPIEKT      120
ISKAKGQPRE PQVYTLPPSR EEMTKNQVSL TCLVKGFYPS DIAVEWESNG QPENNYKTTP      180
PVLDSDGSFF LYSKLTVDKS RWQQGNVFSC SVMHEALHNH YTQKSLSLSP G              231

SEQ ID NO: 43           moltype = AA   length = 231
FEATURE                 Location/Qualifiers
source                  1..231
                        mol_type = protein
                        organism = synthetic construct
SEQUENCE: 43
```

```
EPKSSDKTHT CPPCPAPEAE GAPSVFLFPP KPKDTLMISR TPEVTCVVVD VSHEDPEVKF   60
NWYVDGVEVH NAKTKPREEQ YNSTYRVVSV LTVLHQDWLN GKEYKCKVSN KALPSSIEKT  120
ISKAKGQPRE PQVYTLPPSR EEMTKNQVSL TCLVKGFYPS DIAVEWESNG QPENNYKTTP  180
PVLDSDGSFF LYSKLTVDKS RWQQGNVFSC SVMHEALHNQ YTQKSLSLSP G          231

SEQ ID NO: 44          moltype =    length =
SEQUENCE: 44
000

SEQ ID NO: 45          moltype =    length =
SEQUENCE: 45
000

SEQ ID NO: 46          moltype =    length =
SEQUENCE: 46
000

SEQ ID NO: 47          moltype =    length =
SEQUENCE: 47
000

SEQ ID NO: 48          moltype =    length =
SEQUENCE: 48
000

SEQ ID NO: 49          moltype =    length =
SEQUENCE: 49
000

SEQ ID NO: 50          moltype =    length =
SEQUENCE: 50
000

SEQ ID NO: 51          moltype =    length =
SEQUENCE: 51
000

SEQ ID NO: 52          moltype =    length =
SEQUENCE: 52
000

SEQ ID NO: 53          moltype =    length =
SEQUENCE: 53
000

SEQ ID NO: 54          moltype =    length =
SEQUENCE: 54
000

SEQ ID NO: 55          moltype =    length =
SEQUENCE: 55
000

SEQ ID NO: 56          moltype =    length =
SEQUENCE: 56
000

SEQ ID NO: 57          moltype =    length =
SEQUENCE: 57
000

SEQ ID NO: 58          moltype =    length =
SEQUENCE: 58
000

SEQ ID NO: 59          moltype =    length =
SEQUENCE: 59
000

SEQ ID NO: 60          moltype =    length =
SEQUENCE: 60
000

SEQ ID NO: 61          moltype =    length =
SEQUENCE: 61
000

SEQ ID NO: 62          moltype =    length =
SEQUENCE: 62
```

000

SEQ ID NO: 63          moltype =    length =
SEQUENCE: 63
000

SEQ ID NO: 64          moltype =    length =
SEQUENCE: 64
000

SEQ ID NO: 65          moltype =    length =
SEQUENCE: 65
000

SEQ ID NO: 66          moltype =    length =
SEQUENCE: 66
000

SEQ ID NO: 67          moltype =    length =
SEQUENCE: 67
000

SEQ ID NO: 68          moltype =    length =
SEQUENCE: 68
000

SEQ ID NO: 69          moltype =    length =
SEQUENCE: 69
000

SEQ ID NO: 70          moltype =    length =
SEQUENCE: 70
000

SEQ ID NO: 71          moltype =    length =
SEQUENCE: 71
000

SEQ ID NO: 72          moltype =    length =
SEQUENCE: 72
000

SEQ ID NO: 73          moltype =    length =
SEQUENCE: 73
000

SEQ ID NO: 74          moltype =    length =
SEQUENCE: 74
000

SEQ ID NO: 75          moltype =    length =
SEQUENCE: 75
000

SEQ ID NO: 76          moltype =    length =
SEQUENCE: 76
000

SEQ ID NO: 77          moltype =    length =
SEQUENCE: 77
000

SEQ ID NO: 78          moltype =    length =
SEQUENCE: 78
000

SEQ ID NO: 79          moltype =    length =
SEQUENCE: 79
000

SEQ ID NO: 80          moltype =    length =
SEQUENCE: 80
000

SEQ ID NO: 81          moltype =    length =
SEQUENCE: 81
000

SEQ ID NO: 82          moltype =    length =

```
SEQUENCE: 82
000

SEQ ID NO: 83              moltype =    length =
SEQUENCE: 83
000

SEQ ID NO: 84              moltype =    length =
SEQUENCE: 84
000

SEQ ID NO: 85              moltype =    length =
SEQUENCE: 85
000

SEQ ID NO: 86              moltype =    length =
SEQUENCE: 86
000

SEQ ID NO: 87              moltype =    length =
SEQUENCE: 87
000

SEQ ID NO: 88              moltype =    length =
SEQUENCE: 88
000

SEQ ID NO: 89              moltype =    length =
SEQUENCE: 89
000

SEQ ID NO: 90              moltype =    length =
SEQUENCE: 90
000

SEQ ID NO: 91              moltype =    length =
SEQUENCE: 91
000

SEQ ID NO: 92              moltype =    length =
SEQUENCE: 92
000

SEQ ID NO: 93              moltype =    length =
SEQUENCE: 93
000

SEQ ID NO: 94              moltype =    length =
SEQUENCE: 94
000

SEQ ID NO: 95              moltype =    length =
SEQUENCE: 95
000

SEQ ID NO: 96              moltype =    length =
SEQUENCE: 96
000

SEQ ID NO: 97              moltype =    length =
SEQUENCE: 97
000

SEQ ID NO: 98              moltype =    length =
SEQUENCE: 98
000

SEQ ID NO: 99              moltype =    length =
SEQUENCE: 99
000

SEQ ID NO: 100             moltype =    length =
SEQUENCE: 100
000

SEQ ID NO: 101             moltype = AA  length = 114
FEATURE                    Location/Qualifiers
source                     1..114
                           mol_type = protein
```

```
                        organism = synthetic construct
SEQUENCE: 101
QVQYVESGGG LVQPGGSLRL SCAASGFTFS SYRINWYRQP PGKGRELVGS ITDTGSTNYA   60
DSVKGRFTIS RDNAKNTVYL QMSSLKPEDT AVYYCRAPTI AAYWGQGTQV TVSS        114

SEQ ID NO: 102          moltype = AA  length = 114
FEATURE                 Location/Qualifiers
source                  1..114
                        mol_type = protein
                        organism = synthetic construct
SEQUENCE: 102
QVQLVESGGG LVQPGGSLRL SCAASGFTFS SYRINWFRQA PGQGLEAVAS ITDTGSTNYA   60
DSVKGRFTIS RDNSKNTLYL QMNSLRAEDT AVYYCAAPTI AAYWGQGTLV TVSS        114

SEQ ID NO: 103          moltype = AA  length = 114
FEATURE                 Location/Qualifiers
source                  1..114
                        mol_type = protein
                        organism = synthetic construct
SEQUENCE: 103
QVQLVESGGG LVQPGGSLRL SCAASGFTFS SYRINWFRQA PGQGLELVAS ITDTGSTNYA   60
DSVKGRFTIS RDNSKNTLYL QMNSLRAEDT AVYYCAAPTI AAYWGQGTLV TVSS        114

SEQ ID NO: 104          moltype = AA  length = 114
FEATURE                 Location/Qualifiers
source                  1..114
                        mol_type = protein
                        organism = synthetic construct
SEQUENCE: 104
QVQLVESGGG LVQPGGSLRL SCAASGFTFS SYRINWYRQA PGQGLELVAS ITDTGSTNYA   60
DSVKGRFTIS RDNSKNTLYL QMNSLRAEDT AVYYCAAPTI AAYWGQGTLV TVSS        114

SEQ ID NO: 105          moltype = AA  length = 114
FEATURE                 Location/Qualifiers
source                  1..114
                        mol_type = protein
                        organism = synthetic construct
SEQUENCE: 105
QVQLVESGGG LVQPGGSLRL SCAASGFTFS SYRINWYRQA PGQGRELVAS ITDTGSTNYA   60
DSVKGRFTIS RDNSKNTLYL QMNSLRAEDT AVYYCAAPTI AAYWGQGTLV TVSS        114

SEQ ID NO: 106          moltype = AA  length = 114
FEATURE                 Location/Qualifiers
source                  1..114
                        mol_type = protein
                        organism = synthetic construct
SEQUENCE: 106
QVQLVESGGG LVQPGGSLRL SCAASGFTFS SYRINWYRQP PGKGRELVGS ITDTGSTNYA   60
DSVKGRFTIS RDNSKNTLYL QMNSLRAEDT AVYYCAAPTI AAYWGQGTLV TVSS        114

SEQ ID NO: 107          moltype = AA  length = 8
FEATURE                 Location/Qualifiers
source                  1..8
                        mol_type = protein
                        organism = synthetic construct
SEQUENCE: 107
GFTFSSYR                                                            8

SEQ ID NO: 108          moltype = AA  length = 5
FEATURE                 Location/Qualifiers
source                  1..5
                        mol_type = protein
                        organism = synthetic construct
SEQUENCE: 108
SYRIN                                                               5

SEQ ID NO: 109          moltype = AA  length = 7
FEATURE                 Location/Qualifiers
source                  1..7
                        mol_type = protein
                        organism = synthetic construct
SEQUENCE: 109
GFTFSSY                                                             7

SEQ ID NO: 110          moltype = AA  length = 7
FEATURE                 Location/Qualifiers
source                  1..7
                        mol_type = protein
                        organism = synthetic construct
```

```
SEQUENCE: 110
ITDTGST                                                                      7

SEQ ID NO: 111          moltype = AA  length = 16
FEATURE                 Location/Qualifiers
source                  1..16
                        mol_type = protein
                        organism = synthetic construct
SEQUENCE: 111
SITDTGSTNY ADSVKG                                                           16

SEQ ID NO: 112          moltype = AA  length = 5
FEATURE                 Location/Qualifiers
source                  1..5
                        mol_type = protein
                        organism = synthetic construct
SEQUENCE: 112
TDTGS                                                                        5

SEQ ID NO: 113          moltype = AA  length = 8
FEATURE                 Location/Qualifiers
source                  1..8
                        mol_type = protein
                        organism = synthetic construct
SEQUENCE: 113
AAPTIAAY                                                                     8

SEQ ID NO: 114          moltype = AA  length = 6
FEATURE                 Location/Qualifiers
source                  1..6
                        mol_type = protein
                        organism = synthetic construct
SEQUENCE: 114
PTIAAY                                                                       6

SEQ ID NO: 115          moltype = AA  length = 6
FEATURE                 Location/Qualifiers
source                  1..6
                        mol_type = protein
                        organism = synthetic construct
SEQUENCE: 115
PTIAAY                                                                       6

SEQ ID NO: 116          moltype = AA  length = 345
FEATURE                 Location/Qualifiers
source                  1..345
                        mol_type = protein
                        organism = synthetic construct
SEQUENCE: 116
QVQLVESGGG LVQPGGSLRL SCAASGFTFS SYRINWFRQA PGQGLEAVAS ITDTGSTNYA     60
DSVKGRFTIS RDNSKNTLYL QMNSLRAEDT AVYYCAAPTI AAYWGQGTLV TVSSEPKSSD   120
KTHTCPPCPA PEAEGAPSVF LFPPKPKDTL MISRTPEVTC VVVDVSHEDP EVKFNWYVDG   180
VEVHNAKTKP REEQYNSTYR VVSVLTVLHQ DWLNGKEYKC KVSNKALPSS IEKTISKAKG   240
QPREPQVYTL PPSREEMTKN QVSLTCLVKG FYPSDIAVEW ESNGQPENNY KTTPPVLDSD   300
GSFFLYSKLT VDKSRWQQGN VFSCSVMHEA LHNQYTQKSL SLSPG                   345

SEQ ID NO: 117          moltype = AA  length = 345
FEATURE                 Location/Qualifiers
source                  1..345
                        mol_type = protein
                        organism = synthetic construct
SEQUENCE: 117
QVQLVESGGG LVQPGGSLRL SCAASGFTFS SYRINWFRQA PGQGLELVAS ITDTGSTNYA     60
DSVKGRFTIS RDNSKNTLYL QMNSLRAEDT AVYYCAAPTI AAYWGQGTLV TVSSEPKSSD   120
KTHTCPPCPA PEAEGAPSVF LFPPKPKDTL MISRTPEVTC VVVDVSHEDP EVKFNWYVDG   180
VEVHNAKTKP REEQYNSTYR VVSVLTVLHQ DWLNGKEYKC KVSNKALPSS IEKTISKAKG   240
QPREPQVYTL PPSREEMTKN QVSLTCLVKG FYPSDIAVEW ESNGQPENNY KTTPPVLDSD   300
GSFFLYSKLT VDKSRWQQGN VFSCSVMHEA LHNQYTQKSL SLSPG                   345

SEQ ID NO: 118          moltype = AA  length = 345
FEATURE                 Location/Qualifiers
source                  1..345
                        mol_type = protein
                        organism = synthetic construct
SEQUENCE: 118
QVQLVESGGG LVQPGGSLRL SCAASGFTFS SYRINWYRQA PGQGLELVAS ITDTGSTNYA     60
DSVKGRFTIS RDNSKNTLYL QMNSLRAEDT AVYYCAAPTI AAYWGQGTLV TVSSEPKSSD   120
KTHTCPPCPA PEAEGAPSVF LFPPKPKDTL MISRTPEVTC VVVDVSHEDP EVKFNWYVDG   180
VEVHNAKTKP REEQYNSTYR VVSVLTVLHQ DWLNGKEYKC KVSNKALPSS IEKTISKAKG   240
```

```
QPREPQVYTL PPSREEMTKN QVSLTCLVKG FYPSDIAVEW ESNGQPENNY KTTPPVLDSD    300
GSFFLYSKLT VDKSRWQQGN VFSCSVMHEA LHNQYTQKSL SLSPG                   345

SEQ ID NO: 119          moltype = AA  length = 345
FEATURE                 Location/Qualifiers
source                  1..345
                        mol_type = protein
                        organism = synthetic construct
SEQUENCE: 119
QVQLVESGGG LVQPGGSLRL SCAASGFTFS SYRINWYRQA PGQGRELVAS ITDTGSTNYA    60
DSVKGRFTIS RDNSKNTLYL QMNSLRAEDT AVYYCAAPTI AAYWGQGTLV TVSSEPKSSD   120
KTHTCPPCPA PEAEGAPSVF LFPPKPKDTL MISRTPEVTC VVVDVSHEDP EVKFNWYVDG   180
VEVHNAKTKP REEQYNSTYR VVSVLTVLHQ DWLNGKEYKC KVSNKALPSS IEKTISKAKG   240
QPREPQVYTL PPSREEMTKN QVSLTCLVKG FYPSDIAVEW ESNGQPENNY KTTPPVLDSD   300
GSFFLYSKLT VDKSRWQQGN VFSCSVMHEA LHNQYTQKSL SLSPG                   345

SEQ ID NO: 120          moltype = AA  length = 345
FEATURE                 Location/Qualifiers
source                  1..345
                        mol_type = protein
                        organism = synthetic construct
SEQUENCE: 120
QVQLVESGGG LVQPGGSLRL SCAASGFTFS SYRINWYRQP PGKGRELVGS ITDTGSTNYA    60
DSVKGRFTIS RDNSKNTLYL QMNSLRAEDT AVYYCAAPTI AAYWGQGTLV TVSSEPKSSD   120
KTHTCPPCPA PEAEGAPSVF LFPPKPKDTL MISRTPEVTC VVVDVSHEDP EVKFNWYVDG   180
VEVHNAKTKP REEQYNSTYR VVSVLTVLHQ DWLNGKEYKC KVSNKALPSS IEKTISKAKG   240
QPREPQVYTL PPSREEMTKN QVSLTCLVKG FYPSDIAVEW ESNGQPENNY KTTPPVLDSD   300
GSFFLYSKLT VDKSRWQQGN VFSCSVMHEA LHNQYTQKSL SLSPG                   345

SEQ ID NO: 121          moltype =     length =
SEQUENCE: 121
000

SEQ ID NO: 122          moltype =     length =
SEQUENCE: 122
000

SEQ ID NO: 123          moltype =     length =
SEQUENCE: 123
000

SEQ ID NO: 124          moltype =     length =
SEQUENCE: 124
000

SEQ ID NO: 125          moltype =     length =
SEQUENCE: 125
000

SEQ ID NO: 126          moltype =     length =
SEQUENCE: 126
000

SEQ ID NO: 127          moltype =     length =
SEQUENCE: 127
000

SEQ ID NO: 128          moltype =     length =
SEQUENCE: 128
000

SEQ ID NO: 129          moltype =     length =
SEQUENCE: 129
000

SEQ ID NO: 130          moltype =     length =
SEQUENCE: 130
000

SEQ ID NO: 131          moltype = AA  length = 8
FEATURE                 Location/Qualifiers
source                  1..8
                        mol_type = protein
                        organism = synthetic construct
SEQUENCE: 131
RAPTIAAY                                                              8

SEQ ID NO: 132          moltype =     length =
SEQUENCE: 132
```

000

SEQ ID NO: 133        moltype =    length =
SEQUENCE: 133
000

SEQ ID NO: 134        moltype =    length =
SEQUENCE: 134
000

SEQ ID NO: 135        moltype =    length =
SEQUENCE: 135
000

SEQ ID NO: 136        moltype =    length =
SEQUENCE: 136
000

SEQ ID NO: 137        moltype =    length =
SEQUENCE: 137
000

SEQ ID NO: 138        moltype =    length =
SEQUENCE: 138
000

SEQ ID NO: 139        moltype =    length =
SEQUENCE: 139
000

SEQ ID NO: 140        moltype =    length =
SEQUENCE: 140
000

SEQ ID NO: 141        moltype =    length =
SEQUENCE: 141
000

SEQ ID NO: 142        moltype =    length =
SEQUENCE: 142
000

SEQ ID NO: 143        moltype =    length =
SEQUENCE: 143
000

SEQ ID NO: 144        moltype =    length =
SEQUENCE: 144
000

SEQ ID NO: 145        moltype =    length =
SEQUENCE: 145
000

SEQ ID NO: 146        moltype =    length =
SEQUENCE: 146
000

SEQ ID NO: 147        moltype =    length =
SEQUENCE: 147
000

SEQ ID NO: 148        moltype =    length =
SEQUENCE: 148
000

SEQ ID NO: 149        moltype =    length =
SEQUENCE: 149
000

SEQ ID NO: 150        moltype =    length =
SEQUENCE: 150
000

SEQ ID NO: 151        moltype =    length =
SEQUENCE: 151
000

SEQ ID NO: 152        moltype =    length =

| | | |
|---|---|---|
| SEQUENCE: 152 000 | | |
| SEQ ID NO: 153 SEQUENCE: 153 000 | moltype = | length = |
| SEQ ID NO: 154 SEQUENCE: 154 000 | moltype = | length = |
| SEQ ID NO: 155 SEQUENCE: 155 000 | moltype = | length = |
| SEQ ID NO: 156 SEQUENCE: 156 000 | moltype = | length = |
| SEQ ID NO: 157 SEQUENCE: 157 000 | moltype = | length = |
| SEQ ID NO: 158 SEQUENCE: 158 000 | moltype = | length = |
| SEQ ID NO: 159 SEQUENCE: 159 000 | moltype = | length = |
| SEQ ID NO: 160 SEQUENCE: 160 000 | moltype = | length = |
| SEQ ID NO: 161 SEQUENCE: 161 000 | moltype = | length = |
| SEQ ID NO: 162 SEQUENCE: 162 000 | moltype = | length = |
| SEQ ID NO: 163 SEQUENCE: 163 000 | moltype = | length = |
| SEQ ID NO: 164 SEQUENCE: 164 000 | moltype = | length = |
| SEQ ID NO: 165 SEQUENCE: 165 000 | moltype = | length = |
| SEQ ID NO: 166 SEQUENCE: 166 000 | moltype = | length = |
| SEQ ID NO: 167 SEQUENCE: 167 000 | moltype = | length = |
| SEQ ID NO: 168 SEQUENCE: 168 000 | moltype = | length = |
| SEQ ID NO: 169 SEQUENCE: 169 000 | moltype = | length = |
| SEQ ID NO: 170 SEQUENCE: 170 000 | moltype = | length = |
| SEQ ID NO: 171 SEQUENCE: 171 000 | moltype = | length = |

| | | |
|---|---|---|
| SEQ ID NO: 172<br>SEQUENCE: 172<br>000 | moltype = | length = |
| SEQ ID NO: 173<br>SEQUENCE: 173<br>000 | moltype = | length = |
| SEQ ID NO: 174<br>SEQUENCE: 174<br>000 | moltype = | length = |
| SEQ ID NO: 175<br>SEQUENCE: 175<br>000 | moltype = | length = |
| SEQ ID NO: 176<br>SEQUENCE: 176<br>000 | moltype = | length = |
| SEQ ID NO: 177<br>SEQUENCE: 177<br>000 | moltype = | length = |
| SEQ ID NO: 178<br>SEQUENCE: 178<br>000 | moltype = | length = |
| SEQ ID NO: 179<br>SEQUENCE: 179<br>000 | moltype = | length = |
| SEQ ID NO: 180<br>SEQUENCE: 180<br>000 | moltype = | length = |
| SEQ ID NO: 181<br>SEQUENCE: 181<br>000 | moltype = | length = |
| SEQ ID NO: 182<br>SEQUENCE: 182<br>000 | moltype = | length = |
| SEQ ID NO: 183<br>SEQUENCE: 183<br>000 | moltype = | length = |
| SEQ ID NO: 184<br>SEQUENCE: 184<br>000 | moltype = | length = |
| SEQ ID NO: 185<br>SEQUENCE: 185<br>000 | moltype = | length = |
| SEQ ID NO: 186<br>SEQUENCE: 186<br>000 | moltype = | length = |
| SEQ ID NO: 187<br>SEQUENCE: 187<br>000 | moltype = | length = |
| SEQ ID NO: 188<br>SEQUENCE: 188<br>000 | moltype = | length = |
| SEQ ID NO: 189<br>SEQUENCE: 189<br>000 | moltype = | length = |
| SEQ ID NO: 190<br>SEQUENCE: 190<br>000 | moltype = | length = |
| SEQ ID NO: 191<br>SEQUENCE: 191<br>000 | moltype = | length = |

```
SEQ ID NO: 192          moltype =    length =
SEQUENCE: 192
000

SEQ ID NO: 193          moltype =    length =
SEQUENCE: 193
000

SEQ ID NO: 194          moltype =    length =
SEQUENCE: 194
000

SEQ ID NO: 195          moltype =    length =
SEQUENCE: 195
000

SEQ ID NO: 196          moltype =    length =
SEQUENCE: 196
000

SEQ ID NO: 197          moltype =    length =
SEQUENCE: 197
000

SEQ ID NO: 198          moltype =    length =
SEQUENCE: 198
000

SEQ ID NO: 199          moltype =    length =
SEQUENCE: 199
000

SEQ ID NO: 200          moltype =    length =
SEQUENCE: 200
000

SEQ ID NO: 201          moltype = AA   length = 117
FEATURE                 Location/Qualifiers
source                  1..117
                        mol_type = protein
                        organism = synthetic construct
SEQUENCE: 201
QVQLVESGGG SVQPGGSLRL SCAASGIVFN SDVMGWYRQV PGKPRELVAT ITGGGSTNYA      60
TSVKGRFTIS RDNAKNTVYL QMNSLRPEDT AVYYCNGRRG DSMLAFWAQG TQVTVSS        117

SEQ ID NO: 202          moltype = AA   length = 117
FEATURE                 Location/Qualifiers
source                  1..117
                        mol_type = protein
                        organism = synthetic construct
SEQUENCE: 202
QVQLVESGGG LVQPGGSLRL SCAASGIVFN SDVMGWFRQA PGQGLEAVAT ITGGGSTNYA      60
TSVKGRFTIS RDNSKNTLYL QMNSLRAEDT AVYYCAARRG DSMLAFWGQG TLVTVSS        117

SEQ ID NO: 203          moltype = AA   length = 117
FEATURE                 Location/Qualifiers
source                  1..117
                        mol_type = protein
                        organism = synthetic construct
SEQUENCE: 203
QVQLVESGGG LVQPGGSLRL SCAASGIVFN SDVMGWFRQA PGQGLELVAT ITGGGSTNYA      60
TSVKGRFTIS RDNSKNTLYL QMNSLRAEDT AVYYCAARRG DSMLAFWGQG TLVTVSS        117

SEQ ID NO: 204          moltype = AA   length = 117
FEATURE                 Location/Qualifiers
source                  1..117
                        mol_type = protein
                        organism = synthetic construct
SEQUENCE: 204
QVQLVESGGG LVQPGGSLRL SCAASGIVFN SDVMGWYRQA PGQGLELVAT ITGGGSTNYA      60
TSVKGRFTIS RDNSKNTLYL QMNSLRAEDT AVYYCAARRG DSMLAFWGQG TLVTVSS        117

SEQ ID NO: 205          moltype = AA   length = 117
FEATURE                 Location/Qualifiers
source                  1..117
                        mol_type = protein
                        organism = synthetic construct
SEQUENCE: 205
```

```
QVQLVESGGG LVQPGGSLRL SCAASGIVFN SDVMGWYRQA PGQPRELVAT ITGGGSTNYA    60
TSVKGRFTIS RDNSKNTLYL QMNSLRAEDT AVYYCAARRG DSMLAFWGQG TLVTVSS     117

SEQ ID NO: 206          moltype = AA  length = 117
FEATURE                 Location/Qualifiers
source                  1..117
                        mol_type = protein
                        organism = synthetic construct
SEQUENCE: 206
QVQLVESGGG LVQPGGSLRL SCAASGIVFN SDVMGWYRQV PGKPRELVAT ITGGGSTNYA    60
TSVKGRFTIS RDNSKNTLYL QMNSLRAEDT AVYYCAARRG DSMLAFWGQG TLVTVSS     117

SEQ ID NO: 207          moltype = AA  length = 8
FEATURE                 Location/Qualifiers
source                  1..8
                        mol_type = protein
                        organism = synthetic construct
SEQUENCE: 207
GIVFNSDV                                                             8

SEQ ID NO: 208          moltype = AA  length = 5
FEATURE                 Location/Qualifiers
source                  1..5
                        mol_type = protein
                        organism = synthetic construct
SEQUENCE: 208
SDVMG                                                                5

SEQ ID NO: 209          moltype = AA  length = 7
FEATURE                 Location/Qualifiers
source                  1..7
                        mol_type = protein
                        organism = synthetic construct
SEQUENCE: 209
GIVFNSD                                                              7

SEQ ID NO: 210          moltype = AA  length = 7
FEATURE                 Location/Qualifiers
source                  1..7
                        mol_type = protein
                        organism = synthetic construct
SEQUENCE: 210
ITGGGST                                                              7

SEQ ID NO: 211          moltype = AA  length = 16
FEATURE                 Location/Qualifiers
source                  1..16
                        mol_type = protein
                        organism = synthetic construct
SEQUENCE: 211
TITGGGSTNY ATSVKG                                                   16

SEQ ID NO: 212          moltype = AA  length = 5
FEATURE                 Location/Qualifiers
source                  1..5
                        mol_type = protein
                        organism = synthetic construct
SEQUENCE: 212
TGGGS                                                                5

SEQ ID NO: 213          moltype = AA  length = 11
FEATURE                 Location/Qualifiers
source                  1..11
                        mol_type = protein
                        organism = synthetic construct
SEQUENCE: 213
AARRGDSMLA F                                                        11

SEQ ID NO: 214          moltype = AA  length = 9
FEATURE                 Location/Qualifiers
source                  1..9
                        mol_type = protein
                        organism = synthetic construct
SEQUENCE: 214
RRGDSMLAF                                                            9

SEQ ID NO: 215          moltype = AA  length = 9
FEATURE                 Location/Qualifiers
source                  1..9
```

```
                        mol_type = protein
                        organism = synthetic construct
SEQUENCE: 215
RRGDSMLAF                                                                9

SEQ ID NO: 216          moltype = AA   length = 348
FEATURE                 Location/Qualifiers
source                  1..348
                        mol_type = protein
                        organism = synthetic construct
SEQUENCE: 216
QVQLVESGGG LVQPGGSLRL SCAASGIVFN SDVMGWFRQA PGQGLEAVAT ITGGGSTNYA        60
TSVKGRFTIS RDNSKNTLYL QMNSLRAEDT AVYYCAARRG DSMLAFWGQG TLVTVSSEPK       120
SSDKTHTCPP CPAPEAEGAP SVFLFPPKPK DTLMISRTPE VTCVVVDVSH EDPEVKFNWY       180
VDGVEVHNAK TKPREEQYNS TYRVVSVLTV LHQDWLNGKE YKCKVSNKAL PSSIEKTISK       240
AKGQPREPQV YTLPPSREEM TKNQVSLTCL VKGFYPSDIA VEWESNGQPE NNYKTTPPVL       300
DSDGSFFLYS KLTVDKSRWQ QGNVFSCSVM HEALHNQYTQ KSLSLSPG                    348

SEQ ID NO: 217          moltype = AA   length = 348
FEATURE                 Location/Qualifiers
source                  1..348
                        mol_type = protein
                        organism = synthetic construct
SEQUENCE: 217
QVQLVESGGG LVQPGGSLRL SCAASGIVFN SDVMGWFRQA PGQGLELVAT ITGGGSTNYA        60
TSVKGRFTIS RDNSKNTLYL QMNSLRAEDT AVYYCAARRG DSMLAFWGQG TLVTVSSEPK       120
SSDKTHTCPP CPAPEAEGAP SVFLFPPKPK DTLMISRTPE VTCVVVDVSH EDPEVKFNWY       180
VDGVEVHNAK TKPREEQYNS TYRVVSVLTV LHQDWLNGKE YKCKVSNKAL PSSIEKTISK       240
AKGQPREPQV YTLPPSREEM TKNQVSLTCL VKGFYPSDIA VEWESNGQPE NNYKTTPPVL       300
DSDGSFFLYS KLTVDKSRWQ QGNVFSCSVM HEALHNQYTQ KSLSLSPG                    348

SEQ ID NO: 218          moltype = AA   length = 348
FEATURE                 Location/Qualifiers
source                  1..348
                        mol_type = protein
                        organism = synthetic construct
SEQUENCE: 218
QVQLVESGGG LVQPGGSLRL SCAASGIVFN SDVMGWYRQA PGQGLELVAT ITGGGSTNYA        60
TSVKGRFTIS RDNSKNTLYL QMNSLRAEDT AVYYCAARRG DSMLAFWGQG TLVTVSSEPK       120
SSDKTHTCPP CPAPEAEGAP SVFLFPPKPK DTLMISRTPE VTCVVVDVSH EDPEVKFNWY       180
VDGVEVHNAK TKPREEQYNS TYRVVSVLTV LHQDWLNGKE YKCKVSNKAL PSSIEKTISK       240
AKGQPREPQV YTLPPSREEM TKNQVSLTCL VKGFYPSDIA VEWESNGQPE NNYKTTPPVL       300
DSDGSFFLYS KLTVDKSRWQ QGNVFSCSVM HEALHNQYTQ KSLSLSPG                    348

SEQ ID NO: 219          moltype = AA   length = 348
FEATURE                 Location/Qualifiers
source                  1..348
                        mol_type = protein
                        organism = synthetic construct
SEQUENCE: 219
QVQLVESGGG LVQPGGSLRL SCAASGIVFN SDVMGWYRQA PGQPRELVAT ITGGGSTNYA        60
TSVKGRFTIS RDNSKNTLYL QMNSLRAEDT AVYYCAARRG DSMLAFWGQG TLVTVSSEPK       120
SSDKTHTCPP CPAPEAEGAP SVFLFPPKPK DTLMISRTPE VTCVVVDVSH EDPEVKFNWY       180
VDGVEVHNAK TKPREEQYNS TYRVVSVLTV LHQDWLNGKE YKCKVSNKAL PSSIEKTISK       240
AKGQPREPQV YTLPPSREEM TKNQVSLTCL VKGFYPSDIA VEWESNGQPE NNYKTTPPVL       300
DSDGSFFLYS KLTVDKSRWQ QGNVFSCSVM HEALHNQYTQ KSLSLSPG                    348

SEQ ID NO: 220          moltype = AA   length = 348
FEATURE                 Location/Qualifiers
source                  1..348
                        mol_type = protein
                        organism = synthetic construct
SEQUENCE: 220
QVQLVESGGG LVQPGGSLRL SCAASGIVFN SDVMGWYRQV PGKPRELVAT ITGGGSTNYA        60
TSVKGRFTIS RDNSKNTLYL QMNSLRAEDT AVYYCAARRG DSMLAFWGQG TLVTVSSEPK       120
SSDKTHTCPP CPAPEAEGAP SVFLFPPKPK DTLMISRTPE VTCVVVDVSH EDPEVKFNWY       180
VDGVEVHNAK TKPREEQYNS TYRVVSVLTV LHQDWLNGKE YKCKVSNKAL PSSIEKTISK       240
AKGQPREPQV YTLPPSREEM TKNQVSLTCL VKGFYPSDIA VEWESNGQPE NNYKTTPPVL       300
DSDGSFFLYS KLTVDKSRWQ QGNVFSCSVM HEALHNQYTQ KSLSLSPG                    348

SEQ ID NO: 221          moltype =      length =
SEQUENCE: 221
000

SEQ ID NO: 222          moltype =      length =
SEQUENCE: 222
000

SEQ ID NO: 223          moltype =      length =
```

```
SEQUENCE: 223
000

SEQ ID NO: 224          moltype =   length =
SEQUENCE: 224
000

SEQ ID NO: 225          moltype =   length =
SEQUENCE: 225
000

SEQ ID NO: 226          moltype =   length =
SEQUENCE: 226
000

SEQ ID NO: 227          moltype =   length =
SEQUENCE: 227
000

SEQ ID NO: 228          moltype =   length =
SEQUENCE: 228
000

SEQ ID NO: 229          moltype =   length =
SEQUENCE: 229
000

SEQ ID NO: 230          moltype =   length =
SEQUENCE: 230
000

SEQ ID NO: 231          moltype = AA  length = 11
FEATURE                 Location/Qualifiers
source                  1..11
                        mol_type = protein
                        organism = synthetic construct
SEQUENCE: 231
NGRRGDSMLA F                                                        11

SEQ ID NO: 232          moltype =   length =
SEQUENCE: 232
000

SEQ ID NO: 233          moltype =   length =
SEQUENCE: 233
000

SEQ ID NO: 234          moltype =   length =
SEQUENCE: 234
000

SEQ ID NO: 235          moltype =   length =
SEQUENCE: 235
000

SEQ ID NO: 236          moltype =   length =
SEQUENCE: 236
000

SEQ ID NO: 237          moltype =   length =
SEQUENCE: 237
000

SEQ ID NO: 238          moltype =   length =
SEQUENCE: 238
000

SEQ ID NO: 239          moltype =   length =
SEQUENCE: 239
000

SEQ ID NO: 240          moltype =   length =
SEQUENCE: 240
000

SEQ ID NO: 241          moltype =   length =
SEQUENCE: 241
000
```

-continued

| | | |
|---|---|---|
| SEQ ID NO: 242 SEQUENCE: 242 | moltype = | length = 000 |
| SEQ ID NO: 243 SEQUENCE: 243 | moltype = | length = 000 |
| SEQ ID NO: 244 SEQUENCE: 244 | moltype = | length = 000 |
| SEQ ID NO: 245 SEQUENCE: 245 | moltype = | length = 000 |
| SEQ ID NO: 246 SEQUENCE: 246 | moltype = | length = 000 |
| SEQ ID NO: 247 SEQUENCE: 247 | moltype = | length = 000 |
| SEQ ID NO: 248 SEQUENCE: 248 | moltype = | length = 000 |
| SEQ ID NO: 249 SEQUENCE: 249 | moltype = | length = 000 |
| SEQ ID NO: 250 SEQUENCE: 250 | moltype = | length = 000 |
| SEQ ID NO: 251 SEQUENCE: 251 | moltype = | length = 000 |
| SEQ ID NO: 252 SEQUENCE: 252 | moltype = | length = 000 |
| SEQ ID NO: 253 SEQUENCE: 253 | moltype = | length = 000 |
| SEQ ID NO: 254 SEQUENCE: 254 | moltype = | length = 000 |
| SEQ ID NO: 255 SEQUENCE: 255 | moltype = | length = 000 |
| SEQ ID NO: 256 SEQUENCE: 256 | moltype = | length = 000 |
| SEQ ID NO: 257 SEQUENCE: 257 | moltype = | length = 000 |
| SEQ ID NO: 258 SEQUENCE: 258 | moltype = | length = 000 |
| SEQ ID NO: 259 SEQUENCE: 259 | moltype = | length = 000 |
| SEQ ID NO: 260 SEQUENCE: 260 | moltype = | length = 000 |
| SEQ ID NO: 261 SEQUENCE: 261 | moltype = | length = 000 |

```
SEQ ID NO: 262          moltype =   length =
SEQUENCE: 262
000

SEQ ID NO: 263          moltype =   length =
SEQUENCE: 263
000

SEQ ID NO: 264          moltype =   length =
SEQUENCE: 264
000

SEQ ID NO: 265          moltype =   length =
SEQUENCE: 265
000

SEQ ID NO: 266          moltype =   length =
SEQUENCE: 266
000

SEQ ID NO: 267          moltype =   length =
SEQUENCE: 267
000

SEQ ID NO: 268          moltype =   length =
SEQUENCE: 268
000

SEQ ID NO: 269          moltype =   length =
SEQUENCE: 269
000

SEQ ID NO: 270          moltype =   length =
SEQUENCE: 270
000

SEQ ID NO: 271          moltype =   length =
SEQUENCE: 271
000

SEQ ID NO: 272          moltype =   length =
SEQUENCE: 272
000

SEQ ID NO: 273          moltype =   length =
SEQUENCE: 273
000

SEQ ID NO: 274          moltype =   length =
SEQUENCE: 274
000

SEQ ID NO: 275          moltype =   length =
SEQUENCE: 275
000

SEQ ID NO: 276          moltype =   length =
SEQUENCE: 276
000

SEQ ID NO: 277          moltype =   length =
SEQUENCE: 277
000

SEQ ID NO: 278          moltype =   length =
SEQUENCE: 278
000

SEQ ID NO: 279          moltype =   length =
SEQUENCE: 279
000

SEQ ID NO: 280          moltype =   length =
SEQUENCE: 280
000

SEQ ID NO: 281          moltype =   length =
SEQUENCE: 281
```

000

SEQ ID NO: 282           moltype =    length =
SEQUENCE: 282
000

SEQ ID NO: 283           moltype =    length =
SEQUENCE: 283
000

SEQ ID NO: 284           moltype =    length =
SEQUENCE: 284
000

SEQ ID NO: 285           moltype =    length =
SEQUENCE: 285
000

SEQ ID NO: 286           moltype =    length =
SEQUENCE: 286
000

SEQ ID NO: 287           moltype =    length =
SEQUENCE: 287
000

SEQ ID NO: 288           moltype =    length =
SEQUENCE: 288
000

SEQ ID NO: 289           moltype =    length =
SEQUENCE: 289
000

SEQ ID NO: 290           moltype =    length =
SEQUENCE: 290
000

SEQ ID NO: 291           moltype =    length =
SEQUENCE: 291
000

SEQ ID NO: 292           moltype =    length =
SEQUENCE: 292
000

SEQ ID NO: 293           moltype =    length =
SEQUENCE: 293
000

SEQ ID NO: 294           moltype =    length =
SEQUENCE: 294
000

SEQ ID NO: 295           moltype =    length =
SEQUENCE: 295
000

SEQ ID NO: 296           moltype =    length =
SEQUENCE: 296
000

SEQ ID NO: 297           moltype =    length =
SEQUENCE: 297
000

SEQ ID NO: 298           moltype =    length =
SEQUENCE: 298
000

SEQ ID NO: 299           moltype =    length =
SEQUENCE: 299
000

SEQ ID NO: 300           moltype =    length =
SEQUENCE: 300
000

SEQ ID NO: 301           moltype = AA  length = 122

```
FEATURE                 Location/Qualifiers
source                  1..122
                        mol_type = protein
                        organism = synthetic construct
SEQUENCE: 301
QVQLVESGGG LVQAGDSLRL SCVASDRTFS SYAVGWFRQA PGKEREFVAA ISWNGGRTLY    60
TDSVTGRFTI SRDNAKSTVY LQMNGLKPED TAVYYCAARP AAPTRRLEYD YWGQGTQVTV   120
SS                                                                  122

SEQ ID NO: 302          moltype = AA  length = 122
FEATURE                 Location/Qualifiers
source                  1..122
                        mol_type = protein
                        organism = synthetic construct
SEQUENCE: 302
QVQLVESGGG LVQPGGSLRL SCAASDRTFS SYAVGWFRQA PGQGLEAVAA ISWNGGRTLY    60
TDSVTGRFTI SRDNSKNTLY LQMNSLRAED TAVYYCAARP AAPTRRLEYD YWGQGTLVTV   120
SS                                                                  122

SEQ ID NO: 303          moltype = AA  length = 122
FEATURE                 Location/Qualifiers
source                  1..122
                        mol_type = protein
                        organism = synthetic construct
SEQUENCE: 303
QVQLVESGGG LVQPGGSLRL SCAASDRTFS SYAVGWFRQA PGQGLEFVAA ISWNGGRTLY    60
TDSVTGRFTI SRDNSKNTLY LQMNSLRAED TAVYYCAARP AAPTRRLEYD YWGQGTLVTV   120
SS                                                                  122

SEQ ID NO: 304          moltype = AA  length = 122
FEATURE                 Location/Qualifiers
source                  1..122
                        mol_type = protein
                        organism = synthetic construct
SEQUENCE: 304
QVQLVESGGG LVQPGGSLRL SCAASDRTFS SYAVGWFRQA PGQGREFVAA ISWNGGRTLY    60
TDSVTGRFTI SRDNSKNTLY LQMNSLRAED TAVYYCAARP AAPTRRLEYD YWGQGTLVTV   120
SS                                                                  122

SEQ ID NO: 305          moltype = AA  length = 122
FEATURE                 Location/Qualifiers
source                  1..122
                        mol_type = protein
                        organism = synthetic construct
SEQUENCE: 305
QVQLVESGGG LVQPGGSLRL SCAASDRTFS SYAVGWFRQA PGQEREFVAA ISWNGGRTLY    60
TDSVTGRFTI SRDNSKNTLY LQMNSLRAED TAVYYCAARP AAPTRRLEYD YWGQGTLVTV   120
SS                                                                  122

SEQ ID NO: 306          moltype = AA  length = 122
FEATURE                 Location/Qualifiers
source                  1..122
                        mol_type = protein
                        organism = synthetic construct
SEQUENCE: 306
QVQLVESGGG LVQPGGSLRL SCAASDRTFS SYAVGWFRQA PGKEREFVAA ISWNGGRTLY    60
TDSVTGRFTI SRDNSKNTLY LQMNSLRAED TAVYYCAARP AAPTRRLEYD YWGQGTLVTV   120
SS                                                                  122

SEQ ID NO: 307          moltype = AA  length = 8
FEATURE                 Location/Qualifiers
source                  1..8
                        mol_type = protein
                        organism = synthetic construct
SEQUENCE: 307
DRTFSSYA                                                              8

SEQ ID NO: 308          moltype = AA  length = 5
FEATURE                 Location/Qualifiers
source                  1..5
                        mol_type = protein
                        organism = synthetic construct
SEQUENCE: 308
SYAVG                                                                 5

SEQ ID NO: 309          moltype = AA  length = 7
FEATURE                 Location/Qualifiers
source                  1..7
                        mol_type = protein
```

```
                                        -continued
                         organism = synthetic construct
SEQUENCE: 309
DRTFSSY                                                                    7

SEQ ID NO: 310           moltype = AA   length = 8
FEATURE                  Location/Qualifiers
source                   1..8
                         mol_type = protein
                         organism = synthetic construct
SEQUENCE: 310
ISWNGGRT                                                                   8

SEQ ID NO: 311           moltype = AA   length = 17
FEATURE                  Location/Qualifiers
source                   1..17
                         mol_type = protein
                         organism = synthetic construct
SEQUENCE: 311
AISWNGGRTL YTDSVTG                                                        17

SEQ ID NO: 312           moltype = AA   length = 6
FEATURE                  Location/Qualifiers
source                   1..6
                         mol_type = protein
                         organism = synthetic construct
SEQUENCE: 312
SWNGGR                                                                     6

SEQ ID NO: 313           moltype = AA   length = 15
FEATURE                  Location/Qualifiers
source                   1..15
                         mol_type = protein
                         organism = synthetic construct
SEQUENCE: 313
AARPAAPTRR LEYDY                                                          15

SEQ ID NO: 314           moltype = AA   length = 13
FEATURE                  Location/Qualifiers
source                   1..13
                         mol_type = protein
                         organism = synthetic construct
SEQUENCE: 314
RPAAPTRRLE YDY                                                            13

SEQ ID NO: 315           moltype = AA   length = 13
FEATURE                  Location/Qualifiers
source                   1..13
                         mol_type = protein
                         organism = synthetic construct
SEQUENCE: 315
RPAAPTRRLE YDY                                                            13

SEQ ID NO: 316           moltype = AA   length = 353
FEATURE                  Location/Qualifiers
source                   1..353
                         mol_type = protein
                         organism = synthetic construct
SEQUENCE: 316
QVQLVESGGG LVQPGGSLRL SCAASDRTFS SYAVGWFRQA PGQGLEAVAA ISWNGGRTLY          60
TDSVTGRFTI SRDNSKNTLY LQMNSLRAED TAVYYCAARP AAPTRRLEYD YWGQGTLVTV        120
SSEPKSSDKT HTCPPCPAPE AEGAPSVFLF PPKPKDTLMI SRTPEVTCVV VDVSHEDPEV        180
KFNWYVDGVE VHNAKTKPRE EQYNSTYRVV SVLTVLHQDW LNGKEYKCKV SNKALPSSIE        240
KTISKAKGQP REPQVYTLPP SREEMTKNQV SLTCLVKGFY PSDIAVEWES NGQPENNYKT        300
TPPVLDSDGS FFLYSKLTVD KSRWQQGNVF SCSVMHEALH NQYTQKSLSL SPG               353

SEQ ID NO: 317           moltype = AA   length = 353
FEATURE                  Location/Qualifiers
source                   1..353
                         mol_type = protein
                         organism = synthetic construct
SEQUENCE: 317
QVQLVESGGG LVQPGGSLRL SCAASDRTFS SYAVGWFRQA PGQGLEFVAA ISWNGGRTLY          60
TDSVTGRFTI SRDNSKNTLY LQMNSLRAED TAVYYCAARP AAPTRRLEYD YWGQGTLVTV        120
SSEPKSSDKT HTCPPCPAPE AEGAPSVFLF PPKPKDTLMI SRTPEVTCVV VDVSHEDPEV        180
KFNWYVDGVE VHNAKTKPRE EQYNSTYRVV SVLTVLHQDW LNGKEYKCKV SNKALPSSIE        240
KTISKAKGQP REPQVYTLPP SREEMTKNQV SLTCLVKGFY PSDIAVEWES NGQPENNYKT        300
TPPVLDSDGS FFLYSKLTVD KSRWQQGNVF SCSVMHEALH NQYTQKSLSL SPG               353

SEQ ID NO: 318           moltype = AA   length = 353
```

```
FEATURE                 Location/Qualifiers
source                  1..353
                        mol_type = protein
                        organism = synthetic construct
SEQUENCE: 318
QVQLVESGGG LVQPGGSLRL SCAASDRTFS SYAVGWFRQA PGQGREFVAA ISWNGGRTLY    60
TDSVTGRFTI SRDNSKNTLY LQMNSLRAED TAVYYCAARP AAPTRRLEYD YWGQGTLVTV   120
SSEPKSSDKT HTCPPCPAPE AEGAPSVFLF PPKPKDTLMI SRTPEVTCVV VDVSHEDPEV   180
KFNWYVDGVE VHNAKTKPRE EQYNSTYRVV SVLTVLHQDW LNGKEYKCKV SNKALPSSIE   240
KTISKAKGQP REPQVYTLPP SREEMTKNQV SLTCLVKGFY PSDIAVEWES NGQPENNYKT   300
TPPVLDSDGS FFLYSKLTVD KSRWQQGNVF SCSVMHEALH NQYTQKSLSL SPG          353

SEQ ID NO: 319          moltype = AA   length = 353
FEATURE                 Location/Qualifiers
source                  1..353
                        mol_type = protein
                        organism = synthetic construct
SEQUENCE: 319
QVQLVESGGG LVQPGGSLRL SCAASDRTFS SYAVGWFRQA PGQEREFVAA ISWNGGRTLY    60
TDSVTGRFTI SRDNSKNTLY LQMNSLRAED TAVYYCAARP AAPTRRLEYD YWGQGTLVTV   120
SSEPKSSDKT HTCPPCPAPE AEGAPSVFLF PPKPKDTLMI SRTPEVTCVV VDVSHEDPEV   180
KFNWYVDGVE VHNAKTKPRE EQYNSTYRVV SVLTVLHQDW LNGKEYKCKV SNKALPSSIE   240
KTISKAKGQP REPQVYTLPP SREEMTKNQV SLTCLVKGFY PSDIAVEWES NGQPENNYKT   300
TPPVLDSDGS FFLYSKLTVD KSRWQQGNVF SCSVMHEALH NQYTQKSLSL SPG          353

SEQ ID NO: 320          moltype = AA   length = 353
FEATURE                 Location/Qualifiers
source                  1..353
                        mol_type = protein
                        organism = synthetic construct
SEQUENCE: 320
QVQLVESGGG LVQPGGSLRL SCAASDRTFS SYAVGWFRQA PGKEREFVAA ISWNGGRTLY    60
TDSVTGRFTI SRDNSKNTLY LQMNSLRAED TAVYYCAARP AAPTRRLEYD YWGQGTLVTV   120
SSEPKSSDKT HTCPPCPAPE AEGAPSVFLF PPKPKDTLMI SRTPEVTCVV VDVSHEDPEV   180
KFNWYVDGVE VHNAKTKPRE EQYNSTYRVV SVLTVLHQDW LNGKEYKCKV SNKALPSSIE   240
KTISKAKGQP REPQVYTLPP SREEMTKNQV SLTCLVKGFY PSDIAVEWES NGQPENNYKT   300
TPPVLDSDGS FFLYSKLTVD KSRWQQGNVF SCSVMHEALH NQYTQKSLSL SPG          353

SEQ ID NO: 321          moltype =    length =
SEQUENCE: 321
000

SEQ ID NO: 322          moltype =    length =
SEQUENCE: 322
000

SEQ ID NO: 323          moltype =    length =
SEQUENCE: 323
000

SEQ ID NO: 324          moltype =    length =
SEQUENCE: 324
000

SEQ ID NO: 325          moltype =    length =
SEQUENCE: 325
000

SEQ ID NO: 326          moltype =    length =
SEQUENCE: 326
000

SEQ ID NO: 327          moltype =    length =
SEQUENCE: 327
000

SEQ ID NO: 328          moltype =    length =
SEQUENCE: 328
000

SEQ ID NO: 329          moltype =    length =
SEQUENCE: 329
000

SEQ ID NO: 330          moltype =    length =
SEQUENCE: 330
000

SEQ ID NO: 331          moltype =    length =
```

| | | |
|---|---|---|
| SEQUENCE: 331 000 | | |
| SEQ ID NO: 332 SEQUENCE: 332 000 | moltype = | length = |
| SEQ ID NO: 333 SEQUENCE: 333 000 | moltype = | length = |
| SEQ ID NO: 334 SEQUENCE: 334 000 | moltype = | length = |
| SEQ ID NO: 335 SEQUENCE: 335 000 | moltype = | length = |
| SEQ ID NO: 336 SEQUENCE: 336 000 | moltype = | length = |
| SEQ ID NO: 337 SEQUENCE: 337 000 | moltype = | length = |
| SEQ ID NO: 338 SEQUENCE: 338 000 | moltype = | length = |
| SEQ ID NO: 339 SEQUENCE: 339 000 | moltype = | length = |
| SEQ ID NO: 340 SEQUENCE: 340 000 | moltype = | length = |
| SEQ ID NO: 341 SEQUENCE: 341 000 | moltype = | length = |
| SEQ ID NO: 342 SEQUENCE: 342 000 | moltype = | length = |
| SEQ ID NO: 343 SEQUENCE: 343 000 | moltype = | length = |
| SEQ ID NO: 344 SEQUENCE: 344 000 | moltype = | length = |
| SEQ ID NO: 345 SEQUENCE: 345 000 | moltype = | length = |
| SEQ ID NO: 346 SEQUENCE: 346 000 | moltype = | length = |
| SEQ ID NO: 347 SEQUENCE: 347 000 | moltype = | length = |
| SEQ ID NO: 348 SEQUENCE: 348 000 | moltype = | length = |
| SEQ ID NO: 349 SEQUENCE: 349 000 | moltype = | length = |
| SEQ ID NO: 350 SEQUENCE: 350 000 | moltype = | length = |

| | | |
|---|---|---|
| SEQ ID NO: 351<br>SEQUENCE: 351<br>000 | moltype = | length = |
| SEQ ID NO: 352<br>SEQUENCE: 352<br>000 | moltype = | length = |
| SEQ ID NO: 353<br>SEQUENCE: 353<br>000 | moltype = | length = |
| SEQ ID NO: 354<br>SEQUENCE: 354<br>000 | moltype = | length = |
| SEQ ID NO: 355<br>SEQUENCE: 355<br>000 | moltype = | length = |
| SEQ ID NO: 356<br>SEQUENCE: 356<br>000 | moltype = | length = |
| SEQ ID NO: 357<br>SEQUENCE: 357<br>000 | moltype = | length = |
| SEQ ID NO: 358<br>SEQUENCE: 358<br>000 | moltype = | length = |
| SEQ ID NO: 359<br>SEQUENCE: 359<br>000 | moltype = | length = |
| SEQ ID NO: 360<br>SEQUENCE: 360<br>000 | moltype = | length = |
| SEQ ID NO: 361<br>SEQUENCE: 361<br>000 | moltype = | length = |
| SEQ ID NO: 362<br>SEQUENCE: 362<br>000 | moltype = | length = |
| SEQ ID NO: 363<br>SEQUENCE: 363<br>000 | moltype = | length = |
| SEQ ID NO: 364<br>SEQUENCE: 364<br>000 | moltype = | length = |
| SEQ ID NO: 365<br>SEQUENCE: 365<br>000 | moltype = | length = |
| SEQ ID NO: 366<br>SEQUENCE: 366<br>000 | moltype = | length = |
| SEQ ID NO: 367<br>SEQUENCE: 367<br>000 | moltype = | length = |
| SEQ ID NO: 368<br>SEQUENCE: 368<br>000 | moltype = | length = |
| SEQ ID NO: 369<br>SEQUENCE: 369<br>000 | moltype = | length = |
| SEQ ID NO: 370<br>SEQUENCE: 370<br>000 | moltype = | length = |

| | | |
|---|---|---|
| SEQ ID NO: 371 SEQUENCE: 371 000 | moltype = | length = |
| SEQ ID NO: 372 SEQUENCE: 372 000 | moltype = | length = |
| SEQ ID NO: 373 SEQUENCE: 373 000 | moltype = | length = |
| SEQ ID NO: 374 SEQUENCE: 374 000 | moltype = | length = |
| SEQ ID NO: 375 SEQUENCE: 375 000 | moltype = | length = |
| SEQ ID NO: 376 SEQUENCE: 376 000 | moltype = | length = |
| SEQ ID NO: 377 SEQUENCE: 377 000 | moltype = | length = |
| SEQ ID NO: 378 SEQUENCE: 378 000 | moltype = | length = |
| SEQ ID NO: 379 SEQUENCE: 379 000 | moltype = | length = |
| SEQ ID NO: 380 SEQUENCE: 380 000 | moltype = | length = |
| SEQ ID NO: 381 SEQUENCE: 381 000 | moltype = | length = |
| SEQ ID NO: 382 SEQUENCE: 382 000 | moltype = | length = |
| SEQ ID NO: 383 SEQUENCE: 383 000 | moltype = | length = |
| SEQ ID NO: 384 SEQUENCE: 384 000 | moltype = | length = |
| SEQ ID NO: 385 SEQUENCE: 385 000 | moltype = | length = |
| SEQ ID NO: 386 SEQUENCE: 386 000 | moltype = | length = |
| SEQ ID NO: 387 SEQUENCE: 387 000 | moltype = | length = |
| SEQ ID NO: 388 SEQUENCE: 388 000 | moltype = | length = |
| SEQ ID NO: 389 SEQUENCE: 389 000 | moltype = | length = |
| SEQ ID NO: 390 SEQUENCE: 390 | moltype = | length = |

-continued

```
000

SEQ ID NO: 391          moltype =     length =
SEQUENCE: 391
000

SEQ ID NO: 392          moltype =     length =
SEQUENCE: 392
000

SEQ ID NO: 393          moltype =     length =
SEQUENCE: 393
000

SEQ ID NO: 394          moltype =     length =
SEQUENCE: 394
000

SEQ ID NO: 395          moltype =     length =
SEQUENCE: 395
000

SEQ ID NO: 396          moltype =     length =
SEQUENCE: 396
000

SEQ ID NO: 397          moltype =     length =
SEQUENCE: 397
000

SEQ ID NO: 398          moltype =     length =
SEQUENCE: 398
000

SEQ ID NO: 399          moltype =     length =
SEQUENCE: 399
000

SEQ ID NO: 400          moltype =     length =
SEQUENCE: 400
000

SEQ ID NO: 401          moltype = AA   length = 115
FEATURE                 Location/Qualifiers
source                  1..115
                        mol_type = protein
                        organism = synthetic construct
SEQUENCE: 401
QVQLVESGGG MVQPGGSLRL SCAASGITFS MYSMSWYRQP PGKQRELVAA TTTFGSTNYA    60
DSVKGRFTIS RDNAKNTVYL QMNSLKPEDT AVYLCNARFT SEEYWGQGTQ VTVSS         115

SEQ ID NO: 402          moltype = AA   length = 115
FEATURE                 Location/Qualifiers
source                  1..115
                        mol_type = protein
                        organism = synthetic construct
SEQUENCE: 402
QVQLVESGGG LVQPGGSLRL SCAASGITFS MYSMSWFRQA PGQGLEAVAA TTTFGSTNYA    60
DSVKGRFTIS RDNSKNTLYL QMNSLRAEDT AVYYCAARFT SEEYWGQGTL VTVSS         115

SEQ ID NO: 403          moltype = AA   length = 115
FEATURE                 Location/Qualifiers
source                  1..115
                        mol_type = protein
                        organism = synthetic construct
SEQUENCE: 403
QVQLVESGGG LVQPGGSLRL SCAASGITFS MYSMSWFRQA PGQGLELVAA TTTFGSTNYA    60
DSVKGRFTIS RDNSKNTLYL QMNSLRAEDT AVYYCAARFT SEEYWGQGTL VTVSS         115

SEQ ID NO: 404          moltype = AA   length = 115
FEATURE                 Location/Qualifiers
source                  1..115
                        mol_type = protein
                        organism = synthetic construct
SEQUENCE: 404
QVQLVESGGG LVQPGGSLRL SCAASGITFS MYSMSWYRQA PGQGLELVAA TTTFGSTNYA    60
DSVKGRFTIS RDNSKNTLYL QMNSLRAEDT AVYYCAARFT SEEYWGQGTL VTVSS         115

SEQ ID NO: 405          moltype = AA   length = 115
```

```
FEATURE               Location/Qualifiers
source                1..115
                      mol_type = protein
                      organism = synthetic construct
SEQUENCE: 405
QVQLVESGGG LVQPGGSLRL SCAASGITFS MYSMSWYRQA PGQQRELVAA TTTFGSTNYA    60
DSVKGRFTIS RDNSKNTLYL QMNSLRAEDT AVYYCAARFT SEEYWGQGTL VTVSS        115

SEQ ID NO: 406        moltype = AA  length = 115
FEATURE               Location/Qualifiers
source                1..115
                      mol_type = protein
                      organism = synthetic construct
SEQUENCE: 406
QVQLVESGGG LVQPGGSLRL SCAASGITFS MYSMSWYRQP PGKQRELVAA TTTFGSTNYA    60
DSVKGRFTIS RDNSKNTLYL QMNSLRAEDT AVYYCAARFT SEEYWGQGTL VTVSS        115

SEQ ID NO: 407        moltype = AA  length = 8
FEATURE               Location/Qualifiers
source                1..8
                      mol_type = protein
                      organism = synthetic construct
SEQUENCE: 407
GITFSMYS                                                             8

SEQ ID NO: 408        moltype = AA  length = 5
FEATURE               Location/Qualifiers
source                1..5
                      mol_type = protein
                      organism = synthetic construct
SEQUENCE: 408
MYSMS                                                                5

SEQ ID NO: 409        moltype = AA  length = 7
FEATURE               Location/Qualifiers
source                1..7
                      mol_type = protein
                      organism = synthetic construct
SEQUENCE: 409
GITFSMY                                                              7

SEQ ID NO: 410        moltype = AA  length = 7
FEATURE               Location/Qualifiers
source                1..7
                      mol_type = protein
                      organism = synthetic construct
SEQUENCE: 410
TTTFGST                                                              7

SEQ ID NO: 411        moltype = AA  length = 16
FEATURE               Location/Qualifiers
source                1..16
                      mol_type = protein
                      organism = synthetic construct
SEQUENCE: 411
ATTTFGSTNY ADSVKG                                                   16

SEQ ID NO: 412        moltype = AA  length = 5
FEATURE               Location/Qualifiers
source                1..5
                      mol_type = protein
                      organism = synthetic construct
SEQUENCE: 412
TTFGS                                                                5

SEQ ID NO: 413        moltype = AA  length = 9
FEATURE               Location/Qualifiers
source                1..9
                      mol_type = protein
                      organism = synthetic construct
SEQUENCE: 413
AARFTSEEY                                                            9

SEQ ID NO: 414        moltype = AA  length = 7
FEATURE               Location/Qualifiers
source                1..7
                      mol_type = protein
                      organism = synthetic construct
SEQUENCE: 414
```

```
RFTSEEY                                                                   7

SEQ ID NO: 415          moltype = AA  length = 7
FEATURE                 Location/Qualifiers
source                  1..7
                        mol_type = protein
                        organism = synthetic construct
SEQUENCE: 415
RFTSEEY                                                                   7

SEQ ID NO: 416          moltype = AA  length = 346
FEATURE                 Location/Qualifiers
source                  1..346
                        mol_type = protein
                        organism = synthetic construct
SEQUENCE: 416
QVQLVESGGG LVQPGGSLRL SCAASGITFS MYSMSWFRQA PGQGLEAVAA TTTFGSTNYA          60
DSVKGRFTIS RDNSKNTLYL QMNSLRAEDT AVYYCAARFT SEEYWGQGTL VTVSSEPKSS         120
DKTHTCPPCP APEAEGAPSV FLFPPKPKDT LMISRTPEVT CVVVDVSHED PEVKFNWYVD         180
GVEVHNAKTK PREEQYNSTY RVVSVLTVLH QDWLNGKEYK CKVSNKALPS SIEKTISKAK         240
GQPREPQVYT LPPSREEMTK NQVSLTCLVK GFYPSDIAVE WESNGQPENN YKTTPPVLDS         300
DGSFFLYSKL TVDKSRWQQG NVFSCSVMHE ALHNQYTQKS LSLSPG                       346

SEQ ID NO: 417          moltype = AA  length = 346
FEATURE                 Location/Qualifiers
source                  1..346
                        mol_type = protein
                        organism = synthetic construct
SEQUENCE: 417
QVQLVESGGG LVQPGGSLRL SCAASGITFS MYSMSWFRQA PGQGLELVAA TTTFGSTNYA          60
DSVKGRFTIS RDNSKNTLYL QMNSLRAEDT AVYYCAARFT SEEYWGQGTL VTVSSEPKSS         120
DKTHTCPPCP APEAEGAPSV FLFPPKPKDT LMISRTPEVT CVVVDVSHED PEVKFNWYVD         180
GVEVHNAKTK PREEQYNSTY RVVSVLTVLH QDWLNGKEYK CKVSNKALPS SIEKTISKAK         240
GQPREPQVYT LPPSREEMTK NQVSLTCLVK GFYPSDIAVE WESNGQPENN YKTTPPVLDS         300
DGSFFLYSKL TVDKSRWQQG NVFSCSVMHE ALHNQYTQKS LSLSPG                       346

SEQ ID NO: 418          moltype = AA  length = 346
FEATURE                 Location/Qualifiers
source                  1..346
                        mol_type = protein
                        organism = synthetic construct
SEQUENCE: 418
QVQLVESGGG LVQPGGSLRL SCAASGITFS MYSMSWYRQA PGQGLELVAA TTTFGSTNYA          60
DSVKGRFTIS RDNSKNTLYL QMNSLRAEDT AVYYCAARFT SEEYWGQGTL VTVSSEPKSS         120
DKTHTCPPCP APEAEGAPSV FLFPPKPKDT LMISRTPEVT CVVVDVSHED PEVKFNWYVD         180
GVEVHNAKTK PREEQYNSTY RVVSVLTVLH QDWLNGKEYK CKVSNKALPS SIEKTISKAK         240
GQPREPQVYT LPPSREEMTK NQVSLTCLVK GFYPSDIAVE WESNGQPENN YKTTPPVLDS         300
DGSFFLYSKL TVDKSRWQQG NVFSCSVMHE ALHNQYTQKS LSLSPG                       346

SEQ ID NO: 419          moltype = AA  length = 346
FEATURE                 Location/Qualifiers
source                  1..346
                        mol_type = protein
                        organism = synthetic construct
SEQUENCE: 419
QVQLVESGGG LVQPGGSLRL SCAASGITFS MYSMSWYRQA PGQQRELVAA TTTFGSTNYA          60
DSVKGRFTIS RDNSKNTLYL QMNSLRAEDT AVYYCAARFT SEEYWGQGTL VTVSSEPKSS         120
DKTHTCPPCP APEAEGAPSV FLFPPKPKDT LMISRTPEVT CVVVDVSHED PEVKFNWYVD         180
GVEVHNAKTK PREEQYNSTY RVVSVLTVLH QDWLNGKEYK CKVSNKALPS SIEKTISKAK         240
GQPREPQVYT LPPSREEMTK NQVSLTCLVK GFYPSDIAVE WESNGQPENN YKTTPPVLDS         300
DGSFFLYSKL TVDKSRWQQG NVFSCSVMHE ALHNQYTQKS LSLSPG                       346

SEQ ID NO: 420          moltype = AA  length = 346
FEATURE                 Location/Qualifiers
source                  1..346
                        mol_type = protein
                        organism = synthetic construct
SEQUENCE: 420
QVQLVESGGG LVQPGGSLRL SCAASGITFS MYSMSWYRQP PGKQRELVAA TTTFGSTNYA          60
DSVKGRFTIS RDNSKNTLYL QMNSLRAEDT AVYYCAARFT SEEYWGQGTL VTVSSEPKSS         120
DKTHTCPPCP APEAEGAPSV FLFPPKPKDT LMISRTPEVT CVVVDVSHED PEVKFNWYVD         180
GVEVHNAKTK PREEQYNSTY RVVSVLTVLH QDWLNGKEYK CKVSNKALPS SIEKTISKAK         240
GQPREPQVYT LPPSREEMTK NQVSLTCLVK GFYPSDIAVE WESNGQPENN YKTTPPVLDS         300
DGSFFLYSKL TVDKSRWQQG NVFSCSVMHE ALHNQYTQKS LSLSPG                       346

SEQ ID NO: 421          moltype =     length =
SEQUENCE: 421
000
```

```
SEQ ID NO: 422        moltype =    length =
SEQUENCE: 422
000

SEQ ID NO: 423        moltype =    length =
SEQUENCE: 423
000

SEQ ID NO: 424        moltype =    length =
SEQUENCE: 424
000

SEQ ID NO: 425        moltype =    length =
SEQUENCE: 425
000

SEQ ID NO: 426        moltype =    length =
SEQUENCE: 426
000

SEQ ID NO: 427        moltype =    length =
SEQUENCE: 427
000

SEQ ID NO: 428        moltype =    length =
SEQUENCE: 428
000

SEQ ID NO: 429        moltype =    length =
SEQUENCE: 429
000

SEQ ID NO: 430        moltype =    length =
SEQUENCE: 430
000

SEQ ID NO: 431        moltype = AA  length = 9
FEATURE               Location/Qualifiers
source                1..9
                      mol_type = protein
                      organism = synthetic construct
SEQUENCE: 431
NARFTSEEY                                                                 9

SEQ ID NO: 432        moltype =    length =
SEQUENCE: 432
000

SEQ ID NO: 433        moltype =    length =
SEQUENCE: 433
000

SEQ ID NO: 434        moltype =    length =
SEQUENCE: 434
000

SEQ ID NO: 435        moltype =    length =
SEQUENCE: 435
000

SEQ ID NO: 436        moltype =    length =
SEQUENCE: 436
000

SEQ ID NO: 437        moltype =    length =
SEQUENCE: 437
000

SEQ ID NO: 438        moltype =    length =
SEQUENCE: 438
000

SEQ ID NO: 439        moltype =    length =
SEQUENCE: 439
000

SEQ ID NO: 440        moltype =    length =
SEQUENCE: 440
000
```

| | | |
|---|---|---|
| SEQ ID NO: 441<br>SEQUENCE: 441<br>000 | moltype = | length = |
| SEQ ID NO: 442<br>SEQUENCE: 442<br>000 | moltype = | length = |
| SEQ ID NO: 443<br>SEQUENCE: 443<br>000 | moltype = | length = |
| SEQ ID NO: 444<br>SEQUENCE: 444<br>000 | moltype = | length = |
| SEQ ID NO: 445<br>SEQUENCE: 445<br>000 | moltype = | length = |
| SEQ ID NO: 446<br>SEQUENCE: 446<br>000 | moltype = | length = |
| SEQ ID NO: 447<br>SEQUENCE: 447<br>000 | moltype = | length = |
| SEQ ID NO: 448<br>SEQUENCE: 448<br>000 | moltype = | length = |
| SEQ ID NO: 449<br>SEQUENCE: 449<br>000 | moltype = | length = |
| SEQ ID NO: 450<br>SEQUENCE: 450<br>000 | moltype = | length = |
| SEQ ID NO: 451<br>SEQUENCE: 451<br>000 | moltype = | length = |
| SEQ ID NO: 452<br>SEQUENCE: 452<br>000 | moltype = | length = |
| SEQ ID NO: 453<br>SEQUENCE: 453<br>000 | moltype = | length = |
| SEQ ID NO: 454<br>SEQUENCE: 454<br>000 | moltype = | length = |
| SEQ ID NO: 455<br>SEQUENCE: 455<br>000 | moltype = | length = |
| SEQ ID NO: 456<br>SEQUENCE: 456<br>000 | moltype = | length = |
| SEQ ID NO: 457<br>SEQUENCE: 457<br>000 | moltype = | length = |
| SEQ ID NO: 458<br>SEQUENCE: 458<br>000 | moltype = | length = |
| SEQ ID NO: 459<br>SEQUENCE: 459<br>000 | moltype = | length = |
| SEQ ID NO: 460<br>SEQUENCE: 460 | moltype = | length = |

000

SEQ ID NO: 461          moltype =      length =
SEQUENCE: 461
000

SEQ ID NO: 462          moltype =      length =
SEQUENCE: 462
000

SEQ ID NO: 463          moltype =      length =
SEQUENCE: 463
000

SEQ ID NO: 464          moltype =      length =
SEQUENCE: 464
000

SEQ ID NO: 465          moltype =      length =
SEQUENCE: 465
000

SEQ ID NO: 466          moltype =      length =
SEQUENCE: 466
000

SEQ ID NO: 467          moltype =      length =
SEQUENCE: 467
000

SEQ ID NO: 468          moltype =      length =
SEQUENCE: 468
000

SEQ ID NO: 469          moltype =      length =
SEQUENCE: 469
000

SEQ ID NO: 470          moltype =      length =
SEQUENCE: 470
000

SEQ ID NO: 471          moltype =      length =
SEQUENCE: 471
000

SEQ ID NO: 472          moltype =      length =
SEQUENCE: 472
000

SEQ ID NO: 473          moltype =      length =
SEQUENCE: 473
000

SEQ ID NO: 474          moltype =      length =
SEQUENCE: 474
000

SEQ ID NO: 475          moltype =      length =
SEQUENCE: 475
000

SEQ ID NO: 476          moltype =      length =
SEQUENCE: 476
000

SEQ ID NO: 477          moltype =      length =
SEQUENCE: 477
000

SEQ ID NO: 478          moltype =      length =
SEQUENCE: 478
000

SEQ ID NO: 479          moltype =      length =
SEQUENCE: 479
000

SEQ ID NO: 480          moltype =      length =

```
SEQUENCE: 480
000

SEQ ID NO: 481           moltype =    length =
SEQUENCE: 481
000

SEQ ID NO: 482           moltype =    length =
SEQUENCE: 482
000

SEQ ID NO: 483           moltype =    length =
SEQUENCE: 483
000

SEQ ID NO: 484           moltype =    length =
SEQUENCE: 484
000

SEQ ID NO: 485           moltype =    length =
SEQUENCE: 485
000

SEQ ID NO: 486           moltype =    length =
SEQUENCE: 486
000

SEQ ID NO: 487           moltype =    length =
SEQUENCE: 487
000

SEQ ID NO: 488           moltype =    length =
SEQUENCE: 488
000

SEQ ID NO: 489           moltype =    length =
SEQUENCE: 489
000

SEQ ID NO: 490           moltype =    length =
SEQUENCE: 490
000

SEQ ID NO: 491           moltype =    length =
SEQUENCE: 491
000

SEQ ID NO: 492           moltype =    length =
SEQUENCE: 492
000

SEQ ID NO: 493           moltype =    length =
SEQUENCE: 493
000

SEQ ID NO: 494           moltype =    length =
SEQUENCE: 494
000

SEQ ID NO: 495           moltype =    length =
SEQUENCE: 495
000

SEQ ID NO: 496           moltype =    length =
SEQUENCE: 496
000

SEQ ID NO: 497           moltype =    length =
SEQUENCE: 497
000

SEQ ID NO: 498           moltype =    length =
SEQUENCE: 498
000

SEQ ID NO: 499           moltype =    length =
SEQUENCE: 499
000
```

```
SEQ ID NO: 500          moltype =   length =
SEQUENCE: 500
000

SEQ ID NO: 501          moltype = AA   length = 116
FEATURE                 Location/Qualifiers
source                  1..116
                        mol_type = protein
                        organism = synthetic construct
SEQUENCE: 501
QVQVVESGGG LVQPGGSLTL SCAASGFDFS TYTVNWYRQA PGKEREKVAR ISSTGTTTNY    60
ANSAKGRFTL SRDNAKNRVY LQMNNLKPED TAVYFCNFER FDSNYWGQGT QVTVSS       116

SEQ ID NO: 502          moltype = AA   length = 116
FEATURE                 Location/Qualifiers
source                  1..116
                        mol_type = protein
                        organism = synthetic construct
SEQUENCE: 502
QVQLVESGGG LVQPGGSLRL SCAASGFDFS TYTVNWFRQA PGQGLEAVAR ISSTGTTTNY    60
ANSAKGRFTI SRDNSKNTLY LQMNSLRAED TAVYYCAAER FDSNYWGQGT LVTVSS       116

SEQ ID NO: 503          moltype = AA   length = 116
FEATURE                 Location/Qualifiers
source                  1..116
                        mol_type = protein
                        organism = synthetic construct
SEQUENCE: 503
QVQLVESGGG LVQPGGSLRL SCAASGFDFS TYTVNWFRQA PGQGLEKVAR ISSTGTTTNY    60
ANSAKGRFTI SRDNSKNTLY LQMNSLRAED TAVYYCAAER FDSNYWGQGT LVTVSS       116

SEQ ID NO: 504          moltype = AA   length = 116
FEATURE                 Location/Qualifiers
source                  1..116
                        mol_type = protein
                        organism = synthetic construct
SEQUENCE: 504
QVQLVESGGG LVQPGGSLRL SCAASGFDFS TYTVNWYRQA PGQGLEKVAR ISSTGTTTNY    60
ANSAKGRFTI SRDNSKNTLY LQMNSLRAED TAVYYCAAER FDSNYWGQGT LVTVSS       116

SEQ ID NO: 505          moltype = AA   length = 116
FEATURE                 Location/Qualifiers
source                  1..116
                        mol_type = protein
                        organism = synthetic construct
SEQUENCE: 505
QVQLVESGGG LVQPGGSLRL SCAASGFDFS TYTVNWYRQA PGQEREKVAR ISSTGTTTNY    60
ANSAKGRFTI SRDNSKNTLY LQMNSLRAED TAVYYCAAER FDSNYWGQGT LVTVSS       116

SEQ ID NO: 506          moltype = AA   length = 116
FEATURE                 Location/Qualifiers
source                  1..116
                        mol_type = protein
                        organism = synthetic construct
SEQUENCE: 506
QVQLVESGGG LVQPGGSLRL SCAASGFDFS TYTVNWYRQA PGKEREKVAR ISSTGTTTNY    60
ANSAKGRFTI SRDNSKNTLY LQMNSLRAED TAVYYCAAER FDSNYWGQGT LVTVSS       116

SEQ ID NO: 507          moltype = AA   length = 8
FEATURE                 Location/Qualifiers
source                  1..8
                        mol_type = protein
                        organism = synthetic construct
SEQUENCE: 507
GFDFSTYT                                                              8

SEQ ID NO: 508          moltype = AA   length = 5
FEATURE                 Location/Qualifiers
source                  1..5
                        mol_type = protein
                        organism = synthetic construct
SEQUENCE: 508
TYTVN                                                                 5

SEQ ID NO: 509          moltype = AA   length = 7
FEATURE                 Location/Qualifiers
source                  1..7
                        mol_type = protein
                        organism = synthetic construct
```

-continued

```
SEQUENCE: 509
GFDFSTY                                                                    7

SEQ ID NO: 510          moltype = AA   length = 8
FEATURE                 Location/Qualifiers
source                  1..8
                        mol_type = protein
                        organism = synthetic construct
SEQUENCE: 510
ISSTGTTT                                                                   8

SEQ ID NO: 511          moltype = AA   length = 17
FEATURE                 Location/Qualifiers
source                  1..17
                        mol_type = protein
                        organism = synthetic construct
SEQUENCE: 511
RISSTGTTTN YANSAKG                                                        17

SEQ ID NO: 512          moltype = AA   length = 6
FEATURE                 Location/Qualifiers
source                  1..6
                        mol_type = protein
                        organism = synthetic construct
SEQUENCE: 512
SSTGTT                                                                     6

SEQ ID NO: 513          moltype = AA   length = 9
FEATURE                 Location/Qualifiers
source                  1..9
                        mol_type = protein
                        organism = synthetic construct
SEQUENCE: 513
AAERFDSNY                                                                  9

SEQ ID NO: 514          moltype = AA   length = 7
FEATURE                 Location/Qualifiers
source                  1..7
                        mol_type = protein
                        organism = synthetic construct
SEQUENCE: 514
ERFDSNY                                                                    7

SEQ ID NO: 515          moltype = AA   length = 7
FEATURE                 Location/Qualifiers
source                  1..7
                        mol_type = protein
                        organism = synthetic construct
SEQUENCE: 515
ERFDSNY                                                                    7

SEQ ID NO: 516          moltype = AA   length = 347
FEATURE                 Location/Qualifiers
source                  1..347
                        mol_type = protein
                        organism = synthetic construct
SEQUENCE: 516
QVQLVESGGG LVQPGGSLRL SCAASGFDFS TYTVNWFRQA PGQGLEAVAR ISSTGTTTNY          60
ANSAKGRFTI SRDNSKNTLY LQMNSLRAED TAVYYCAAER FDSNYWGQGT LVTVSSEPKS         120
SDKTHTCPPC PAPEAEGAPS VFLFPPKPKD TLMISRTPEV TCVVVDVSHE DPEVKFNWYV         180
DGVEVHNAKT KPREEQYNST YRVVSVLTVL HQDWLNGKEY KCKVSNKALP SSIEKTISKA         240
KGQPREPQVY TLPPSREEMT KNQVSLTCLV KGFYPSDIAV EWESNGQPEN NYKTTPPVLD         300
SDGSFFLYSK LTVDKSRWQQ GNVFSCSVMH EALHNQYTQK SLSLSPG                       347

SEQ ID NO: 517          moltype = AA   length = 347
FEATURE                 Location/Qualifiers
source                  1..347
                        mol_type = protein
                        organism = synthetic construct
SEQUENCE: 517
QVQLVESGGG LVQPGGSLRL SCAASGFDFS TYTVNWFRQA PGQGLEKVAR ISSTGTTTNY          60
ANSAKGRFTI SRDNSKNTLY LQMNSLRAED TAVYYCAAER FDSNYWGQGT LVTVSSEPKS         120
SDKTHTCPPC PAPEAEGAPS VFLFPPKPKD TLMISRTPEV TCVVVDVSHE DPEVKFNWYV         180
DGVEVHNAKT KPREEQYNST YRVVSVLTVL HQDWLNGKEY KCKVSNKALP SSIEKTISKA         240
KGQPREPQVY TLPPSREEMT KNQVSLTCLV KGFYPSDIAV EWESNGQPEN NYKTTPPVLD         300
SDGSFFLYSK LTVDKSRWQQ GNVFSCSVMH EALHNQYTQK SLSLSPG                       347

SEQ ID NO: 518          moltype = AA   length = 347
FEATURE                 Location/Qualifiers
```

```
source                  1..347
                        mol_type = protein
                        organism = synthetic construct
SEQUENCE: 518
QVQLVESGGG LVQPGGSLRL SCAASGFDFS TYTVNWYRQA PGQGLEKVAR ISSTGTTTNY   60
ANSAKGRFTI SRDNSKNTLY LQMNSLRAED TAVYYCAAER FDSNYWGQGT LVTVSSEPKS  120
SDKTHTCPPC PAPEAEGAPS VFLFPPKPKD TLMISRTPEV TCVVVDVSHE DPEVKFNWYV  180
DGVEVHNAKT KPREEQYNST YRVVSVLTVL HQDWLNGKEY KCKVSNKALP SSIEKTISKA  240
KGQPREPQVY TLPPSREEMT KNQVSLTCLV KGFYPSDIAV EWESNGQPEN NYKTTPPVLD  300
SDGSFFLYSK LTVDKSRWQQ GNVFSCSVMH EALHNQYTQK SLSLSPG                347

SEQ ID NO: 519          moltype = AA  length = 347
FEATURE                 Location/Qualifiers
source                  1..347
                        mol_type = protein
                        organism = synthetic construct
SEQUENCE: 519
QVQLVESGGG LVQPGGSLRL SCAASGFDFS TYTVNWYRQA PGQEREKVAR ISSTGTTTNY   60
ANSAKGRFTI SRDNSKNTLY LQMNSLRAED TAVYYCAAER FDSNYWGQGT LVTVSSEPKS  120
SDKTHTCPPC PAPEAEGAPS VFLFPPKPKD TLMISRTPEV TCVVVDVSHE DPEVKFNWYV  180
DGVEVHNAKT KPREEQYNST YRVVSVLTVL HQDWLNGKEY KCKVSNKALP SSIEKTISKA  240
KGQPREPQVY TLPPSREEMT KNQVSLTCLV KGFYPSDIAV EWESNGQPEN NYKTTPPVLD  300
SDGSFFLYSK LTVDKSRWQQ GNVFSCSVMH EALHNQYTQK SLSLSPG                347

SEQ ID NO: 520          moltype = AA  length = 347
FEATURE                 Location/Qualifiers
source                  1..347
                        mol_type = protein
                        organism = synthetic construct
SEQUENCE: 520
QVQLVESGGG LVQPGGSLRL SCAASGFDFS TYTVNWYRQA PGKEREKVAR ISSTGTTTNY   60
ANSAKGRFTI SRDNSKNTLY LQMNSLRAED TAVYYCAAER FDSNYWGQGT LVTVSSEPKS  120
SDKTHTCPPC PAPEAEGAPS VFLFPPKPKD TLMISRTPEV TCVVVDVSHE DPEVKFNWYV  180
DGVEVHNAKT KPREEQYNST YRVVSVLTVL HQDWLNGKEY KCKVSNKALP SSIEKTISKA  240
KGQPREPQVY TLPPSREEMT KNQVSLTCLV KGFYPSDIAV EWESNGQPEN NYKTTPPVLD  300
SDGSFFLYSK LTVDKSRWQQ GNVFSCSVMH EALHNQYTQK SLSLSPG                347

SEQ ID NO: 521          moltype =     length =
SEQUENCE: 521
000

SEQ ID NO: 522          moltype =     length =
SEQUENCE: 522
000

SEQ ID NO: 523          moltype =     length =
SEQUENCE: 523
000

SEQ ID NO: 524          moltype =     length =
SEQUENCE: 524
000

SEQ ID NO: 525          moltype =     length =
SEQUENCE: 525
000

SEQ ID NO: 526          moltype =     length =
SEQUENCE: 526
000

SEQ ID NO: 527          moltype =     length =
SEQUENCE: 527
000

SEQ ID NO: 528          moltype =     length =
SEQUENCE: 528
000

SEQ ID NO: 529          moltype =     length =
SEQUENCE: 529
000

SEQ ID NO: 530          moltype =     length =
SEQUENCE: 530
000

SEQ ID NO: 531          moltype = AA  length = 9
FEATURE                 Location/Qualifiers
```

```
source                          1..9
                                mol_type = protein
                                organism = synthetic construct
SEQUENCE: 531
NFERFDSNY                                                                       9

SEQ ID NO: 532                  moltype = AA   length = 509
FEATURE                         Location/Qualifiers
source                          1..509
                                mol_type = protein
                                organism = synthetic construct
SEQUENCE: 532
APLVCRAGCS PEHGFCEQPG ECRCLEGWTG PLCTVPVSTS SCLSPRGPSS ATTGCLVPGP              60
GPCDGNPCAN GGSCSETPRS FECTCPRGFY GLRCEVSGVT CADGPCFNGG LCVGGADPDS             120
AYICHCPPGF QGSNCEKRVD RCSLQPCRNG GLCLDLGHAL RCRCRAGFAG PRCEHDLDDC             180
AGRACANGGT CVEGGGAHRC SCALGFGGRD CRERADPCAA RPCAHGGRCY AHFSGLVCAC             240
APGYMGARCE FPVHPDGASA LPAAPPGLRP GDPQRYLARG PTIKPCPPCK CPAPNLLGGP             300
SVFIFPPKIK DVLMISLSPI VTCVVVDVSE DDPDVQISWF VNNVEVHTAQ TQTHREDYNS             360
TLRVVSALPI QHQDWMSGKE FKCKVNNKDL PAPIERTISK PKGSVRAPQV YVLPPPEEEM             420
TKKQVTLTCM VTDFMPEDIY VEWTNNGKTE LNYKNTEPVL DSDGSYFMYS KLRVEKKNWV             480
ERNSYSCSVV HEGLHNHHTT KSFSRTPGK                                               509

SEQ ID NO: 533                  moltype = AA   length = 5
FEATURE                         Location/Qualifiers
source                          1..5
                                mol_type = protein
                                organism = synthetic construct
SEQUENCE: 533
GSGGS                                                                           5

SEQ ID NO: 534                  moltype = AA   length = 5
FEATURE                         Location/Qualifiers
source                          1..5
                                mol_type = protein
                                organism = synthetic construct
SEQUENCE: 534
GGGGS                                                                           5

SEQ ID NO: 535                  moltype = AA   length = 4
FEATURE                         Location/Qualifiers
source                          1..4
                                mol_type = protein
                                organism = synthetic construct
SEQUENCE: 535
GGGS                                                                            4

SEQ ID NO: 536                  moltype = AA   length = 7
FEATURE                         Location/Qualifiers
source                          1..7
                                mol_type = protein
                                organism = synthetic construct
SEQUENCE: 536
AAEPKSS                                                                         7

SEQ ID NO: 537                  moltype = AA   length = 17
FEATURE                         Location/Qualifiers
source                          1..17
                                mol_type = protein
                                organism = synthetic construct
SEQUENCE: 537
AAEPKSSDKT HTCPPCP                                                             17

SEQ ID NO: 538                  moltype = AA   length = 4
FEATURE                         Location/Qualifiers
source                          1..4
                                mol_type = protein
                                organism = synthetic construct
SEQUENCE: 538
GGGG                                                                            4

SEQ ID NO: 539                  moltype = AA   length = 14
FEATURE                         Location/Qualifiers
source                          1..14
                                mol_type = protein
                                organism = synthetic construct
SEQUENCE: 539
GGGGDKTHTC PPCP                                                                14
```

POLYPEPTIDE COMPRISING A SINGLE-DOMAIN ANTIBODY VARIABLE REGION THAT BINDS DELTA-LIKE LIGAND 3 (DLL3) AND METHOD OF USE THEREOF TO MAKE A RADIONUCLIDE COMPLEX

CROSS REFERENCE

This application is a continuation of International Application No. PCT/US2023/072586 filed Aug. 21, 2023, which claims the benefit of priority to U.S. Provisional App. No. 63/373,184 filed Aug. 22, 2022, and 63/477,261 filed on Dec. 27, 2022, all of which are incorporated by reference herein in their entirety.

SEQUENCE LISTING

The instant application contains a Sequence Listing which has been submitted electronically in XML format and is hereby incorporated by reference in its entirety. The XML copy, created on Aug. 31, 2023, is named 60924715601_seq.xml and is 212,543 bytes in size.

BACKGROUND

The exquisite specificity of antibodies, such as IgGs, to their antigens makes antibodies a premier targeting platform for therapeutics; however, the typical serum half-life of at least three weeks for an IgG is disadvantageous for the delivery of radioisotopes including alpha-emitting isotopes such as Ac-225 and beta-emitting isotopes such as Lu-177 and Y-90, in particular due to prolonged exposure and chronic off-target toxicities. 225-Ac is among the most cytotoxic of the α-emitting radioisotopes, and a single decay event can effectively destroy a cancer cell by causing double-strand DNA breaks and subsequent cell death. The potency of α-emitting radioisotopes makes them attractive as cell killing agents, capable of overcoming the acquired resistance observed in response to other therapies.

Moreover, there are additional issues for targeted radioscope delivering platforms, including for alpha-emitting and beta-emitting radioisotopes, requiring simultaneous optimization when designing such platforms, such as, e.g., immunogenicity, specificity, tissue penetration, stability, ease of manufacturing, and acceptable therapeutic window.

SUMMARY

The present disclosure relates to DLL3 binding molecules (e.g., VHHs). The present disclosure additionally relates to immunoconjugates or radioimmunoconjugate, compositions comprising DLL3 binding regions and methods of using such immunoconjugates and compositions. These DLL3 binding molecules and antigen binding regions may be advantageously formatted as VHH-Fc containing molecules with: 1) reduced size enabling greater tissue penetrance; and 2) with altered FcRn binding allowing for serum half-life reduction that reduce radiotoxicities.

The present disclosure addresses a number of challenges inherent in the targeted delivery of alpha particle emitters in vivo through the selection and particular combination of specific delivery platform components. The alpha particle emitting radioisotope-delivery platforms of the present disclosure provide shorter half-lives compared to traditional IgGs, but longer half-lives than smaller monomeric antibody fragment formats. Such half-lives allow for a reduction in toxicity due to the alpha emitter, while preserving the antibody fragment long enough in the body to exert therapeutic activity. For example, the alpha particle emitting radioisotope-delivery platforms of the current disclosure exhibit enhanced tumor targeting and reduced accumulation in radiosensitive tissues such as the bone-marrow and kidney. Further and surprisingly, the alpha particle emitting radioisotope-delivery platforms of the present disclosure exhibit excellent tumor binding and labeling properties for tumors with different antigen densities, which can be a limitation for some use of some immunoconjugates.

Describe herein in one aspect is a polypeptide comprising an antigen binding region that binds DLL3, wherein the antigen binding region comprises: (a) a heavy chain complementarity determining region 1 (HCDR1) comprising an amino acid sequence set forth in any one of SEQ ID NO: 107 to SEQ ID NO: 109, SEQ ID NO: 207 to SEQ ID NO: 209, SEQ ID NO: 307 to SEQ ID NO: 309, SEQ ID NO: 407 to SEQ ID NO: 409, or SEQ ID NO: 507 to SEQ ID NO: 509; (b) a heavy chain complementarity determining region 2 (HCDR2) comprising an amino acid sequence set forth in any one of SEQ ID NO: 110 to SEQ ID NO: 112, SEQ ID NO: 210 to SEQ ID NO: 212, SEQ ID NO: 310 to SEQ ID NO: 312, SEQ ID NO: 410 to SEQ ID NO: 412, or SEQ ID NO: 510 to SEQ ID NO: 512; and/or (c) a heavy chain complementarity determining region 3 (HCDR3) comprising an amino acid sequence set forth in any one of SEQ ID NO: 113 to SEQ ID NO: 115, SEQ ID NO: 213 to SEQ ID NO: 215, SEQ ID NO: 313 to SEQ ID NO: 315, SEQ ID NO: 413 to SEQ ID NO: 415, or SEQ ID NO: 513 to SEQ ID NO: 515, SEQ ID NO: 131, SEQ ID NO: 231, SEQ ID NO: 431, or SEQ ID NO: 531. In certain embodiments, the antigen binding region comprises a heavy chain variable region, wherein the heavy chain variable region comprises an amino acid sequence at least about 80%, 85%, 90%, 95%, 97%, 98%, 99%, or 100% identical set to that set forth in any one of SEQ ID NO: 101 to 106, 201 to 206, 301 to 306, 401 to 306, and 501 to 506. In certain embodiments, the antigen binding region comprises: (a) a heavy chain complementarity determining region 1 (HCDR1) comprising an amino acid sequence set forth in any one of SEQ ID NO: 107 to SEQ ID NO: 109; (b) a heavy chain complementarity determining region 2 (HCDR2) comprising an amino acid sequence set forth in any one of SEQ ID NO: 110 to SEQ ID NO: 112; (c) a heavy chain complementarity determining region 3 (HCDR3) comprising an amino acid sequence set forth in any one of SEQ ID NO: 113 to SEQ ID NO: 115, or SEQ ID NO: 131. In certain embodiments, the antigen binding region comprises a heavy chain variable region, wherein the heavy chain variable region comprises an amino acid sequence at least about 80%, 85%, 90%, 95%, 97%, 98%, or 99% identical to that set forth in any one of SEQ ID NO: 101 to SEQ ID NO: 106. In certain embodiments, the antigen binding region comprises a heavy chain variable region, wherein the heavy chain variable region comprises the amino acid sequence of any one of SEQ ID NO: 101 to SEQ ID NO: 106. In certain embodiments, the antigen binding region comprises: (a) a heavy chain complementarity determining region 1 (HCDR1) comprising an amino acid sequence set forth in any one of SEQ ID NO: 207 to SEQ ID NO: 209; (b) a heavy chain complementarity determining region 2 (HCDR2) comprising an amino acid sequence set forth in any one of SEQ ID NO: 210 to SEQ ID NO: 212; (c) a heavy chain complementarity determining region 3 (HCDR3) comprising an amino acid sequence set forth in any one of SEQ ID NO: 213 to SEQ ID NO: 215, or SEQ ID NO: 231. In certain embodiments, the antigen binding region comprises a heavy chain variable region, wherein the heavy chain variable region comprises an amino acid sequence at least about 80%, 85%, 90%, 95%, 97%, 98%, or 99% identical to that set forth in any one of SEQ ID NO: 201 to SEQ ID NO: 206. In certain embodiments, the antigen binding region comprises a heavy chain variable region, wherein the heavy chain variable region comprises the amino acid sequence set forth in any one of SEQ ID NO: 201 to SEQ ID NO: 206. In certain embodiments, the antigen binding region comprises: (a) a heavy chain complementarity determining region 1 (HCDR1) comprising an amino acid sequence set forth in any one of SEQ ID NO: 307 to SEQ ID NO: 309; (b) a heavy chain complementarity determining region 2 (HCDR2) comprising an amino acid sequence set forth in any one of SEQ ID NO: 310 to SEQ ID NO: 312; (c) a heavy chain complementarity determining region 3 (HCDR3) comprising an amino acid sequence set forth in any one of SEQ ID NO: 313 to SEQ ID NO: 315. In certain embodiments, the antigen binding region comprises a heavy chain variable region, wherein the heavy chain variable region comprises an amino acid sequence at least about 80%, 85%, 90%, 95%, 97%, 98%, or 99% identical to that set forth in any one of SEQ ID NO: 301 to SEQ ID NO: 306. In certain embodiments, the antigen binding region comprises a heavy chain variable region, wherein the heavy chain variable region comprises the amino acid sequence set forth in any one of SEQ ID NO: 301 to SEQ ID NO: 306. In certain embodiments, the antigen binding region comprises: (a) a heavy chain complementarity determining region 1 (HCDR1) comprising an amino acid sequence set forth in any one of SEQ ID NO: 407 to SEQ ID NO: 409; (b) a heavy chain complementarity determining region 2 (HCDR2) comprising an amino acid sequence set forth in any one of SEQ ID NO: 410 to SEQ ID NO: 412; (c) a heavy chain complementarity determining region 3 (HCDR3) comprising an amino acid sequence set forth in any one of SEQ ID NO: 413 to SEQ ID NO: 415, or SEQ ID NO: 431. In certain embodiments, the antigen binding region comprises a heavy chain variable region, wherein the heavy chain variable region comprises an amino acid sequence at least about 80%, 85%, 90%, 95%, 97%, 98%, or 99% identical to that set forth in any one of SEQ ID NO: 401 to SEQ ID NO: 406. In certain embodiments, the antigen binding region comprises a heavy chain variable region, wherein the heavy chain variable region comprises the amino acid sequence set forth in any one of SEQ ID NO: 401 to SEQ ID NO: 406. In certain embodiments, the antigen binding region comprises: (a) a heavy chain complementarity determining region 1 (HCDR1) comprising an amino acid sequence set forth in any one of SEQ ID NO: 507 to SEQ ID NO: 509; (b) a heavy chain complementarity determining region 2 (HCDR2) comprising an amino acid sequence set forth in any one of SEQ ID NO: 510 to SEQ ID NO: 512; (c) a heavy chain complementarity determining region 3 (HCDR3) comprising an amino acid sequence set forth in any one of SEQ ID NO: 513 to SEQ ID NO: 515, or SEQ ID NO: 531. In certain embodiments, the antigen binding region comprises a heavy chain variable region, wherein the heavy chain variable region comprises an amino acid sequence at least about 80%, 85%, 90%, 95%, 97%, 98%, or 99% identical to that set forth in any one of SEQ ID NO: 501 to SEQ ID NO: 506. In certain embodiments, the antigen binding region comprises a heavy chain variable region, wherein the heavy chain variable region comprises the amino acid sequence set forth in any one of SEQ ID NO: 501 to SEQ ID NO: 506. In certain embodiments, the antigen binding region is humanized. In certain embodiments, the antigen binding region does not comprise an immunoglobulin light chain. In certain embodiments, the antigen binding region comprises a VHH. In certain embodiments, the polypeptide comprises an immunoglobulin heavy chain constant region. In certain embodiments, the immunoglobulin heavy chain constant region comprises a CH2 domain of an immunoglobulin, CH3 domain of an immunoglobulin, or a CH2 and a CH3 domain of an immunoglobulin. In certain embodiments, the immunoglobulin heavy chain constant region comprises a CH2 and a CH3 domain of an immunoglobulin. In certain embodiments, the immunoglobulin heavy chain constant region is an IgA, IgG1, IgG2, IgG3, or IgG4 isotype. In certain embodiments, the immunoglobulin heavy chain constant region is an IgG1 isotype. In certain embodiments, the immunoglobulin heavy chain constant region is an IgG4 isotype. In certain embodiments, the immunoglobulin heavy chain constant region comprises an alteration to one or more amino acid residues that reduces an effector function of the immunoglobulin heavy chain constant region or alters binding of the polypeptide to the neonatal Fc receptor (FcRn). In certain embodiments, the immunoglobulin heavy chain constant region comprises an alteration to one or more amino acid residues that reduces an effector function of the immunoglobulin heavy chain constant region and alters binding of the polypeptide to the neonatal Fc receptor (FcRn). In certain embodiments, the immunoglobulin heavy chain constant region comprises an alteration to one or more amino acid residues that reduces an effector function of the immunoglobulin heavy chain constant region. In certain embodiments, the immunoglobulin heavy chain constant region comprises an alteration to one or more amino acid residues that alters binding of the polypeptide to the neonatal Fc receptor (FcRn). In certain embodiments, the alteration to one or more amino acid residues that reduces the effector function of the immunoglobulin heavy chain constant region is an alteration that reduces complement dependent cytotoxicity (CDC), antibody-dependent cell-cytotoxicity (ADCC), antibody-dependent cell-phagocytosis ADCP, or a combination thereof. In certain embodiments, the alteration to one or more amino acid residues that reduces the effector function of the immunoglobulin heavy chain constant region is selected from the list consisting of: (a) 297A, 297Q, 297G, or 297D, (b) 279F, 279K, or 279L, (c) 228P, (d) 235A, 235E, 235G, 235Q, 235R, or 235S, (e) 237A, 237E, 237K, 237N, or 237R, (f) 234A, 234V, or 234F, (g) 233P, (h) 328A, (i) 327Q or 327T, j) 329A, 329G, 329Y, or 329R (k) 331S, (l) 236F or 236R, (m) 238A, 238E, 238G, 238H, 238I, 238V, 238W, or 238Y, (n) 248A, (o) 254D, 254E, 254G, 254H, 254I, 254N, 254P, 254Q, 254T, or 254V, (p) 255N, (q) 256H, 256K, 256R, or 256V, (r) 264S, (s) 265H, 265K, 265S, 265Y, or 265A, (t) 267G, 267H, 267I, or 267K, (u) 268K, (v) 269N or 269Q, (w) 270A, 270G, 270M, or 270N, (x) 271T, (y) 272N, (z) 292E, 292F, 292G, or 292I, (aa) 293S, (bb) 301W, (cc) 304E, (dd) 311E, 311G, or 311S, (ee) 316F, (ff) 328V, (gg) 330R, (hh) 339E or 339L, (ii) 343I or 343V, (jj) 373A, 373G, or 373S, (kk) 376E, 376W, or 376Y, (ll) 380D, (mm) 382D or 382P, (nn) 385P, (oo) 424H, 424M, or 424V, (pp) 434I, (qq) 438G, (rr) 439E, 439H, or 439Q, (ss) 440A, 440D, 440E, 440F, 440M, 440T, or 440V, (tt) K322A, (uu) L235E, (vv) L234A and L235A, (ww) L234A, L235A, and G237A, (xx) L234A, L235A, and P329G, (yy) L234F, L235E, and P331S, (zz) L234A, L235E, and G237A, (aaa), L234A, L235E, G237A, and P331S (bbb) L234A, L235A, G237A, P238S, H268A, A330S, and P331S, (ccc) L234A, L235A, and P329A, (ddd) G236R and L328R, (eee) G237A, (fff) F241A, (ggg) V264A, (hhh) D265A, (iii) D265A and N297A, (jjj) D265A and N297G, (kkk) D270A, (lll)

A330L, (mmm) P331A or P331S, or (nnn) E233P, (ooo) L234A, L235E, G237A, A330S, and P331S or (ppp) any combination of (a)-(ppp), per EU numbering. In certain embodiments, the alteration to one or more amino acid residues that reduces the effector function of the immunoglobulin heavy chain constant region comprises L234A, L235E, G237A, A330S, and P331S per EU numbering. In certain embodiments, the amino acid alteration to one or more amino acid residues that alters binding of the polypeptide to the neonatal Fc receptor (FcRn) reduces the serum half-life of the polypeptide. In certain embodiments, the alteration to one or more amino acid residues that alters binding of the polypeptide to the neonatal Fc receptor (FcRn) is to an amino acid residue selected from the list consisting of: 251, 252, 253, 254, 255, 288, 309, 310, 312, 385, 386, 388, 400, 415, 433, 435, 436, 439, 447, and combinations thereof per EU numbering. In certain embodiments, the alteration to one or more amino acid residues that alters binding of the polypeptide to the neonatal Fc receptor (FcRn) is to an amino acid residue selected from the list consisting of: 253, 254, 310, 435, 436 and combinations thereof per EU numbering. In certain embodiments, the alteration to one or more amino acid residues that alters binding of the polypeptide to the neonatal Fc receptor (FcRn) is to an amino acid residue selected from the list consisting of: I253A, I253D, I253P, S254A, H310A, H310D, H310E, H310Q, H435A, H435Q, Y436A, and combinations thereof per EU numbering. In certain embodiments, the alteration to one or more amino acid residues that alters binding of the polypeptide to the neonatal Fe receptor (FcRn) is to an amino acid residue selected from the list consisting of: I253A, S254A, H310A, H435Q, Y436A and combinations thereof per EU numbering. In certain embodiments, the alteration to one or more amino acid residues that alters binding of the polypeptide to the neonatal Fe receptor (FcRn) is to an amino acid residue selected from the list consisting of: I253A, H310A, H435Q, and combinations thereof per EU numbering. In certain embodiments, the alteration to one or more amino acid residues that alters binding of the polypeptide to the neonatal Fc receptor (FcRn) comprises I253A per EU numbering. In certain embodiments, the alteration to one or more amino acid residues that alters binding of the polypeptide to the neonatal Fe receptor (FcRn) comprises H310A per EU numbering. In certain embodiments, the alteration to one or more amino acid residues that alters binding of the polypeptide to the neonatal Fc receptor (FcRn) comprises H435Q per EU numbering. In certain embodiments, comprising a linker amino acid sequence or a human IgG hinge region. In certain embodiments, the antigen binding region is coupled to the immunoglobulin heavy chain constant region by a human IgG hinge region. In certain embodiments, the human IgG hinge region comprises the amino acid sequence set forth in SEQ ID NO: 41. In certain embodiments, the polypeptide comprises an amino acid sequence at least about 80%, 85%, 90%, 95%, 97%, 98%, or 99% identical to any one of SEQ ID NO: 116 to SEQ ID NO: 120, SEQ ID NO: 216 to SEQ ID NO: 220, SEQ ID NO: 316 to SEQ ID NO: 320, SEQ ID NO: 416 to SEQ ID NO: 420, and SEQ ID NO: 516 to SEQ ID NO: 520. In certain embodiments, the polypeptide comprises an amino acid sequence identical to any one of SEQ ID NO: 116 to SEQ ID NO: 120, SEQ ID NO: 216 to SEQ ID NO: 220, SEQ ID NO: 316 to SEQ ID NO: 320, SEQ ID NO: 416 to SEQ ID NO: 420, and SEQ ID NO: 516 to SEQ ID NO: 520. In certain embodiments, the polypeptide comprises an amino acid sequence at least about 80%, 85%, 90%, 95%, 97%, 98%, or 99% identical to SEQ ID NO: 116 to SEQ ID NO: 120. In certain embodiments, the polypeptide comprises an amino acid sequence identical to SEQ ID NO: 116 to SEQ ID NO: 120. In certain embodiments, the polypeptide comprises an amino acid sequence at least about 80%, 85%, 90%, 95%, 97%, 98%, or 99% identical to SEQ ID NO: 216 to SEQ ID NO: 220. In certain embodiments, the polypeptide comprises an amino acid sequence identical to SEQ ID NO: 216 to SEQ ID NO: 220. In certain embodiments, the polypeptide comprises an amino acid sequence at least about 80%, 85%, 90%, 95%, 97%, 98%, or 99% identical to SEQ ID NO: 316 to SEQ ID NO: 320. In certain embodiments, the polypeptide comprises an amino acid sequence identical to SEQ ID NO: 316 to SEQ ID NO: In certain embodiments, the polypeptide comprises an amino acid sequence at least about 80%, 85%, 90%, 95%, 97%, 98%, or 99% identical to SEQ ID NO: 416 to SEQ ID NO: 420. In certain embodiments, the polypeptide comprises an amino acid sequence identical to SEQ ID NO: 416 to SEQ ID NO: 420. In certain embodiments, the polypeptide comprises an amino acid sequence at least about 80%, 85%, 90%, 95%, 97%, 98%, or 99% identical to SEQ ID NO: 516 to SEQ ID NO: 520. In certain embodiments, the polypeptide comprises an amino acid sequence identical to SEQ ID NO: 516 to SEQ ID NO: 520. In certain embodiments, the polypeptide possess a KD of 10 nanomolar or less. In certain embodiments, the polypeptide possess a KD of 5 nanomolar or less. In certain embodiments, the polypeptide possess a KD of 2 nanomolar or less. In certain embodiments, the polypeptide possess a KD of 1 nanomolar or less. In certain embodiments, described herein is an immunoconjugate comprising the polypeptide and a chelating agent. In certain embodiments, the molecular weight of the immunoconjugate is between 60 and 110 kDa. In certain embodiments, the immunoconjugate has a serum half-life of less than 15 days. In certain embodiments, the immunoconjugate has a serum half-life of less than 10 days. In certain embodiments, the immunoconjugate has a serum half-life of less than 120 hours. In certain embodiments, the immunoconjugate has a serum half-life of less than 72 hours. In certain embodiments, the chelating agent is a radioisotope chelating agent. In certain embodiments, the chelating agent is a alpha emitter chelating agent. In certain embodiments, the chelating agent is a beta- or gamma-emitter chelating agent. In certain embodiments, the chelating agent is selected from the list consisting of: DOTA, DO3A, DOTAGA, DOTAGA anhydride, Py4Pa, Py4Pa-NCS, Crown, Macropa, Macropa-NCS, HEHA, CHXoctapa, Bispa, Noneunpa, and combinations thereof. In certain embodiments, the chelating agent is selected from the list consisting of: DOTMA, DOTPA, DO3AM-acetic acid, DOTP, DOTMP, DOTA-4AMP, CB-TE2A, NOTA, NOTP, TETPA, TETA, PEPA, H4Octapa, H2Dedpa, DO2P, EDTA, DTPA-BMA, 3,2,3-LI(HOPO), 3,2-HOPO, Neunpa, Neunpa-NCS, Octapa, PyPa, Porphyrin, Deferoxamine, DFO*, and combinations thereof. In certain embodiments, the chelating agent is DOTA. In certain embodiments, the chelating agent is DOTAGA. In certain embodiments, the chelating agent is Py4 Pa. In certain embodiments, the chelating agent is directly coupled to the antigen binding region and/or the immunoglobulin heavy chain constant region. In certain embodiments, the chelating agent is coupled to the antigen binding region and/or the immunoglobulin heavy chain constant region by a linker. In certain embodiments, the linker is selected from: 6-maleimidocaproyl (MC), maleimidopropanoyl (MP), valine-citrulline (val-cit), alanine-phenylalanine (ala-phe), p-aminobenzyloxycarbonyl (PAB), and those resulting from conjugation with linker reagents: N-Succinimidyl 4-(2-pyridylthio) pentanoate forming linker moiety 4-mercaptopentanoic acid (SPP), Succinimidyl 4-(N-maleimidomethyl)cyclohexane-1-carboxylate (SMCC), N-Succinimidyl 4-(2-pyridyldithio) butanoate (SPDB), N-Succinimidyl (4-iodo-acetyl) aminobenzoate (SIAB), polyethylene glycol (PEG), a polyethylene glycol polymers (PEGn), and S-2-(4-Isothiocyanatobenzyl) (SCN). In certain embodiments, the linker is selected from: polyethylene glycol (PEG), a polyethylene glycol polymers (PEG), and S-2-(4-isothiocyanatobenzyl) (SCN). In certain embodiments, the linker is PEG5. In certain embodiments, the linker is SCN. In certain embodiments, the chelating agent is a linker-chelator selected from the list consisting of: TFP-Ad-PEG5-DOTAGA, p-SCN-Bn-DOTA, p-SCN-Ph-Et-Py4 Pa, and TFP-Ad-PEG5-Ac-Py4 Pa. In certain embodiments, the chelating agent is TFP-Ad-PEG5-DOTAGA. In certain embodiments, the chelating agent is p-SCN-Bn-DOTA. In certain embodiments, the chelating agent is p-SCN-Ph-Et-Py4 Pa. In certain embodiments, the chelating agent is TFP-Ad-PEG5-Ac-Py4 Pa. In certain embodiments, the chelating agent is coupled to the antigen binding region and/or the immunoglobulin heavy chain constant region at a ratio of 1:1 to 8:1. In certain embodiments, the chelating agent is coupled to the antigen binding region and/or the immunoglobulin heavy chain constant region at a ratio of 1:1 to 6:1. In certain embodiments, the chelating agent is coupled to the antigen binding region and/or the immunoglobulin heavy chain constant region at a ratio of 2:1 to 6:1. In certain embodiments, the immunoconjugate further comprises a radioisotope. In certain embodiments, the radioisotope is an alpha emitter. In certain embodiments, the radioisotope is an alpha emitter selected from the list consisting of 225-Ac, 223-Ra, 224-Ra, 227-Th, 212-Pb, 212-Bi, and 213-Bi. In certain embodiments, the radioisotope is 225-Ac. In certain embodiments, the radioisotope is a beta emitter. In certain embodiments, the radioisotope is a beta emitter selected from 177-Lu, 90-Y, 67-Cu, and 153-Sm. In certain embodiments, the radioisotope is a gamma emitter. In certain embodiments, the radioisotope is a gamma emitter selected from 111-In, 89-Zn, 123-I, 99m-Tc, and 68-Ga. In certain embodiments, the molecular weight of the immunoconjugate is between 60 and 100 kDa. In certain embodiments, the molecular weight of the immunoconjugate is between 60 and 90 kDa. In certain embodiments, the molecular weight of the immunoconjugate is between 65 and 90 kDa. In certain embodiments, the molecular weight of the immunoconjugate is between 70 and 90 kDa. In certain embodiments, the immunoconjugate forms a dimer with another immunoconjugate. In certain embodiments, the immunoconjugate further comprises a pharmaceutically acceptable excipient or carrier. In certain embodiments, the immunoconjugate is formulated for intravenous administration.

Also described herein is a method of making the immunoconjugate, comprising loading the immunoconjugate with a radioisotope. In certain embodiments, the radioisotope is an alpha emitter. In certain embodiments, the radioisotope is an alpha emitter selected from the list consisting of 225-Ac, 223-Ra, 224-Ra, 227-Th, 212-Pb, 212-Bi, and 213-Bi. In certain embodiments, the radioisotope is 225-Ac. In certain embodiments, the radioisotope is a beta emitter. In certain embodiments, the radioisotope is a beta emitter selected from 177-Lu, 90-Y, 67-Cu, and 153-Sm. In certain embodiments, the radioisotope is 177-Lu. In certain embodiments, the radioisotope is a gamma emitter. In certain embodiments, the radioisotope is a gamma emitter selected from 111-In, 89-Zn, 123-I, 99m-Tc, and 68-Ga.

Also described herein is a method of treating a cancer or a tumor in an individual comprising administering to the individual the immunoconjugate, thereby treating the cancer or the tumor. In certain embodiments, the individual is a human individual. In certain embodiments, the cancer or tumor is a solid cancer or tumor. In certain embodiments, the cancer or the tumor comprises lung cancer, breast cancer, ovarian cancer, or a neuroendocrine cancer. In certain embodiments the method further comprises administering from 0.5 µCi to 30.0 µCi per kilogram to the individual. In certain embodiments, the cancer or tumor expresses an antigen specifically bound by the immunoconjugate.

Also described herein is the immunoconjugate for use in a method of treating a cancer or a tumor in an individual. In certain embodiments, the individual is a human individual. In certain embodiments, the cancer or tumor is a solid cancer or tumor. In certain embodiments, the cancer or the tumor comprises lung cancer, breast cancer, ovarian cancer, or a neuroendocrine cancer. In certain embodiments, from 0.5 µCi to 30.0 µCi per kilogram is administered to the individual. In certain embodiments, the cancer or tumor expresses an antigen specifically bound by the immunoconjugate.

Also described herein is a method of killing a cancer cell in an individual comprising administering to the individual the immunoconjugate, thereby killing the cancer cell. In certain embodiments, the individual is a human individual. In certain embodiments, the cancer cell comprises a lung cancer cell, a breast cancer cell, an ovarian cancer cell, or a neuroendocrine cancer cell. In certain embodiments, the method comprises administering from 0.1 µCi to 30.0 µCi per kilogram to the individual. In certain embodiments, the method comprises administering from 10 mCi to 75 mCi per meter squared of body area to the individual. In certain embodiments, the cancer cell expresses an antigen specifically bound by the immunoconjugate.

Also described herein is use of the immunoconjugate in a method of killing a cancer cell in an individual. In certain embodiments, the individual is a human individual. In certain embodiments, the cancer cell comprises a lung cancer cell, a breast cancer cell, an ovarian cancer cell, or a neuroendocrine cancer cell. In certain embodiments, the method comprises administering from 0.5 µCi to 30.0 µCi per kilogram to the individual. In certain embodiments, the cancer cell expresses an antigen specifically bound by the immunoconjugate.

Also described herein is a method of delivering a radioisotope to a cancer cell or a tumor cell in an individual comprising administering to the individual the immunoconjugate, thereby delivering the radioisotope to the cancer cell or the tumor cell. In certain embodiments, the individual is a human individual. In certain embodiments, the cancer cell or the tumor cell comprises a lung cancer cell, a breast cancer cell, an ovarian cancer cell, or a neuroendocrine cancer cell. In certain embodiments, the method comprises administering from 0.5 µCi to 30.0 µCi per kilogram to the individual. In certain embodiments, the cancer cell or the tumor cell expresses an antigen specifically bound by the immunoconjugate.

Also described herein is the immunoconjugate for use in delivering a radioisotope to a cancer cell or a tumor cell in an individual. In certain embodiments, the individual is a human individual. In certain embodiments, the cancer cell or the tumor cell comprises a lung cancer cell, a breast cancer cell, an ovarian cancer, or a neuroendocrine cancer cell. In certain embodiments, the cancer cell or the tumor cell expresses an antigen specifically bound by the immunoconjugate.

Also described herein is a method of imaging a tumor in an individual comprising administering to the individual the immunoconjugate. In certain embodiments, the individual is a human individual. In certain embodiments, the cancer or the tumor comprises lung cancer, breast cancer, ovarian cancer, or a neuroendocrine cancer. In certain embodiments, the tumor expresses an antigen specifically bound by the immunoconjugate.

Also described herein is the immunoconjugate for use in a method of imaging a tumor in an individual. In certain embodiments, the individual is a human individual. In certain embodiments, the cancer or the tumor comprises lung cancer, breast cancer, ovarian cancer, or a neuroendocrine cancer. In certain embodiments, the tumor expresses an antigen specifically bound by the immunoconjugate.

Also described herein is a nucleic acid encoding the immunoconjugate. In certain embodiments, an expression vector comprises the nucleic acid. In certain embodiments, A cell comprises the nucleic acid or the expression vector. In certain embodiments, the cell is a eukaryotic cell. In certain embodiments, the eukaryotic cell is a CHO cell.

In some embodiments, the subject radioisotope delivery platforms have a molecular size large enough (e.g., 60 kDa to 110 kDa) to substantially reduce off-target toxicities, especially renal damage (e.g., from an alpha emitting isotope cargo) and a small enough size for increased tissue penetration as compared to traditional IgGs, with maintained target specificity, and increased probability of first decay event in target tissue. Such sizes provide for preferential elimination by the liver as opposed to the kidney, sparing the kidney from radiotoxicity.

In some embodiments, the subject radioisotope delivery platforms are useful for in vivo targeted delivery of alpha emitters safely and effectively by, in part, reducing certain adverse effects caused by platforms having half-lives over 5 days and/or molecular weights under 60 kDa.

These and other features, aspects and advantages of the present disclosure will become better understood with regard to the following description and appended claims. The aforementioned elements of this disclosure may be individually combined or removed freely in order to make other embodiments of this disclosure, without any statement to object to such combination or removal hereinafter.

BRIEF DESCRIPTION OF THE DRAWINGS

FIG. 8 shows a comparison of imaging with $^{111}$In labeled VHH-Fc compared to biodistribution of $^{225}$Ac labeled VHH-Fc.

FIG. 12 shows whole body clearance of VHH-Fc (H101) and VHH-Fc variants (H105, H107, and H108) labeled with $^{111}$In.

FIG. 20A shows SHP-77 cell binding of humanized VHHFcs.

FIG. 20B shows SHP-77 cell internalization of humanized VHHFcs.

FIG. 23 shows results from a membrane protein array.

FIG. 31 shows the structure of hDLL3 (SEQ ID NO: 532). The N-terminal domain is presented by aa 27-175 (in italics), the DSL domain is aa 176-215 (bold underline), and EGF1-6 is aa 216-492 (normal text).

DETAILED DESCRIPTION

Figure 1A:
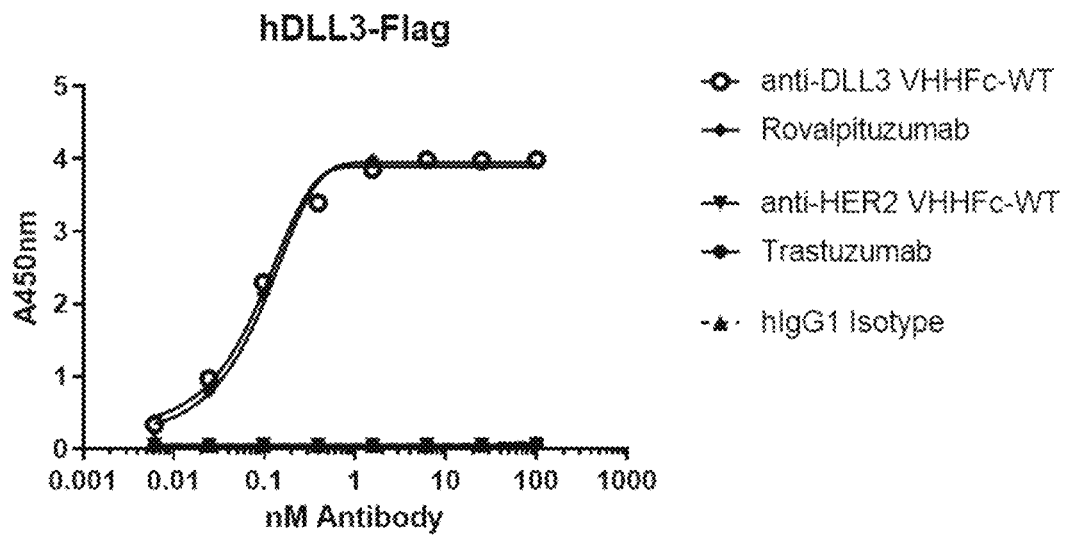
FIGS. 1A and 1B show binding of anti-HER2 and anti-DLL3 VHH-Fc constructs.

The present invention is described more fully hereinafter using illustrative, non-limiting embodiments. This invention may, however, be embodied in many different forms and should not be construed as to be limited to the embodiments set forth below. Rather, these embodiments are provided so that this disclosure is thorough and conveys the scope of the invention to those skilled in the art. In order that the present invention may be more readily understood, certain terms are defined below. Additional definitions may be found within the detailed description of the invention.

Described herein in one aspect are binding molecules and binding regions that specifically bind to DLL3. These binding regions may be further incorporated into a polypeptide comprising an; a) immunoglobulin hinge region, an immunoglobulin Fc region, or both (e.g., VHH-Fc). The VHH-Fcs of this disclosure may dimerize (through their respective Fc regions) to form a bivalent binding molecule. These bivalent VHH-Fcs can be further conjugated with a cytotoxic moiety (e.g., a radionuclide) by a chelator coupled to the bivalent VHH-Fc. Certain radionuclides such as alpha or beta emitters can be loaded onto he chelators such that the bivalent VHH-Fcs can be used to target a tumor for imaging or therapeutic purposes.

In particular, in embodiments, the present disclosure addresses a number of challenges inherent in the targeted delivery of radioisotopes in vivo through the selection and particular assembly of specific immunoconjugate and radioimmunoconjugate components. The radioisotope-delivering platforms of the present disclosure provide shorter half-lives compared to traditional IgGs, but longer half-lives than smaller monomeric antibody fragment formats. In some embodiments, the subject radioisotope delivering platforms have a molecular size large enough (e.g., 60 kDa to 110 kDa) to substantially reduce off-target toxicities, especially renal damage (e.g., from an alpha- or beta-emitting isotope cargo) and a small enough size for increased tissue penetration as compared to traditional IgGs, with maintained target specificity, and increased probability of first decay event in target tissue. In some embodiments, the subject radioisotope delivering platforms are useful for in vivo targeted delivery of radioisotopes (such as alpha- or beta-emitters) safely and effectively by, in part, reducing certain adverse effects caused by platforms having half-lives over 5 days and/or molecular weights under 60 kDa. In some embodiments, the subject radioisotope delivering platforms are useful for in vivo targeted delivery of radioisotopes (such as alpha- or beta-emitters) safely and effectively, in part, by exhibiting decreased loss of targeting capacity due to radiolysis as compared to other possible delivery platforms. In some embodiments, the subject radioisotope delivering platforms are useful for in vivo targeted delivery of radioisotopes (such as alpha- or beta-emitters) safely and effectively, in part, by exhibiting increased stability in manufacturing under the temperatures required for certain radiolabeling processes (e.g., high temperature chelation with certain chelators) as compared to other possible delivery platforms using antibody fragments.

Immunoconjugates

In one aspect, this disclosure provides immunoconjugates that specifically bind to a target antigen with high affinity. In some embodiments, the present disclosure provides an immunoconjugate that specifically binds to a cell-surface antigen of a cancer cell. In some embodiments, the immunoconjugate comprises three, four, five, six, or more CDRs or HVRs (Kabat). In some embodiments, the immunoconjugate binds a specific antigen and/or epitope with an affinity characterized by a $K_D$ of $\leq 1$ μM, <100 nM, <10 nM, <1 nM, <0.1 nM, <0.01 nM, or <0.001 nM (e.g. $10^{-8}$ M or less, e.g. from $10^{-8}$ M to $10^{-13}$ M, e.g., from $10^{-9}$ M to $10^{-13}$ M). In certain embodiments, the polypeptide or immunoconjugate possess a KD of 10 nanomolar or less. In certain embodiments, the polypeptide or immunoconjugate possess a KD of 5 nanomolar or less. In certain embodiments, the polypeptide or immunoconjugate possess a KD of 2 nanomolar or less. In certain embodiments, the polypeptide or immunoconjugate possess a KD of 1 nanomolar or less. In certain embodiments, the polypeptide or immunoconjugate possess a KD of 0.1 nanomolar or greater. In certain embodiments, the polypeptide or immunoconjugate possess a KD of 0.5 nanomolar or greater In one embodiment, an immunoconjugate of the current disclosure comprises a: a) DLL3 antigen binding region; and b) an immunoglobulin heavy chain constant region. In one embodiment, an immunoconjugate of the current disclosure comprises a: a) DLL3 antigen binding region; b) an immunoglobulin heavy chain constant region; and c) a chelating agent. In one embodiment, an immunoconjugate of the current disclosure comprises a: a) DLL3 antigen binding region; b) an immunoglobulin heavy chain constant region; and c) a radioisotope chelating agent. In one embodiment an immunoconjugate of the current disclosure comprises an: a) antigen binding region; b) an immunoglobulin heavy chain constant region; and c) a radioisotope chelating agent; wherein the molecular weight of said immunoconjugate is between 60 and 110 kDa.

In one embodiment, an immunoconjugate of the current disclosure comprises a: a) VHH antigen binding region that specifically binds DLL3; and b) an immunoglobulin heavy chain constant region. In one embodiment an immunoconjugate of the current disclosure comprises an: a) VHH antigen binding region that specifically binds DLL3; b) an immunoglobulin heavy chain constant region; and c) a chelating agent. In one embodiment, an immunoconjugate of the current disclosure comprises an: a) VHH antigen binding region that specifically binds DLL3; b) an immunoglobulin heavy chain constant region; and c) a radioisotope chelating agent. In one embodiment an immunoconjugate of the current disclosure comprises an: a) VHH antigen binding region that specifically binds DLL3; b) an immunoglobulin heavy chain constant region; and c) a radioisotope chelating agent; wherein the molecular weight of said immunoconjugate is between 60 and 110 kDa.

In one embodiment an immunoconjugate of the current disclosure comprises an: a) VHH antigen binding region; and b) a variant immunoglobulin Fc region. In one embodiment an immunoconjugate of the current disclosure comprises an: a) VHH antigen binding region that specifically binds DLL3; b) a variant immunoglobulin Fc region; and c) a chelating agent. In one embodiment an immunoconjugate of the current disclosure comprises an: a) VHH antigen binding region that specifically binds DLL3; b) a variant immunoglobulin Fc region; and c) a radioisotope chelating agent. In one embodiment an immunoconjugate of the current disclosure comprises an: a) VHH antigen binding region that specifically binds DLL3; b) a variant immunoglobulin Fc region; and c) a radioisotope chelating agent; wherein the molecular weight of said immunoconjugate is between 60 and 110 kDa. In certain embodiments, the variant immunoglobulin Fc region comprises one or more amino acid alterations to reduce the serum or plasma half-life of the immunoconjugate. In certain embodiments, the variant immunoglobulin Fc region comprises one or more amino acid alterations to reduce the serum or plasma half-life of the immunoconjugate and to reduce an effector function of the Fc (e.g., ADCC, CDC or ADCP.

In some embodiments, the radioisotope delivering platforms have sizes larger than about 60 kDa, in order to avoid certain toxicities from an alpha emitting isotope cargo, such as, e.g., off-target renal toxicities. In some embodiments, the radioisotope delivering platforms have sizes less than about 110 kDa in order to improve tumor penetration. In some embodiments, the radioisotope delivering platform has size between 60 and 110 kDa due to its dimeric structure of two individual antigen binding arms each having a VHH polypeptide fused to a hinge region and a wild-type or variant constant region. In some embodiments, the variant constant region has specific amino acid substitution(s) relatively to a wildtype Fc region in order to reduce half-life and/or eliminate Fc effector function(s).

In one embodiment, the antibody construct of the immunoconjugate consists of two antigen binding arms that are covalently linked to each other (for example via a disulfide linkage between associated heavy chain constant regions or immunoglobulin hinge regions). Each of the antigen binding arms independently consists of an antigen binding region, a hinge region, and a variant constant region. Within each antigen binding arm, the antigen binding region of the arm is covalently linked to the hinge region of the arm and the hinge region of the arm is covalently linked to the variant constant region of the arm, such that the hinge region is interposed between and thereby links the antigen binding region and the variant constant region within the antigen binding arm. In certain embodiments, the variant constant region comprises one or more amino acid alterations to reduce the serum or plasma half-life of the immunoconjugate and to reduce an effector function of the Fc (e.g., ADCC, CDC or ADCP.

DLL3 Antigen Binding Regions

Described herein are polypeptides that bind to Delta-like protein 3 (DLL3). In certain embodiments, the polypeptides bind to human DLL3. In certain embodiments, the polypeptides bind to cynomolgus DLL3. The sequence of the human DLL3 protein is available, for instance, at UniProt website, entry Q9NYJ7. In certain embodiments, the DLL3 binding polypeptides comprise a heavy chain binding region, such as a VHH. In certain embodiments, the DLL3 binding polypeptides do not comprise an immunoglobulin light chain.

In certain embodiments, the polypeptides described herein comprise an antigen binding region that binds DLL3, wherein the antigen binding region comprises: (a) a heavy chain complementarity determining region 1 (HCDR1) comprising an amino acid sequence set forth in any one of SEQ ID NO: 107 to SEQ ID NO: 109, SEQ ID NO: 207 to SEQ ID NO: 209, SEQ ID NO: 307 to SEQ ID NO: 309, SEQ ID NO: 407 to SEQ ID NO: 409, or SEQ ID NO: 507 to SEQ ID NO: 509; (b) a heavy chain complementarity determining region 2 (HCDR2) comprising an amino acid sequence set forth in any one of SEQ ID NO: 110 to SEQ ID NO: 112, SEQ ID NO: 210 to SEQ ID NO: 212, SEQ ID NO: 310 to SEQ ID NO: 312, SEQ ID NO: 410 to SEQ ID NO: 412, or SEQ ID NO: 510 to SEQ ID NO: 512; and/or (c) a heavy chain complementarity determining region 3 (HCDR3) comprising an amino acid sequence set forth in any one of SEQ ID NO: 113 to SEQ ID NO: 115, SEQ ID NO: 213 to SEQ ID NO: 215, SEQ ID NO: 313 to SEQ ID NO: 315, SEQ ID NO: 413 to SEQ ID NO: 415, or SEQ ID NO: 513 to SEQ ID NO: 515, SEQ ID NO: 131, SEQ ID NO: 231, SEQ ID NO: 431, or SEQ ID NO: 531. In certain embodiments, the polypeptides described herein comprise an antigen binding region that binds DLL3, wherein the antigen binding region comprises: (a) a heavy chain complementarity determining region 1 (HCDR1) comprising an amino acid sequence set forth in any one of SEQ ID NO: 107 to SEQ ID NO: 109, SEQ ID NO: 207 to SEQ ID NO: 209, SEQ ID NO: 307 to SEQ ID NO: 309, SEQ ID NO: 407 to SEQ ID NO: 409, or SEQ ID NO: 507 to SEQ ID NO: 509; (b) a heavy chain complementarity determining region 2 (HCDR2) comprising an amino acid sequence set forth in any one of SEQ ID NO: 110 to SEQ ID NO: 112, SEQ ID NO: 210 to SEQ ID NO: 212, SEQ ID NO: 310 to SEQ ID NO: 312, SEQ ID NO: 410 to SEQ ID NO: 412, or SEQ ID NO: 510 to SEQ ID NO: 512; and/or (c) a heavy chain complementarity determining region 3 (HCDR3) comprising an amino acid sequence set forth in any one of SEQ ID NO: 113 to SEQ ID NO: 115, SEQ ID NO: 213 to SEQ ID NO: 215, SEQ ID NO: 313 to SEQ ID NO: 315, SEQ ID NO: 413 to SEQ ID NO: 415, or SEQ ID NO: 513 to SEQ ID NO: 515. In certain embodiments, the antigen binding region comprises a heavy chain variable region, wherein the heavy chain variable region comprises an amino acid sequence at least about 80%, 85%, 90%, 95%, 97%, 98%, 99%, or 100% identical set to that set forth in any one of SEQ ID NO: 101 to 106, 201 to 206, 301 to 306, 401 to 306, and 501 to 506.

In certain embodiments, the polypeptides described herein comprise an antigen binding region that binds DLL3, wherein the antigen binding region comprises: (a) a heavy chain complementarity determining region 1 (HCDR1) comprising an amino acid sequence set forth in any one of SEQ ID NO: 107 to SEQ ID NO: 109; (b) a heavy chain complementarity determining region 2 (HCDR2) comprising an amino acid sequence set forth in any one of SEQ ID NO: 110 to SEQ ID NO: 112; (c) a heavy chain complementarity determining region 3 (HCDR3) comprising an amino acid sequence set forth in any one of SEQ ID NO: 113 to SEQ ID NO: 115. In certain embodiments, the antigen binding region comprises a heavy chain variable region, wherein the heavy chain variable region comprises an amino acid sequence at least about 80%, 85%, 90%, 95%, 97%, 98%, or 99% identical to that set forth in any one of SEQ ID NO: 101 to SEQ ID NO: 106. In certain embodiments, the antigen binding region comprises a heavy chain variable region, wherein the heavy chain variable region comprises the amino acid sequence of any one of SEQ ID NO: 101 to SEQ ID NO: 106.

In certain embodiments, the polypeptides described herein comprise an antigen binding region that binds DLL3, wherein the antigen binding region comprises: (a) a heavy chain complementarity determining region 1 (HCDR1) comprising an amino acid sequence set forth in any one of SEQ ID NO: 207 to SEQ ID NO: 209; (b) a heavy chain complementarity determining region 2 (HCDR2) comprising an amino acid sequence set forth in any one of SEQ ID NO: 210 to SEQ ID NO: 212; (c) a heavy chain complementarity determining region 3 (HCDR3) comprising an amino acid sequence set forth in any one of SEQ ID NO: 213 to SEQ ID NO: 215. In certain embodiments, the antigen binding region comprises a heavy chain variable region, wherein the heavy chain variable region comprises an amino acid sequence at least about 80%, 85%, 90%, 95%, 97%, 98%, or 99% identical to that set forth in any one of SEQ ID NO: 201 to SEQ ID NO: 206. In certain embodiments, the antigen binding region comprises a heavy chain variable region, wherein the heavy chain variable region comprises the amino acid sequence set forth in any one of SEQ ID NO: 201 to SEQ ID NO: 206.

In certain embodiments, the polypeptides described herein comprise an antigen binding region that binds DLL3, wherein the antigen binding region comprises: (a) a heavy chain complementarity determining region 1 (HCDR1) comprising an amino acid sequence set forth in any one of SEQ ID NO: 307 to SEQ ID NO: 309; (b) a heavy chain complementarity determining region 2 (HCDR2) comprising an amino acid sequence set forth in any one of SEQ ID NO: 310 to SEQ ID NO: 312; (c) a heavy chain complementarity determining region 3 (HCDR3) comprising an amino acid sequence set forth in any one of SEQ ID NO: 313 to SEQ ID NO: 315. In certain embodiments, the antigen binding region comprises a heavy chain variable region, wherein the heavy chain variable region comprises an amino acid sequence at least about 80%, 85%, 90%, 95%, 97%, 98%, or 99% identical to that set forth in any one of SEQ ID NO: 301 to SEQ ID NO: 306. In certain embodiments, the antigen binding region comprises a heavy chain variable region, wherein the heavy chain variable region comprises the amino acid sequence set forth in any one of SEQ ID NO: 301 to SEQ ID NO: 306.

In certain embodiments, the antigen binding region comprises a heavy chain variable region, wherein the heavy chain variable region comprises an amino acid sequence at least about 80%, 85%, 90%, 95%, 97%, 98%, or 99% identical to that set forth in SEQ ID NO: 303.

The polypeptide according to any one of claims 1, 2 or 9, wherein the antigen binding region comprises a heavy chain variable region, wherein the heavy chain variable region comprises an amino acid sequence set forth in SEQ ID NO: 303.

In certain embodiments, the antigen binding region comprises a heavy chain variable region, wherein the heavy chain variable region comprises an amino acid sequence at least about 80%, 85%, 90%, 95%, 97%, 98%, or 99% identical to that set forth in SEQ ID NO: 304.

In certain embodiments, the antigen binding region comprises a heavy chain variable region, wherein the heavy chain variable region comprises an amino acid sequence set forth in SEQ ID NO: 304.

In certain embodiments, the antigen binding region comprises a heavy chain variable region, wherein the heavy chain variable region comprises an amino acid sequence at least about 80%, 85%, 90%, 95%, 97%, 98%, or 99% identical to that set forth in SEQ ID NO: 305.

In certain embodiments, the polypeptides described herein comprise an antigen binding region that binds DLL3, wherein the antigen binding region comprises: (a) a heavy chain complementarity determining region 1 (HCDR1) comprising an amino acid sequence set forth in any one of SEQ ID NO: 407 to SEQ ID NO: 409; (b) a heavy chain complementarity determining region 2 (HCDR2) comprising an amino acid sequence set forth in any one of SEQ ID NO: 410 to SEQ ID NO: 412; (c) a heavy chain complementarity determining region 3 (HCDR3) comprising an amino acid sequence set forth in any one of SEQ ID NO: 413 to SEQ ID NO: 415. In certain embodiments, the antigen binding region comprises a heavy chain variable region, wherein the heavy chain variable region comprises an amino acid sequence at least about 80%, 85%, 90%, 95%, 97%, 98%, or 99% identical to that set forth in any one of SEQ ID NO: 401 to SEQ ID NO: 406. In certain embodiments, the antigen binding region comprises a heavy chain variable region, wherein the heavy chain variable region comprises the amino acid sequence set forth in any one of SEQ ID NO: 401 to SEQ ID NO: 406.

In certain embodiments, the antigen binding region comprises a heavy chain variable region, wherein the heavy chain variable region comprises an amino acid sequence at least about 80%, 85%, 90%, 95%, 97%, 98%, or 99% identical to that set forth in SEQ ID NO: 403.

In certain embodiments, the antigen binding region comprises a heavy chain variable region, wherein the heavy chain variable region comprises the amino acid sequence set forth in SEQ ID NO: 403.

In certain embodiments, the polypeptides described herein comprise an antigen binding region that binds DLL3, wherein the antigen binding region comprises: (a) a heavy chain complementarity determining region 1 (HCDR1) comprising an amino acid sequence set forth in any one of SEQ ID NO: 507 to SEQ ID NO: 509; (b) a heavy chain complementarity determining region 2 (HCDR2) comprising an amino acid sequence set forth in any one of SEQ ID NO: 510 to SEQ ID NO: 512; (c) a heavy chain complementarity determining region 3 (HCDR3) comprising an amino acid sequence set forth in any one of SEQ ID NO: 513 to SEQ ID NO: 515. In certain embodiments, the antigen binding region comprises a heavy chain variable region, wherein the heavy chain variable region comprises an amino acid sequence at least about 80%, 85%, 90%, 95%, 97%, 98%, or 99% identical to that set forth in any one of SEQ ID NO: 501 to SEQ ID NO: 506. In certain embodiments, the antigen binding region comprises a heavy chain variable region, wherein the heavy chain variable region comprises the amino acid sequence set forth in any one of SEQ ID NO: 501 to SEQ ID NO: 506.

The DLL3 antigen binding region confers specificity to the immunoconjugate and may suitably comprise a small antigen binding polypeptide. Such small antigen binding polypeptides confer advantages such as reducing the overall size of the immunoconjugate molecule allowing for tumor penetration and labeling. The small antigen binding polypeptide may lack certain regions dispensable for binding such as a light chain constant region, a heavy chain constant region, a CH1 region or a hinge region. In certain embodiments, the antigen binding region may lack a light chain variable region. In certain embodiments, the small antigen binding region may possess a molecular weight of between 10 kDa and 40 kDa.

In some embodiments, the small antigen binding region possesses a molecular weight of about 10 kDa to about 40 kDa. In some embodiments, the small antigen binding region possesses a molecular weight of about 10 kDa to about 15 kDa, about 10 kDa to about 20 kDa, about 10 kDa to about 25 kDa, about 10 kDa to about 30 kDa, about 10 kDa to about 35 kDa, about 10 kDa to about 40 kDa, about 15 kDa to about 20 kDa, about 15 kDa to about 25 kDa, about 15 kDa to about 30 kDa, about 15 kDa to about 35 kDa, about 15 kDa to about 40 kDa, about 20 kDa to about 25 kDa, about 20 kDa to about 30 kDa, about 20 kDa to about 35 kDa, about 20 kDa to about 40 kDa, about 25 kDa to about 30 kDa, about 25 kDa to about 35 kDa, about 25 kDa to about 40 kDa, about 30 kDa to about 35 kDa, about 30 kDa to about 40 kDa, or about 35 kDa to about 40 kDa. In some embodiments, the small antigen binding region possesses a molecular weight of about 10 kDa, about 15 kDa, about 20 kDa, about 25 kDa, about 30 kDa, about 35 kDa, or about 40 kDa. In some embodiments, the small antigen binding region possesses a molecular weight of at least about 10 kDa, about 15 kDa, about 20 kDa, about 25 kDa, about 30 kDa, or about 35 kDa. In some embodiments, the small antigen binding region possesses a molecular weight of at most about 15 kDa, about 20 kDa, about 25 kDa, about 30 kDa, about 35 kDa, or about 40 kDa.

The antigen binding region may comprise a VHH polypeptide, an scFv polypeptide, or a VNAR polypeptide. In certain embodiments, the antigen binding region comprises a VHH polypeptide. In certain embodiments, the antigen binding region comprises a ScFv polypeptide. In certain embodiments, the antigen binding region comprises a VNAR polypeptide. In certain embodiments, the antigen binding region is humanized. In certain embodiments, the antigen binding region does not comprise an immunoglobulin light chain.

In some embodiments, the immunoconjugate of the present disclosure comprises a synthetically engineered antibody derivate, such as, e.g. a protein or polypeptide comprising an autonomous $V_H$ domain (such as, e.g., from camelids, murine, or human sources), single-domain antibody domain (sdAb), heavy-chain antibody domains derived from a camelid (VHH fragment or $V_H$ domain fragment), heavy-chain antibody domains derived from a camelid VHH fragments or $V_H$ domain fragments, heavy-chain antibody domain derived from a cartilaginous fish, immunoglobulin new antigen receptor (IgNAR), VNAR fragment, single-chain variable (scFv) fragment, nanobody, "camelized" or "camelised" scaffold comprising a $V_H$ domain, Fd fragment consisting of the heavy chain and CH1 domains, single chain Fv-$C_H$3 minibody, Fc antigen binding domain (Fcabs), scFv-Fc fusion, multimerizing scFv fragment (diabodies, triabodies, tetrabodies), disulfide-stabilized antibody variable (Fv) fragment (dsFv), disulfide-stabilized antigen-binding (Fab) fragment consisting of the $V_L$, $V_H$, $C_L$ and $C_H$1 domains, scFv comprising a disulfide-stabilized heavy and light chain (sc-dsFvs), bivalent nanobodies, bivalent minibodies, bivalent F(ab')$_2$ fragments (Fab dimers), bispecific tandem VHH fragments, bispecific tandem scFv fragments, bispecific nanobodies, bispecific minibodies, and any genetically manipulated counterparts of the foregoing that retain paratope and target antigen binding function.

In some embodiments, the immunoconjugate is monovalent. In other embodiments, the immunoconjugate is multivalent, such as, e.g., bivalent. In some further embodiments, the immunoconjugate is bivalent and dimeric. In some further embodiments, the bivalent immunoconjugate is homodimeric.

In one aspect, the present disclosure provides antibody constructs (alone or in the context of immunoconjugates, radioimmunoconjugates, or targeted imaging complexes, each of this disclosure), comprising a VHH fragment comprising a heavy chain variable region comprising three heavy chain CDRs derived from a camelid, which bind to an antigen with specificity and high affinity.

In some embodiments, the antibody construct, immunoconjugate, radioimmunoconjugate, or targeted imaging complex specifically binds to at least one extracellular part of an antigen expressed on a cellular surface. In some embodiments, the immunoconjugate specifically binds to at least one extracellular part of antigen expressed by a target cell, such as, e.g., a tumor cell.

In some embodiments, this disclosure provides immunoconjugate that specifically binds to an antigen. In some embodiments, the immunoconjugate comprises an antibody construct comprising a heavy chain variable region (HVR-H) comprising three CDRs: hCDR1, hCDR2, and hCDR3, such as, e.g., derived from a camelid antibody or IgNAR. In some embodiments, the immunoconjugate comprises: (a) a light chain variable region (HVR-L) comprising three CDRs: lCDR1, lCDR2, and lCDR3, and (b) a heavy chain variable region (HVR-H) comprising three CDRs: hCDR1, hCDR2, and hCDR3. In some embodiments, the antibody construct is chimeric or humanized.

In some embodiments, the immunoconjugate of the present disclosure comprises an antibody construct comprising an antigen binding domain which is an antibody fragment, including but not limited to, e.g., a Fv, Fab, Fab', scFv, HcAb fragment, VHH fragment, sdAb fragment, diabody, or F(ab')2 fragment. In some further embodiments, the immunoconjugate of the present disclosure comprises a multimer of two or more antibody fragments, such as, e.g., a homodimer or heterodimer comprising two antibody fragments each capable of binding to an antigen with specificity and high affinity and each comprising a heavy chain variable region (HVR-H) comprising three CDRs: hCDR1, hCDR2, and hCDR3.

Heavy Chain Constant Regions

The antigen binding regions of the immunoconjugates described herein may comprise an Fc or heavy chain constant region. The antigen binding molecules can be coupled to the Fc or heavy chain constant region directly, by a suitable linker, or by an IgG hinge region. The inclusion of the heavy chain constant region or Fc region confers such advantages as allowing for optimization and tuning of serum half-life, the addition of additional sites to conjugate a chelating or cytotoxic agent, and allow for purification of the immunoconjugates using standard processes and methods. The addition of a heavy chain constant region also increases the size which may shift the catabolisis and elimination of the immunoconjugate to the liver from the kidney. This can confer safety advantages especially for radioimmunoconjugates as the kidney is more sensitive to radiation than the liver. Alterations, that affect the effector function or the serum half-life of can be made to residues present in the heavy chain constant region responsible for binding the neonatal Fc receptor (FcRn). Binding to the FcRn, in general contributes to the increased half-life of molecules that comprise an immunoglobulin Fc, thus reducing binding to FcRn can reduce the half-life of molecules comprising an Fc. Reduction in FcRn binding can confer advantages such as a reduction in the half-life of immunoconjugates, and, thus, subsequent toxicity attributed to cytotoxic agents or radioisotopes. In certain embodiments, the immunoglobulin constant region comprises or consists of an Fc region. In certain embodiments, the immunoglobulin heavy chain constant region comprises a CH2 domain of an immunoglobulin, CH3 domain of an immunoglobulin, or a CH2 and a CH3 domain of an immunoglobulin. In certain embodiments, the immunoglobulin heavy chain constant region comprises a CH2 and a CH3 domain of an immunoglobulin. For treatment or imaging of human individuals the immunoglobulin heavy chain constant region may be human, preventing or reducing an endogenous immune response against the immunoconjugate. In certain embodiments, the immunoglobulin heavy chain constant region is a human immunoglobulin heavy chain constant region. In certain embodiments, the immunoglobulin heavy chain constant region is an IgA, IgG1, IgG2, IgG3, or IgG4 isotype. In certain embodiments, the immunoglobulin heavy chain constant region is an IgG1 isotype. In certain embodiments, the immunoglobulin heavy chain constant region is an IgG4 isotype.

In some embodiments, this disclosure contemplates a variant of an immunoconjugate of this disclosure that comprises a Fc region wherein the variant possesses some but not all effector functions, which make it a desirable candidate for applications in which the half-life of the immunoconjugate in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the immunoconjugate lacks FcγγR binding (hence likely lacking ADCC activity), but retains FcRn binding ability. The primary cells for mediating ADCC, NK cells, express FcγγRIII only, whereas monocytes express FcγγRI, FcγγRII and FcγRIII. FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see e.g. Hellstrom, I. et al. Proc Natl Acad Sci USA 83:7059-7063 (1986)) and Hellstrom, I et al., Proc Natl Acad Sci USA 82:1499-1502 (1985); 5,821,337 (see Bruggemann, M. et al., J. Exp. Med. 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and Cyto-Tox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. Proc Natl Acad Sci USA 95:652-656 (1998). C1q binding assays may also be carried out to confirm that the immunoconjugate is unable to bind C1q and hence lacks CDC activity (see e.g., C1q and C3c binding ELISA in WO 2006/029879 and WO 2005/100402). To assess complement activation, a CDC assay may be performed (see e.g., Gazzano-Santoro et al., J. Immunol. Methods 202:163 (1996); Cragg, M. S. et al., Blood 101:1045-1052 (2003); Cragg, M. S. and M. J. Glennie, Blood 103:2738-2743 (2004)). FcRn binding and in vivo clearance/half-life determinations can also be performed using methods known in the art (see e.g., Petkova, S. B. et al., Int'l. Immunol. 18(12): 1759-1769 (2006)).

The immunoglobulin heavy chain constant region can be a variant constant region that comprises one or more alterations to an amino acid residues that confers additional utility and advantageous properties to the immunoconjugates described herein. In certain embodiments, the immunoglobulin heavy chain constant region comprises an alteration to one or more amino acid residues that reduces an effector function of the immunoglobulin heavy chain constant region or alters binding of the immunoconjugate to the neonatal Fc receptor (FcRn). In certain embodiments, the immunoglobulin heavy chain constant region comprises an alteration to one or more amino acid residues that reduces an effector function of the immunoglobulin heavy chain constant region or reduces binding of the immunoconjugate to the neonatal Fc receptor (FcRn). In certain embodiments, the immunoglobulin heavy chain constant region comprises an alteration to one or more amino acid residues that reduces an effector function of the immunoglobulin heavy chain constant region and reduces binding of the immunoconjugate to the neonatal Fc receptor (FcRn). In certain embodiments, the immunoglobulin heavy chain constant region comprises an alteration to one or more amino acid residues that reduces an effector function of the immunoglobulin heavy chain constant region. In certain embodiments, the immunoglobulin heavy chain constant region comprises an alteration to one or more amino acid residues that reduces binding of the immunoconjugate to the neonatal Fc receptor (FcRn).

The alterations to heavy chain constant regions of the immunoconjugate can reduce effector function associated with a heavy chain constant region, such as, the ability to fix complement, promote phagocytosis, or recruit other immune effector cells (e.g., NK cells) to the heavy chain constant region. In certain embodiments, the alteration to one or more amino acid residues that reduces the effector function of the immunoglobulin heavy chain constant region is an alteration that reduces complement dependent cytotoxicity (CDC), antibody-dependent cell-cytotoxicity (ADCC), antibody-dependent cell-phagocytosis ADCP, or a combination thereof. In certain embodiments, the alteration to one or more amino acid residues that reduces the effector function of the immunoglobulin heavy chain constant region is selected from the list consisting of: (a) 297A, 297Q, 297G, or 297D, (b) 279F, 279K, or 279L, (c) 228P, (d) 235A, 235E, 235G, 235Q, 235R, or 235S, (e) 237A, 237E, 237K, 237N, or 237R, (f) 234A, 234V, or 234F, (g) 233P, (h) 328A, (i) 327Q or 327T, (j) 329A, 329G, 329Y, or 329R (k) 331S, (l) 236F or 236R, (m) 238A, 238E, 238G, 238H, 238I, 238V, 238W, or 238Y, (n) 248A, (o) 254D, 254E, 254G, 254H, 254I, 254N, 254P, 254Q, 254T, or 254V, (p) 255N, (q) 256H, 256K, 256R, or 256V, (r) 264S, (s) 265H, 265K, 265S, 265Y, or 265A, (t) 267G, 267H, 267I, or 267K, (u) 268K, (v) 269N or 269Q, (w) 270A, 270G, 270M, or 270N, (x) 271T, (y) 272N, (z) 292E, 292F, 292G, or 292I, (aa) 293S, (bb) 301W, (cc) 304E, (dd) 311E, 311G, or 311S, (ee) 316F, (ff) 328V, (gg) 330R, (hh) 339E or 339L, (ii) 343I or 343V, (jj) 373A, 373G, or 373S, (kk) 376E, 376W, or 376Y, (ll) 380D, (mm) 382D or 382P, (nn) 385P, (oo) 424H, 424M, or 424V, (pp) 434I, (qq) 438G, (rr) 439E, 439H, or 439Q, (ss) 440A, 440D, 440E, 440F, 440M, 440T, or 440V, (tt) K322A, (uu) L235E, (vv) L234A and L235A, (ww) L234A, L235A, and G237A, (xx) L234A, L235A, and P329G, (yy) L234F, L235E, and P331S, (zz) L234A, L235E, and G237A, (aaa), L234A, L235E, G237A, and P331S (bbb) L234A, L235A, G237A, P238S, H268A, A330S, and P331S, (ccc) L234A, L235A, and P329A, (ddd) G236R and L328R, (eee) G237A, (fff) F241A, (ggg) V264A, (hhh) D265A, (iii) D265A and N297A, (jjj) D265A and N297G, (kkk) D270A, (lll) A330L, (mmm) P331A or P331S, or (nnn) E233P, (ooo) L234A, L235E, G237A, A330S, and P331S or (ppp) any combination of (a)-(ooo), per EU numbering. In certain embodiments, the alteration to one or more amino acid residues that reduces the effector function of the immunoglobulin heavy chain constant region comprises L234A, L235E, G237A, A330S, and P331S per EU numbering.

The alterations to heavy chain constant regions of the immunoconjugate can reduce the serum half-life of the immunoconjugate. In certain embodiments, the amino acid alteration that alters or reduces binding of the immunoconjugate to the neonatal Fc receptor (FcRn) reduces the serum half-life of the immunoconjugate. In certain embodiments, the alteration that alters or reduces binding of the immunoconjugate to the neonatal Fc receptor (FcRn) is to an amino acid residue selected from the list consisting of: 251, 252, 253, 254, 255, 288, 309, 310, 312, 385, 386, 388, 400, 415, 433, 435, 436, 439, 447, and combinations thereof per EU numbering. In certain embodiments, the alteration that alters or reduces binding of the immunoconjugate to the neonatal Fc receptor (FcRn) is to an amino acid residue selected from the list consisting of: 253, 254, 310, 435, 436 and combinations thereof per EU numbering. In certain embodiments, the alteration that alters or reduces binding of the immunoconjugate to the neonatal Fc receptor (FcRn) is to an amino acid residue selected from the list consisting of: I253A, I253D, I253P, S254A, H310A, H310D, H310E, H310Q, H435A, H435Q, Y436A, and combinations thereof per EU numbering. In certain embodiments, the alteration that alters or reduces binding of the immunoconjugate to the neonatal Fc receptor (FcRn) is to an amino acid residue selected from the list consisting of: I253A, S254A, H310A, H435Q, Y436A and combinations thereof per EU numbering. In certain embodiments, the alteration that alters or reduces binding of the immunoconjugate to the neonatal Fc receptor (FcRn) is to an amino acid residue selected from the list consisting of: I253A, H310A, H435Q, and combinations thereof per EU numbering. In certain embodiments, the alteration that alters or reduces binding of the immunoconjugate to the neonatal Fc receptor (FcRn) is to an amino acid residue selected from the list consisting of: H310A, H435Q, and combinations thereof per EU numbering.

In certain embodiments, a heavy chain constant regions of the immunoconjugate comprises a sequence at least 90%, 95%, 97%, 98%, or 99% identical to the sequence set forth in SEQ ID NO: 1. In certain embodiments, a heavy chain constant regions of the immunoconjugate comprises a sequence identical to SEQ ID NO: 1. In certain embodiments, a heavy chain constant regions of the immunoconjugate comprises a sequence at least 90%, 95%, 97%, 98%, or 99% identical to the sequence set forth in SEQ ID NO: 1, wherein the heavy chain constant region comprises an I253A substitution per EU numbering.

In certain embodiments, a heavy chain constant regions of the immunoconjugate comprises a sequence at least 90%, 95%, 97%, 98%, or 99% identical to the sequence set forth in SEQ ID NO: 2. In certain embodiments, a heavy chain constant regions of the immunoconjugate comprises a sequence identical to SEQ ID NO: 2. In certain embodiments, a heavy chain constant regions of the immunoconjugate comprises a sequence at least 90%, 95%, 97%, 98%, or 99% identical to the sequence set forth in SEQ ID NO: 2, wherein the heavy chain constant region comprises an S254A substitution per EU numbering.

In certain embodiments, a heavy chain constant regions of the immunoconjugate comprises a sequence at least 90%, 95%, 97%, 98%, or 99% identical to the sequence set forth in SEQ ID NO: 3. In certain embodiments, a heavy chain constant regions of the immunoconjugate comprises a sequence identical to SEQ ID NO: 3. In certain embodiments, a heavy chain constant regions of the immunoconjugate comprises a sequence at least 90%, 95%, 97%, 98%, or 99% identical to the sequence set forth in SEQ ID NO: 3, wherein the heavy chain constant region comprises an H310A substitution per EU numbering.

In certain embodiments, a heavy chain constant regions of the immunoconjugate comprises a sequence at least 90%, 95%, 97%, 98%, or 99% identical to the sequence set forth in SEQ ID NO: 4. In certain embodiments, a heavy chain constant regions of the immunoconjugate comprises a sequence identical to SEQ ID NO: 4. In certain embodiments, a heavy chain constant regions of the immunoconjugate comprises a sequence at least 90%, 95%, 97%, 98%, or 99% identical to the sequence set forth in SEQ ID NO: 4, wherein the heavy chain constant region comprises an H435Q substitution per EU numbering.

In certain embodiments, a heavy chain constant regions of the immunoconjugate comprises a sequence at least 90%, 95%, 97%, 98%, or 99% identical to the sequence set forth in SEQ ID NO: 5. In certain embodiments, a heavy chain constant regions of the immunoconjugate comprises a sequence identical to SEQ ID NO: 5. In certain embodiments, a heavy chain constant regions of the immunoconjugate comprises a sequence at least 90%, 95%, 97%, 98%, or 99% identical to the sequence set forth in SEQ ID NO: 5, wherein the heavy chain constant region comprises an Y436A substitution per EU numbering.

In certain embodiments, a heavy chain constant regions of the immunoconjugate comprises a sequence at least 90%, 95%, 97%, 98%, or 99% identical to the sequence set forth in SEQ ID NO: 6. In certain embodiments, a heavy chain constant regions of the immunoconjugate comprises a sequence identical to SEQ ID NO: 6. In certain embodiments, a heavy chain constant regions of the immunoconjugate comprises a sequence at least 90%, 95%, 97%, 98%, or 99% identical to the sequence set forth in SEQ ID NO: 6, wherein the heavy chain constant region comprises an H310A/H435Q substitution per EU numbering.

In certain embodiments, a heavy chain constant regions of the immunoconjugate comprises a sequence at least 90%, 95%, 97%, 98%, or 99% identical to the sequence set forth in SEQ ID NO: 7. In certain embodiments, a heavy chain constant regions of the immunoconjugate comprises a sequence identical to SEQ ID NO: 7. In certain embodiments, a heavy chain constant regions of the immunoconjugate comprises a sequence at least 90%, 95%, 97%, 98%, or 99% identical to the sequence set forth in SEQ ID NO: 7, wherein the heavy chain constant region comprises a L234A, L235E, G237A, A330S, and P331S substitution per EU numbering.

In certain embodiments, a heavy chain constant regions of the immunoconjugate comprises a sequence at least 90%, 95%, 97%, 98%, or 99% identical to the sequence set forth in SEQ ID NO: 8. In certain embodiments, a heavy chain constant regions of the immunoconjugate comprises a sequence identical to SEQ ID NO: 8, wherein the heavy chain constant region comprises a L234A, L235E, G237A, H310A, A330S, and P331S substitution per EU numbering.

In certain embodiments, a heavy chain constant regions of the immunoconjugate comprises a sequence at least 90%, 95%, 97%, 98%, or 99% identical to the sequence set forth in SEQ ID NO: 9. In certain embodiments, a heavy chain constant regions of the immunoconjugate comprises a sequence identical to SEQ ID NO: 9. In certain embodiments, a heavy chain constant regions of the immunoconjugate comprises a sequence identical to SEQ ID NO: 9, wherein the heavy chain constant region comprises a L234A, L235E, G237A, H435Q, A330S, and P331S substitution per EU numbering.

In certain embodiments, a heavy chain constant regions of the immunoconjugate comprises a sequence at least 90%, 95%, 97%, 98%, or 99% identical to the sequence set forth in SEQ ID NO: 10. In certain embodiments, a heavy chain constant regions of the immunoconjugate comprises a sequence identical to SEQ ID NO: 10 per EU numbering.

In one embodiment, each of the two variant constant regions has at least one FcRn binding mutation. In one embodiment, each of the two variant constant regions has the same FcRn binding mutation. In one embodiment, each of the two variant constant regions has a different FcRn binding mutation.

In one embodiment, at least one of the variant constant regions in the immunoconjugate has at least one FcRn binding mutation. In an embodiment, each of the two variant constant regions of the immunoconjugate has at least one FcRn binding mutation, which FcRn binding mutations are the same or different.

Alterations that effect FcRn binding can reduce the serum half-life of the immunoconjugate, thus allowing the skilled artisan to choose a half-life that is suitable for a particular imaging or therapeutic goal. In certain embodiments, the immunoconjugate has a serum half-life of about 12 hours to about 120 hours. In certain embodiments, the immunoconjugate has a serum half-life of about 12 hours to about 24 hours, about 12 hours to about 36 hours, about 12 hours to about 48 hours, about 12 hours to about 60 hours, about 12 hours to about 72 hours, about 12 hours to about 84 hours, about 12 hours to about 96 hours, about 12 hours to about 108 hours, about 12 hours to about 120 hours, about 24 hours to about 36 hours, about 24 hours to about 48 hours, about 24 hours to about 60 hours, about 24 hours to about 72 hours, about 24 hours to about 84 hours, about 24 hours to about 96 hours, about 24 hours to about 108 hours, about 24 hours to about 120 hours, about 36 hours to about 48 hours, about 36 hours to about 60 hours, about 36 hours to about 72 hours, about 36 hours to about 84 hours, about 36 hours to about 96 hours, about 36 hours to about 108 hours, about 36 hours to about 120 hours, about 48 hours to about 60 hours, about 48 hours to about 72 hours, about 48 hours to about 84 hours, about 48 hours to about 96 hours, about 48 hours to about 108 hours, about 48 hours to about 120 hours, about 60 hours to about 72 hours, about 60 hours to about 84 hours, about 60 hours to about 96 hours, about 60 hours to about 108 hours, about 60 hours to about 120 hours, about 72 hours to about 84 hours, about 72 hours to about 96 hours, about 72 hours to about 108 hours, about 72 hours to about 120 hours, about 84 hours to about 96 hours, about 84 hours to about 108 hours, about 84 hours to about 120 hours, about 96 hours to about 108 hours, about 96 hours to about 120 hours, or about 108 hours to about 120 hours. In certain embodiments, the immunoconjugate has a serum half-life of about 12 hours, about 24 hours, about 36 hours, about 48 hours, about 60 hours, about 72 hours, about 84 hours, about 96 hours, about 108 hours, or about 120 hours. In certain embodiments, the immunoconjugate has a serum half-life of at least about 12 hours, about 24 hours, about 36 hours, about 48 hours, about 60 hours, about 72 hours, about 84 hours, about 96 hours, or about 108 hours. In certain embodiments, the immunoconjugate has a serum half-life of at most about 24 hours, about 36 hours, about 48 hours, about 60 hours, about 72 hours, about 84 hours, about 96 hours, about 108 hours, or about 120 hours.

In certain embodiments, the immunoconjugate has a serum half-life of about 1 day to about 10 days. In certain embodiments, the immunoconjugate has a serum half-life of about 1 day to about 2 days, about 1 day to about 3 days, about 1 day to about 4 days, about 1 day to about 5 days, about 1 day to about 6 days, about 1 day to about 7 days, about 1 day to about 8 days, about 1 day to about 9 days, about 1 day to about 10 days, about 2 days to about 3 days, about 2 days to about 4 days, about 2 days to about 5 days, about 2 days to about 6 days, about 2 days to about 7 days, about 2 days to about 8 days, about 2 days to about 9 days, about 2 days to about 10 days, about 3 days to about 4 days, about 3 days to about 5 days, about 3 days to about 6 days, about 3 days to about 7 days, about 3 days to about 8 days, about 3 days to about 9 days, about 3 days to about 10 days, about 4 days to about 5 days, about 4 days to about 6 days, about 4 days to about 7 days, about 4 days to about 8 days, about 4 days to about 9 days, about 4 days to about 10 days, about 5 days to about 6 days, about 5 days to about 7 days, about 5 days to about 8 days, about 5 days to about 9 days, about 5 days to about 10 days, about 6 days to about 7 days, about 6 days to about 8 days, about 6 days to about 9 days, about 6 days to about 10 days, about 7 days to about 8 days, about 7 days to about 9 days, about 7 days to about 10 days, about 8 days to about 9 days, about 8 days to about 10 days, or about 9 days to about 10 days. In certain embodiments, the immunoconjugate has a serum half-life of about 1 day, about 2 days, about 3 days, about 4 days, about 5 days, about 6 days, about 7 days, about 8 days, about 9 days, or about 10 days. In certain embodiments, the immunoconjugate has a serum half-life of at least about 1 day, about 2 days, about 3 days, about 4 days, about 5 days, about 6 days, about 7 days, about 8 days, or about 9 days. In certain embodiments, the immunoconjugate has a serum half-life of at most about 2 days, about 3 days, about 4 days, about 5 days, about 6 days, about 7 days, about 8 days, about 9 days, or about 10 days.

In certain embodiments, the heavy chain constant region has a molecular weight of about 10 kDa to about 25 kDa. In certain embodiments, the heavy chain constant region has a molecular weight of about 10 kDa to about 15 kDa, about 10 kDa to about 20 kDa, about 10 kDa to about 25 kDa, about 15 kDa to about 20 kDa, about 15 kDa to about 25 kDa, or about 20 kDa to about 25 kDa. In certain embodiments, the heavy chain constant region has a molecular weight of about 10 kDa, about 15 kDa, about 20 kDa, or about 25 kDa. In certain embodiments, the heavy chain constant region has a molecular weight of at least about 10 kDa, about 15 kDa, or about 20 kDa. In certain embodiments, the heavy chain constant region has a molecular weight of at most about 15 kDa, about 20 kDa, or about 25 kDa.

In some embodiments, the immunoconjugate of the present disclosure comprises a linker or hinge region, which is a polypeptide linking an antigen binding region to a heavy chain constant region or a variant constant region in the instant disclosure. Naturally occurring and synthetic hinge regions linking immunoglobulin components are well known in the art and available for use in the present disclosure. For example, see U.S. Pat. No. 8,067,548 and references therein.

In one embodiment, the hinge regions of the immunoconjugate are the same. In one embodiment, the hinge regions of the immunoconjugate are different.

The antigen binding regions and the heavy chain constant regions (with or without an altered amino acid sequence) can be connected by a suitable hinge or linker sequence. In certain embodiments, the antigen binding region is coupled to the immunoglobulin heavy chain constant region by a linker amino acid sequence or a human IgG hinge region. Appropriate IgG hinge regions comprise and include IgG1 or IgG4 hinge regions. In certain embodiments, the hinge region is an IgG1 hinge region. In certain embodiments, the hinge region is an IgG1 hinge regions with a with a C220S substitution per EU numbering. In certain embodiments, the hinge region is an IgG1 hinge regions with a with a C220P substitution per EU numbering. Suitable hinge regions include those described in Wu et al., "Multimerization of a chimeric anti-CD20 single-chain Fv-Fc fusion protein is mediated through variable domain exchange," *Protein Engineering, Design and Selection*, Volume 14, Issue 12, December 2001, Pages 1025-1033; Shu et al, "Secretion of a single-gene-encoded immunoglobulin from myeloma cells." *Proceedings of the National Academy of Sciences* September 1993, 90 (17) 7995-7999; Davis et al., "Abatacept binds to the Fc receptor CD64 but does not mediate complement-dependent cytotoxicity or antibody-dependent cellular cytotoxicity." *J Rheumatol.* 2007 November; 34(11):2204-10. Appropriate hinges may also include a non-IgG based polypeptide linker. The linker amino acid sequence may predominantly include the following amino acid residues: Gly, Ser, Ala, or Thr. The linker peptide should have a length that is adequate to link two molecules in such a way that they assume the correct conformation relative to one another, and so that they retain the desired activity. In one embodiment, the linker is from about 1 to 50 amino acids in length or about 1 to 30 amino acids in length. In one embodiment, linkers of 1 to 20 amino acids in length may be used. Useful linkers include glycine-serine polymers, including for example (GS)n, (GSGGS)n (SEQ ID NO: 533), (GGGGS)n (SEQ ID NO: 534), and (GGGS)n (SEQ ID NO: 535), where n is an integer of at least one, glycine-alanine polymers, alanine-serine polymers, and other flexible linkers. Exemplary, linkers for linking antibody fragments or single chain variable fragments can include AAEPKSS (SEQ ID NO: 536), AAEPKSSDKTHTCPPCP (SEQ ID NO: 537), GGGG (SEQ ID NO: 538), or GGGGDKTHTCPPCP (SEQ ID NO: 539). Alternatively, a variety of non-proteinaceous polymers, including but not limited to polyethylene glycol (PEG), polypropylene glycol, polyoxyalkylenes, or copolymers of polyethylene glycol and polypropylene glycol, may find use as linkers. In certain embodiments, the human IgG hinge region comprises the amino acid sequence set forth in SEQ ID NO: 40 or 41. In certain embodiments, the human IgG hinge region comprises the amino acid sequence set forth in SEQ ID NO: 40. In certain embodiments, the human IgG hinge region comprises the amino acid sequence set forth in SEQ ID NO: 41.

The total size of the immunoconjugate may be such that it promotes tissue penetration, stability, and/or clearance. In certain embodiments, the immunoconjugate has a molecular weight of about 60 kDa to about 120 kDa. In certain embodiments, the immunoconjugate has a molecular weight of about 60 kDa to about 65 kDa, about 60 kDa to about 70 kDa, about 60 kDa to about 75 kDa, about 60 kDa to about 80 kDa, about 60 kDa to about 90 kDa, about 60 kDa to about 100 kDa, about 60 kDa to about 110 kDa, about 60 kDa to about 120 kDa, about 65 kDa to about 70 kDa, about 65 kDa to about 75 kDa, about 65 kDa to about 80 kDa, about 65 kDa to about 90 kDa, about 65 kDa to about 100 kDa, about 65 kDa to about 110 kDa, about 65 kDa to about 120 kDa, about 70 kDa to about 75 kDa, about 70 kDa to about 80 kDa, about 70 kDa to about 90 kDa, about 70 kDa to about 100 kDa, about 70 kDa to about 110 kDa, about 70 kDa to about 120 kDa, about 75 kDa to about 80 kDa, about 75 kDa to about 90 kDa, about 75 kDa to about 100 kDa, about 75 kDa to about 110 kDa, about 75 kDa to about 120 kDa, about 80 kDa to about 90 kDa, about 80 kDa to about 100 kDa, about 80 kDa to about 110 kDa, about 80 kDa to about 120 kDa, about 90 kDa to about 100 kDa, about 90 kDa to about 110 kDa, about 90 kDa to about 120 kDa, about 100 kDa to about 110 kDa, about 100 kDa to about 120 kDa, or about 110 kDa to about 120 kDa. In certain embodiments, the immunoconjugate has a molecular weight of about 60 kDa, about 65 kDa, about 70 kDa, about 75 kDa, about 80 kDa, about 90 kDa, about 100 kDa, about 110 kDa, or about 120 kDa. In certain embodiments, the immunoconjugate has a molecular weight of at least about 60 kDa, about 65 kDa, about 70 kDa, about 75 kDa, about 80 kDa, about 90 kDa, about 100 kDa, or about 110 kDa. In certain embodiments, the immunoconjugate has a molecular weight of at most about 65 kDa, about 70 kDa, about 75 kDa, about 80 kDa, about 90 kDa, about 100 kDa, about 110 kDa, or about 120 kDa.

In some embodiments, the immunoconjugate has a molecular weight greater than 60, 70, 75, 80, 82, 83, 85, 86, 87, 88 or 89 kDa. In some embodiments, the immunoconjugate has a molecular weight less than 110, 100, 95, 93, 91, 90, 89, 88, 87, 86, 85, 84, 83, 82, 81, or 80 kDa. In some embodiments, the immunoconjugate has a molecular weight greater than 60, 65, 70, 71, 72, 73, 74, 75, 76, 77, 78, or 79 kDa and less than 110, 100, 95, 93, 91, or 90 kDa.

The sizes of the immunoconjugates and/or the heavy chain constant region variants described herein allow for an increased safety profile or therapeutic index of the immunoconjugates included herein. Such a safety profile may be reflected in the reduction of accumulation of radiation in radio sensitive major tissues such as kidney and bone marrow and/or an increase in radiation accumulation in target tissues (i.e., a tumor or cancerous tissue) or more radio tolerant organs such as the liver.

In certain embodiments, the immunoconjugates of this disclosure result in a total radiation exposure per treatment as measured in Gray (Gy). In certain embodiments, the kidney is exposed to 20 Gy or less per treatment. In certain embodiments, the kidney is exposed to 19 Gy or less per treatment. In certain embodiments, the kidney is exposed to 18 Gy or less per treatment. In certain embodiments, the kidney is exposed to 17 Gy or less per treatment. In certain embodiments, the kidney is exposed to 16 Gy or less per treatment. In certain embodiments, the kidney is exposed to 15 Gy or less per treatment. In certain embodiments, the kidney is exposed to 14 Gy or less per treatment. In certain embodiments, the kidney is exposed to 13 Gy or less per treatment. In certain embodiments, the kidney is exposed to 12 Gy or less per treatment. In certain embodiments, the kidney is exposed to 11 Gy or less per treatment. In certain embodiments, the kidney is exposed to 10 Gy or less per treatment. In certain embodiments, the kidney is exposed to 9 Gy or less per treatment. In certain embodiments, the kidney is exposed to 8 Gy or less per treatment. In certain embodiments, the kidney is exposed to 5 Gy or less per treatment.

In certain embodiments, the immunoconjugates of this disclosure result in a total radiation exposure per treatment as measured in Gray (Gy). In certain embodiments, the bone marrow is exposed to 4 Gy or less per treatment. In certain embodiments, the bone marrow is exposed to 3 Gy or less per treatment. In certain embodiments, the bone marrow is exposed to 2 Gy or less per treatment. In certain embodiments, the bone marrow is exposed to 1.5 Gy or less per treatment. In certain embodiments, the bone marrow is exposed to 1.0 Gy or less per treatment. In certain embodiments, the bone marrow is exposed to 0.5 Gy or less per treatment.

In certain embodiments, the immunoconjugates of this disclosure result in an increased amount of radiation in the tumor compared to the kidney when measured as a percent injected dose per gram. In certain embodiments, the ratio of tumor percent injected dose per gram to kidney percent injected dose per gram is greater than 2:1, 3:1, 4:1, 5:1, 6:1, 7:1, 8:1, 9:1, or 10:1.

In certain embodiments, the immunoconjugates of this disclosure result in an increased amount of radiation in the tumor compared to the blood when measured as percent injected dose per gram. In certain embodiments, the ratio of tumor percent injected dose per gram to blood percent injected dose per gram is greater than 2:1, 3:1, 4:1, 5:1, 6:1, 7:1, 8:1, 9:1, or 10:1.

In certain embodiments, the immunoconjugates of this disclosure result in an increased amount of radiation in the tumor compared to the bone marrow when measured as percent injected dose per gram. In certain embodiments, the ratio of tumor percent injected dose per gram to bone marrow percent injected dose per gram is greater than 2:1, 3:1, 4:1, 5:1, 6:1, 7:1, 8:1, 9:1, or 10:1.

In certain embodiments, the immunoconjugates of this disclosure result in an increased amount of radiation in the liver compared to the kidney when measured as an injected dose per gram. In certain embodiments, the ratio of tumor percent injected dose per gram to bone marrow percent injected dose per gram is greater than 3:1, 4:1, 5:1, 6:1, 7:1, 8:1, 9:1, or 10:1.

As will be recognized by the person of ordinary skill in the art, certain teachings herein apply to antibody constructs, targeted imaging complexes, immunoconjugates and radio-immunoconjugates of this disclosure, notwithstanding that reference is made in the text to one only or two such compositions (e.g., immunoconjugate) as a non-limiting example. All such applications and embraced by the present disclosure.

The immunoconjugates herein may comprise a polypeptide comprising a VHH region, a hinge region, a CH2 region, and a CH3 region. In certain embodiments, the polypeptide may comprise a homodimer with another poly peptide to create a dimeric bivalent polypeptide. In certain embodiments, the polypeptide comprises an amino acid sequence at least about 80%, 85%, 90%, 95%, 97%, 98%, or 99% identical to any one of SEQ ID NO: 116 to SEQ ID NO: 120, SEQ ID NO: 216 to SEQ ID NO: 220, SEQ ID NO: 316 to SEQ ID NO: 320, SEQ ID NO: 416 to SEQ ID NO: 420, and SEQ ID NO: 516 to SEQ ID NO: 520. In certain embodiments, the polypeptide comprises an amino acid sequence identical to any one of SEQ ID NO: 116 to SEQ ID NO: 120, SEQ ID NO: 216 to SEQ ID NO: 220, SEQ ID NO: 316 to SEQ ID NO: 320, SEQ ID NO: 416 to SEQ ID NO: 420, and SEQ ID NO: 516 to SEQ ID NO: 520. In certain embodiments, the polypeptide comprises an amino acid sequence at least about 80%, 85%, 90%, 95%, 97%, 98%, or 99% identical to SEQ ID NO: 116 to SEQ ID NO: 120. In certain embodiments, the polypeptide comprises an amino acid sequence identical to SEQ ID NO: 116 to SEQ ID NO: 120. In certain embodiments, the polypeptide comprises an amino acid sequence at least about 80%, 85%, 90%, 95%, 97%, 98%, or 99% identical to SEQ ID NO: 216 to SEQ ID NO: 220. In certain embodiments, the polypeptide comprises an amino acid sequence identical to SEQ ID NO: 216 to SEQ ID NO: 220. In certain embodiments, the polypeptide comprises an amino acid sequence at least about 80%, 85%, 90%, 95%, 97%, 98%, or 99% identical to SEQ ID NO: 316 to SEQ ID NO: 320. In certain embodiments, the polypeptide comprises an amino acid sequence identical to SEQ ID NO: 316 to SEQ ID NO: In certain embodiments, the polypeptide comprises an amino acid sequence at least about 80%, 85%, 90%, 95%, 97%, 98%, or 99% identical to SEQ ID NO: 416 to SEQ ID NO: 420. In certain embodiments, the polypeptide comprises an amino acid sequence identical to SEQ ID NO: 416 to SEQ ID NO: 420. In certain embodiments, the polypeptide comprises an amino acid sequence at least about 80%, 85%, 90%, 95%, 97%, 98%, or 99% identical to SEQ ID NO: 516 to SEQ ID NO: 520. In certain embodiments, the polypeptide comprises an amino acid sequence identical to SEQ ID NO: 516 to SEQ ID NO: 520.

In certain embodiments, the polypeptide comprises an amino acid sequence at least about 80%, 85%, 90%, 95%, 97%, 98%, or 99% identical to SEQ ID NO: 317.

In certain embodiments, the polypeptide comprises an amino acid sequence set forth in SEQ ID NO: 317.

In certain embodiments, the polypeptide comprises an amino acid sequence at least about 80%, 85%, 90%, 95%, 97%, 98%, or 99% identical to SEQ ID NO: 318.

In certain embodiments, the polypeptide comprises an amino acid sequence set forth in SEQ ID NO: 318.

In certain embodiments, the polypeptide comprises an amino acid sequence at least about 80%, 85%, 90%, 95%, 97%, 98%, or 99% identical to SEQ ID NO: 319.

In certain embodiments, the polypeptide comprises an amino acid sequence set forth in SEQ ID NO: 319.

In certain embodiments, the polypeptide comprises an amino acid sequence at least about 80%, 85%, 90%, 95%, 97%, 98%, or 99% identical to SEQ ID NO: 417.

In certain embodiments, the polypeptide comprises an amino acid sequence set forth in SEQ ID NO: 417.

Chelating Agents

As described herein a chelating agent can be coupled to the immunoconjugates, the antigen binding region/immunoglobulin heavy chain constant region molecules, the VHH antigen binding region/immunoglobulin heavy chain constant region molecules (wild type or variant), the VHH antigen binding region/immunoglobulin Fc molecules (wild type or variant). The chelating agent allows for the immunoconjugate to be loaded with an appropriate radioisotope, such as a beta emitter or an alpha emitter. The chelator can be coupled to the immunoconjugate by the antigen binding region, the heavy chain constant region, the immunoglobulin Fc region, or any combination thereof. Such coupling can suitably be by a covalent attachment to one or more amino acids of the immunoconjugate, the antigen binding region, the heavy chain constant region, the immunoglobulin Fc region, or any combination thereof.

In one embodiment, a chelating agent of the immunoconjugate is covalently linked to an antigen binding region, the heavy chain constant region, the immunoglobulin Fc region, or any combination thereof. In one embodiment, a chelating agent is covalently linked to the antigen binding region, the heavy chain constant region, the immunoglobulin Fc region, or any combination thereof directly (e.g., without the use of a spacer, stretcher or linker). In one embodiment the chelating agent is covalently linked to the antigen binding arm through a linker that is covalently linked to the chelating agent and covalently linked to the antigen binding arm. In one embodiment, the linker is hydrophilic (e.g., a PEG chain). In one embodiment, the linker is hydrophobic (e.g., an alkyl or alkene chain). Chelators may be linked or coupled to the immunoconjugates as described in Sadiki, A. et al. "Site-specific conjugation of native antibody." *Antibody Therapeutics* 2020, 3, 271-284.

In some embodiments, the immunoconjugate is formed through the attachment of the chelator-linker in a site-specific manner, directed into a specific amino acid or glycan residue. In some embodiments, the site-specific conjugation involves directed functionalization of a specific lysine residue in the framework region with the chelator-linker. In other embodiments, this residue may be functionalized with a different reactive functional group which then reacts in a second step with chelator-linker to furnish the immunoconjugate. In some embodiments, this reactive functional group is thiopropionate.

In some embodiments, a non-native cysteine residue is engineered into the framework of the antibody as a site for thiol directed conjugation to furnish the immunoconjugate. In some embodiments, other non-native amino acids or an amino acid sequence is engineered into the framework to serve as the attachment site for the chelator-linker or for a secondary reactive group upon which the chelator-linker will be conjugated to furnish the immunoconjugate.

In some embodiments, a non-natural amino acid containing a cross-linking group is engineered into the framework for attachment of the chelator-linker. In some embodiments, this non-natural amino-acid contains an azide.

In some embodiments, the chelator-linker is attached to a glutamine residue through the action of a transglutaminase enzyme. In other embodiments, a secondary reactive group is attached by transglutaminase upon which the chelator-linker is added to furnish the immunoconjugate.

In some embodiments, the chelator-linker is attached by modifying one or more N-glycans with a reactive functional group through the action of a glycosidase, then conjugation of the chelator-linker to that site. In some embodiments, the glycan is modified through the action of β-galactosidase. In some embodiments, the glycan is modified with a glycoside that contains an azide for attachment of a properly functionalized chelator-linker.

In one embodiment, the immunoconjugate comprises more than one chelating agent, which are the same or different.

In one embodiment, an immunoconjugate having more than one chelating agent has more than one chelating agent attached to the same antigen binding arm.

In one embodiment, an immunoconjugate having more than one chelating agent and less than eleven chelating agents has more than two chelating agents, more than three chelating agents, more than four chelating agents, more than five chelating agents, more than six chelating agents, more than seven chelating agents, more than eight chelating agents, or more than nine chelating agents. In one embodiment, the chelating agents are the same. In one embodiment, each antigen binding arm is linked directly or indirectly to more than one chelating agent.

In one embodiment, the chelating agent comprises a radioisotope chelating component and a functional group that allows for covalent attachment to the antigen binding arm. In one embodiment, the functional group is directly attached to the radioisotope chelating component. In one embodiment the chelating agent further comprises a linker between the functional group and the radioisotope chelating component.

In one embodiment, the radioisotope chelating component comprises DOTA or a DOTA derivative. In one embodiment, the radioisotope chelating component comprises DOTAGA. In one embodiment, the radioisotope chelating component comprises macropa or a macropa derivative. In one embodiment, the radioisotope chelating component comprises Py4 Pa or a Py4 Pa derivative.

In an embodiment, the chelating agent of an immunoconjugate is not attached to the antigen binding region in the antigen binding arm of the immunoconjugate.

In one embodiment, the chelating agent of the immunoconjugate is non-covalently associated with an antigen binding arm. In an embodiment, the chelator is not associated with the antigen binding region in the antigen binding arm of the immunoconjugate.

In one embodiment, the chelating agent comprises DOTA or a DOTA derivative. In one embodiment, the chelating agent comprises DOTAGA. In one embodiment, the chelating agent comprises macropa or a macropa derivative. In one embodiment, the chelating agent comprises Py4 Pa or a Py4 Pa derivative. In one embodiment, the chelating agent comprises siderocalin or a siderocalin derivative.

In certain embodiments, described herein is an immunoconjugate coupled to a chelating agent. In certain embodiments, the chelating agent is a radioisotope chelating agent. In certain embodiments, the radioisotope chelating agent is selected from the list consisting of: tetraazacyclododecane-1,4,7,10-tetraacetic acid (DOTA), α-(2-Carboxyethyl)-1,4,7,10-tetraazacyclododecane-1,4,7,10-tetraacetic acid (DOTAGA), or (Py4 Pa). In certain embodiments, the radioisotope chelating agent is DOTA. In certain embodiments, the radioisotope chelating agent is DOTAGA. In certain embodiments, the radioisotope chelating agent is Py4 Pa. In certain embodiments, the radioisotope wherein the radioisotope chelating agent is directly coupled to the antigen binding region and/or the immunoglobulin heavy chain constant region. In certain embodiments, the radioisotope chelating agent is coupled to the antigen binding region or the immunoglobulin heavy chain constant region by a linker. In certain embodiments, the linker is selected from: 6-maleimidocaproyl (MC), maleimidopropanoyl (MP), valine-citrulline (val-cit), alanine-phenylalanine (ala-phe), p-aminobenzyloxycarbonyl ( PAB), and those resulting from conjugation with linker reagents: N-Succinimidyl 4-(2-pyridylthio) pentanoate forming linker moiety 4-mercaptopentanoic acid (SPP), Succinimidyl 4-(N-maleimidomethyl) cyclohexane-1-carboxylate (SMCC), N-Succinimidyl 4-(2-pyridyldithio)butanoate (SPDB), N-Succinimidyl (4-iodoacetyl) aminobenzoate (SIAB), polyethylene glycol (PEG), a polyethylene glycol polymers (PEGn), and S-2-(4-Isothiocyanatobenzyl) (SCN). In certain embodiments, the linker is selected from: polyethylene glycol (PEG), a polyethylene glycol polymers (PEG), and S-2-(4-isothiocyanatobenzyl) (SCN). In certain embodiments, the linker is PEG5. In certain embodiments, the linker is SCN. In certain embodiments, the radioisotope chelating agent is a linker-chelator selected from the list consisting of: TFP-Ad-PEG5-DOTAGA, p-SCN-Bn-DOTA, p-SCN-Ph-Et-Py4 Pa, and TFP-Ad-PEG5-Ac-Py4 Pa.

The chelator may be conjugated at a ratio of protein or antigen binding region and/or the immunoglobulin heavy chain constant. In certain embodiments, the radioisotope chelating agent is coupled to the antigen binding region and/or the immunoglobulin heavy chain constant region at a ratio of 1:1 to 8:1. In certain embodiments, the radioisotope chelating agent is coupled to the antigen binding region and/or the immunoglobulin heavy chain constant region at a ratio of 1:1 to 6:1. In certain embodiments, the radioisotope chelating agent is coupled to the antigen binding region and/or the immunoglobulin heavy chain constant region at a ratio of 2:1 to 6:1.

In some embodiments, the immunoconjugate of the present disclosure comprises a linker, such as, e.g., to join an antigen binding arm to a chelating agent (interchangeably, "chelator") or to a radioisotope or to cargo (e.g., a cytotoxin). A linker may comprise one or more linker components. In some embodiments, the immunoconjugate of this disclosure is engineered to have a terminal lysine available for conjugation to the chelating agent or linker.

For example, a bifunctional chelator is used to conjugate a radioisotope to a radioisotope delivery platform of this disclosure to create an immunoconjugate of this disclosure. (See e.g., Scheinberg D, McDevitt M, *Curr Radiopharm* 4: 306-20 (2011)). Examples of bifunctional chelators known in the art include DOTA, DTPA, DO3A-NHS, DOTAGA-NHS, DOTAGA-anhydride DOTAGA-TFP, p-SCN-Bn-DOTA, p-SCN-Bn-DTPA, p-SCN-Bn-CHX'A"-DTPA, p-SCN-Bn-TCMC, macropa-NCS, crown, p-SCN-Ph-Et-Py4 Pa, 3,2-HOPO, and TCMC.

Examples of bifunctional chelators are 1,4,7,10-tetraazacyclododecane-1,4,7,10-tetraacetic acid (DOTA), diethylene triamine pentaacetic acid (DTPA), and related analogs of the aforementioned. Such chelators are suitable for coordinating metal ions like α and β-emitting radionuclides.

In some embodiments the chelating agent of an immunoconjugate or radioimmunoconjugate of this disclosure is selected from the group comprising bifunctional chelator, DOTA, DO3A-NHS, DOTAGA-NHS, DOTAGA-anhydride DOTAGA-TFP, p-SCN-Bn-DOTA, p-SCN-Bn-DTPA, p-SCN-Bn-CHX-A"-DTPA, p-SCN-Bn-TCMC, macropa-NCS (Thiele N A, et al. Angew. Chem. Int. Ed. 56:1 (2017)), crown (Yang H, et al. Chem. Eur. J. 26:11435 (2020)), P—SCN-Ph-Et-Py4 Pa (Li L, et al. Bioconjugate Chem. ASAP (2020)), 3,2-HOPO (Wickstroem K, et al. Int. J. Rad. Onc. Biol. Phys. 105:410 (2019)) (For a review of these and other bifunctional chelators See e.g., Price E W and Orvig C Chem. Soc. Rev., 2014, 43:260 (2014) and Brechbiel M W Q. J. Nucl. Med. Mol. Imaging 52:166 (2008)).

In some embodiments the chelating agent of an immunoconjugate or radioimmunoconjugate of this disclosure is selected from the group consisting of bifunctional chelator, DOTA, DO3A-NHS, DOTAGA-NHS, DOTAGA-anhydride DOTAGA-TFP, p-SCN-Bn-DOTA, p-SCN-Bn-DTPA, p-SCN-Bn-CHX-A"-DTPA, p-SCN-Bn-TCMC, macropa-NCS (Thiele N A, et al. Angew. Chem. Int. Ed. 56:1 (2017)), crown (Yang H, et al. Chem. Eur. J. 26:11435 (2020)), P—SCN-Ph-Et-Py4 Pa (Li L, et al. Bioconjugate Chem. ASAP (2020)), 3,2-HOPO (Wickstroem K, et al. Int. J. Rad. Onc. Biol. Phys. 105:410 (2019)) (For a review of these and other bifunctional chelators see e.g., Price E W and Orvig C Chem. Soc. Rev., 2014, 43:260 (2014) and Brechbiel MW Q. J. Nucl. Med. Mol. Imaging 52:166 (2008)).

For 225-Ac immunoconjugates, there are a variety of acyclic and cyclic ligands known in the art as suitable chelators (see e.g., Davis I, et al., *Nucl Med Biol* 26: 581 (1999); Chappell L, et al., *Bioconjug Chem* 11: 510 (2000); Chappell, L, et al., *Nucl Med Biol* 30: 581 (2003); McDevitt M, et al., *Appl Radiat Isot* 57: 841 (2002); Gouin S, et al., *Org Biomol Chem* 3: 453 (2005); Thiele N, et al., *Angew Chem Int Ed Engl* 56: 14712 (2017)).

In certain embodiments, the chelator is a chelator suitable for alpha emitter chelation. Some chelators suitable for alpha emitters are described in Yang et al, "Harnessing α-Emitting Radionuclides for Therapy: Radiolabeling Method Review." *J Nucl Med.* 2022 January; 63(1):5-13.

In certain embodiments the, chelator suitable for alpha emitter chelation is selected from the list consisting of: DOTA 1,4,7,10-tetraazacyclododecane-1,4,7,10-tetraacetic acid; DO3A 1,4,7-Tris(carboxymethyl)-1,4,7,10-tetraazacyclododecane; DOTAGA α-(2-Carboxyethyl)-1,4,7,10-tetraazacyclododecane-1,4,7,10-tetraacetic acid; DOTAGA anhydride (2,2',2"-(10-(2,6-dioxotetrahydro-2H-pyran-3-yl)-1,4,7,10-tetraazacyclododecane-1,4,7-triyl)triacetic acid; Py4 Pa 6,6',6"',6"''-(((pyridine-2,6-diylbis(methylene)) bis(azanetriyl))tetrakis(methylene))tetrapicolinic acid; Py4 Pa-NCS is 6,6'-((((4-isothiocyanatopyridine-2,6-diyl)bis (methylene))bis((carboxymethyl)azanediyl))bis(methylene))dipicolinic acid; Crown 2,2',2",2"'-(1,10-dioxa-4,7,13, 16-tetraazacyclooctadecane-4,7,13,16-tetrayl)tetraacetic acid; Macropa 6,6'-((1,4,10,13-tetraoxa-7,16-diazacyclooctadecane-7,16-diyl)bis(methylene))dipicolinic acid; Macropa-NCS 6-((16-((6-carboxypyridin-2-yl)methyl)-1,4,10, 13-tetraoxa-7,16-diazacyclooctadecan-7-yl)methyl)-4-isothiocyanatopicolinic acid; HEHA 1,4,7,10,13,16-hexaazacyclohexadecane-1,4,7,10,13,16-hexaacetic acid; CHXoctapa 6,6'-[(1R,2R)-1,2-Cyclohexanediylbis[[(carboxymethyl)imino]methylene]]bis[2-pyridinecarboxylic acid]; Bispa 3,7-Diazabicyclo[3.3.1]nonane-1,5-dicarboxylic acid, 7-[(6-carboxy-2-pyridinyl)methyl]-9-hydroxy-3-methyl-2,4-di-2-pyridinyl-, 1,5-dimethyl ester; Noneunpa 6,6'-(((oxybis(ethane-2,1-diyl))bis((carboxymethyl) azanediyl))bis(methylene))dipicolinic acid; and combinations thereof.

In certain embodiments, the chelator is a chelator suitable for an beta- or gamma-emitter chelation. In certain embodiments the, chelator suitable for an beta- or gamma-emitter chelation is selected from the list consisting of: DOTMA (1R,4R,7R,10R)-a, a', a", a"'-tetramethyl-1,4,7,10-tetraazacyclododecane-1,4,7,10-tetraacetic acid DOTAM (1,4,7,10-tetrakis(carbamoylmethyl)-1,4,7,10-tetraazacyclododecane); DOTPA 1,4,7,10-tetraazacyclododecane-1, 4,7,10-tetra propionic acid; DO3AM-acetic acid (2-(4,7,10-tris(2-amino-2-oxoethyl)-1,4,7,10-tetraazacyclododecan-1-yl) acetic acid); DOTP 1,4,7,10-tetraazacyclododecane-1,4,7, 10-tetra(methylene phosphonic acid); DOTMP 1,4,6,10-tetraazacyclodecane-1,4,7,10-tetramethylene phosphonic acid; DOTA-4AMP 1,4,7,10-tetraazacyclododecane-1,4,7, 10-tetrakis(acetamido-methylenephosphonic acid); CB-TE2A (1,4,8,11-tetraazabicyclo[6.6.2]hexadecane-4,11-diacetic acid); NOTA 1,4,7-triazacyclononane-1,4,7-triacetic acid; NOTP 1,4,7-triazacyclononane-1,4,7-tri(methylene phosphonic acid); TETPA 1,4,8,11-tetraazacyclotetradecane-1,4,8,11-tetrapropionic acid; TETA 1,4,8,11-tetraazacyclotetradecane-1,4,8,11-tetraacetic acid; PEPA 1,4,7,10,13-pentaazacyclopentadecane-N,N',N", N"',N""-pentaacetic acid; H4Octapa N,N'-bis(6-carboxy-2-pyridylmethyl)-ethylenediamine-N,N'-diacetic acid; H2Dedpa 1,2-[[6-(carboxy)-pyridin-2-yl]-methylamino]ethane; H6phospa N,N'-(methylenephosphonate)-N,N'-[6-(methoxycarbonyl)pyridin-2-yl]-methyl-1,2-diaminoethane; TTHA triethylenetetramine-N,N,N',N",N"',N"'-hexaacetic acid; DO2P tetraazacyclododecane dimethanephosphonic acid; HP-DO3A hydroxypropyltetraazacyclododecanetriacetic acid; EDTA ethylenediaminetetraacetic acid; DTPA diethylenetriaminepentaacetic acid; DTPA-BMA diethylenetriaminepentaacetic acid-bismethylamide; HOPO octadentate hydroxypyridinones; 3,2,3-LI(HOPO) N,N'-(butane-1,4-diyl)bis(1-hydroxy-N-(3-(1-hydroxy-6-oxo-1,6-dihydropyridine-2-carboxamido) propyl)-6-oxo-1,6-dihydropyridine-2-carboxamide); 3,2-HOPO N,N'-(((2-(4-aminobenzyl)-3-((2-(3-hydroxy-1-methyl-2-oxo-1,2-dihydropyridine-4-carboxamido)ethyl) (2-(3-hydroxy-2-oxo-1,2-dihydropyridine-4-carboxamido) ethyl)amino)propyl)azanediyl)bis(ethane-2,1-diyl))bis(3-hydroxy-1-methyl-2-oxo-1,2-dihydropyridine-4-carboxamide); Neunpa 6,6'-(((azanediylbis(ethane-2,1-diyl))bis((carboxymethyl)azanediyl))bis(methylene)) dipicolinic acid; Neunpa-NCS=6,6'-(((((4-isothiocyanatophenethyl)azanediyl)bis(ethane-2,1-diyl))bis ((carboxymethyl)azanediyl))bis(methylene))dipicolinic acid; Octapa 6,6'-((ethane-1,2-diylbis((carboxymethyl) azanediyl))bis(methylene))dipicolinic acid; Octox 2,2'-(ethane-1,2-diylbis(((8-hydroxyquinolin-2-yl)methyl) azanediyl))diacetic acid; PyPa 6,6'-(((pyridine-2,6-diylbis (methylene))bis((carboxymethyl)azanediyl))bis (methylene))dipicolinic acid; Porphyrin 21,22,23,24-Tetraazapentacyclo[16.2.1.13,6.18,11.113,16]tetracosa-1,3, 5,7,9,11(23),12,14,16,18(21),19-undecaene; Deferoxamine 30-Amino-3,14,25-trihydroxy-3,9,14,20,25-pentaazatriacontane-2,10,13,21,24-pentaone; DFO*N1-[5-(Acetylhydroxyamino)pentyl]-N26-(5-aminopentyl)-N26,5,16-trihydroxy-4,12,15,23-tetraoxo-5,11,16,22-tetraazahexacosanediamide; and combinations thereof.

Alternatively, or in addition, an isothiocyanate linker may be used, such as p-SCN-Bn-DOTA, involving a lysine residue within an immunoconjugate of this disclosure.

Exemplary linker components include 6-maleimidocaproyl ("MC"), maleimidopropanoyl ("MP"), valine-citrulline ("val-cit" or "vc"), alanine-phenylalanine ("ala-phe"), p-aminobenzyloxycarbonyl (a "PAB"), and those resulting from conjugation with linker reagents: N-Succinimidyl 4-(2-pyridylthio) pentanoate forming linker moiety 4-mercaptopentanoic acid ("SPP"), N-succinimidyl 4-(N-maleimidomethyl) cyclohexane-1 carboxylate forming linker moiety 4-((2,5-dioxopyrrolidin-1-yl)methyl)cyclohexanecarboxylic acid ("SMCC", also referred to herein as "MCC"), 2,5- dioxopyrrolidin-1-yl 4-(pyridin-2-yldisulfanyl) butanoate forming linker moiety 4-mercaptobutanoic acid ("SPDB"), N-Succinimidyl (4-iodo-acetyl) aminobenzoate ("SIAB"), ethyleneoxy —CH$_2$CH$_2$O— as one or more repeating units ("EO," "PEO," or "PEG"). Additional linker components are known in the art and some are described herein. Various linker components are known in the art, some of which are described below.

Figure 18:
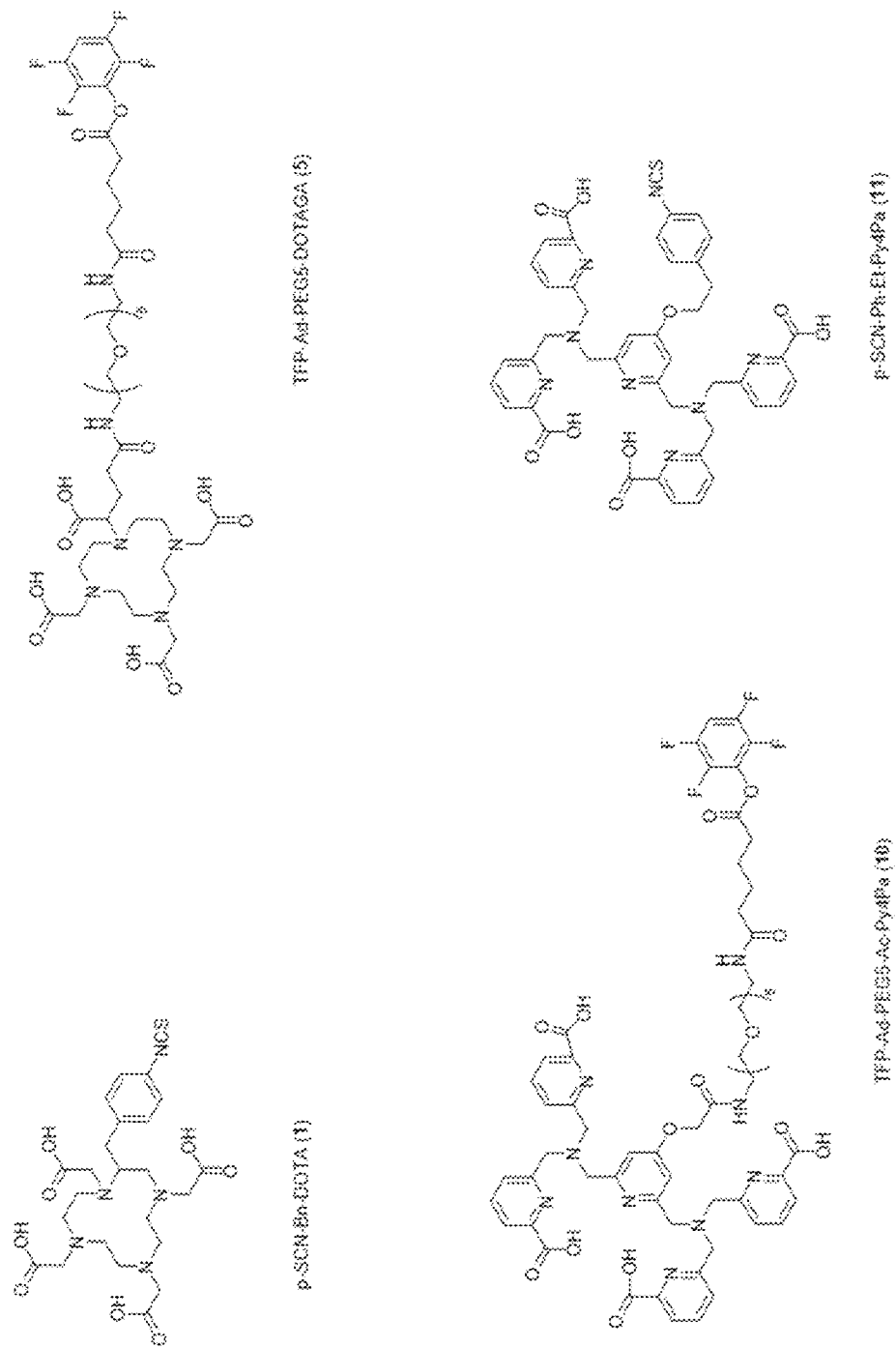
FIG. 18 shows the chemical structures of certain linker chelators described herein.

In certain embodiments, the linker is SCN. In certain embodiments, the chelating agent is a linker-chelator selected from the list consisting of: TFP-Ad-PEG5-DOTAGA, p-SCN-Bn-DOTA, p-SCN-Ph-Et-Py4 Pa, and TFP-Ad-PEG5-Ac-Py4 Pa. In certain embodiments, the chelating agent is TFP-Ad-PEG5-DOTAGA. In certain embodiments, the chelating agent is p-SCN-Bn-DOTA. In certain embodiments, the chelating agent is p-SCN-Ph-Et-Py4 Pa. In certain embodiments, the chelating agent is TFP-Ad-PEG5-Ac-Py4 Pa. Such linkers are shown in FIG. 18.

A linker may be a "cleavable linker," facilitating release of a drug in the cell. For example, an acid-labile linker (e.g., hydrazone), protease-sensitive (e.g., peptidase-sensitive) linker, photolabile linker, dimethyl linker or disulfide-containing linker (Chari et al., Cancer Research 52:127-31 (1992); U.S. Pat. No. 5,208,020) may be used.

In certain embodiments, a linker is as shown in the following formula (Formula I):

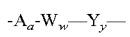

wherein A is a stretcher unit, and a is an integer from 0 to 1; W is an amino acid unit, and w is an integer from 0 to 12; Y is a spacer unit, and y is 0, 1, or 2; and Ab, D, and p are defined as above for Formula I. Exemplary embodiments of such linkers are described in US 20050238649.

In some embodiments, a linker component may comprise a "stretcher unit" that links an immunoconjugate to another linker component or to a drug moiety. Exemplary stretcher units are shown below (wherein the wavy line indicates sites of covalent attachment to an immunoconjugate):

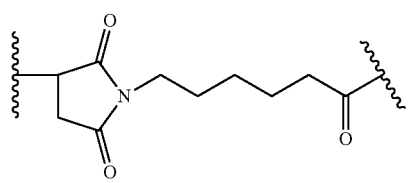

MC

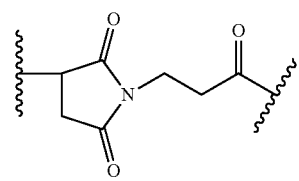

MP

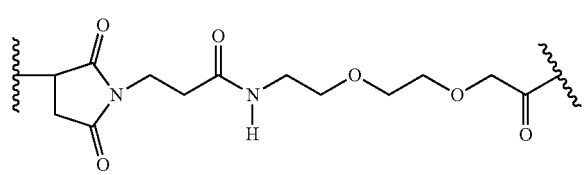

MPEG

-continued

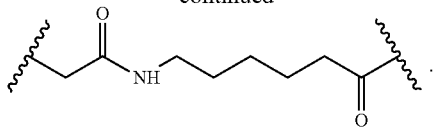

In some embodiments, a linker may be conjugated to an antibody through a cysteine bridging functionality such as ThioBridge® or DBM (dibromomaleimide). These linkers can act to restabilize intrachain disulfides after reduction and conjugation (Bird M, et al., Antibody-Drug Conjugates pp. 113-129 (2019) and Behrens C R, et al. Mol. Pharmaceutics 12:3986 (2015)). Exemplary rebridging stretcher elements are shown below (wherein the wavy line indicates sites of covalent attachment to an immunoconjugate):

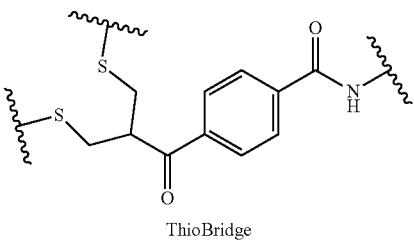

ThioBridge

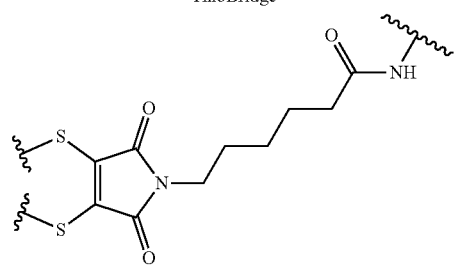

DBM

In some embodiments, a linker component may comprise an amino acid unit. In one such embodiment, the amino acid unit allows for cleavage of the linker by a protease, thereby facilitating release of the drug from the immunoconjugate upon exposure to intracellular proteases, such as lysosomal enzymes (see, e.g., Doronina et al. (2003) Nat. Biotechnol. 21: 778-4. Exemplary amino acid units include, but are not limited to, a dipeptide, a tripeptide, a tetrapeptide, and a pentapeptide. Exemplary dipeptides include: valine-citrulline (vc or val-cit), alanine-phenylalanine (af or ala-phe); phenylalanine-lysine (fk or phe-lys); or N-methyl-valine-citrulline (Me-val-cit). Exemplary tripeptides include: glycine-valine-citrulline (gly-val-cit) and glycine-glycine-glycine (gly-gly-gly). An amino acid unit may comprise amino acid residues that occur naturally, as well as minor amino acids and non-naturally occurring amino acid analogs, such as citrulline. Amino acid units can be designed and optimized in their selectivity for enzymatic cleavage by a particular enzyme, for example, a tumor-associated protease, cathepsin B, C and D, or a plasmin protease.

In some embodiments, a linker component may comprise a "spacer" unit that links the immunoconjugate to a drug moiety, either directly or by way of a stretcher unit and/or an amino acid unit. A spacer unit may be "self-immolative" or a "non-self-immolative." A "non-self-immolative" spacer unit is one in which part or all of the spacer unit remains bound to the drug moiety upon enzymatic (e.g., proteolytic)

cleavage of the ADC. Examples of non-self-immolative spacer units include, but are not limited to, a glycine spacer unit and a glycine-glycine spacer unit. Other combinations of peptidic spacers susceptible to sequence-specific enzymatic cleavage are also contemplated. For example, enzymatic cleavage of an ADC containing a glycine-glycine spacer unit by a tumor-cell associated protease would result in release of a glycine-glycine-drug moiety from the remainder of the ADC. In one such embodiment, the glycine-glycine-drug moiety is then subjected to a separate hydrolysis step in the tumor cell, thus cleaving the glycine-glycine spacer unit from the drug moiety.

A "self-immolative" spacer unit allows for release of the drug moiety without a separate hydrolysis step. In certain embodiments, a spacer unit of a linker comprises a p-aminobenzyl unit. In one such embodiment, a p-aminobenzyl alcohol is attached to an amino acid unit via an amide bond, and a carbamate, methylcarbamate, or carbonate is made between the benzyl alcohol and a cytotoxic agent (see, e.g., Hamann et al. (2005) Expert Opin. Ther. Patents (2005) 15: 1087-103. In one embodiment, the spacer unit is p-aminobenzyloxycarbonyl (PAB). In certain embodiments, the phenylene portion of a p-amino benzyl unit is substituted with Qm, wherein Q is —$C_1$-$C_8$ alkyl, —O—($C_1$-$C_8$ alkyl), -halogen, -nitro or -cyano; and m is an integer ranging from 0-4. Examples of self-immolative spacer units further include, but are not limited to, aromatic compounds that are electronically similar to p-aminobenzyl alcohol (see, e.g., US 2005/0256030 A1), such as 2-aminoimidazol-5-methanol derivatives (Hay et al. (1999) Bioorg. Med. Chem. Lett. 9: 2237) and ortho- or para-aminobenzylacetals. Spacers can be used that undergo cyclization upon amide bond hydrolysis, such as substituted and unsubstituted 4-aminobutyric acid amides (Rodrigues et al., Chemistry Biology, 1995, 2, 223); appropriately substituted bicyclo[2.2.1] and bicyclo [2.2.2] ring systems (Storm, et al., J. Amer. Chem. Soc., 1972, 94: 5815); and 2-aminophenylpropionic acid amides (Amsberry, et al., J. Org. Chem., 1990, 55: 5867). Elimination of amine-containing drugs that are substituted at the α-position of glycine (Kingsbury, et al., J. Med. Chem., 1984, 27: 1447) are also examples of self-immolative spacers useful in ADCs.

In one embodiment, a spacer unit is a branched bis (hydroxymethyl)styrene (BHMS) unit as depicted below, which can be used to incorporate and release multiple drugs.

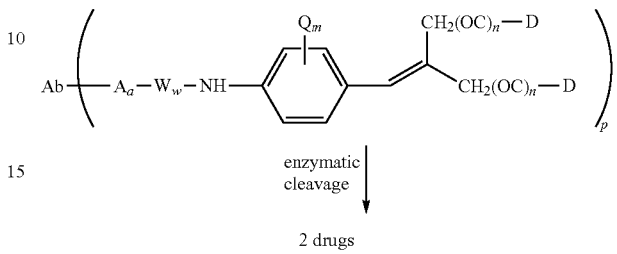

wherein Q is —$C_1$-$C_8$alkyl, —O—($C_1$-$C_8$ alkyl), -halogen, -nitro or -cyano; m is an integer ranging from 0-4; n is 0 or 1; and p ranges ranging from 1 to about 20.

In some embodiments, the immunoconjugate comprises a linker, such as, e.g., a dendritic type linker for covalent attachment of more than one drug moiety through a branching, multifunctional linker moiety to an antibody (Sun et al (2002) Bioorganic & Medicinal Chemistry Letters 12: 2213-5; Sun et al (2003) Bioorganic & Medicinal Chemistry 11: 1761-8). Dendritic linkers can increase the molar ratio of drug to antibody, i.e. loading, which is related to the potency of the ADC. Thus, where a cysteine-engineered antibody bears only one reactive cysteine thiol group, a multitude of drug moieties may be attached through a dendritic linker.

Examples of linker components and combinations thereof are shown below, which are also suitable for use in the formula above:

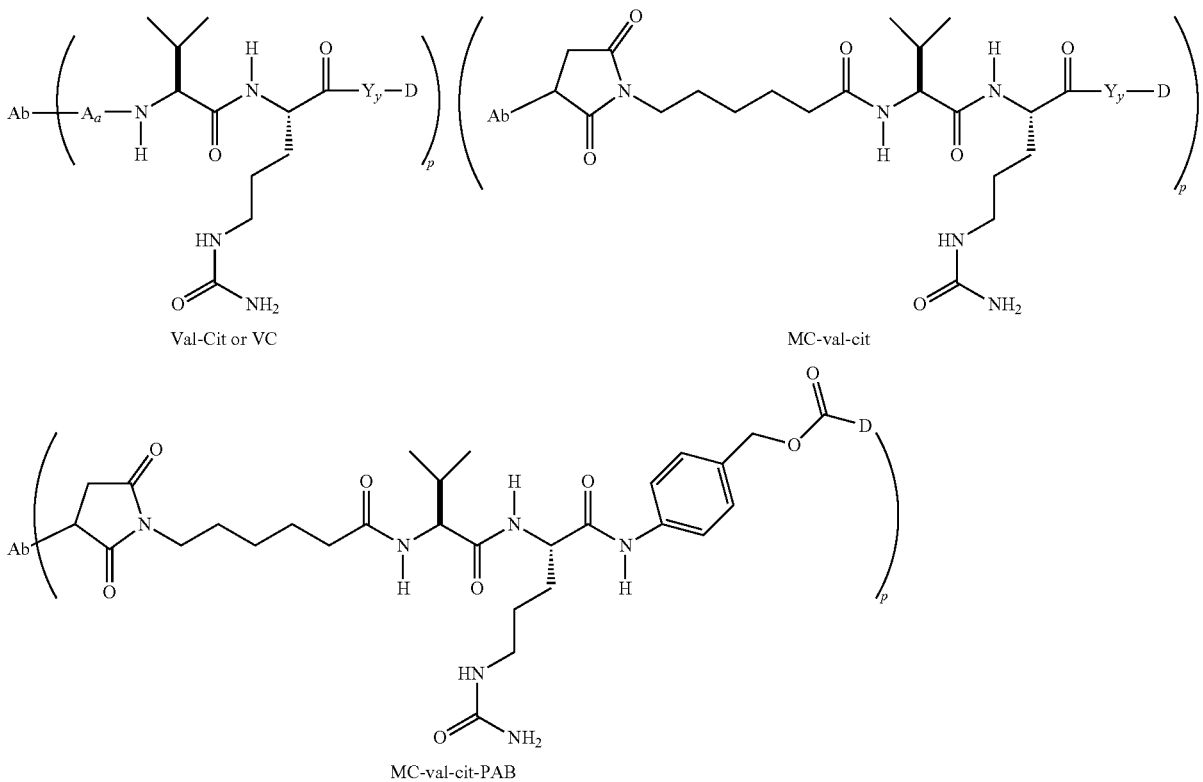

Additional non-limiting examples of linkers include those described in WO 2015095953.

Linkers components, including stretcher, spacer, and amino acid units, may be synthesized by methods known in the art, such as those described in US 20050238649.

In some embodiments the chelating agent comprises a linker and is selected from and one of the compounds described in U.S. Application No. 63/373,189, filed Aug. 22, 2022, or a U.S. non-provisional application or international application claiming priority thereto, which are hereby incorporated by reference for such compounds. In some embodiments the chelating agent comprises a linker and is selected from: Compound 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, and 1-34 of U.S. Application No. 63/373,189, filed Aug. 22, 2022, which is hereby incorporated by reference for such compounds.

In some embodiments the chelating agent comprises a linker and is selected from and one of the compounds described in U.S. Application No. 63/373,183, filed Aug. 22, 2022, or a U.S. non-provisional application or international application claiming priority thereto, which are hereby incorporated by reference for such compounds. In some embodiments the chelating agent comprises a linker and is selected from: Compound 2-1, 2-2, 2-3, 2-4, 2-5, 2-6, 2-7, 2-8, 2-9, 2-10, 2-11, 2-12, and 2-13 of U.S. Application No. 63/373,183, filed Aug. 22, 2022, which is hereby incorporated by reference for such compounds.

In some embodiments the chelating agent comprises a linker and is selected from and one of the compounds described in U.S. Application No. 63/373,190, filed Aug. 22, 2022, or a U.S. non-provisional application claiming priority thereto, which are hereby incorporated by reference for such compounds. In some embodiments the chelating agent comprises a linker and is selected from: Compound 3-1, 3-2, 3-3, 3-4, 3-5, 3-13, 3-16 of U.S. Application No. 63/373,190, filed Aug. 22, 2022, which is hereby incorporated by reference in its entirety for such compounds.

Radioimmunoconjugates

In one embodiment, this disclosure provides immunoconjugates. In one embodiment, the immunoconjugates are capable of delivering α-emitters in vivo when so labeled, linked or loaded with an α-emitter. In one embodiment, the immunoconjugates are also capable of delivering other radioisotopes (β-emitters, and/or γ-emitters), and/or other atoms in vivo, when so labeled, linked or loaded. In one embodiment, the immunoconjugates are capable of delivering imaging metals (e.g., 111-In, 89-Zr, 64-Cu, 68-Ga or 134-Ce) in vivo when so labeled, linked or loaded.

The immunoconjugates of the current disclosure may be loaded with a radioisotope for a therapeutic or diagnostic effect. In certain embodiments, the chelator may further comprise a radioisotope. In certain embodiments, the radioisotope is an alpha emitter. In certain embodiments, the radioisotope is an alpha emitter selected from the list consisting of 225-Ac, 223-Ra, 224-Ra, 227-Th, 212-Pb, 212-Bi, and 213-Bi. In certain embodiments, the radioisotope is 225-Ac. In certain embodiments, the radioisotope is an beta emitter. In certain embodiments, the radioisotope is a beta emitter selected from 177-Lu, 90-Y, 67-Cu, and 153-Sm.

Also described herein is a method of making a radioimmunoconjugate comprising loading or complexing an immunoconjugate of the current disclosure to a radioisotope. In certain embodiments, the radioisotope is an alpha emitter. In certain embodiments, the radioisotope is an alpha emitter selected from the list consisting of 225-Ac, 223-Ra, 224-Ra, 227-Th, 212-Pb, 212-Bi, and 213-Bi. In certain embodiments, the radioisotope is 225-Ac. In certain embodiments, the radioisotope is an beta emitter. In certain embodiments, the radioisotope is a beta emitter selected from 177-Lu, 90-Y, 67-Cu, and 153-Sm.

In one aspect, this disclosure provides a radioimmunoconjugate, comprising an immunoconjugate of this disclosure and an α-emitting radioisotope. In one embodiment, the α-emitting radioisotope of the radioimmunoconjugate is selected from the group comprising: 225-Ac, 223-Ra, 224-Ra, 227-Th, 212-Pb, 212-Bi, and 213-Bi. In one embodiment, the α-emitting radioisotope of the radioimmunoconjugate is selected from the group consisting of: 225-Ac, 223-Ra, 224-Ra, 227-Th, 212-Pb, 212-Bi, and 213-Bi. In one embodiment, the α-emitting radioisotope of the radioimmunoconjugate is 225-Ac. In one embodiment, the α-emitting radioisotope of the radioimmunoconjugate is 223-Ra. In one embodiment, the α-emitting radioisotope of the radioimmunoconjugate is 224-Ra. In one embodiment, the α-emitting radioisotope of the radioimmunoconjugate is 227-Th. In one embodiment, the α-emitting radioisotope of the radioimmunoconjugate is 212-Pb. In one embodiment, the α-emitting radioisotope of the radioimmunoconjugate is 212-Bi. In one embodiment, the α-emitting radioisotope of the radioimmunoconjugate is 213-Bi.

In some embodiments, the immunoconjugate of the present disclosure is combined with a radioisotope to provide a radioimmunoconjugate of this disclosure. In some embodiments, the radioisotope is 225-Ac, 86-Y, 90-Y, 177-Lu, 186-Re, 188-Re, 89-Sr, 153-Sm, 213-Bi, 213-Po, 212-Bi, 223-Ra, 224-Ra, 227-Th, 149-Tb, 68-Ga, 64-Cu, 67-Cu, 89-Zr, 137-Cs, 212-Pb, or 103-Pd. In some embodiments, the radioisotope is an alpha emitter, such as, e.g., 225-Ac, 223-Ra, 224-Ra, 227-Th, 212-Pb, 212-Bi, and 213-Bi. In some embodiments, the radioisotope is a beta particle emitter, such as, e.g., 177-Lu, 90-Y, 67-Cu, 153-Sm. In some embodiments, the radioisotope is both an alpha particle emitter and a beta and/or gamma particle emitter. In some embodiments, the radioisotope is both a beta particle emitter and a gamma particle and/or photon emitter. In some embodiments, the radioimmunoconjugate is labeled, linked or loaded with, and accordingly comprises, both an α-emitter and a β-emitter. In some embodiments, the radioisotope is selected for use in radio-imaging, such as, e.g., from among 68-Ga, 64-Cu, 89-Zr, 111-In, 134-Ce.

The immunoconjugates and radioimmunoconjugates of this disclosure may comprise other cargos or payloads besides a radioisotope, including various cytotoxic agents, such as, e.g., a small molecule chemotherapeutic agent, cytotoxic antibiotic, alkylating agent, antimetabolite, topoisomerase inhibitor, and/or tubulin inhibitor. For example, an immunoconjugate of this disclosure may be used to deliver a non-radioisotope cytotoxin to a target cell. Non-limiting examples of cytotoxic agents include aziridines, cisplatins, tetrazines, procarbazine, hexamethylmelamine, *vinca* alkaloids, taxanes, camptothecins, etoposide, doxorubicin, mitoxantrone, teniposide, novobiocin, aclarubicin, anthracyclines, actinomycin, bleomycin, plicamycin, mitomycin, daunorubicin, epirubicin, idarubicin, dolastatins, maytansines, docetaxel, adriamycin, calicheamicin, auristatins, pyrrolobenzodiazepine, carboplatin, 5-fluorouracil (5-FU), capecitabine, mitomycin C, paclitaxel, 1,3-Bis(2-chloroethyl)-1-nitrosourea (BCNU), rifampicin, cisplatin, methotrexate, and gemcitabine.

In some embodiments, a radioimmunoconjugate of this disclosure comprises a radioisotope selected from the group comprising 225-Ac, 86-Y, 90-Y, 177-Lu, 186-Re, 188-Re, 89-Sr, 153-Sm, 213-Bi, 213-Po, 211-At, 212-Bi, 223-Ra, 224-Ra, 227-Th, 149-Tb, 68-Ga, 64-Cu, 67-Cu, 89-Zr, 137-Cs, 212-Pb, and 103-Pd.

In some embodiments, a radioimmunoconjugate of this disclosure comprises a radioisotope selected from the group consisting of 225-Ac, 86-Y, 90-Y, 177-Lu, 186-Re, 188-Re, 89-Sr, 153-Sm, 213-Bi, 213-Po, 211-At, 212-Bi, 223-Ra, 224-Ra, 227-Th, 149-Tb, 68-Ga, 64-Cu, 67-Cu, 89-Zr, 137-Cs, 212-Pb, and 103-Pd.

In some embodiments, the radioisotope is an alpha-particle-emitting radioisotope comprises 225-Ac, 223-Ra, 224-Ra, 227-Th, 212-Pb, 212-Bi, or 213-Bi.

In some embodiments, the radioisotope is an alpha-particle-emitting radioisotope selected from the group consisting of 225-Ac, 223-Ra, 224-Ra, 227-Th, 212-Pb, 212-Bi, and 213-Bi.

In some embodiments, the immunoconjugate of the present disclosure comprises an antibody construct (used as an antigen binding region herein) comprising a humanized immunoglobulin domain(s).

Humanized forms of non-human (e.g., camelid, murine, or rabbit) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as a camelid, mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody may also comprise at least a portion of an immunoglobulin constant region (Fc), typically that of a human immunoglobulin (Jones et al., Nature, 321: 522-5 (1986); Riechmann et al., Nature, 332: 323-9 (1988); and Presta, Curr. Op. Struct. Biol., 2: 593-6 (1992)).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

According to another method, antigen binding may be restored during humanization of antibodies through the selection of repaired hypervariable regions (see, e.g., U.S. application Ser. No. 11/061,841, filed Feb. 18, 2005). The method includes incorporating non-human hypervariable regions onto an acceptor framework and further introducing one or more amino acid substitutions in one or more hypervariable regions without modifying the acceptor framework sequence. Alternatively, the introduction of one or more amino acid substitutions may be accompanied by modifications in the acceptor framework sequence.

Any cysteine residue not involved in maintaining the proper conformation of the immunoconjugate of this disclosure also may be substituted, generally with serine, to improve the oxidative stability of the molecule and prevent aberrant crosslinking. Conversely, cysteine bond(s) may be added to the immunoconjugate of this disclosure to improve its stability (particularly where the antibody is an antibody fragment such as an Fv fragment or VHH fragment).

In some embodiments, it may be desirable to create cysteine engineered immunoconjugates in which one or more residues of an immunoconjugate are substituted with cysteine residues. In some embodiments, the substituted residues occur at accessible sites of the immunoconjugate. By substituting those residues with cysteine, reactive thiol groups are thereby positioned at accessible sites of the immunoconjugate and may be used to conjugate the immunoconjugate to other moieties, such as drug moieties or linker-drug moieties. In some embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

In some embodiments, an immunoconjugate provided herein is altered to increase or decrease the extent to which the immunoconjugate is glycosylated and/or to change the glycosylation pattern. "Altering the native glycosylation pattern" is intended for purposes herein to mean deleting one or more carbohydrate moieties found in a parental immunoconjugate of this disclosure (either by removing the underlying glycosylation site or by deleting the glycosylation by chemical and/or enzymatic means), and/or adding one or more glycosylation sites that are not present in the native sequence immunoconjugate of this disclosure. In addition, the phrase includes qualitative changes in the glycosylation of the native proteins, involving a change in the nature and proportions of the various carbohydrate moieties present.

Where the immunoconjugate comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region (see e.g., Wright et al. TIBTECH 15:26-32 (1997)). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an immunoconjugate of this disclosure may be made in order to create immunoconjugate variants with certain improved properties.

Described herein in one embodiment is a radioimmunoconjugate comprising an antigen binding region and an immunoglobulin heavy chain constant region wherein the immunoglobulin heavy chain constant region comprises an immunoglobulin hinge region, a CH2 and a CH3 domain of an immunoglobulin, wherein the antigen binding region comprises a VHH, wherein the VHH comprises a heavy chain complementarity determining region 1 (HCDR1) comprising an amino acid sequence set forth in any one of SEQ ID NO: 407 to SEQ ID NO: 409; a heavy chain complementarity determining region 2 (HCDR2) comprising an amino acid sequence set forth in any one of SEQ ID NO: 410 to SEQ ID NO: 412; and a heavy chain complementarity determining region 3 (HCDR3) comprising an amino acid sequence set forth in any one of SEQ ID NO: 413 to SEQ ID NO: 415, or SEQ ID NO: 431, wherein the hinge region comprises a C220S substitution according to EU numbering, wherein the immunoglobulin heavy chain constant region comprises L234A, L235E, G237A, A330S, P331S and H435Q substitutions per EU numbering, wherein the radioimmunoconjugate comprises a chelating agent. In certain embodiments, the chelating agent comprises DOTA. In certain embodiments, the chelating agent is p-SCN-Bn-DOTA. In certain embodiments, the chelating agent is complexed to an alpha, beta, or gamma emitting radioisotope. In certain embodiments, the alpha emitting radioisotope is 225-Ac. In certain embodiments, the beta emitting radioisotope is 177-Lu. In certain embodiments, the gamma emitting radioisotope is 111-In.

Described herein in one embodiment is a radioimmunoconjugate comprising an antigen binding region and an immunoglobulin heavy chain constant region wherein the immunoglobulin heavy chain constant region comprises an immunoglobulin hinge region, a CH2 and a CH3 domain of an immunoglobulin, wherein the antigen binding region comprises a VHH, wherein the VHH comprises a heavy chain complementarity determining region 1 (HCDR1) comprising an amino acid sequence set forth in any one of SEQ ID NO: 307 to SEQ ID NO: 309; a heavy chain complementarity determining region 2 (HCDR2) comprising an amino acid sequence set forth in any one of SEQ ID NO: 310 to SEQ ID NO: 312; a heavy chain complementarity determining region 3 (HCDR3) comprising an amino acid sequence set forth in any one of SEQ ID NO: 313 to SEQ ID NO: 315, wherein the hinge region comprises a C220S substitution according to EU numbering, wherein the immunoglobulin heavy chain constant region comprises L234A, L235E, G237A, A330S, P331S and H435Q substitutions per EU numbering, wherein the radioimmunoconjugate comprises a chelating agent. In certain embodiments, the chelating agent comprises DOTA. In certain embodiments, the chelating agent is p-SCN-Bn-DOTA. In certain embodiments, the chelating agent is complexed to an alpha, beta, or gamma emitting radioisotope. In certain embodiments, the alpha emitting radioisotope is 225-Ac. In certain embodiments, the beta emitting radioisotope is 177-Lu. In certain embodiments, the gamma emitting radioisotope is 111-In.

Described herein in one embodiment is a radioimmunoconjugate comprising an antigen binding region and an immunoglobulin heavy chain constant region wherein the immunoglobulin heavy chain constant region comprises an immunoglobulin hinge region, a CH2 and a CH3 domain of an immunoglobulin, wherein the antigen binding region comprises a VHH, wherein the VHH comprises an amino acid sequence at least about 80%, 85%, 90%, 95%, 97%, 98%, or 99% identical to that set forth in SEQ ID NO: 403, wherein the hinge region comprises a C220S substitution according to EU numbering, wherein the immunoglobulin heavy chain constant region comprises L234A, L235E, G237A, A330S, P331S and H435Q substitutions per EU numbering, wherein the radioimmunoconjugate comprises a chelating agent. In certain embodiments, the chelating agent comprises DOTA. In certain embodiments, the chelating agent is p-SCN-Bn-DOTA. In certain embodiments, the chelating agent is complexed to an alpha, beta, or gamma emitting radioisotope. In certain embodiments, the alpha emitting radioisotope is 225-Ac. In certain embodiments, the beta emitting radioisotope is 177-Lu. In certain embodiments, the gamma emitting radioisotope is 111-In.

Described herein in one embodiment is a radioimmunoconjugate comprising an antigen binding region and an immunoglobulin heavy chain constant region wherein the immunoglobulin heavy chain constant region comprises an immunoglobulin hinge region, a CH2 and a CH3 domain of an immunoglobulin, wherein the antigen binding region comprises a VHH, wherein the VHH comprises an amino acid sequence set forth in SEQ ID NO: 403, wherein the hinge region comprises a C220S substitution according to EU numbering, wherein the immunoglobulin heavy chain constant region comprises L234A, L235E, G237A, A330S, P331S and H435Q substitutions per EU numbering, wherein the radioimmunoconjugate comprises a chelating agent. In certain embodiments, the chelating agent comprises DOTA. In certain embodiments, the chelating agent is p-SCN-Bn-DOTA. In certain embodiments, the chelating agent is complexed to an alpha, beta, or gamma emitting radioisotope. In certain embodiments, the alpha emitting radioisotope is 225-Ac. In certain embodiments, the beta emitting radioisotope is 177-Lu. In certain embodiments, the gamma emitting radioisotope is 111-In.

Described herein in one embodiment is a radioimmunoconjugate comprising an antigen binding region and an immunoglobulin heavy chain constant region wherein the immunoglobulin heavy chain constant region comprises an immunoglobulin hinge region, a CH2 and a CH3 domain of an immunoglobulin, wherein the antigen binding region comprises a VHH, wherein the VHH comprises an amino acid sequence at least about 80%, 85%, 90%, 95%, 97%, 98%, or 99% identical to that set forth in SEQ ID NO: 317, wherein the hinge region comprises a C220S substitution according to EU numbering, wherein the immunoglobulin heavy chain constant region comprises L234A, L235E, G237A, A330S, P331S and H435Q substitutions per EU numbering, wherein the radioimmunoconjugate comprises a chelating agent. In certain embodiments, the chelating agent comprises DOTA. In certain embodiments, the chelating agent is p-SCN-Bn-DOTA. In certain embodiments, the chelating agent is complexed to an alpha, beta, or gamma emitting radioisotope. In certain embodiments, the alpha emitting radioisotope is 225-Ac. In certain embodiments, the beta emitting radioisotope is 177-Lu. In certain embodiments, the gamma emitting radioisotope is 111-In.

Described herein in one embodiment is a radioimmunoconjugate comprising an antigen binding region and an immunoglobulin heavy chain constant region wherein the immunoglobulin heavy chain constant region comprises an immunoglobulin hinge region, a CH2 and a CH3 domain of an immunoglobulin, wherein the antigen binding region comprises a VHH, wherein the VHH comprises an amino acid sequence set forth in SEQ ID NO: 317, wherein the hinge region comprises a C220S substitution according to EU numbering, wherein the immunoglobulin heavy chain constant region comprises L234A, L235E, G237A, A330S, P331S and H435Q substitutions per EU numbering, the radioimmunoconjugate comprises a chelating agent. In certain embodiments, the chelating agent comprises DOTA.

In certain embodiments, the chelating agent is p-SCN-Bn-DOTA. In certain embodiments, the chelating agent is complexed to an alpha, beta, or gamma emitting radioisotope. In certain embodiments, the alpha emitting radioisotope is 225-Ac. In certain embodiments, the beta emitting radioisotope is 177-Lu. In certain embodiments, the gamma emitting radioisotope is 111-In.

Described herein in one embodiment is a radioimmunoconjugate comprising an antigen binding region and an immunoglobulin heavy chain constant region wherein the immunoglobulin heavy chain constant region comprises an immunoglobulin hinge region, a CH2 and a CH3 domain of an immunoglobulin, wherein the antigen binding region comprises a VHH, wherein the VHH comprises an amino acid sequence at least about 80%, 85%, 90%, 95%, 97%, 98%, or 99% identical to that set forth in SEQ ID NO: 318, wherein the hinge region comprises a C220S substitution according to EU numbering, wherein the immunoglobulin heavy chain constant region comprises L234A, L235E, G237A, A330S, P331S and H435Q substitutions per EU numbering, wherein the radioimmunoconjugate comprises a chelating agent. In certain embodiments, the chelating agent comprises DOTA. In certain embodiments, the chelating agent is p-SCN-Bn-DOTA. In certain embodiments, the chelating agent is complexed to an alpha, beta, or gamma emitting radioisotope. In certain embodiments, the alpha emitting radioisotope is 225-Ac. In certain embodiments, the beta emitting radioisotope is 177-Lu. In certain embodiments, the gamma emitting radioisotope is 111-In.

Described herein in one embodiment is a radioimmunoconjugate comprising an antigen binding region and an immunoglobulin heavy chain constant region wherein the immunoglobulin heavy chain constant region comprises an immunoglobulin hinge region, a CH2 and a CH3 domain of an immunoglobulin, wherein the antigen binding region comprises a VHH, wherein the VHH comprises an amino acid sequence set forth in SEQ ID NO: 318, wherein the hinge region comprises a C220S substitution according to EU numbering, wherein the immunoglobulin heavy chain constant region comprises L234A, L235E, G237A, A330S, P331S and H435Q substitutions per EU numbering, wherein the radioimmunoconjugate comprises a chelating agent. In certain embodiments, the chelating agent comprises DOTA. In certain embodiments, the chelating agent is p-SCN-Bn-DOTA. In certain embodiments, the chelating agent is complexed to an alpha, beta, or gamma emitting radioisotope. In certain embodiments, the alpha emitting radioisotope is 225-Ac. In certain embodiments, the beta emitting radioisotope is 177-Lu. In certain embodiments, the gamma emitting radioisotope is 111-In.

Described herein in one embodiment is a radioimmunoconjugate comprising an antigen binding region and an immunoglobulin heavy chain constant region wherein the immunoglobulin heavy chain constant region comprises an immunoglobulin hinge region, a CH2 and a CH3 domain of an immunoglobulin, wherein the antigen binding region comprises a VHH, wherein the VHH comprises an amino acid sequence at least about 80%, 85%, 90%, 95%, 97%, 98%, or 99% identical to that set forth in SEQ ID NO: 319, wherein the hinge region comprises a C220S substitution according to EU numbering, wherein the immunoglobulin heavy chain constant region comprises L234A, L235E, G237A, A330S, P331S and H435Q substitutions per EU numbering, wherein the radioimmunoconjugate comprises a chelating agent. In certain embodiments, the chelating agent comprises DOTA. In certain embodiments, the chelating agent is p-SCN-Bn-DOTA. In certain embodiments, the chelating agent is complexed to an alpha, beta, or gamma emitting radioisotope. In certain embodiments, the alpha emitting radioisotope is 225-Ac. In certain embodiments, the beta emitting radioisotope is 177-Lu. In certain embodiments, the gamma emitting radioisotope is 111-In.

Described herein in one embodiment is a radioimmunoconjugate comprising an antigen binding region and an immunoglobulin heavy chain constant region wherein the immunoglobulin heavy chain constant region comprises an immunoglobulin hinge region, a CH2 and a CH3 domain of an immunoglobulin, wherein the antigen binding region comprises a VHH, wherein the VHH comprises an amino acid sequence set forth in SEQ ID NO: 319, wherein the hinge region comprises a C220S substitution according to EU numbering, wherein the immunoglobulin heavy chain constant region comprises L234A, L235E, G237A, A330S, P331S and H435Q substitutions per EU numbering, wherein the radioimmunoconjugate comprises a chelating agent. In certain embodiments, the chelating agent comprises DOTA. In certain embodiments, the chelating agent is p-SCN-Bn-DOTA. In certain embodiments, the chelating agent is complexed to an alpha, beta, or gamma emitting radioisotope. In certain embodiments, the alpha emitting radioisotope is 225-Ac. In certain embodiments, the beta emitting radioisotope is 177-Lu. In certain embodiments, the gamma emitting radioisotope is 111-In.

Immunoconjugate Derivatives and Other Modifications

Covalent modifications of the immunoconjugates of this disclosure are included within the scope of this disclosure. One type of covalent modification includes reacting targeted amino acid residues of an immunoconjugate of this disclosure with an organic derivatizing agent that is capable of reacting with selected side chains or the N- or C-terminal residues of the immunoconjugate. Derivatization with bifunctional agents is useful, for instance, for crosslinking an immunoconjugate of this disclosure to a water-insoluble support matrix or surface for use in the method for purifying the immunconjugates of this disclosure, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W. H. Freeman & Co., San Francisco, pp. 79-86 (1983)), acetylation of the N-terminal amine, and amidation of any C-terminal carboxyl group.

In some embodiments, an immunoconjugate provided herein may be further modified to contain additional non-proteinaceous moieties that are known in the art and readily available. The moieties suitable for derivatization of the immunoconjugate include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1, 3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the immunoconjugate may vary, and if more than one polymer are attached, they can be the same or different molecules. In general, the number and/or type of polymers used for derivatization can be determined based on considerations including, but not limited to, the particular properties or functions of the immunoconjugate to be improved, whether the immunoconjugate derivative will be used in a therapy under defined conditions, etc.

PEG derivatized immunoconjugates of this disclosure may comprise linkers comprising one or more —$CH_2CH_2O$— and can be used to alter biodistribution and pharmacokinetics of the immunoconjugate. PEGs can be prepared in a polymeric form or as discrete oligomers. Bifunctionalized versions of these polymers can link immunoconjugatess with a chelating agent and/or provide additional size and/or solubility to the overall molecule. In some embodiments, the PEG derivatized immunoconjugates exhibit reduced immunogenicity compared to their un-derivatized parental molecules.

Methods of Producing the Immunoconjugates of the Present Disclosure

The present disclosure provides a composition comprising one or more of the immunoconjugates according to any of the above embodiments or described herein. In another aspect, this disclosure provides an isolated nucleic acid encoding a radioisotope delivering platform as described herein. Also provided herein are nucleic acids encoding the protein components of the immunoconjugates of the present disclosure, expression vectors comprising the aforementioned nucleic acid, and host cells comprising the aforementioned expression vectors.

In another aspect, this disclosure provides a host cell comprising a nucleic acid and/or vector as provided herein. In some embodiments, the host cell of the present disclosure is isolated or purified. In some embodiments, the host cell of the present disclosure is in a cell culture medium. The nucleic acids, expression vectors, and host cells of this disclosure may be used to produce a composition comprising one or more of the immunoconjugates of this disclosure. In some embodiments, the host cell is eukaryotic. In some embodiments, the host cell is mammalian. In some embodiments, the host cell is a Chinese Hamster Ovary (CHO) cell. In some embodiments, the host cell is prokaryotic. In some embodiments, the host cell is *E. coli.*

A description follows as to illustrative techniques for the production of the immunoconjugates and radioimmunoconjugates of the present disclosure for use in accordance with the methods of the present disclosure. In some embodiments, this disclosure provides a process for making an immunoconjugate of the present disclosure, the method comprising culturing a host cell as provided herein under conditions suitable for the expression vector encoding the radioisotope delivery platform and recovering or purifying the radioisotope delivery platform. In some embodiments, the method further comprises radiolabeling the radioisotope delivery platform with an appropriate isotope, such as, e.g., an alpha or beta particle emitter.

Immunoconjugate Production; Host Cells and Expression Vectors of this Disclosure The description below relates primarily to production of the antibody constructs of this disclosure by culturing cells transformed or transfected with a vector-containing immunoconjugate of this disclosure-encoding nucleic acid. It is, of course, contemplated that alternative methods, which are well known in the art, may be employed to prepare the antibody constructs of this disclosure. For instance, the appropriate amino acid sequence, or portions thereof, may be produced by direct peptide synthesis using solid-phase techniques (e.g., Stewart et al., *Solid-Phase Peptide Synthesis*, W. H. Freeman Co., San Francisco, CA (1969); Merrifield, J, *Am. Chem. Soc.,* 85: 2149-54 (1963)). In vitro protein synthesis may be performed using manual techniques or by automation. Automated synthesis may be accomplished, for instance, using an Applied Biosystems Peptide Synthesizer (Foster City, CA) using manufacturer's instructions. Various portions of the immunoconjugate of this disclosure may be chemically synthesized separately and combined using chemical or enzymatic methods to produce the desired immunoconjugate of this disclosure.

Antibody constructs may be produced using recombinant methods and compositions, e.g., as described in U.S. Pat. No. 4,816,567. In one embodiment, isolated nucleic acid encoding an antibody described herein is provided. Such nucleic acid may encode an amino acid sequence comprising the VH of the antibody and/or comprising the VL amino acid sequence (e.g., the light and/or heavy chains of the antibody). In a further embodiment, one or more vectors (e.g., expression vectors) comprising such nucleic acid are provided. In a further embodiment, a host cell comprising such nucleic acid is provided. In some embodiments, a host cell comprises (e.g., has been transformed with): (1) a vector comprising a nucleic acid that encodes an amino acid sequence comprising the VH of the antibody. In some other embodiments, a host cell comprises: (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g., a Chinese Hamster Ovary (CHO) cell or lymphoid cell (e.g., YO, NSO, Sp20 cell). In one embodiment, a method of making an immunoconjugate of this disclosure is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an immunoconjugate of the present disclosure, nucleic acid encoding an antibody construct, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and/or light chains of the antibody). Nucleic acid molecules encoding amino acid sequence of the immunoconjugate of the present disclosure (including sequence variants) may be prepared by a variety of methods known to the skilled worker. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody construct.

Manipulation of Host Cells for Immunoconjugate Production

Host cells are transfected or transformed with expression or cloning vectors described herein for immunoconjugate of this disclosure production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Suitable host cells for cloning or expression of immunoconjugate-encoding nucleic acids and vectors include prokaryotic or eukaryotic cells described herein. For example, antibodies may be produced in bacteria, in particular when glycosylation and Fc effector function are not needed. For expression of antibody fragments and polypeptides in bacteria, see e.g., U.S. Pat. Nos. 5,648,237; 5,789,199; 5,840,523; and Charlton, *Methods in Molecular Biology*, Vol. 248 (B.K.C. Lo, ed., Humana Press, Totowa, NJ, 2003), pp. 245-254, describing expression of antibody fragments in *E. coli*). After expression, the immunoconjugate may be isolated from the bacterial cell paste in a soluble fraction and can be further purified.

Selection and Use of a Replicable Vector

For recombinant production of a radioisotope delivery platform of this disclosure, the nucleic acid (e.g., cDNA or genomic DNA) encoding it is isolated and inserted into a replicable vector for further cloning (amplification of the DNA) or for expression. DNA encoding the immunoconjugate is readily isolated and sequenced using conventional procedures (e.g., by using oligonucleotide probes that are capable of binding specifically to genes encoding the heavy and light chains of an antibody). Many vectors are available. The choice of vector depends in part on the host cell to be used. Generally, suitable host cells are of either prokaryotic or eukaryotic (generally mammalian) origin.

The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The immunoconjugate of the invention may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the immunoconjugate encoded by a DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Purification of an Immunoglobulin-Derived Structure of this Disclosure

Forms of immunoconjugate of this disclosure may be recovered from culture medium or from host cell lysates. If membrane-bound, it can be released from the membrane using a suitable detergent solution (e.g., Triton-X 100) or by enzymatic cleavage. Cells employed in expression of immunoconjugate of this disclosure can be disrupted by various physical or chemical means, such as freeze-thaw cycling, sonication, mechanical disruption, or cell lysing agents.

It may be desired to purify immunoconjugate of this disclosure from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the immunoconjugate of this disclosure. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular immunoconjugate of this disclosure produced.

When using recombinant techniques, the immunoconjugate can be produced intracellularly, in the periplasmic space, or directly secreted into the medium. If the immunoconjugate is produced intracellularly, as a first step, the particulate debris, either host cells or lysed fragments, are removed, for example, by centrifugation or ultrafiltration. Carter et al., *Bio/Technology* 10: 163-7 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the immunoconjugate is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The immunoconjugate composition prepared from the cells can be purified using, for example, hydroxylapatite chromatography, gel electrophoresis, dialysis, and affinity chromatography, with affinity chromatography being a preferred purification technique. The suitability of protein A as an affinity ligand depends on the species and isotype of any immunoglobulin Fc domain that is present in the immunoconjugate. Protein A can be used to purify antibodies that are based on human γ1, γ2 or γ4 heavy chains (Lindmark et al., *J. Immunol. Meth.* 62: 1-13 (1983)). Protein G is recommended for all mouse isotypes and for human γ3 (Guss et al., *EMBO J.* 5: 15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the immunoconjugate comprises a CH3 domain, the Bakerbond ABX™ resin (J. T. Baker, Phillipsburg, NJ) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the immunoconjugate to be recovered.

Following any preliminary purification step(s), the mixture comprising the immunoconjugate of interest and contaminants may be subjected to low pH hydrophobic interaction chromatography using an elution buffer at a pH between about 2.5-4.5, and generally at low salt concentrations (e.g., from about 0-0.25M salt).

Immunoconjugation Using Chelators and/or Linkers

Methods for affixing a radioisotope to an immunoconjugate or antibody construct (i.e., "labeling" an antibody with a radioisotope) are well known to the skilled worker. Certain of these methods are described, for example, in WO 2017/155937.

Bifunctional chelators, such as, e.g., DOTA, DTPA, and related analogs are suitable for coordinating metal ions like α and β-emitting radionuclides. For example, these chelating molecules can be linked to the targeting molecule by forming a new amide bond between an amine on the antibody construct (e.g., a functional group of a lysine residue) and a carboxylate on the DOTA/DTPA. In the case of peptide synthesis, characterization and purification of the linker addition can be part of the overall synthesis of an antibody platform or immunoconjugate for radioisotope conjugation.

For some embodiment, the method of producing an immunoconjugate involves a click chemistry step described by Poty, S et al., *Chem Commun.* (Camb) 54: 2599 (2018).

For some embodiments, a peptide may be biosynthesized or may be synthesized by chemical amino acid synthesis using suitable amino acid precursors involving, for example, fluorine-19 in place of hydrogen. In some embodiments, radiolabels may be incorporated into peptide. In some embodiments, radiolabels may be linked to peptide. The IODOGEN method (Fraker et al. (1978) *Biochem Biophys Res Commun.* 80: 49-57 can be used to incorporate iodine-123. "Monoclonal Antibodies in Immunoscintigraphy" (Chatal, CRC Press 1989) describes other methods in detail.

Characterization of Immunoconjugates of the Present Invention

Immunoconjugates of the present invention may be identified, screened for, or characterized for their physical/chemical properties and/or biological activities by various assays known in the art. The immunoconjugates and antibody constructs of this disclosure may be characterized for their physical/chemical properties and/or biological activities by various assays known in the art. Immunoconjugates of this disclosure can be characterized by a series of assays including, but not limited to, polypeptide sequence determination, amino acid analysis, non-denaturing size exclusion high pressure liquid chromatography (HPLC), mass spectrometry, ion exchange chromatography, and papain digestion.

Antigen Binding

An immunoconjugate of the present invention may be tested for its antigen binding activity by methods known in the art, e.g., ELISA, Western blot, etc. The binding affinity of an antibody can, for example, be determined by the Scatchard analysis described in Munson et al., *Anal Biochem.* 107: 220 (1980). Further, the antigen binding ability of an immunoconjugate of this disclosure may be quantitated using methods known in the art, e.g., a quantitative ELISA, quantitative Western blot, surface plasmon resonance assay, and/or a Scatchard analysis.

In one embodiment, the KD of an immunoconjugate is measured using a radiolabeled antigen ELISA performed with the immunoconjugate. According to another embodiment, the $K_D$ is measured by using surface-plasmon resonance assays using a BIACORE®-2000 or a BIACORE®-3000 instrument (BIAcore, Inc., Piscataway, N.J.), e.g., using immobilized antigen CM5 chips at 25° C. and 10 response units.

In another aspect, binding competition assays may be used to identify immunoconjugates that compete for binding to the same antigen, or epitope thereof. In some embodiments, such a competing antibody binds to the same epitope (e.g., a linear or a conformational epitope) of an immunoconjugate of this disclosure (see e.g., Harlow and Lane (1988) *Antibodies: A Laboratory Manual*, Ch. 14 (Cold Spring Harbor Laboratory, Cold Spring Harbor, NY)).

The epitope and/or contact residues within an antigen bound by an immunoconjugate of this disclosure can be identified or mapped using methods known to the skilled worker. Detailed exemplary methods for mapping an epitope to which an antibody binds are provided in Morris (1996) "Epitope Mapping Protocols," in *Methods in Molecular Biology* (3$^{rd}$ ed., Humana Press, Totowa, NJ).

Pharmaceutical Compositions and Formulations of the Present Disclosure

As will be recognized by the person of ordinary skill in the art, certain teachings herein below apply to immunoconjugates and radioimmunoconjugates of this disclosure, notwithstanding the specific textual reference to one type of invention, and such applications are embraced in entirety by this disclosure.

In another aspect, this disclosure provides a composition comprising an immunoconjugate or radioimmunoconjugate of the present invention. This disclosure further provides pharmaceutical compositions and formulations comprising at least one immunoconjugate of the present invention and at least one pharmaceutically acceptable excipient or carrier. In some embodiments, a pharmaceutical formulation comprises (1) an immunoconjugate or radioimmunoconjugate of this disclosure, and (2) a pharmaceutically acceptable carrier.

An immunoconjugate or radioimmunoconjugate is formulated in any suitable form for delivery to a target cell/tissue. Pharmaceutical formulations of an immunoconjugate of the present invention are prepared by mixing such immunoconjugate having the desired degree of purity with one or more optional pharmaceutically acceptable carriers, diluents, and/or excipients (*Remington's Pharmaceutical Sciences* 16th edition, Osol, A. Ed. (1980)), in the form of lyophilized formulations or aqueous solutions. Pharmaceutically acceptable carriers, diluents, and excipients are generally nontoxic to recipients at the dosages and concentrations employed, and include, but are not limited to: sterile water, buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG).

Pharmaceutical formulations to be used for in vivo administration are generally sterile. This is readily accomplished by filtration through sterile filtration membranes.

Examples of lyophilized antibody formulations are described in U.S. Pat. No. 6,267,958. Aqueous antibody formulations include those described in U.S. Pat. No. 6,171, 586 and WO 2006/044908, the latter formulations including a histidine-acetate buffer.

Pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). In one aspect, a sHASEGP is combined with one or more additional glycosaminoglycanases such as chondroitinases.

The formulation herein may also contain more than one active ingredient as necessary for the particular indication being treated, preferably those with complementary activities that do not adversely affect each other. Such active ingredients are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methyl-methacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences,* 16th edition, Osol, A. Ed. (1980).

In some embodiments, immunoconjugates may be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the immunoconjugate are prepared by methods known in the art, such as described in Epstein et al., *Proc Natl Acad Sci USA* 82: 3688 (1985); Hwang et al., *Proc Natl Acad Sci USA* 77: 4030 (1980); U.S. Pat. Nos. 4,485,045 and 4,544,545; and WO1997/38731 published Oct. 23, 1997. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. A chemotherapeutic agent is optionally contained within the liposome (see Gabizon et al., *J. National Cancer Inst.* 81: 1484 (1989)). Liposomes with enhanced circulation time are disclosed in U.S. Pat. No. 5,013,556.

Sustained-release preparations may be prepared. Suitable examples of sustained-release preparations include semipermeable matrices of solid hydrophobic polymers containing the antibody, which matrices are in the form of shaped articles, e.g., films, or microcapsules.

Methods of Using Immunoconjugates and Radioimmunoconjugates and Compositions Thereof In one aspect, this disclosure provides a method of treating a disease, disorder, or condition in a patient in need thereof, the method comprising administering to a subject in need thereof a pharmaceutically effective amount of an immunoconjugate or radioimmunoconjugate or composition of the present invention. For some further embodiments, the method is for inhibiting the growth and/or the killing of a cancer cell or tumor. In another aspect, this disclosure provides for the use of an immunoconjugate described herein for the preparation and/or manufacture of a medicament for treating a disease, disorder, or condition in a subject, such as, e.g., cancer.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

In one embodiment, an immunoconjugate or radioimmunoconjugate or composition of this disclosure can be used in a method for binding target antigen in an individual suffering from a disorder associated with increased target antigen expression and/or activity, the method comprising administering to the individual the immunoconjugate or radioimmunoconjugate or composition such that target antigen in the individual is bound. In one embodiment, the target antigen is human target antigen, and the individual is a human individual. An immunoconjugate or radioimmunoconjugate or composition of this disclosure can be administered to a human for therapeutic purposes. Moreover, an immunoconjugate or radioimmunoconjugate or composition of this disclosure can be administered to a non-human mammal expressing target antigen with which the immunoconjugate or radioimmunoconjugate cross-reacts (e.g., a primate, pig, rat, or mouse) for veterinary purposes or as an animal model of human disease. Regarding the latter, such animal models may be useful for evaluating the therapeutic efficacy of an immunoconjugate or radioimmunoconjugate or composition of this disclosure (e.g., testing of dosages and time courses of administration).

An immunoconjugate or radioimmunoconjugate or composition of this disclosure (and any additional therapeutic agent or adjuvant) can be administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the antibody is suitably administered by pulse infusion, particularly with declining doses of the antibody. Dosing can be by any suitable route, e.g., by injections, such as intravenous or subcutaneous injections, depending in part on whether the administration is brief or chronic.

Immunoconjugate or radioimmunoconjugate or compositions of this disclosure would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The immunoconjugates of this disclosure are administered to a human patient, in accordance with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. For some embodiments, intravenous or subcutaneous administration of the immunoconjugate or radioimmunoconjugate or composition of this disclosure is preferred.

For the prevention or treatment of disease, the dosage and mode of administration will be chosen by the physician according to known criteria. The appropriate dosage of immunoconjugate or radioimmunoconjugate or composition of this disclosure will depend on the type of disease to be treated, as defined above, the severity and course of the disease, whether the immunoconjugate or radioimmunoconjugate or composition of this disclosure is administered for preventive or therapeutic purposes, previous therapy, the patient's clinical history and response to the immunoconjugate or radioimmunoconjugate or composition, and the discretion of the attending physician. The immunoconjugate or radioimmunoconjugate or composition of this disclosure is suitably administered to the patient at one time or over a series of treatments. Preferably, the immunoconjugate or radioimmunoconjugate or composition is administered by intravenous infusion or by subcutaneous injections. Depending on the type and severity of the disease, about 1 µg/kg to about 50 mg/kg body weight (e.g., about 0.1-15 mg/kg/dose) of immunoconjugate or radioimmunoconjugate or composition can be an initial candidate dosage for administration to the patient, whether, for example, by one or more separate administrations, or by continuous infusion. A dosing regimen can comprise administering an initial loading dose of about 4 mg/kg, followed by a weekly maintenance dose of about 2 mg/kg of the immunoconjugate or radioimmunoconjugate or composition of this disclosure. However, other dosage regimens may be useful. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. The progress of this therapy can be readily monitored by conventional methods and assays and based on criteria known to the physician or other persons of skill in the art.

The dose and administration schedule may be selected and adjusted based on the level of disease, or tolerability in the subject, which may be monitored during the course of treatment. The conjugates of the present invention may administered once per day, once per week, multiple times per week, but less than once per day, multiple times per month but less than once per day, multiple times per month but less than once per week, once per month, once per five weeks, once per six weeks, once per seven weeks, once per eight weeks, once per nine weeks, once per ten weeks, or intermittently to relieve or alleviate symptoms of the disease. Administration may continue at any of the disclosed intervals until remission of the tumor or symptoms of the cancer being treated. Administration may continue after remission or relief of symptoms is achieved where such remission or relief is prolonged by such continued administration.

For some embodiments, the effective amount of the immunoconjugate or radioimmunoconjugate or composition may be provided as a single dose.

The Immunoconjugates and radioimmunoconjugates of the present invention maybe used in combination with conventional and/or novel methods of treatment or therapy or separately as a monotherapy.

Immunoconjugates and radioimmunoconjugates of the present invention may (i) inhibit the growth or proliferation of a cell to which they bind; (ii) induce the death of a cell to which they bind; (iii) inhibit the delamination of a cell to which they bind; (iv) inhibit the metastasis of a cell to which they bind; or (v) inhibit the vascularization of a tumor comprising a cell to which they bind. In this context, "inhibiting cell growth or proliferation" means decreasing a cell's growth or proliferation by at least 10%, 20%, 30%, 40%, 50%, 60%, 70%, 80%, 90%, 95%, or 100%, and includes inducing cell death.

By way of example, an immunoconjugate that inhibits the growth of a tumor cell is one that results in measurable growth inhibition of a tumor cell (e.g., a cancer cell). In one embodiment, an immunoconjugate or radioimmunoconjugate of this disclosure is capable of inhibiting the growth of cancer cells displaying the antigen bound by the immunoconjugate or radioimmunoconjugate. Preferred growth inhibitory immunoconjugates or radioimmunoconjugates inhibit growth of antigen-expressing tumor cells by greater than 20%, preferably from about 20% to about 50%, and even more preferably, by greater than 50% (e.g., from about 50% to about 100%) as compared to the appropriate control, the control typically being tumor cells not treated with the immunoconjugate or radioimmunoconjugate being tested.

For some embodiments, a majority of the immunoconjugate or radioimmunoconjugate or composition administered to a subject typically consists of non-labeled immunoconjugate, with the minority being labeled radioimmunoconjugate. The ratio of labeled radioimmunoconjugate to non-labeled immunoconjugate can be adjusted using known methods. Thus, accordingly to certain aspects of the present invention, the immunoconjugate/radioimmunoconjugate may be provided in a total protein amount of up to 100 mg, such as less than 60 mg, or from 5 mg to 45 mg, or a total protein amount of between 0.1 µg/kg to 1 mg/kg patient weight, such as 1 µg/kg to 1 mg/kg patient weight, or 10 µg/kg to 1 mg/kg patient weight, or 100 µg/kg to 1 mg/kg patient weight, or 0.1 µg/kg to 100 µg/kg patient weight, or 0.1 µg/kg to 50 µg/kg patient weight, or 0.1 µg/kg to 10 µg/kg patient weight, or 0.1 µg/kg to 40 µg/kg patient weight, or 1 µg/kg to 40 µg/kg patient weight, or 0.1 mg/kg to 1.0 mg/kg patient weight, such as from 0.2 mg/kg patient weight to 0.6 mg/kg patient weight.

In certain embodiments, the immunoconjugate/radioimmunoconjugate may be administered from about 0.5 mg/kg to about 30 mg/kg. In certain embodiments, the immunoconjugate/radioimmunoconjugate may be administered from about 0.5 mg/kg to about 1 mg/kg, about 0.5 mg/kg to about 2 mg/kg, about 0.5 mg/kg to about 5 mg/kg, about 0.5 mg/kg to about 10 mg/kg, about 0.5 mg/kg to about 3 mg/kg, about 0.5 mg/kg to about 4 mg/kg, about 0.5 mg/kg to about 5 mg/kg, about 0.5 mg/kg to about 10 mg/kg, about 0.5 mg/kg to about 20 mg/kg, about 0.5 mg/kg to about 30 mg/kg, about 1 mg/kg to about 2 mg/kg, about 1 mg/kg to about 5 mg/kg, about 1 mg/kg to about 10 mg/kg, about 1 mg/kg to about 3 mg/kg, about 1 mg/kg to about 4 mg/kg, about 1 mg/kg to about 5 mg/kg, about 1 mg/kg to about 10 mg/kg, about 1 mg/kg to about 20 mg/kg, about 1 mg/kg to about 30 mg/kg, about 2 mg/kg to about 5 mg/kg, about 2 mg/kg to about 10 mg/kg, about 2 mg/kg to about 3 mg/kg, about 2 mg/kg to about 4 mg/kg, about 2 mg/kg to about 5 mg/kg, about 2 mg/kg to about 10 mg/kg, about 2 mg/kg to about 20 mg/kg, about 2 mg/kg to about 30 mg/kg, about 5 mg/kg to about 10 mg/kg, about 5 mg/kg to about 3 mg/kg, about 5 mg/kg to about 4 mg/kg, about 5 mg/kg to about 5 mg/kg, about 5 mg/kg to about 10 mg/kg, about 5 mg/kg to about 20 mg/kg, about 5 mg/kg to about 30 mg/kg, about 10 mg/kg to about 3 mg/kg, about 10 mg/kg to about 4 mg/kg, about 10 mg/kg to about 5 mg/kg, about 10 mg/kg to about 10 mg/kg, about 10 mg/kg to about 20 mg/kg, about 10 mg/kg to about 30 mg/kg, about 3 mg/kg to about 4 mg/kg, about 3 mg/kg to about 5 mg/kg, about 3 mg/kg to about 10 mg/kg, about 3 mg/kg to about 20 mg/kg, about 3 mg/kg to about 30 mg/kg, about 4 mg/kg to about 5 mg/kg, about 4 mg/kg to about 10 mg/kg, about 4 mg/kg to about 20 mg/kg, about 4 mg/kg to about 30 mg/kg, about 5 mg/kg to about 10 mg/kg, about 5 mg/kg to about 20 mg/kg, about 5 mg/kg to about 30 mg/kg, about 10 mg/kg to about 20 mg/kg, about 10 mg/kg to about 30 mg/kg, or about 20 mg/kg to about 30 mg/kg. In certain embodiments, the immunoconjugate/radioimmunoconjugate may be administered at about 0.5 mg/kg, about 1 mg/kg, about 2 mg/kg, about 5 mg/kg, about 10 mg/kg, about 3 mg/kg, about 4 mg/kg, about 5 mg/kg, about 10 mg/kg, about 20 mg/kg, or about 30 mg/kg. In certain embodiments, the immunoconjugate/radioimmunoconjugate may be administered at least about 0.5 mg/kg, about 1 mg/kg, about 2 mg/kg, about 5 mg/kg, about 10 mg/kg, about 3 mg/kg, about 4 mg/kg, about 5 mg/kg, about 10 mg/kg, or about 20 mg/kg. In certain embodiments, the immunoconjugate/radioimmunoconjugate may be administered at most about 1 mg/kg, about 2 mg/kg, about 5 mg/kg, about 10 mg/kg, about 3 mg/kg, about 4 mg/kg, about 5 mg/kg, about 10 mg/kg, about 20 mg/kg, or about 30 mg/kg.

In some embodiments, the method comprises administering the effective amount of a radioimmunoconjugate comprising 225-Ac that is from 0.01 to 0.1 mCi, or 0.1 mCi to 1.0 mCi, or from 1.0 mCi to 2.0 mCi, or from 2.0 mCi to 4.0 mCi.

In some embodiments, the method comprises administering the effective amount of a radioimmunoconjugate comprising 225-Ac that is from 0.1 µCi/kg to 2.0 µCi/kg subject weight, or from 0.1 µCi/kg to 1.0 µCi/kg subject weight, or from 1.0 µCi/kg to 3.0 µCi/kg subject weight, or from 3.0 µCi/kg to 10.0 µCi/kg subject weight, or from 10.0 µCi/kg to 20.0 µCi/kg subject weight, or from 10.0 µCi/kg to 30.0 µCi/kg subject weight.

In certain embodiments, the effective amount of 225-Ac is about 0.1 microcurie to about 20 microcurie. In certain embodiments, the effective amount of 225-Ac is about 0.1 microcurie to about 0.2 microcurie, about 0.1 microcurie to about 0.5 microcurie, about 0.1 microcurie to about 1 microcurie, about 0.1 microcurie to about 2 microcurie, about 0.1 microcurie to about 3 microcurie, about 0.1 microcurie to about 4 microcurie, about 0.1 microcurie to about 5 microcurie, about 0.1 microcurie to about 10 microcurie, about 0.1 microcurie to about 20 microcurie, about 0.2 microcurie to about 0.5 microcurie, about 0.2 microcurie to about 1 microcurie, about 0.2 microcurie to about 2 microcurie, about 0.2 microcurie to about 3 microcurie, about 0.2 microcurie to about 4 microcurie, about 0.2 microcurie to about 5 microcurie, about 0.2 microcurie to about 10 microcurie, about 0.2 microcurie to about 20 microcurie, about 0.5 microcurie to about 1 microcurie, about 0.5 microcurie to about 2 microcurie, about 0.5 microcurie to about 3 microcurie, about 0.5 microcurie to about 4 microcurie, about 0.5 microcurie to about 5 microcurie, about 0.5 microcurie to about 10 microcurie, about 0.5 microcurie to about 20 microcurie, about 1 microcurie to about 2 microcurie, about 1 microcurie to about 3 microcurie, about 1 microcurie to about 4 microcurie, about 1 microcurie to about 5 microcurie, about 1 microcurie to about 10 microcurie, about 1 microcurie to about 20 microcurie, about 2 microcurie to about 3 microcurie, about 2 microcurie to about 4 microcurie, about 2 microcurie to about 5 microcurie, about 2 microcurie to about 10 microcurie, about 2 microcurie to about 20 microcurie, about 3 microcurie to about 4 microcurie, about 3 microcurie to about 5 microcurie, about 3 microcurie to about 10 microcurie, about 3 microcurie to about 20 microcurie, about 4 microcurie to about 5 microcurie, about 4 microcurie to about 10 microcurie, about 4 microcurie to about 20 microcurie, about 5 microcurie to about 10 microcurie, about 5 microcurie to about 20 microcurie, or about 10 microcurie to about 20 microcurie. In certain embodiments, the effective amount of 225-Ac is about 0.1 microcurie, about 0.2 microcurie, about 0.5 microcurie, about 1 microcurie, about 2 microcurie, about 3 microcurie, about 4 microcurie, about 5 microcurie, about 10 microcurie, or about 20 microcurie. In certain embodiments, the effective amount of 225-Ac is at least about 0.1 microcurie, about 0.2 microcurie, about 0.5 microcurie, about 1 microcurie, about 2 microcurie, about 3 microcurie, about 4 microcurie, about 5 microcurie, or about 10 microcurie. In certain embodiments, the effective amount of 225-Ac is at most about 0.2 microcurie, about 0.5 microcurie, about 1 microcurie, about 2 microcurie, about 3 microcurie, about 4 microcurie, about 5 microcurie, about 10 microcurie, or about 20 microcurie. According to aspects where the radioisotope of the radioimmunoconjugate is 111-In, the effective amount is below, for example, 15.0 mCi (i.e., where the amount of 111-In administered to the subject delivers a total body radiation dose of below 15.0 mCi).

According to aspects where the radioisotope of the radioimmunoconjugate is 111-In, the effective amount is below 15.0 mCi, below 14.0 mCi, below 13.0 mCi, below 12.0 mCi, below 11.0 mCi, below 10.0 mCi., below 9.0 mCi, below 8.0 mCi, below 7.0 mCi, below 6.0 mCi, below 5.0 mCi, below 4.0 mCi, below 3.5 mCi, below 3.0 mCi, below 2.5 mCi, below 2.0 mCi, below 1.5 mCi, below 1.0 mCi, below 0.5 mCi, below 0.4 mCi, below 0.3 mCi, below 0.2 mCi, or below 0.1 mCi.

According to aspects where the radioisotope of the radioimmunoconjugate is 111-In, the effective amount is from 0.1 mCi to 1.0 mCi, from 0.1 mCi to 2.0 mCi, from 1.0 mCi to 2.0 mCi, from 1.0 mCi to 3.0 mCi, from 1.0 mCi to 4.0 mCi, from 1.0 mCi to 5.0 mCi, from 1.0 mCi to 10.0 mCi, from 1.0 mCi to 15.0 mCi, from 1.0 mCi to 20.0 mCi, from 2.0 mCi to 3.0 mCi, from 3.0 mCi to 4.0 mCi, from 4.0 mCi to 5.0 mCi, from 5.0 mCi to 10.0 mCi, from 5.0 mCi to 15.0 mCi, from 5.0 mCi to 20.0 mCi, from 6.0 mCi to 14.0 mCi, from 7.0 mCi to 13.0 mCi, from 8.0 mCi to 12.0 mCi, from 9.0 mCi to 11.0 mCi, or from 10.0 mCi to 15.0 mCi.

According to aspects where the radioisotope of the radioimmunoconjugate is 111-In, the effective amount is 15.0 mCi, 14.0 mCi, 13.0 mCi, 12.0 mCi, 11.0 mCi, 10.0 mCi, 9.0 mCi, 8.0 mCi, 7.0 mCi, 6.0 mCi, 5.0 mCi, 4.0 mCi, 3.5 mCi, 3.0 mCi, 2.5 mCi, 2.0 mCi, 1.5 mCi, 1.0 mCi, 0.5 mCi, 0.4 mCi, 0.3 mCi, 0.2 mCi, or 0.1 mCi.

According to aspects where the radioisotope of the radioimmunoconjugate is 225-Ac, the effective amount is below, for example, 30.0 µCi/kg (i.e., where the amount of 225-Ac administered to the subject delivers a radiation dose of below 30.0 µCi per kilogram of subject's body weight).

According to aspects where the radioisotope of the radioimmunoconjugate is 225-Ac, the effective amount is below 30 µCi/kg, 25 µCi/kg, 20 µCi/kg, 17.5 µCi/kg, 15.0 µCi/kg, 12.5 Ci/kg, 10.0 µCi/kg, 9 µCi/kg, 8 µCi/kg, 7 µCi/kg, 6 µCi/kg, 5 µCi/kg, 4.5 µCi/kg, 4.0 µCi/kg, 3.5 µCi/kg, 3.0 µCi/kg, 2.5 µCi/kg, 2.0 µCi/kg, 1.5 µCi/kg, 1.0 µCi/kg, 0.9 µCi/kg, 0.8 µCi/kg, 0.7 µCi/kg, 0.6 µCi/kg, 0.5 µCi/kg, 0.4 µCi/kg, 0.3 µCi/kg, 0.2 µCi/kg, 0.1 µCi/kg, or 0.05 µCi/kg.

According to aspects where the radioisotope of the radioimmunoconjugate is 225-Ac, the effective amount is from 0.05 µCi/kg to 0.1 µCi/kg, from 0.1 µCi/kg to 0.2 µCi/kg, from 0.2 µCi/kg to 0.3 µCi/kg, from 0.3 µCi/kg to 0.4 µCi/kg, from 0.4 µCi/kg to 0.5 µCi/kg, from 0.5 µCi/kg to 0.6 µCi/kg, from 0.6 µCi/kg to 0.7 µCi/kg, from 0.7 µCi/kg to 0.8 µCi/kg, from 0.8 µCi/kg to 0.9 µCi/kg, from 0.9 µCi/kg to 1.0 µCi/kg, from 1.0 µCi/kg to 1.5 µCi/kg, from 1.5 µCi/kg to 2.0 µCi/kg, from 2.0 µCi/kg to 2.5 µCi/kg, from 2.5 µCi/kg to 3.0 µCi/kg, from 3.0 µCi/kg to 3.5 µCi/kg, from 3.5 µCi/kg to 4.0 µCi/kg, from 4.0 µCi/kg to 4.5 µCi/kg, or from 4.5 µCi/kg to 5.0 µCi/kg.

According to aspects where the radioisotope of the radioimmunoconjugate is 225-Ac, the effective amount is 0.05 µCi/kg, 0.1 µCi/kg, 0.2 µCi/kg, 0.3 µCi/kg, 0.4 µCi/kg, 0.5 µCi/kg, 0.6 µCi/kg, 0.7 µCi/kg, 0.8 µCi/kg, 0.9 µCi/kg, 1.0 µCi/kg, 1.5 µCi/kg, 2.0 µCi/kg, 2.5 µCi/kg, 3.0 µCi/kg, 3.5 µCi/kg, 4.0 µCi/kg or 4.5 µCi/kg, 5.0 µCi/kg, 6.0 µCi/kg, 7.0 µCi/kg, 8.0 µCi/kg, 9.0 µCi/kg, 10.0 µCi/kg, 12.5 µCi/kg, 15.0 µCi/kg, 17.5 µCi/kg, 20.0 µCi/kg, 25 µCi/kg, or 30 µCi/kg.

In certain embodiments where the radioisotope of the radioimmunoconjugate is 177-Lu the effective amount is from 0.1 µCi to 100 mCi per meter squared of body surface area.

In certain embodiments where the radioisotope of the radioimmunoconjugate is 177-Lu the effective amount is from 1 mCi to 100 mCi per meter squared of body surface area. In certain embodiments, the effective amount is about 1 per meter squared to about 100 per meter squared. In certain embodiments, the effective amount is about 1 per meter squared to about 5 per meter squared, about 1 per meter squared to about 10 per meter squared, about 1 per meter squared to about 15 per meter squared, about 1 per meter squared to about 20 per meter squared, about 1 per meter squared to about 25 per meter squared, about 1 per meter squared to about 75 per meter squared, about 1 per meter squared to about 100 per meter squared, about 5 per meter squared to about 10 per meter squared, about 5 per meter squared to about 15 per meter squared, about 5 per meter squared to about 20 per meter squared, about 5 per meter squared to about 25 per meter squared, about 5 per meter squared to about 75 per meter squared, about 5 per meter squared to about 100 per meter squared, about 10 per meter squared to about 15 per meter squared, about 10 per meter squared to about 20 per meter squared, about 10 per meter squared to about 25 per meter squared, about 10 per meter squared to about 75 per meter squared, about 10 per meter squared to about 100 per meter squared, about 15 per meter squared to about 20 per meter squared, about 15 per meter squared to about 25 per meter squared, about 15 per meter squared to about 75 per meter squared, about 15 per meter squared to about 100 per meter squared, about 20 per meter squared to about 25 per meter squared, about 20 per meter squared to about 75 per meter squared, about 20 per meter squared to about 100 per meter squared, about 25 per meter squared to about 75 per meter squared, about 25 per meter squared to about 100 per meter squared, or about 75 per meter squared to about 100 per meter squared. In certain embodiments, the effective amount is about 1 per meter squared, about 5 per meter squared, about 10 per meter squared, about 15 per meter squared, about 20 per meter squared, about 25 per meter squared, about 75 per meter squared, or about 100 per meter squared. In certain embodiments, the effective amount is at least about 1 per meter squared, about 5 per meter squared, about 10 per meter squared, about 15 per meter squared, about 20 per meter squared, about 25 per meter squared, or about 75 per meter squared. In certain embodiments, the effective amount is at most about 5 per meter squared, about 10 per meter squared, about 15 per meter squared, about 20 per meter squared, about 25 per meter squared, about 75 per meter squared, or about 100 per meter squared.

According to certain aspects of the present invention, a preparation of radioimmunoconjugate of this disclosure, or a composition thereof (e.g., a pharmaceutical composition), may comprise a radiolabeled fraction (radioimmunoconjugate) and an unlabeled fraction (immunoconjugate), wherein the ratio of labeled:unlabeled may be from about 1:1000 to 1:1.

Moreover, the pharmaceutical compositions may be provided as a single dose composition tailored to a specific patient, i.e., as a patient specific therapeutic composition, wherein the amount of labeled and unlabeled immunoconjugate (labeled immunoconjugate, for clarity, being the same as radioimmunoconjugate herein) in the composition may depend on at least a patient weight, height, body surface area, age, gender, and/or disease state or health status. As such, a total volume of the patient specific therapeutic composition may be provided in a vial that is configured to be wholly administered to the patient in one treatment session, such that little to no composition remains in the vial after administration.

Currently, depending on the stage of the cancer, cancer treatment involves one or a combination of the following therapies: surgery to remove the cancerous tissue, radiation therapy, and chemotherapy. Therapy using radioimmunoconjugate of this disclosure (interchangeably, "radiolabeled immunoconjugate") may be especially desirable in elderly patients who do not tolerate the toxicity and side effects of chemotherapy well and in metastatic disease where radiation therapy has limited usefulness. For some embodiments, therapy using radiolabeled immunoconjugate of this disclosure are useful to alleviate target antigen-expressing cancers upon initial diagnosis of the disease or during relapse.

In some embodiments, determining whether a cancer is amenable to treatment by methods disclosed herein involves detecting the presence of the target antigen in a subject or in a sample from a subject. To determine target antigen expression in a cancer, various detection assays are available. In one embodiment, target antigen overexpression is analyzed by immunohistochemistry (IHC). Parrafin embedded tissue sections from a tumor biopsy are subjected to the IHC assay and accorded a target antigen staining intensity criteria. Alternatively, or additionally, FISH assays such as the INFORM® (sold by Ventana, AZ, U.S.A.) or PATHVISION® (Vysis, IL, U.S.A.) may be carried out on formalin-fixed, paraffin-embedded tumor tissue to determine the extent (if any) of target antigen overexpression in the tumor.

Target antigen overexpression or amplification may be evaluated using an in vivo detection assay, e.g., by administering a molecule (such as an antibody construct or immunoconjugate of this disclosure) which binds the molecule to be detected and is tagged with a detectable label (e.g., a radioactive isotope or a fluorescent label) and externally scanning the patient for localization of the label.

An immunoconjugate or radioimmunoconjugate of this disclosure may be used in, for example, in vitro, ex vivo, and in vivo methods. In one aspect, this disclosure provides methods for inhibiting cell growth or proliferation, either in vivo or in vitro, the method comprising exposing a cell to an immunoconjugate or radioimmunoconjugate of this disclosure under conditions permissive for binding of the immunoconjugate or radioimmunoconjugate to a target antigen. The immunoconjugate or radioimmunoconjugate of this disclosure may also (i) inhibit the growth or proliferation of a cell to which they bind; (ii) induce the death of a cell to which they bind; (iii) inhibit the delamination of a cell to which they bind; (iv) inhibit the metastasis of a cell to which they bind; or (v) inhibit the vascularization of a tumor comprising a cell to which they bind.

In one aspect, this disclosure provides a method of killing an antigen expressing cell, the method comprising contacting the cell with an immunoconjugate or radioimmunoconjugate of the present invention (or a composition thereof). This method can be used, e.g., to kill, deplete, or eliminate target antigen-expressing cells from a population of mixed cells. This method can be used, e.g., to kill, deplete, or eliminate target antigen-expressing cells from a population of mixed cells as a step in the purification of other cells. This method can be performed in vitro or in vivo, including ex vivo on primary patient cell or tissue compositions to prepare such compositions for transplantation.

In one aspect, an immunoconjugate or radioimmunoconjugate of this disclosure is used to treat or prevent a cell proliferative disorder. In certain embodiments, the cell proliferative disorder comprises a solid tumor cancer. A solid tumor cancer is a cancer comprising an abnormal mass of tissue, e.g., carcinomas and sarcomas. In certain other embodiments, the cell proliferative disorder comprises a liquid tumor cancer or hematological cancer, Used interchangeably, such cancers present in the body fluid, e.g., leukemias and lymphomas. In certain embodiments, the cell proliferative disorder is associated with increased expression and/or activity of a target antigen. For example, in certain embodiments, the cell proliferative disorder is associated with increased expression of target antigen on the surface of a cell. In certain embodiments, the cell proliferative disorder is a tumor or a cancer. In certain embodiments, the cell proliferative disorder comprises a solid tumor cancer. A solid tumor cancer is a cancer comprising an abnormal mass of tissue, e.g., carcinomas and sarcomas. In certain other embodiments, the cell proliferative disorder comprises a liquid tumor cancer or hematological cancer, Used interchangeably, such cancers present in the body fluid, e.g., leukemias and lymphomas.

In one aspect, this disclosure provides methods for treating a cell proliferative disorder comprising administering to an individual an effective amount of an immunoconjugate or radioimmunoconjugate of this disclosure.

In addition to direct cell killing of target cells expressing cell-surface antigen specifically bound by the immunoconjugate or radioimmunoconjugate of this disclosure, the immunoconjugate or radioimmunoconjugate of the present invention optionally may be used for delivery of additional cargos to the vicinity of or the interiors of target cells. The delivery of additional exogenous materials may be used, e.g., for cytotoxic, cytostatic, information gathering, and/or diagnostic functions. Non-cytotoxic variants of the immunoconjugate or radioimmunoconjugate of this disclosure, or optionally toxic variants, may be used to deliver cargos to and/or label the interiors of cells expressing the target antigen. Non-limiting examples of cargos include cytotoxic agents, detection-promoting agents, and small molecule chemotherapeutic agents.

As described herein, in some embodiments, the antibody constructs, immunoconjugates, radioimmunoconjugates and targeted imaging complexes of the present invention have various non-therapeutic applications. In some embodiments, the compositions of this disclosure may be used to identify patient populations predicted to benefit from a specific therapeutic approach or modality, such as, e.g., treatment with an immunoconjugates or radioimmunoconjugates of this disclosure. In some embodiments, the compositions of this disclosure can be useful for staging of target antigen expressing cancers (e.g., by radioimaging) or as prognostic indicators of disease progression. In some embodiments, the compositions are also useful for detection and quantitation of a target epitope in vitro, e.g., in an ELISA or a Western blot, as well as purification or immunoprecipitation of a target antigen from cells or a tissue sample.

For some embodiments, the immunoconjugate or radioimmunoconjugate of this disclosure is used in a method to detect the presence of or level of an antigen, such as, e.g., in vitro in a biological sample or in vivo using an imagine technique. Immunoconjugate and radioimmunoconjugate detection can be achieved via different techniques known to the skilled worker and as described herein, e.g., IHC and PET imaging. When an immunoconjugate or radiolabeled immunoconjugate of this disclosure is used for detection, it may comprise a radioactive atom for scintigraphic studies, for example 99m-Tc or 111-In.

Another embodiment of the present invention is directed to a method of diagnosing the presence of a tumor in a subject, wherein the method comprises (a) contacting a test sample comprising tissue cells obtained from the mammal with an immunoconjugate that binds to a target antigen and (b) detecting the formation of a complex between the immunoconjugate and the target antigen in the test sample, wherein the formation of a complex is indicative of the presence of a tumor in the mammal. Optionally, the immunoconjugate is detectably labeled, attached to a solid support, or the like, and/or the test sample of tissue cells is obtained from an individual suspected of having a cancerous tumor.

In some embodiments, the immunoconjugates of the present invention, including compositions comprising the aforementioned and/or provided herein are useful for detecting the presence of a target antigen, e.g., in vivo or in a biological sample. The immunoconjugates of this disclosure can be used in a variety of different assays, including but not limited to ELISA, bead-based immunoassays, and mass spectrometry.

Kits and Articles of Manufacture of the Present Invention

Another aspect of the present invention is an article of manufacture containing materials useful for the treatment, prevention and/or diagnosis of diseases and disorders characterized by target antigen-expressing cells (e.g., a cancer cell). The article of manufacture of this disclosure comprises a container and a label or package insert on or associated with the container. Suitable containers include, for example, bottles, vials, syringes, etc. The containers may be formed from a variety of materials such as glass or plastic. The container holds a composition which is effective for treating, preventing and/or diagnosing the cancer condition and may have a sterile access port (for example the container may be an intravenous solution bag or a vial having a stopper pierceable by a hypodermic injection needle). At least one active agent in the composition is an immunoconjugate of this disclosure. The label or package insert indicates that the composition is used for treating cancer. The label or package insert will further comprise instructions for administering the immunoconjugate composition to the cancer patient. Additionally, the article of manufacture may further comprise a second container comprising a pharmaceutically-acceptable buffer, such as bacteriostatic water for injection (BWFI), phosphate-buffered saline, Ringer's solution and dextrose solution. The article of manufacture may further include other materials desirable from a commercial and user standpoint, including other buffers, diluents, filters, needles, and syringes.

In another aspect, this disclosure provides a kit comprising any of the immunoconjugates described herein and an additional reagent or pharmaceutical device. In some further embodiments, the kit comprises a composition as provided herein (e.g., a pharmaceutical or diagnostic composition). Another aspect of the present invention is a kit useful for various purposes, e.g., target antigen-expressing cell killing; for target antigen-expressing cell detection; quantification, purification, or immunoprecipitation of target antigen from cells.

In some embodiments, the kit of this disclosure is an immunoassay kit for specifically detecting an antigen in a biological sample, comprising: (a) an immunoconjugate as described herein and/or a composition thereof; and (b) instructions for detecting said immunoconjugate. A target antigen detection assays of the present invention can be provided in the form of a kit. In some embodiments, such a kit comprises an immunoconjugate of the present invention, or a composition comprising the aforementioned, such as one described herein. The kit may further comprise a solid support for the capture reagents, which may be provided as a separate element or to which the capture reagents are already immobilized. For isolation and purification of a target antigen, the kit may contain an immunoconjugate of this disclosure coupled to beads (e.g., sepharose beads). This disclosure provides kits that contain an antibody for the detection and/or quantitation of target antigen in vitro, e.g., in an ELISA or a Western blot. In some embodiments, the capture reagents (e.g., the immunoconjugate of this disclosure) are coated on or attached to a solid material (e.g., to beads, a microtiter plate, or a comb). The detectable antibodies may be labeled antibodies detected directly or unlabeled antibodies that are detected by labeled antibodies directed against the unlabeled antibodies, such as, e.g., antibodies raised in a different species. Where the label is an enzyme, the kit will ordinarily include substrates and cofactors required by the enzyme; where the label is a fluorophore, a dye precursor that provides the detectable chromophore; and where the label is biotin, an avidin such as avidin, streptavidin, or streptavidin conjugated to HRP or β-galactosidase with MUG.

As with the article of manufacture of this disclosure, the kit of this disclosure comprises a container and a label or package insert on or associated with the container. The container holds a composition comprising at least one immunoconjugate of this disclosure. Additional containers may be included that contain, e.g., diluents and buffers, control immunconjugates or antibodies. The label or package insert may provide a description of the composition as well as instructions for the intended in vitro or detection use. The kit also typically contains additives such as stabilizers, washing and incubation buffers, and the like for performing the assay method(s). The components of the kit will be provided in predetermined ratios, with the relative amounts of the various reagents suitably varied to provide for concentrations in solution of the reagents that substantially maximize the sensitivity of the assay(s). Particularly, the reagents may be provided as dry powders, usually lyophilized, including excipients, which on dissolution will provide for a reagent solution having the appropriate concentration for combining with the sample to be tested.

The present invention is further illustrated by the following non-limiting examples of immunoconjugates comprising the aforementioned structures and functions, in particular platforms having VHH polypeptides, a molecular weight between 60 and 110 kDa, a serum half-life of less than 96 hours, which in some embodiments exhibit enhanced stability during the temperatures required for certain radiolabeling processes relative to other antibody fragment platforms, and which in some embodiments exhibit decreased loss of targeting capacity due to radiolysis as compared to other possible delivery platforms.

Certain Definitions

In this description, certain specific details are set forth in order to provide a thorough understanding of various embodiments. However, one skilled in the art will understand that the embodiments provided may be practiced without these details. Unless the context requires otherwise, throughout the specification and claims which follow, the word "comprise" and variations thereof, such as, "comprises" and "comprising" are to be construed in an open, inclusive sense, that is, as "including, but not limited to." As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. Further, headings provided herein are for convenience only and do not interpret the scope or meaning of the claimed embodiments.

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001). The skilled worker will recognize many methods and materials similar or equivalent to those described herein, which could be used in the practice of the present invention. Indeed, the present invention is in no way limited to the methods and materials described. For purposes of the present invention, some terms are defined below.

As used in the specification and the appended claims, the terms "a," "an" and "the" include both singular and the plural referents unless the context clearly dictates otherwise.

Throughout this specification, the term "including" is used to mean "including but not limited to." "Including" and "including but not limited to" are used interchangeably.

The term "about" as used herein refers to the usual error range for the respective value readily known to the skilled person in this technical field. Reference to "about" a value or parameter herein includes (and describes) embodiments that are directed to that value or parameter per se. The term "about" when used before a numerical designation, e.g., a numerical temperature, time, amount, or concentration, including a range, indicates approximations which may vary by ±10%.

The term "amino acid residue" or "amino acid" includes reference to an amino acid that is incorporated into a protein, polypeptide, and/or peptide. The term "polypeptide" includes any polymer of amino acids or amino acid residues. The term "polypeptide sequence" refers to a series of amino acids or amino acid residues which physically comprise a polypeptide and can be any length. A "protein" is a macromolecule comprising one or more polypeptides or polypeptide "chains." A "peptide" is a small polypeptide of a size of 2 to 20 amino acid residues. The term "amino acid sequence" refers to a series of amino acids or amino acid residues which physically comprise a peptide or polypeptide depending on the length. Unless otherwise indicated, polypeptide and protein sequences disclosed herein are written from left to right representing their order from an amino terminus to a carboxy terminus.

The terms "amino acid," "amino acid residue," "amino acid sequence," or polypeptide sequence include naturally occurring amino acids (including L and D isosteriomers) and, unless otherwise limited, also include known analogs of natural amino acids that can function in a similar manner as the common natural amino acids, such as selenocysteine, pyrrolysine, N-formylmethionine, gamma-carboxyglutamate, hydroxyprolinehypusine, pyroglutamic acid, and selenomethionine (see, e.g., Ho J et al., *ACS Synth Biol* 5: 163-71 (2016); Wang Y, Tsao M, *Chembiochem* 17: 2234-9 (2016)). The amino acids referred to herein are described by shorthand designations as follows in Table A:

As used herein, the term "radioisotope" includes, but is not limited to, an alpha emitting isotope (interchangeably, α-emitting isotope), beta-emitting isotope (interchangeably, β-emitting isotope), and/or gamma-emitting isotope (interchangeably, γ-emitting isotope), such as, e.g., any one of 86-Y, 90-Y, 177-Lu, 186-Re, 188-Re, 89-Sr, 153-Sm, 225-Ac, 213-Bi, 213-Po, 212-Bi, 223-Ra, 224-Ra, 227-Th, 149-Tb, 68-Ga, 64-Cu, 67-Cu, 89-Zr, 137-Cs, 212-Pb, 103-Pd, 111-In, 89-Zn, 123-I, and 99m-Tc.

As used herein, the term "radioimmunoconjugate" refers to a molecular complex comprising (1) an immunoconjugate according to the present disclosure and (2) a radioisotope. In a preferred embodiment, the radioisotope is an α-emitting radioisotope. In another embodiment, the radioisotope is a β-emitting radioisotope. In another embodiment, the radioisotope is a γ-emitting isotope. In another embodiment, this disclosure provides radioimmunoconjugates comprising α-emitting and β-emitting radioisotopes. The term "radioconjugate" is used interchangeably with the term "radioimmunoconjugate" herein. In one embodiment, the radioisotope is associated with a chelating agent of the radioimmunoconjugate. In one embodiment, the radioisotope is directly linked to the immunoconjugate.

As used herein, the term "immunoconjugate" refers to a molecular complex comprising an at least one antigen binding region derived from an antibody (e.g., variable regions or complementarity determining regions) further coupled to at least one non-antibody derived molecule, such as a chelator or cytotoxic agent. Non-antibody derived molecules may for example be conjugated to one or more lysine or cysteine resides of the antigen binding region or to a constant region coupled (by peptide linkage or otherwise) to the antigen binding region. In some embodiments, the immunoconjugate further comprises a chelating agent (interchangeably, "chelator"). In one embodiment, an immunoconjugate comprises an antibody construct of this disclosure linked directly or indirectly to a cytotoxic agent or radioisotope.

The immunoconjugates and radioimmunoconjugates described herein comprise antigen binding regions. These antigen binding regions can be derived from an "antibody." The term "antibody" herein is used in the broadest sense and includes monoclonal antibodies, and includes intact antibodies and functional (antigen-binding) antibody fragments thereof, including fragment antigen binding (Fab) fragments, F(ab')₂ fragments, Fab' fragments, Fv fragments, recombinant IgG (rIgG) fragments, single chain antibody fragments, including single chain variable fragments (sFv or scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD. The antibody can comprise a human IgG1 constant region. The antibody can comprise a human IgG4 constant region.

The terms "complementarity determining region," and "CDR," which are synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4). The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) *JMB* 273,927-948 ("Chothia" numbering scheme); MacCallum et al., *J. Mol. Biol.* 262:732-745 (1996), "Antibody-antigen interactions: Contact analysis and binding site topography," *J. Mol. Biol.* 262, 732-745." ("Contact" numbering scheme); Lefranc M P et al., "IMGT unique numbering for immunoglobulin and T cell receptor variable domains and Ig superfamily V-like domains," Dev Comp *Immunol,* 2003 January; 27(1):55-77 ("IMGT" numbering scheme); Honegger A and Plückthun A, "Yet another numbering scheme for immunoglobulin variable domains: an automatic modeling and analysis tool," *J Mol Biol,* 2001 Jun. 8; 309(3):657-70, ("Aho" numbering scheme); and Whitelegg N R and Rees A R, "WAM: an improved algorithm for modelling antibodies on the WEB,"

*Protein Eng.* 2000 December; 13(12):819-24 ("AbM" numbering scheme. In certain embodiments, the CDRs of the antibodies described herein can be defined by a method selected from Kabat, Chothia, IMGT, Aho, AbM, or combinations thereof.

The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme.

The term "variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three CDRs (See e.g., Kindt et al. Kuby *Immunology*, 6th ed., W. H. Freeman and Co., page 91(2007)). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively (See e.g., Portolano et al., *J. Immunol.* 150:880-887 (1993); Clarkson et al., *Nature* 352:624-628 (1991)).

The antigen binding regions of the immunoconjugates described herein may be humanized. "Humanized" in reference to an immunoconjugate refers to an antigen binding region in which all or substantially all CDR amino acid residues are derived from non-human CDRs and all or substantially all FR amino acid residues are derived from human FRs. A humanized immunoconjugate optionally may include at least a portion of an antibody constant region derived from a human antibody.

Among the provided immunoconjugates are human immunoconjugates. A "human immunoconjugates" is an immunoconjugates possessing an antigen binding region with an amino acid sequence corresponding to that of an antibody produced by a human or a human cell, or non-human source that utilizes human antibody repertoires or other human antibody-encoding sequences, including human antibody libraries. The term excludes humanized forms of non-human antibodies comprising non-human antigen-binding regions, such as those in which all or substantially all CDRs are non-human.

The phrase "antigen binding arm", as used herein, refers to a single polypeptide chain, comprising an "antigen binding region", a hinge region, and a variant constant region. Other elements (e.g., a chelating agent; an imaging metal) may be attached to the antigen binding arm directly or through one or more linkers in compositions of this disclosure. Immunoconjugates of this disclosure comprise two antigen binding arms that are covalently linked together. In one embodiment, the antigen binding arms are linked through the hinge region. In one embodiment, the antigen binding arms are linked through an immunoglobulin heavy chain constant region. In one embodiment, the antigen binding arms are linked through the variant constant region.

In one embodiment, the antigen binding arms are linked via a disulfide linkage (e.g., via a cysteine residue in a hinge region).

The phrase "antigen binding region", as used herein, refers to the region of an immunoconjugate responsible for specific binding to an antigen, such region one or more antigen binding domains comprising complementarity determining regions, variable regions and framework regions, which may be derived from, modeled on, or may mimic, antibodies or fragments thereof, as are known by the person of ordinary skill in the art. In one embodiment, the "antigen binding region" of an antigen binding arm contains one or two antigen binding domains. In a preferred embodiment, the "antigen binding region" of an antigen binding arm consists of a single antigen binding domain, which antigen binding domain is preferably a VHH polypeptide. In a preferred embodiment, the antigen binding regions of both antigen binding arms of an immunoconjugate independently consist of a single antigen binding domain, which antigen binding domain is preferably a VHH polypeptide, which VHH polypeptides are the same or different.

The term "VHH polypeptide" as used herein encompasses natural and synthetic compositions and refers to a polypeptide constituting a VHH fragment as it is known in the art, i.e., a polypeptide that constitutes a single domain heavy chain only variable domain fragment, or a polypeptide that structurally and functionally resembles a VHH fragment, as such structure is further described below and has the ability to specifically bind antigen is described below, and as both are well known in the art. In preferred embodiments, the VHH polypeptides comprise a heavy chain variable region comprising three heavy chain CDR's; in one embodiment the VHH polypeptide is derived from a camelid; in another embodiment the VHH polypeptide is derived from a library; VHH polypeptides bind to antigens with specificity and high affinity. In a preferred embodiment, the VHH polypeptide is a single heavy chain variable domain comprising the arrangement: FR1, CDR1, FR2, CDR2, FR3, CDR3, and FR4. VHH polypeptides may be obtained, for example, as the antigen binding fragments of heavy chain only antibodies generated in vivo (e.g., in camelids). VHH polypeptides may also be obtained from synthetic libraries, e.g., phage display libraries. For example, see McMahon et al., Nature Structural & Molecular Biology|VOL 25|March 2018|289-296 *Yeast surface display platform for rapid discovery of conformationally selective nanobodies*; Moutel et al., eLife 2016; 5:e16228 NaLi-H1: *A universal synthetic library of humanized nanobodies providing highly functional antibodies and intrabodies*. De Genst E, Saerens D, Muyldermans S, Conrath K. Antibody repertoire development in camelids. Dev Comp Immunol. 2006; 30(1-2):187-98. doi: 10.1016/j.dci.2005.06.010. PMID: 16051357. Vincke C, Gutiérrez C, Wernery U, Devoogdt N, Hassanzadeh-Ghassabeh G, Muyldermans S. Generation of single domain antibody fragments derived from camelids and generation of manifold constructs. Methods Mol Biol. 2012; 907:145-76. doi: 10.1007/978-1-61779-974-7_8. PMID: 22907350. Arbabi Ghahroudi M, Desmyter A, Wyns L, Hamers R, Muyldermans S. Selection and identification of single domain antibody fragments from camel heavy-chain antibodies. FEBS Lett. 1997 Sep. 15; 414(3):521-6. doi: 10.1016/s0014-5793(97)01062-4. PMID: 9323027.

For VHH humanization, see, for example, Vincke C, Loris R, Saerens D, Martinez-Rodriguez S, Muyldermans S, Conrath K. General strategy to humanize a camelid single-domain antibody and identification of a universal humanized nanobody scaffold. J Biol Chem. 2009 Jan. 30; 284(5):3273-84. doi: 10.1074/jbc.M806889200. Epub 2008 Nov. 14. PMID: 19010777.

For VHH stability, see, for example, Kunz P, Flock T, Soler N, Zaiss M, Vincke C, Sterckx Y, Kastelic D, Muyldermans S, Hoheisel J D. Exploiting sequence and stability information for directing nanobody stability engineering. Biochim Biophys Acta Gen Subj. 2017 September; 1861(9):2196-2205. doi: 10.1016/j.bbagen.2017.06.014. Epub 2017 Jun. 20. PMID: 28642127; PMCID: PMC5548252; Kunz P, Zinner K, Miicke N, Bartoschik T, Muyldermans S, Hoheisel J D. The structural basis of nanobody unfolding reversibility and thermoresistance. Sci Rep. 2018 May 21; 8(1):7934. doi: 10.1038/s41598-018-26338-z. PMID: 29784954; PMCID: PMC5962586.

A "linker" herein is also referred to as "linker sequence" "spacer" "tethering sequence" or grammatical equivalents thereof. A "linker" as referred herein connects two distinct molecules that by themselves possess target binding, catalytic activity, or are naturally expressed and assembled as separate polypeptides or comprise separate domains of the same polypeptide. For example, two distinct binding moieties or a heavy-chain/light-chain pair or an antigen binding region and an immunoglobulin heavy chain constant region. A number of strategies may be used to covalently link molecules together. Linkers described herein may be utilized to join a light chain variable region and a heavy chain variable region in an scFv molecule; or may be used to tether an scFv or other antigen binding fragment on the N- or C-terminus of an antibody heavy chain. These include but are not limited to polypeptide linkages between N- and C-termini of proteins or protein domains, linkage via disulfide bonds, and linkage via chemical cross-linking reagents. In one aspect of this embodiment, the linker is a peptide bond, generated by recombinant techniques or peptide synthesis.

An antibody that "binds" an antigen or epitope of interest is one that binds the antigen or epitope with sufficient affinity that is measurably different from a non-specific interaction. Specific binding can be measured, for example, by determining binding of a molecule compared to binding of a control molecule, which generally is a molecule of similar structure that does not have binding activity (e.g., an isotype control).

"Specific binding" refers to an antibody or immunoconjugate that is capable of binding antigen with sufficient affinity such that the antibody is useful as a diagnostic and/or therapeutic agent in targeting that antigen. In one embodiment, the extent of binding of an antibody to an unrelated protein is less than about 10% of the binding of the antibody to its antigen as measured, e.g., by a radioimmunoassay. An "antigen specific" antibody or immunoconjugate, as used herein, is one that specifically binds to the antigen with sufficient specificity and affinity to be useful in targeting a therapeutic, targeting diagnostic, or method of detecting the antigen in a biological sample from a subject. In some embodiments, an immunoconjugate or antibody construct or target imaging complex or radioimmunoconjugate that binds to its target antigen has a dissociation constant ($K_D$) of ≤1 µM, <100 nM, <10 nM, <1 nM, <0.1 nM, <0.01 nM, or <0.001 nM (e.g., $10^{-8}$ M or less, e.g., from $10^{-8}$ M to $10^{-13}$ M, e.g., from $10^{-9}$ M to $10^{-13}$ M). In some embodiments, an immunoconjugate or antibody construct or target imaging complex or radioimmunoconjugate of the present invention binds to multiple antigens, such as, e.g., an epitope conserved among homologs from different species, such as wherein the amino acid identity of the epitope is non-identical in different species.

As used herein, the term "variant constant region" refers to a polypeptide comprising of a portion of an immunoglobulin heavy chain constant region that has been modified from native immunoglobulin amino acid sequence, preferably at from one to several amino acid positions. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, MD (1991). Modifications to Fc regions for various purposes are well known in the art. For example, see Kevin O. Saunders, Frontiers in Immunology, June 2019|Volume 10|Article 1296, titled "Conceptual Approaches to Modulating Antibody Effector Functions and Circulation Half-Life".

Percent (%) sequence identity with respect to a reference polypeptide sequence is the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways using available computer software. Appropriate parameters for aligning sequences are able to be determined, including algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "cytotoxic agent" as used herein refers to a substance that inhibits or prevents a cellular function and/or causes cell death or destruction. Cytotoxic agents include, but are not limited to, radioactive isotopes; chemotherapeutic agents or drugs (e.g., methotrexate, adriamicin, *vinca* alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various cytotoxic agents described herein.

The term "affinity" refers to the strength of the sum total of noncovalent interactions between a single binding site of a molecule (e.g., an antibody) and its binding partner (e.g., an antigen or epitope). Unless indicated otherwise, as used herein, "binding affinity" refers to intrinsic binding affinity which reflects a 1:1 interaction between members of a binding pair (e.g., antibody and antigen or epitope). The affinity of a molecule X for its partner Y can generally be represented by the dissociation constant ($K_D$). Affinity can be measured by common methods known in the art, including those described herein. Specific illustrative embodiments for measuring binding affinity are described herein.

The term "antagonist" is used in the broadest sense, and includes any molecule that partially or fully blocks, inhibits, or neutralizes a biological activity of antigen. Suitable antagonist molecules specifically include antagonist antibodies or antibody fragments, or derivatives thereof.

A "blocking" antibody or an "antagonist" antibody is an antibody that inhibits or reduces biological activity of the antigen it binds or a protein complex comprising the antigen. Preferred blocking antibodies or antagonist antibodies substantially or completely inhibit the biological activity of the antigen or protein complex comprising the antigen.

The term "tumor" as used herein refers to all neoplastic cell growth and proliferation, whether malignant or benign, and all pre-cancerous and cancerous cells and tissues.

The terms "cancer" and "cancerous" as used herein refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), skin cancer, melanoma, lung cancer including small-cell lung cancer, non-small cell lung cancer ("NSCLC"), small cell neuroendocrine lung cancer, large cell neuroendocrine lung cancer, adenocarcinoma of the lung and squamous carcinoma of the lung, cancer of the peritoneum, hepatocellular cancer, gastric or stomach cancer including gastrointestinal cancer, pancreatic cancer (e.g., pancreatic ductal adenocarcinoma), glioblastoma, cervical cancer, ovarian cancer (e.g., high grade serous ovarian carcinoma), liver cancer (e.g., hepatocellular carcinoma (HCC)), bladder cancer (e.g., urothelial bladder cancer), testicular (germ cell tumor) cancer, hepatoma, breast cancer, brain cancer (e.g., astrocytoma), colon cancer, rectal cancer, colorectal cancer, endometrial or uterine carcinoma, salivary gland carcinoma, kidney or renal cancer (e.g., renal cell carcinoma, nephroblastoma or Wilms' tumor), prostate cancer, vulval cancer, thyroid cancer, hepatic carcinoma, anal carcinoma, penile carcinoma, as well as head and neck cancer. Additional examples of cancer include, without limitation, retinoblastoma, thecomas, arrhenoblastomas, hepatoma, hematologic malignancies including non-Hodgkins lymphoma (NHL), multiple myeloma and acute hematologic malignancies, endometrial or uterine carcinoma, endometriosis, fibrosarcomas, choriocarcinoma, salivary gland carcinoma, vulval cancer, thyroid cancer, esophageal carcinomas, hepatic carcinoma, anal carcinoma, penile carcinoma, nasopharyngeal carcinoma, laryngeal carcinomas, Kaposi's sarcoma, melanoma, skin carcinomas, Schwannoma, oligodendroglioma, neuroblastomas, rhabdomyosarcoma, osteogenic sarcoma, leiomyosarcomas, urinary tract carcinomas, anaplastic astrocytoma, basal cell carcinoma (basal cell epithelioma), bile duct cancer, small cell bladder cancer, metastatic breast cancer, metastatic colorectal cancer, epithelial ovarian cancer, fallopian tube cancer, gastric adenocarcinoma, glioblastoma multiforme (GBM), recurrent glioblastoma multiforme (GBM), gliomas, gliosarcoma, head and neck squamous cell carcinoma (HNSCC), recurrent head and neck cancer squamous cell carcinoma, malignant pleural mesothelioma head and neck cancer, Hodgkin lymphoma, metastatic renal cell carcinoma, metastatic renal clear cell carcinoma, squamous non-small cell lung cancer, squamous carcinoma of the lung, relapsed or refractory small-cell lung cancer, treatment-resistant melanoma, metastatic melanoma, Merkel cell carcinoma, neuroendocrine cancer, large cell neuroendocrine cancer, neuroendocrine tumors (NETS), ovarian carcinoma, papillary carcinoma, peritoneal cancer, neuroendocrine prostate cancer, hormone-refractory prostate cancer, castration-resistant prostate cancer, soft tissue sarcoma, and squamous cell carcinoma.

The term "metastatic cancer" means the state of cancer where the cancer cells of a tissue of origin are transmitted from the original site to one or more sites elsewhere in the body, by the blood vessels or lymphatics, to form one or more secondary tumors in one or more organs besides the tissue of origin. A prominent example is a metastatic breast cancer.

The terms "cell proliferative disorder" and "proliferative disorder" refer to disorders that are associated with some degree of abnormal cell proliferation. In one embodiment, the cell proliferative disorder is cancer.

The terms "associated," "associating," "linked," or "linking" with regard to the claimed invention refers to the state of two or more components of a molecule being joined, attached, connected, or otherwise coupled to form a single molecule (or single molecular complex) or the act of making two molecules associated with each other to form a single molecule (or single molecular complex) by creating an association, linkage, attachment, and/or any other connection between the two molecules. For example, the term "linked" may refer to two or more components associated by one or more atomic interactions such that a single molecule is formed and wherein the individual atomic interactions may be covalent or non-covalent. Non-limiting examples of covalent associations between two components include peptide bonds and cysteine-cysteine disulfide bonds. Non-limiting examples of non-covalent associations between two molecular components include ionic bonds.

A "bispecific" antibody refers to an antibody that has binding specificities for at least two different epitopes, regardless of whether the plurality of epitopes are in the same molecule and/or partially overlapping. In some embodiments, the bispecific immunoconjugate of the present invention binds to two different epitopes of a single antigen described herein.

As used herein, the terms "expressed," "expressing," or "expresses," and grammatical variants thereof, refer to translation of a polynucleotide or nucleic acid into a protein. The expressed protein may remain intracellular, become a component of the cell surface membrane or be secreted into an extracellular space.

For purposes of the present invention, the phrase "derived from" when referring to a polypeptide or polypeptide region means that the polypeptide or polypeptide region comprises highly similar amino acid sequences originally found in a "parental" protein and which may now comprise certain amino acid residue additions, deletions, truncations, rearrangements, or other alterations relative to the original polypeptide or polypeptide region as long as a certain function(s) (e.g., antigen binding affinity) and a structure(s) of the "parental" molecule are substantially conserved. The skilled worker will be able to identify a parental molecule (e.g., an antibody sequence) from which a polypeptide or polypeptide region (e.g., a VHH polypeptide, CDR, HVR, $V_H$, and/or $V_L$) was derived using techniques known in the art, e.g., protein sequence alignment software.

As used herein, cells which express an extracellular target biomolecule or antigen on at least one cellular surface are "target positive cells" or "target+ cells" and are cells physically coupled to the specified, extracellular target biomolecule. Additional target biomolecule description is provided below. "Target biomolecule", "target antigen molecule", "target antigen", "antigen of interest", and grammatical variants and equivalents are used interchangeably herein as will be recognized by the person of ordinary skill in the art viewing the context of usage, and include the molecular determinants of antibody binding. Such antigens can be bound by the immunoconjugates described herein though the antigen binding region or antigen binding arm of the immunoconjugate.

The term "pharmaceutical formulation" or "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

An "isolated" antibody or immunoconjugate or radio immunoconjugate is one which has been separated from a component of its natural environment or artificial production. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). Routine methods for assessment of antibody purity in a composition are known to the skilled worker, see e.g., Flatman et al., *J. Chromatogr. B* 848:79-87 (2007). In particular, unwanted components (contaminants) to be purified away from are such components that would interfere with desired uses for the antibody, such as, e.g., a therapeutic use, and may include, inter alia, bacterial factors, enzymes, hormones, and other proteinaceous or non-proteinaceous solutes.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present at extrachromosomal location or at a chromosomal location that is different from its natural chromosomal location.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As used herein, the term "administer", with respect to an immunoconjugate or composition thereof (e.g., a radioimmunoconjugate, a pharmaceutical composition, or a diagnostic composition), means to deliver the immunoconjugate, or composition thereof, to a subject's body via any known method suitable for delivery of immunoconjugate or composition thereof. Specific modes of administration include, without limitation, intravenous, transdermal, subcutaneous, intraperitoneal and intrathecal administration.

An "effective amount" of an agent, e.g., a pharmaceutical formulation, refers to an amount effective, at dosages and for periods of time necessary, to achieve the desired therapeutic or prophylactic result.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, radioimmunoconjugates of this disclosure are used to delay development of a disease or to slow the progression of a disease.

A "therapeutically effective amount" is at least the minimum concentration required to effect a measurable improvement or prevention of a particular disorder. A therapeutically effective amount herein may vary according to factors such as the disease state, age, sex, and weight of the patient, and the ability of a composition of this disclosure to elicit a desired response in the individual. A therapeutically effective amount is also one in which any toxic or detrimental effects of the composition of this disclosure are outweighed by the therapeutically beneficial effects.

The terms "predictive" and "prognostic" as used herein are interchangeable. In one sense, the methods for prediction or prognostication are to allow the person practicing a predictive/prognostic method of this disclosure to select patients that are deemed (usually in advance of treatment, but not necessarily) more likely to respond to treatment with an immunoconjugate of the present invention or a composition of the aforementioned (e.g., a pharmaceutical composition).

The term "detecting" is used in the broadest sense to include both qualitative and quantitative measurements of a target antigen molecule. In one aspect, the detecting method as described herein is used to identify the mere presence of the antigen of interest in a biological sample. In another aspect, the method is used to test whether the antigen of interest in a sample is present at a detectable level. In yet another aspect, the method can be used to quantify the amount of the antigen of interest in a sample and further to compare the antigen levels from different samples. In another aspect, the method can be used in vivo to determine the location of a target cell, for example, using a targeted imaging complex of this disclosure.

The term "biological sample" refers to any biological substance that might contain an antigen of interest. A sample can be biological fluid, such as whole blood or whole blood components including red blood cells, white blood cells, platelets, serum and plasma, ascites, itreous fluid, lymph fluid, synovial fluid, follicular fluid, seminal fluid, amniotic fluid, milk, saliva, sputum, tears, perspiration, mucus, cerebrospinal fluid, and other constituents of the body that might contain the antigen of interest. In various embodiments, the sample is a biological sample from any animal. In some embodiments, the sample is from a mammal. In some embodiments, the sample is from a human subject. In some embodiments, the biological sample is serum from a clinical patient. In some embodiments, the biological sample is biopsy material. In some embodiments, the biological sample is biopsy material from a clinical patient. In some embodiments, the biological sample is serum from a clinical patient. In some embodiments, the biological sample is primary cell culture material. In some embodiments, the biological sample is primary cell culture material from a clinical patient. In some embodiments, the biological sample is from clinical patients or patients treated with a composition of this disclosure e.g., a radioimmunoconjugate, or treated with a different therapeutic agent, such as an antibody-drug conjugate targeting the antigen of interest or β-irradiation or a small molecule therapeutic.

The term "package insert" is used to refer to instructions customarily included in commercial packages of therapeutic products, that contain information about the indications, usage, dosage, administration, combination therapy, contraindications and/or warnings concerning the use of such therapeutic products.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

EXAMPLES

The following illustrative examples are representative of embodiments of the compositions and methods described herein and are not meant to be limiting in any way.

The Examples below describe radioisotope-delivering platforms having sizes between 60 and 110 kDa and which have shorter half-lives (e.g., 4 days or less) compared to traditional IgGs but longer half-lives than smaller monomeric antibody fragment formats (e.g., greater than 10 hours). Furthermore, certain radioisotope-delivering platforms provided herein exhibit high stability in vitro or in vivo, low immunogenicity, and suitable therapeutic windows. These radioisotope-delivering platforms are preferred for targeting radioisotopes in vivo in order to treat disease. These radioisotope-delivering platforms are particularly useful for targeted delivery of alpha emitters safely and effectively in a subject by exhibiting reduced adverse effects as compared to antibodies having half-lives over 4 days and/or molecular weights under 60 kDa.

Below, in certain phrases, "Fc portion" is used in reference to variant constant domain and "hinge" is used in reference to "hinge region" as will be understood by the person of ordinary skill in the art.

Example 1. Antibody Production

VHH-Fc plasmids were generated by cloning the VHH sequence, with a hinge and Fc portion (human IgG1 $C_H2$-$C_H3$) into a mammalian expression vector. In some instances, mutations were introduced into the Fc portion. To produce recombinant VHH-Fc and variants thereof, plasmid was transfected into HEK23.SUS cells (ATUM, or similar). After 3-5 days of secretion, the antibody-containing supernatant was cleared of cells by centrifugation and sterile filtration. Antibodies were purified using Mab Select SuRe PCC column (GE, Cat #: 11003495) and buffer exchange into PBS, pH 7.0. Proteins were quantified using A280 or BCA. The purity of the antibodies were tested by SDS-PAGE, capillary electrophoresis, HPLC-SEC and LC-MS using standard protocols. Regarding VHH polypeptides, see, for example, McMahon et al., Nature Structural & Molecular Biology|VOL 25|March 2018|289-296 *Yeast surface display platform for rapid discovery of conformationally selective nanobodies*; Moutel et al., eLife 2016; 5:e16228 NaLi-H1: *A universal synthetic library of humanized nanobodies providing highly functional antibodies and intrabodies*. De Genst E, Saerens D, Muyldermans S, Conrath K. Antibody repertoire development in camelids. Dev Comp Immunol. 2006; 30(1-2):187-98. doi: 10.1016/j.dci.2005.06.010. PMID: 16051357. Vincke C, Gutiérrez C, Wernery U, Devoogdt N, Hassanzadeh-Ghassabeh G, Muyldermans S. Generation of single domain antibody fragments derived from camelids and generation of manifold constructs. Methods Mol Biol. 2012; 907:145-76. doi: 10.1007/978-1-61779-974-7_8. PMID: 22907350. Arbabi Ghahroudi M, Desmyter A, Wyns L, Hamers R, Muyldermans S. Selection and identification of single domain antibody fragments from camel heavy-chain antibodies. FEBS Lett. 1997 Sep. 15; 414(3):521-6. doi: 10.1016/s0014-5793(97)01062-4. PMID: 9323027.

For VHH humanization, see, for example, Vincke C, Loris R, Saerens D, Martinez-Rodriguez S, Muyldermans S, Conrath K. General strategy to humanize a camelid single-domain antibody and identification of a universal humanized nanobody scaffold. J Biol Chem. 2009 Jan. 30; 284(5):3273-84. doi: 10.1074/jbc.M806889200. Epub 2008 Nov. 14. PMID: 19010777.

For VHH stability, see, for example, Kunz P, Flock T, Soler N, Zaiss M, Vincke C, Sterckx Y, Kastelic D, Muyldermans S, Hoheisel J D. Exploiting sequence and stability information for directing nanobody stability engineering. Biochim Biophys Acta Gen Subj. 2017 September; 1861(9): 2196-2205. doi: 10.1016/j.bbagen.2017.06.014. Epub 2017 Jun. 20. PMID: 28642127; PMCID: PMC5548252; Kunz P, Zinner K, Mucke N, Bartoschik T, Muyldermans S, Hoheisel J D. The structural basis of nanobody unfolding reversibility and thermoresistance. Sci Rep. 2018 May 21; 8(1):7934. doi: 10.1038/s41598-018-26338-z. PMID: 29784954; PMCID: PMC5962586.

A number of VHH-Fc prototypes and variants were engineered using VHH sequences such as the anti-HER2 clone 2RS15d VHH (See. e.g., WO2016/016021) (SEQ ID NO: 20), and the anti-DLL3 clone hz10D9v7.251 VHH sequences (See e.g., WO2020/07967) (SEQ ID NO: 30), unless otherwise stated herein the data collected and shown was obtained using VHH antigen binding regions of these clones.

TABLE 1

| VHH Fc name | FcRn Mutant | Fc Effector Mutant | Target |
|---|---|---|---|
| H101 | wt | wt | HER2 |
| D102 | wt | wt | DLL3 |
| H105 | I253A | wt | HER2 |
| H106 | S254A | wt | HER2 |
| H107 | H310A | wt | HER2 |
| H108 | H435Q | wt | HER2 |
| H109 | Y463A | wt | HER2 |
| D111 | I253A | wt | DLL3 |
| D112 | S254A | wt | DLL3 |
| D113 | H310A | wt | DLL3 |
| D114 | H435Q | wt | DLL3 |
| D115 | Y463A | wt | DLL3 |
| H133 | wt | AEASS | HER2 |
| D134 | wt | AEASS | DLL3 |
| H135 | H310A | AEASS | HER2 |
| D136 | H310A | AEASS | DLL3 |
| H137 | H435Q | AEASS | HER2 |
| D138 | H435Q | AEASS | DLL3 |

Variants per EU numbering; AEASS = L234A, L235E, G237A, A330S, and P331S

Figure 1B:
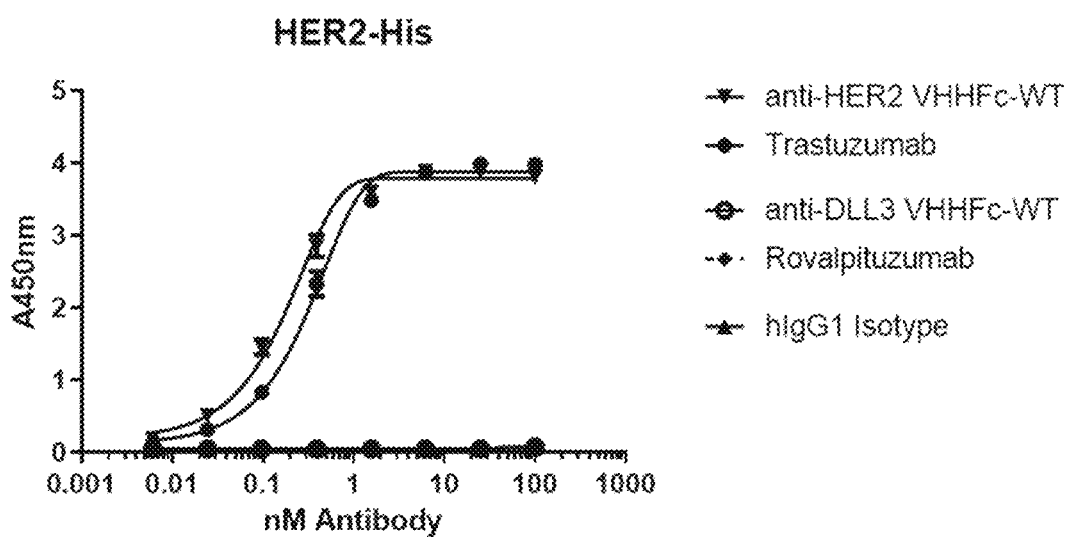

Example 2. Antibody Binding Properties: Assays for Target Protein and Target Cells The VHH-Fcs were assessed by ELISA for binding to Target soluble protein-human, murine and cynomolgous orthologs as appropriate, according to standard protocols. Antigens were sourced commercially or produced by cloning known antigen sequences (Uniprot) into mammalian expression vectors with a HIS, FLAG or equivalent tag for purification and detection purposes. A commercially available control anti-target IgG was included. Plates (96-well maxisorp, Corning 3368) were coated with 50 to 100 μL of each Target protein of interest at a concentration optimized for coating. Purified VHH-Fc and hIgG1 isotype control (Sigma, Cat #I5154) were prepared at starting concentrations of 200 to 400 nM and titrated 1:4 down. Following primary antibody incubation for 1 hour at room temperature (RT), and washing, 0.2 ug/ml of secondary HRP-labelled antibody was added and incubated for 1 h at RT (goat anti human-IgG-Fc-HRP Jackson, Cat #109-035-098). Reaction was detected using 50 L/well of TMB (Neogen, Cat #308177). The color development was stopped with 1 M HCl (50 μl). Optical density (OD) was measured at 450 nm using Spectromax plate reader and data were processed using SoftMaxPro. Data shows anti-Target VHH-Fcs bind to human, murine and cynomolgous target protein. Recombinant DLL3 protein used was human DLL3.FLAG (Adipogen #AG-40B-0151, amino acid 27-466), or human DLL3.HIS (abeam #ab255797, amino acid 27-492), or murine DLL3.HIS (IPA custom, amino acid 25-477) or cynomolgous DLL3.HIS (Acrobiosystems #, amino acid 27-490). Control antibodies for DLL3 binding was Rovalpituzumab (Creative Biolabs #TAB-216CL) Recombinant HER2 protein used was human Her2.HIS (Sinobiologics, #10004-H08H) and murine HER2.HIS (Sinobiologics #50714-M08H). Control antibody for HER2 binding was Trastuzumab (DIN: 02240692, ROCHE).). FIGS. 1A and 1B show Anti-Her2 and anti-DLL3 VHH-Fcs binding specifically to soluble target antigen in an ELISA, additional VHH-Fcs comprising mutations in the Fc region to decrease effector function and/or FcRn binding were tested but did not significantly affect binding to target antigen.

Figure 2A:
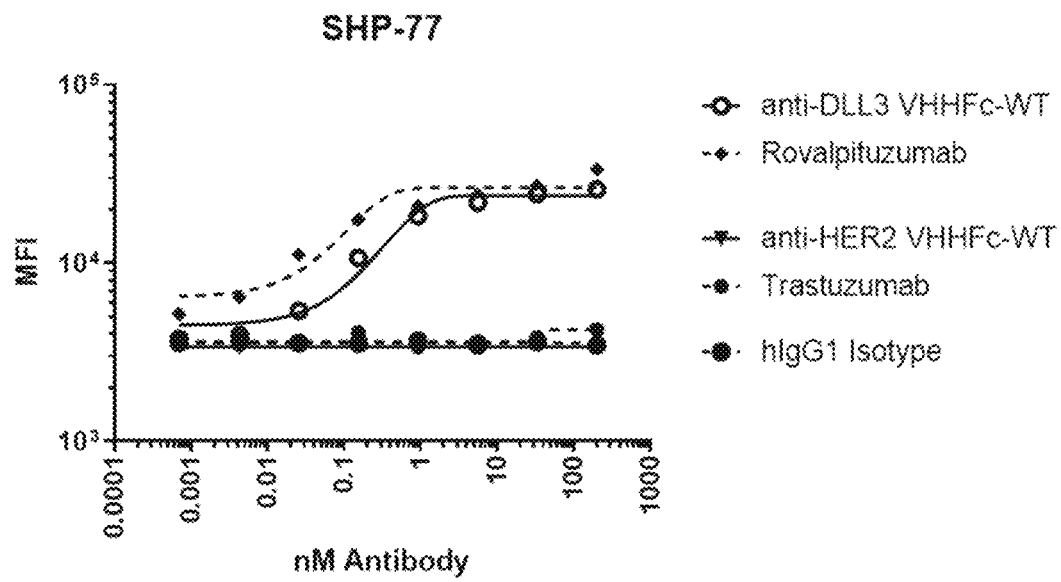
FIGS. 2A, 2B, and 2C show binding of anti-HER2 and anti-DLL3 VHH-Fc constructs to cells expressing HER2 and/or DLL3.
Figure 2B:
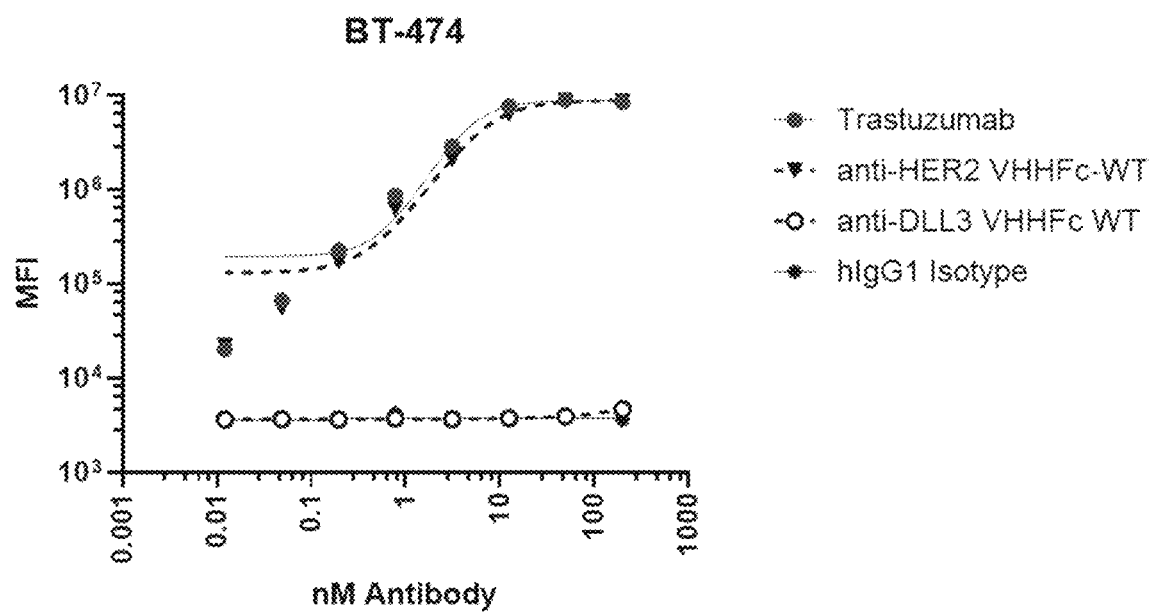
Figure 2C:
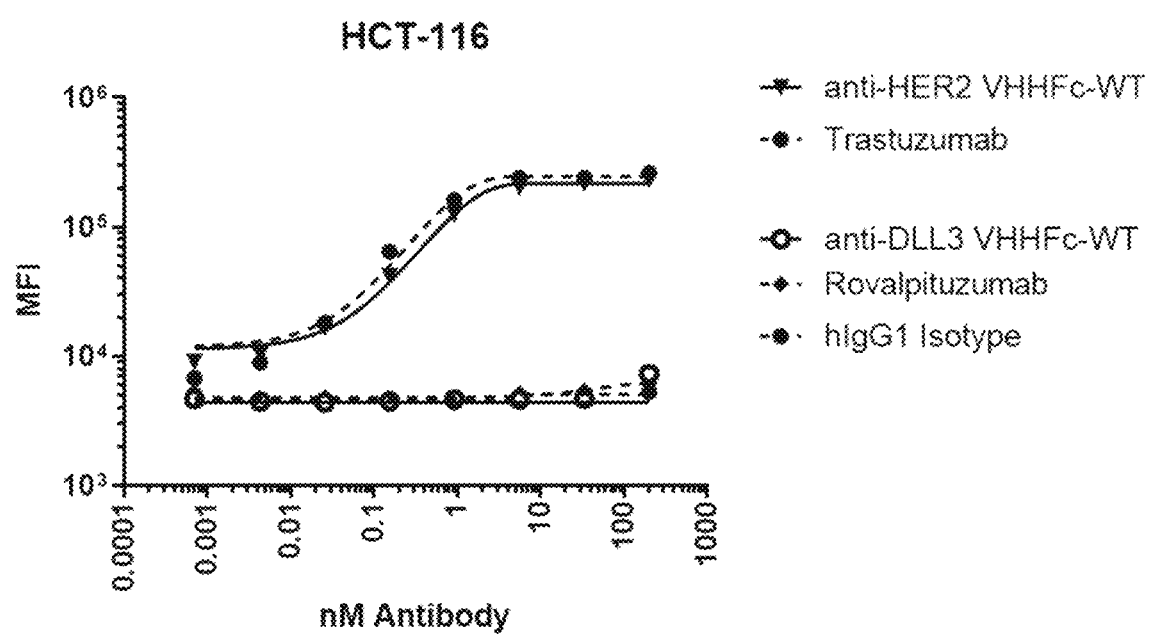

VHH-Fcs were screened for binding to a range of target-positive cancer cell lines by flow cytometry. All cell lines were sourced from ATCC unless otherwise noted, and cultured according to manufacturers instructions and recommended media. HER2-positive cell lines used were SKBR3 (ATCC #HTB-30) and BT474(ATCC #HTB-20) and HEK293-6E(NRC) cells. DLL3-positive cell lines tested include SHP-77(ATCC CRl-2195), NCI-H82(ATCC HTB-175), NCI-H69(ATCC HTB-119), HEK-DLL3 (Creative Biogene #CSC-R00531). HER2-negative cell lines tested included SHP-77. DLL3-negative cell lines tested included HCT-116 (CCL-247), BT-474 and SKBR3. Primary antibodies diluted in same manner as for ELISA were added to cells and incubated for 1 hour on ice. Cells were washed twice with 1% FBS in PBS, centrifuged at 450G for 4 minutes and incubated with 2 μg/mL AlexaFluor 647 conjugated anti-human IgG (Jackson, Cat #109-605-098) or AlexaFluor 647 conjugated anti-mouse IgG (Jackson, Cat #115-605-164) with 1:1000 DAPI (Biolegend, Cat #422801) for 30 minutes on ice. Following two further washes, cells were resuspended, and analyzed by flow cytometry on the iQue screener platform (Intellicyt), and data was processed with Forecyt, according to standard protocols. FIGS. 2A, 2B and 2C show binding to target-positive cell lines and shows that binding was specific to Target-positive cells (i.e., through binding comparison to negative controls cells). Further experiments indicated that Fc mutations to reduce effector function and/or FcRn binding did not impact binding to cancer cells as compared to wildtype Fcs.

Example 3. Internalization Assays

Figure 3A:
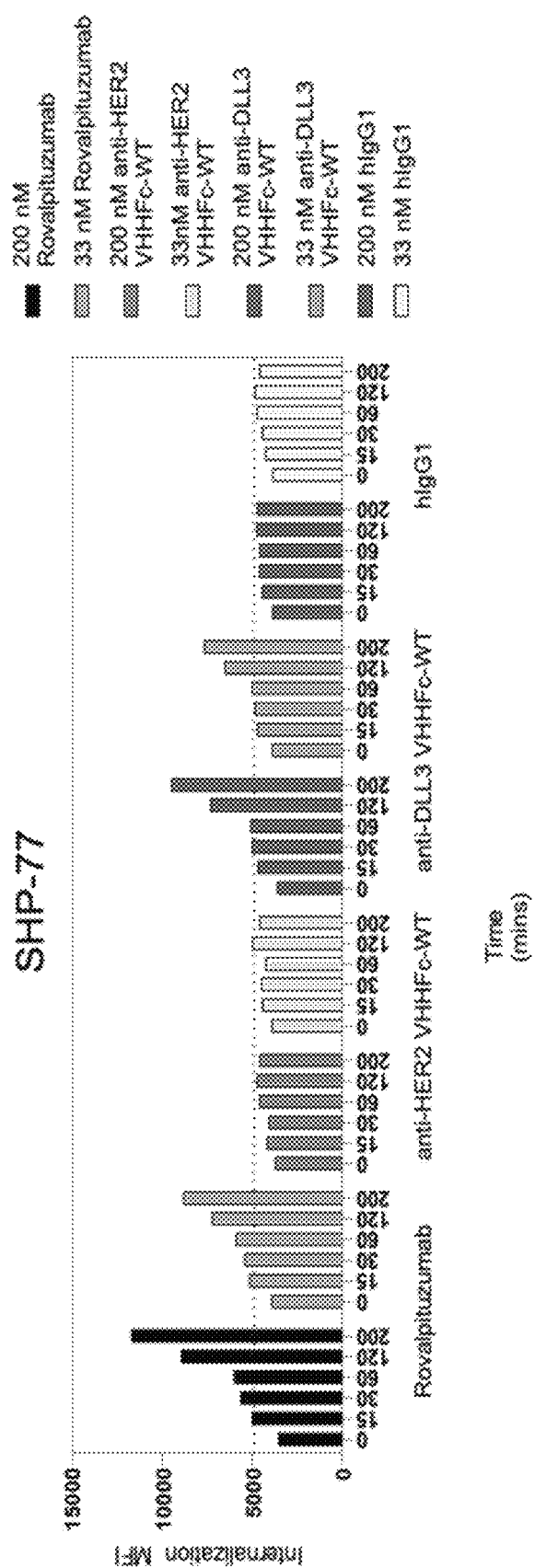
FIGS. 3A and 3B show internalization of anti-HER2 and anti-DLL3 VHH-Fc constructs in cells expressing HER2 and DLL3.
Figure 3B:
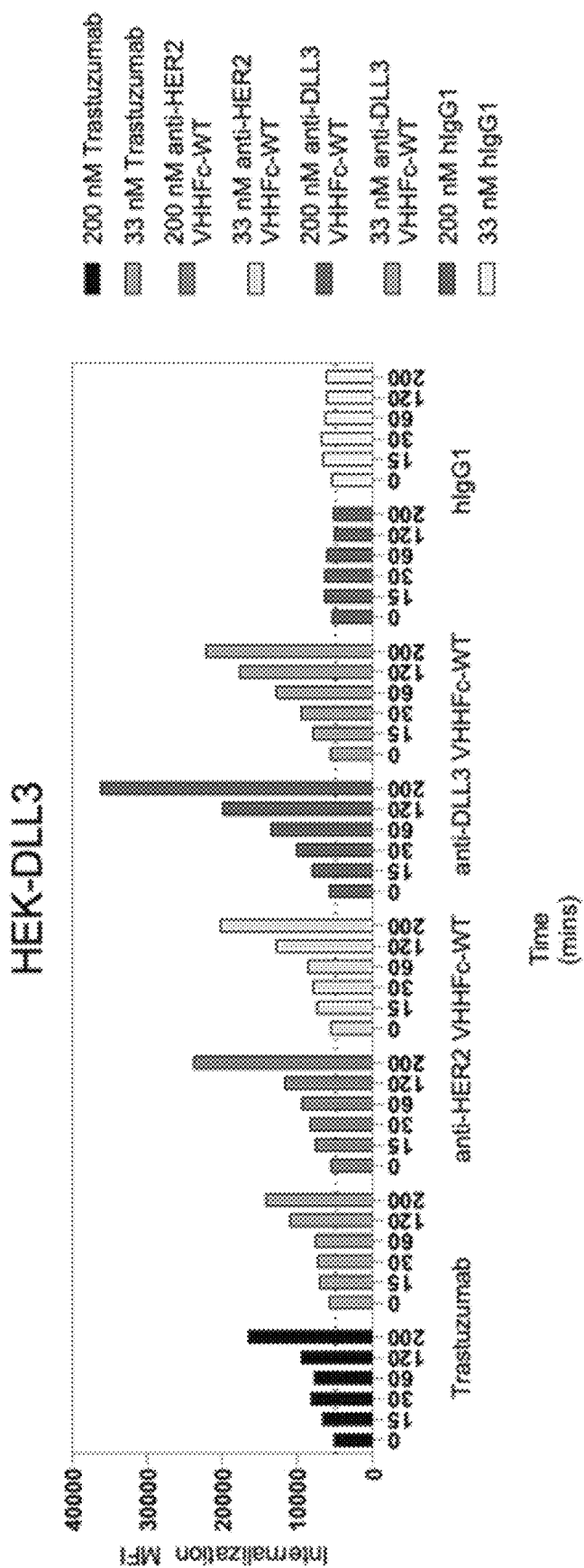

VHH-Fcs were tested for internalization by target-expressing cells using a secondary antibody conjugated to a pH sensitive dye. Goat anti-hu IgG-Fc secondary antibody was amine-conjugated to a pH sensitive pHAb dye (Promega Cat #G9845) according to the manufacturer's instructions. The pHAb dye has low or no fluorescence at pH>7 but fluoresces in acidic environment upon antibody internalization. Target-positive cells and target-negative cells were plated at 1.0× 106/mL in a 96-well V bottom plate. VHH-Fcs and hIgG1 isotype control were diluted in media to 75 nM. Cells were spun to remove supernatant, resuspended with the prepared primary antibodies and incubated on ice for 1 hour. Excess primary antibody was washed off from cells and then incubated with pHAb labelled secondary antibody on ice for 30 minutes. Excess secondary was then washed off and cells were resuspended in media. One set of samples was placed in an incubator at 37° C. to allow internalization, and another set was left on ice (0° C.) as a binding only control. Cells were sampled at different time points ranging from 0 to 24 hours. Cells were stained with DAPI and read by flow cytometry on 572/28 channel with iQue screener platform. The VHH-Fcs show higher fluorescence than the negative controls (isotype, buffer) on target-positive cells. FIGS. 3A and 3B show that H101 and were D102 internalized by SHP-77 and HEK-DLL3 cells.

Example 4. Antibody Thermal Stability Determination

Denaturing temperatures (Tm) of VHH-Fcs were determined from differential scanning fluorimetry (DSF) using Protein Thermo Shift Dye Kit™ (ThermoFisher, Cat #: 4461146). Briefly, A total of 1 μg of antibody was used in each reaction. Melting curves of the antibodies were generated using an Applied Biosystems QuantStudio 7 Flex Real-Time PCR System with the recommended settings stated in the kit manual. The Tm's of the antibodies in Table 1 were then determined by using the ThermoFisher Protein Thermal Shift software (v.1.3). Tm1 of the VHH-Fcs was determined by DSF. Both H101 and D102 showed good thermostability of 67.5±0.1 Celsius. Additional, VHH-Fcs comprising mutations in the Fc region to decrease effector function and/or FcRn binding were tested for thermostability and resulted in slightly lower thermostability (1 to 2 degrees Celsius), but were still within acceptable ranges.

Example 5. Receptor Density Determination

In order to test efficacy of the immunoconjugate binding with respect to target density receptor density was measured on target positive cell lines. Target density was measured using the ABC (Antibody Binding Capacity) assay. Cancer cells expressing the target of interest, as well as a negative control cell line, were harvested with cell dissociation buffer, seeded at about 5×104 cells per well into 96-well V bottom plate (Sarstedt 82.1583.001). Cells were tested for receptor expression using QuantiBRITE PE beads (BD Cat #340495) and a PE-conjugated anti-hu IgG (Biolegend clone HP6017) following the manufacturers' instructions. In brief, VHH-Fc and isotype control antibodies were prepared at suitable saturating concentrations based on previous experiments. Antibody sample dilutions were incubated with the panel of cell lines on ice for 1 hour. Cells were washed twice with 1% FBS in 1×PBS (FACS buffer), centrifuged at 400 G for 4 min. Cells were then incubated with 4 µg/mL mouse PE-conjugated anti-hu and DAPI (1:1000) for 30 minutes on ice. Cells were washed twice with FACS buffer, centrifuged at 400 G for 4 minutes and resuspended in FACS buffer. Fluorescence intensity on the PE channel was measured on the iQue Screener platform, and data were processed with ForeCyt software. The amount of PE signal generated from the different primary antibody was then fit to a standard curve based off of known PE molecules/Quantibrite bead samples to determine the number of antibody-binding sites per cell. Relative antibody binding sites correlate to the number of antigens or receptors on cell surface. Table 2 shows receptor density numbers for anti-DLL3 and anti-HER2 VHH-Fcs binding to a panel of cancer cell lines and were similar ranges to those reported in literature.

TABLE 2

Estimated number of epitopes/cell for each binder and cell line

| | | SHP-77 | HEK-DLL3 | BT474 | H82 | HEK293-6E | HCT-116 |
|---|---|---|---|---|---|---|---|
| Anti-DLL3 | Rova | 969 | 1679 | — | 936 | — | — |
| | D102 | 807 | 1734 | — | 794 | — | — |
| Anti-HER2 | Tmab | 625 | 1575 | 356690 | — | 1969 | 2790 |
| | H101 | 572 | 1490 | 401604 | — | 1935 | 2604 |

Example 6. Affinity of Antibodies to Target Protein

Antibody affinity was assessed using Octet Red96e (ForteBio). The association rate constant (ka), dissociation rate constant (kd) and affinity constant (KD) were measured by biolayer interferometry with anti-hIgG Fcc (AHC) capture biosensors (Fortebio cat #18-5063). Each cycle was performed with orbital shake speed of 1,000 rpm. Antigen was titrated 1:2 from a suitable starting concentration in kinetics buffer (Fortebio, Cat #18-1105). A set of AHC biosensors was dipped in kinetics buffer for baseline step of 60 s. Anti-Target VHH-Fc (5 µg/mL, in kinetics buffer) was loaded onto the biosensors for 240 s followed by a second baseline step of 30 s. The IgG captured sensors were dipped into buffer for single reference subtraction to compensate natural dissociation of capture IgG. Each biosensor was then dipped into corresponding concentration of target protein (human, murine or cynomolgus monomeric protein) for 600 s, followed by 1800 s of dissociation time in kinetics buffer, or conditions as optimized. A new set of AHC biosensors was used for every VHH-Fc. The data was analysed by global fit 1:1 model for the association and dissociation step, (Octet software version v11.0). Table 3 shows binding affinity data.

TABLE 3

Affinity of H101 and D102 to target proteins

| VHH-Fc | Analyte | KD (nM) |
|---|---|---|
| D102 | Human DLL3-Flag | 0.472 |
| D102 | Mouse DLL3-His | 8.75 |
| H101 | Human HER2-His | 3.79 |

Example 7. FcRn and Fc Effector Mutation Affinity Determination

FcRn affinity of VHH-Fc can generally be used to predict the half-life of antibody serum clearance. (See, e.g., Datta-Mannan A et al. "FcRn affinity-pharmacokinetic relationship of five human IgG4 antibodies engineered for improved in vitro FcRn binding properties in cynomolgus monkeys-."*Drug Metab Dispos.* 2012 August; 40(8):1545-55). Briefly, 10 nM of biotinylated hFcRn (Sino Biological, Cat #: CT071-H27H-B) was captured with the SA biosensor using Octet RED96e (Fortebio). The hFcRN coated biosensor was dipped into the sample solutions in sodium phosphate buffer (100 mM Na2HPO4,150 mM NaCl w/0.05% Tween-20, pH 6.0) with serial concentrations of tested antibodies and the association measured. The dissociation was measured by dipping the biosensors into sodium phosphate buffer without antibody. The KD values were determined using Octet Data Analysis HT 11.0 software. 2:1 (Heterogeneous Ligand) binding model was used in analysis. Table 4 shows FCRN affinity for wildtype VHH-Fcs, and the impact of specific mutations in the Fc on affinity for the mutants. Changes in FcRn affinity were consistent across targets. Constructs with Fc Effector mutation only have no impact on FcRn affinity. Addition of Fc Effector mutations to FcRn mutation constructs does not affect FcRn affinity. Table 4A shows affinities of VHH-Fcs and Fc variants to FcRn.

TABLE 4A

Affinity of FcRn VHH-Fcs and Fc variants to FcRn

| VHH.Fc | FcRn Mutant | KD (nM) |
|---|---|---|
| H101 | wt | 3.7 |
| D102 | wt | 3.8 |
| H105 | I253A | Weak |
| H106 | S254A | 13 |
| H107 | H310A | No binding |
| H108 | H435Q | Weak |
| H109 | Y463A | 13 |
| H110 | H310A/H435Q | No binding |
| D111 | I253A | Weak |

TABLE 4A-continued

Affinity of FcRn VHH-Fcs and Fc variants to FcRn

| VHH.Fc | FcRn Mutant | KD (nM) |
|---|---|---|
| D112 | S254A | 19 |
| D113 | H310A | No binding |
| D114 | H435Q | Weak |
| D115 | Y463A | 20 |
| D116 | H310A/H435Q | No binding |
| H133 | wt | 2.1 |
| D134 | wt | 1.9 |
| H135 | H310A | No binding |
| D136 | H310A | No binding |
| H137 | H435Q | Weak |
| D138 | H435Q | Weak |

VHH-Fcs were also tested for affinity to FcγRs by biolayer interferometry using the Octet Red96e platform. Each cycle is performed with orbital shake speed of 1,000 rpm. Streptavidin (SA) biosensors (Sartorius 18-5019) were rehydrated for 10 mins using kinetics buffer (PBS+0.1% BSA+ 0.02% Tween-20). Biotinylated-FcγRs (Acro Biosystems) were then loaded for 40-100 s onto SA biosensors at concentrations ranging between 1-5 µg/mL diluted in PBS. VHH-Fcs were serially diluted 1:2 in sample buffer (PBS+ 0.02% Tween-20) with starting concentrations ranging between 5000 nM to 37.5 nM. Loaded biosensors were then associated with VHH-Fcs for 60-120 s. VHH-Fc dissociation was measured for 30-900 s in sample buffer. Bound VHH-Fcs were then removed using 3 cycles of 5 s regeneration buffer (150 mM NaCl, 300 mM Sodium Citrate) and 5 s sample buffer. The data was analyzed either using a globally-fitted 1:1 Langmuir binding model (FcγRI) or steady state analysis (Octet software version HT v11.1).

Analysis shows reduction in binding (represented by a higher KD) to FcγRs for constructs with those mutations incorporated as shown in Table 4B.

TABLE 4B

Affinity of FcRn VHH-Fcs and Fc variants to Fc receptors

| | Fc mutation | FcγRI nM KD | FcγRIIa (H167) nM KD | FcγRIIa (R167) nM KD | FcγRIIb/c nM KD | FcγRIIIa (F176) nM KD | FcγRIIIa (V176) nM KD |
|---|---|---|---|---|---|---|---|
| Trastuzumab | wt | 0.92 | 270 | 520 | 3700 | 630 | 110 |
| H101 | wt | 1.01 | 340 | 160 | 450 | 1600 | 480 |
| H133 | AEASS | — | — | 2300 | weak | — | — |
| H135 | AEASS + H310A | — | — | 1200 | weak | — | — |
| H137 | AEASS + H435Q | — | — | 1200 | weak | — | — |
| D102 | wt | 1.27 | 390 | 530 | 430 | 1200 | 730 |
| D134 | AEASS | — | weak | 460 | 1100 | — | — |
| D136 | AEASS + H310A | — | weak | 570 | 2200 | — | — |
| D138 | AEASS + H435Q | — | weak | 520 | 770 | — | — |

(—) indicates no binding detected

Example 8. Self-Association Studies Using AC-SINS

Figure 4:
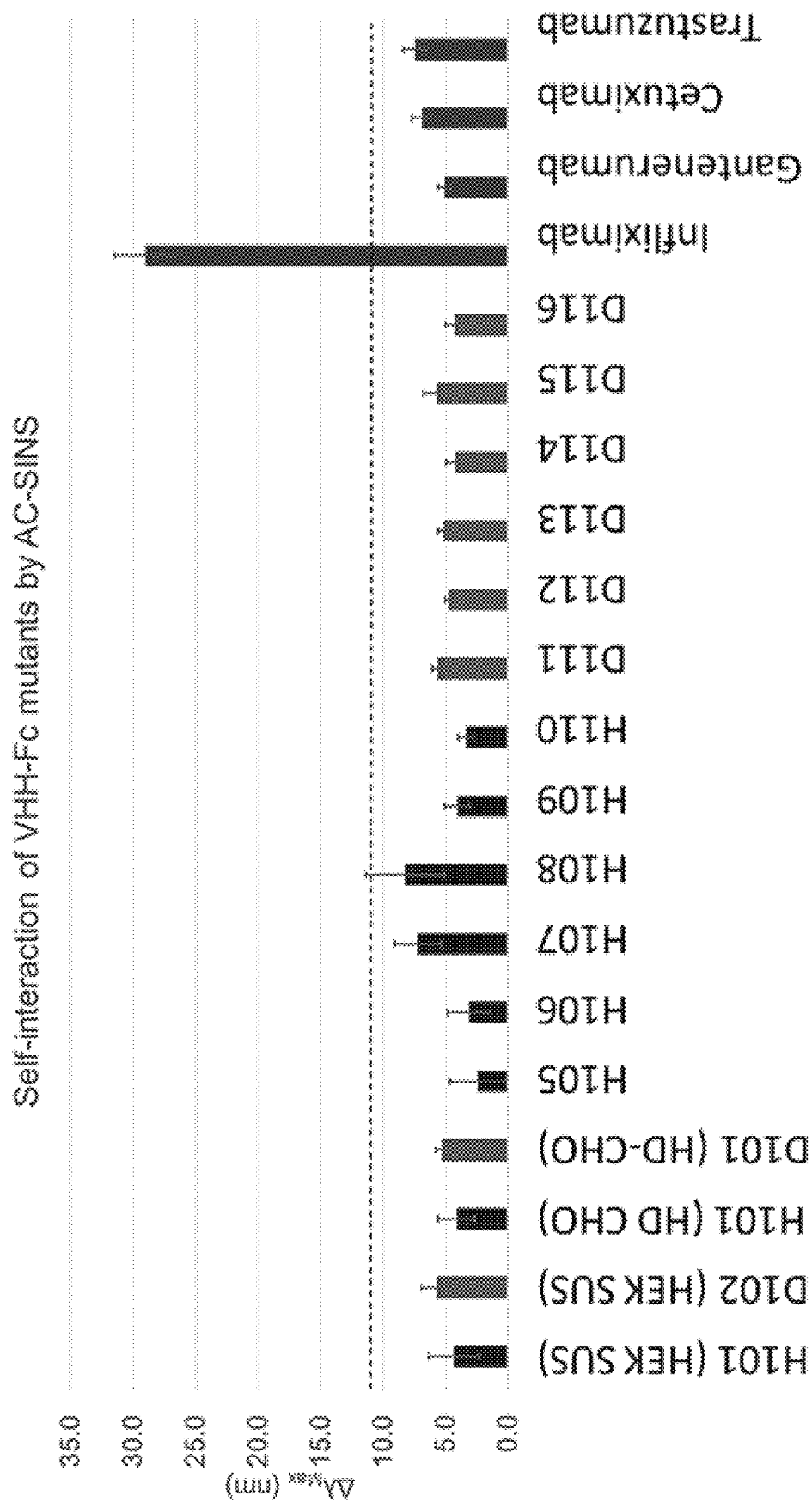
FIG. 4 shows self-interaction data for anti-HER2 and anti-DLL3 VHH-Fc constructs.

Propensities of self-association of VHH-Fcs was determined from affinity-capture self-interaction nanoparticle spectroscopy (AC-SINS) using gold nanoparticles (Au—NP) (Ted Pella, Cat #: 15705). (PMID: 24492294, 30395473) Briefly, goat IgG and goat anti-human Fc IgG (1:4 mole ratio) were used to coat the Au—NP. Conjugated Au—NP was mixed with 5 µg of each VHH-Fc, in quadruplicates, in a 96-well plate. The wavelength scan was measured with Synergy Neo2 plate reader. The difference of maximum absorbance ($\Delta\lambda max$) was calculated by subtracting $\lambda max$ of each reaction with that of PBS buffer. The data was analyzed with Linest function in Excel using second-order polynomial fitting. Control antibodies with known high ACSINS score (above the literature established cut-off of 11 for IgGs) were included in the assay. FIG. 4 shows ACSINS scores for test articles and controls.

Example 9. Polyreactivity Studies

Polyreactivity of VHH-Fcs against negatively charged biomolecules was determined by ELISA (As in Avery et al., "Establishing in vitro in vivo correlations to screen monoclonal antibodies for physicochemical properties related to favorable human pharmacokinetics." *MAbs.* 2018 February/March; 10(2):244-255). Briefly, ELISA plate was coated with 5 g/mL of human insulin (SigmaAlrich, Cat #: 19278) and 10 µg/mL of double stranded DNA (SigmaAlrich, Cat #: D1626-250MG) overnight. The plate was blocked with ELISA buffer (PBS, 1 mM EDTA, 0.05% Tween-20, pH 7.4). 10 µg/mL of test VHH-Fcs was loaded onto the plates in quadruplicates and incubated for 2 hours. Goat anti-human Fc (0.01 ug/ml) conjugated with HRP was then added and the plate incubated for 1 hour. The signal was developed with TMB and A450 absorbance was measured with Synergy Neo2 plate reader. The signal was normalized with the signal of non-coated well for each antibody tested. Table 5 shows the polyreactivity score, in comparison to control antibodies.

TABLE 5

Polyreactivity Assay Scores

| VHH.Fc | Insulin | dsDNA |
|---|---|---|
| H101 | 1.176 | 1.406 |
| D102 | 2.311 | 2.248 |
| H105 | 1.207 | |
| H106 | 1.321 | 1.446 |

TABLE 5-continued

Polyreactivity Assay Scores

| VHH.Fc | Insulin | dsDNA |
|---|---|---|
| H107 | 1.306 | 1.678 |
| H108 | 1.420 | 1.663 |
| H109 | 1.244 | 1.579 |
| H110 | 1.181 | 1.317 |
| D111 | 2.202 | |
| D112 | 3.461 | 2.970 |
| D113 | 2.829 | 2.594 |
| D114 | 3.161 | 3.015 |
| D115 | 2.503 | 2.252 |
| D116 | 2.446 | 2.302 |
| Gantenerumab | >10 | >10 |

Example 10. Fc Variants Effectively Reduce VHH-Fc Half-Life

In certain instances, reducing the drug half-life of alpha emitters is important for safety and to avoid unwanted toxicity associated with treatment. However, antibodies generally have a half-life upwards of 14 days or greater. Therefore, the half-life of the VHH-Fc variants was tested in order to observe and measure any reductions in half-life.

Twenty eight (28) 8 week old male B6.Cg-Fcgrt$^{tm1Dcr}$ Tg(FCGRT)32Dcr/DcrJ (Tg32 hom, JAX stock #014565) mice were distributed into 7 groups with 4 mice per group as outlined in the table. Tg32 mice comprise a humanized FcRn and are generally viewed as a surrogate for human pharmacokinetics of antibodies when compared to non-human primates. (See, e.g., Avery L B et al. "Utility of a human FcRn transgenic mouse model in drug discovery for early assessment and prediction of human pharmacokinetics of monoclonal antibodies."*MAbs*. 2016 August-September; 8(6):1064-78). On Day 0, body weights were measured and test articles were IV administered to all mice at 3 mg/kg and 5 ml/kg. 25 µL blood samples were collected from each mouse at time intervals. The blood samples were collected into 1 µL K$_3$EDTA, processed to plasma, diluted ¹/₁₀ in 50% glycerol in PBS, transferred into specialized 96 well storage plates, and stored at −20° C. All plasma samples were assessed via a hIgG ELISA chosen for its high sensitivity for all seven test articles.

TABLE 6

Pharmacokinetic parameter summary for HER2 VHH-Fc

| | Terminal Half-Life days | Clearance mL/days | Cmax µg/mL | AUC µg-days/mL | Volume of Distribution mL |
|---|---|---|---|---|---|
| H105 | 1.12 | 152.1 | 63.9 | 841 | 137 |
| sem | 0.03 | 3.4 | 3.6 | 29 | 1 |
| H106 | 7.10 | 19.8 | 53.5 | 2193 | 177 |
| sem | 0.31 | 0.8 | 0.4 | 29 | 3 |
| H107 | 0.41 | 304.4 | 62.4 | 516 | 82 |
| sem | 0.01 | 15.0 | 4.3 | 22 | 3 |
| H108 | 1.57 | 117.5 | 46.6 | 903 | 174 |
| sem | 0.10 | 6.6 | 0.7 | 40 | 6 |
| H109 | 6.92 | 18.2 | 52.2 | 2519 | 152 |
| sem | 0.34 | 0.6 | 0.8 | 28 | 4 |
| H101 | 6.91 | 28.7 | 57.0 | 1946 | 218 |
| sem | 0.77 | 5.2 | 1.6 | 231 | 35 |
| trastuzumab | 14.54 | 5.9 | 59.0 | 4108 | 108 |
| sem | 1.12 | 0.5 | 2.3 | 109 | 2 |

As observed in Table 6, the introduction of mutations within the FcRn was generally able to reduce the half-life of the anti-HER2 VHH-Fc. Interestingly, contrary to published results in the field, not all Fc variants when included in the immunoconjugates tested showed a reduction in half-life consistent with previously published results found in the literature. (See, e.g., Burvenich I J et al., "Cross-species analysis of Fc engineered anti-Lewis-Y human IgG1 variants in human neonatal receptor transgenic mice reveal importance of S254 and Y436 in binding human neonatal Fc receptor."*MAbs*. 2016 May-June; 8(4):775-86).

TABLE 7

Pharmacokinetic summary for DLL3 VHH-Fc

| | Terminal Half-Life days | Clearance mL/days |
|---|---|---|
| D111 | 10.2 | 10.8 |
| SEM | 4.4 | 10.5 |
| D112 | 14.2 | 7.8 |
| SEM | 3.2 | 1.0 |
| D113 | 1.1 | 254.8 |
| SEM | 0.2 | 27.0 |
| D114 | 2.5 | 46.9 |
| SEM | 0.1 | 3.6 |
| D115 | 11.0 | 6.9 |
| SEM | 13.2 | 1.1 |
| D102 | 13.3 | 10.3 |
| SEM | 3.3 | 3.8 |
| trastuzumab | 18.4 | 3.7 |
| SEM | 5.9 | 0.9 |

As observed in Table 7, the introduction of mutations within the FcRn was generally able to reduce the half-life of the anti-DLL3 VHH-Fc. Similarly to HER2 binding immunoconjugates and contrary to published results, not all Fc variants showed a reduction in half-life consistent with previously published results found in the literature.

Example 11. VHH-Fc Intact Mass Analysis

Conjugates were deglycosylated prior to analysis with in-house Endo-S enzyme (final concentration of 10 µg/mL) at 37° C. for 1 hour.

For analysis of the intact mass, 8 µL samples were injected on a Waters Acquity UPLC-Q-TOF with a UPLC BEH200 SEC 1.7 µM 4.6×150 mm column. These samples were eluted with a mobile phase of water/ACN (70/30, v/v) with 0.1% TFA and 0.1% FA (formic acid) for 11 min with a flow rate of 0.25 mL/min.

Example 12. Sourcing Bifunctional Chelators

Several chelators are known to practitioners of the art which are pre-functionalized for antibody conjugation. p-SCN-Bn-DOTA (1) is available from Macrocyclics (Plano, TX). Other linker variations of DOTA can be produced from the advanced intermediate DOTAGA-tetra(t-Bu ester) (2) (Macrocyclics, Plano, TX) following the general procedure below.

Other reagents used in these procedures are available from Millipore Sigma, CombiBlocks, Chem-Impex, and Broadpharm. All solvents were obtained from VWR and used as is with no anhydrous handling conditions unless indicated. Mass spectra were taken with an Agilent HPLC-MS or Waters HPCS-MS with C18 reverse phase column and an acetonitrile/water (+0.1% formic acid) gradient. Flash chromatography was performed using a Biotage IsoleraOne instrument with an appropriately sized normal phase silica gel cartridge with fraction collection at 254 nm. Final compounds were purified by an Agilent prep-scale HPLC using an acetonitrile/water (+0.1% TFA) gradient. NMR spectra were taken with a Bruker 400 MHz NMR instrument and processed with MestReNova v.14. Detailed NMR Data was compiled with the multiplet analysis function used in manual mode.

Figure 5:
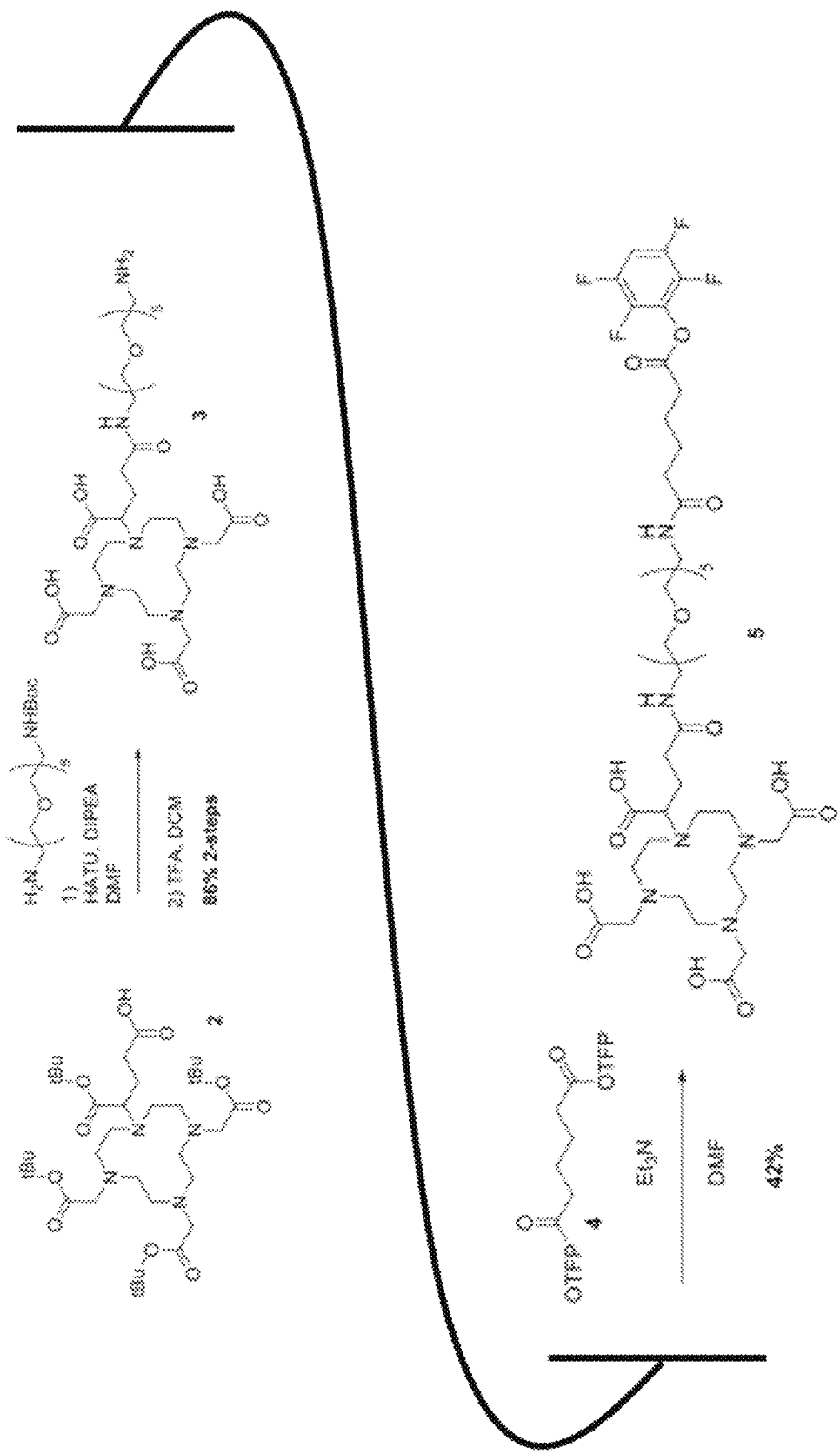
FIG. 5 shows a diagram for chemical synthesis of linker molecules.

FIG. 5 shows PEG5-DOTA synthesis, including compounds numbered (2)-(5), as described below. Compound 3 was prepared through a HATU coupling, followed by TFA deprotection. Available without chromatographic purification.

Synthesis of Compound (3) 4-({2-[2-(2-aminoethoxy)ethoxy]ethyl}carbamoyl)-2-[4,7,10-tris(carboxymethyl)-1,4,7,10-tetraazacyclododecan-1-yl]butanoic acid; tetrakis (trifluoroacetic acid): Compound 2 (100 mg, 0.143 mmol) was taken up in DMF (2 mL), HATU (65.1 mg, 0.171 mmol) was added, then DIPEA (0.099 mL, 73.8 mg, 0.57 mmol) was added. After 3 min, a solution of Boc-NH-PEG5-amine (65.1 mg, 0.17 mmol), was added to the reaction. After stirring for 10 min, HPLC showed the reaction to be complete. After 1 h, the reaction was quenched with about 5 mL NaHCO$_3$(sat), then 5 mL of water was added and the mixture was extracted 4×30 mL Et$_2$O. The combined organics were washed with saturated brine, dried over sodium sulfate, filtered, and concentrated in vacuo to yield the crude protected intermediate in good purity. m/z found=1063.6 (M+H).

The above intermediate was directly taken up in DCM (5 mL) and TFA (5 mL) was added. The reaction was stirred for 24 h until HPLC indicated complete removal of Boc and tBu esters. The reaction solution was concentrated in vacuo and co-evaporated 2× with 25 mL DCM. The residue was precipitated from DCM with Et$_2$O, then the remaining solid was triturated extensively with sonication (15-30 min) to yield the title compound (128 mg, 86% two-steps) as an off-white powder in good purity. $^1$H NMR (400 MHz, Deuterium Oxide) δ 4.15-3.68 (m, 7H), 3.62 (d, J=4.7 Hz, 2H), 3.59-3.49 (m, 20H), 3.47 (t, J=5.5 Hz, 2H), 3.35-2.78 (m, 16H), 2.52-2.37 (m, 2H), 1.97-1.79 (m, 2H). m/z found=739.5 (M+H).

Synthesis of Compound (4) Bis(2,3,5,6-tetrafluorophenyl) hexanedioate: Adipic Acid (1.00 g, 6.84 mmol) and EDC (3.28 g, 17.1 mmol) were taken up in 20 mL DCM and cooled to 0C on an ice bath, then a solution of 2,3,5,6-tetrafluorophenol in 20 mL DCM was added. Conversion to product was observed by TLC (R$_f$=0.5; 75% DCM/Hexanes). The reaction mixture was concentrated in vacuo and purified by flash chromatography (0-100% DCM/Hexanes) to yield the title compound (2.48 g, 82%) as a crystalline white powder. $^1$H NMR (400 MHz, Chloroform-d) δ 7.03 (tt, J=9.9, 7.0 Hz, 2H), 3.00-2.63 (m, 4H), 1.95 (t, J=3.3 Hz, 4H). This compound has poor signal by LCMS.

Compound (5)-{[2-(2-{2-[6-oxo-6-(2,3,5,6 tetrafluorophenoxy)hexanamido]ethoxy}ethoxy)ethyl]carbamoyl}-2-[4,7,10-tris(carboxymethyl)1,4,7,10tetraazacyclododecan-1-yl]butanoic acid: To a solution of compound 3 (22.1 mg, 0.017 mmol) in DMF (1.5 mL) was added bis(2,3,5,6-tetrafluorophenyl) hexanedioate (4) (45.2 mg, 0.102 mmol) and triethylamine (0.0086 mL, 6.2 mg, 0.061 mmol). Full conversion to product was confirmed by HPLC. After stirring for 2 h, the reaction was diluted with DMSO (1.5 mL) and purified by direct injection onto prep-HPLC (Agilent, Hanover, CT) with a gradient of 15-50% MeCN/water+ 0.1% TFA to yield the title compound (10.6 mg, 50%) as a white powder (2×TFA salt). $^1$H NMR (400 MHz, Deuterium Oxide) δ 7.20 (tt, J=10.4, 7.2 Hz, 1H), 3.97-3.65 (m, 5H), 3.58-3.51 (m, 20H), 3.49 (q, J=5.1 Hz, 2H), 3.43-3.32 (m, 6H), 3.26 (t, J=5.3 Hz, 2H), 3.20-2.82 (m, 12H), 2.69 (t, J=6.8 Hz, 2H), 2.52-2.34 (m, 2H), 2.19 (t, J=6.8 Hz, 2H), 1.99-1.82 (m, 2H), 1.75-1.46 (m, 4H). m/z found=1015.3 (M+H).

Figure 6:
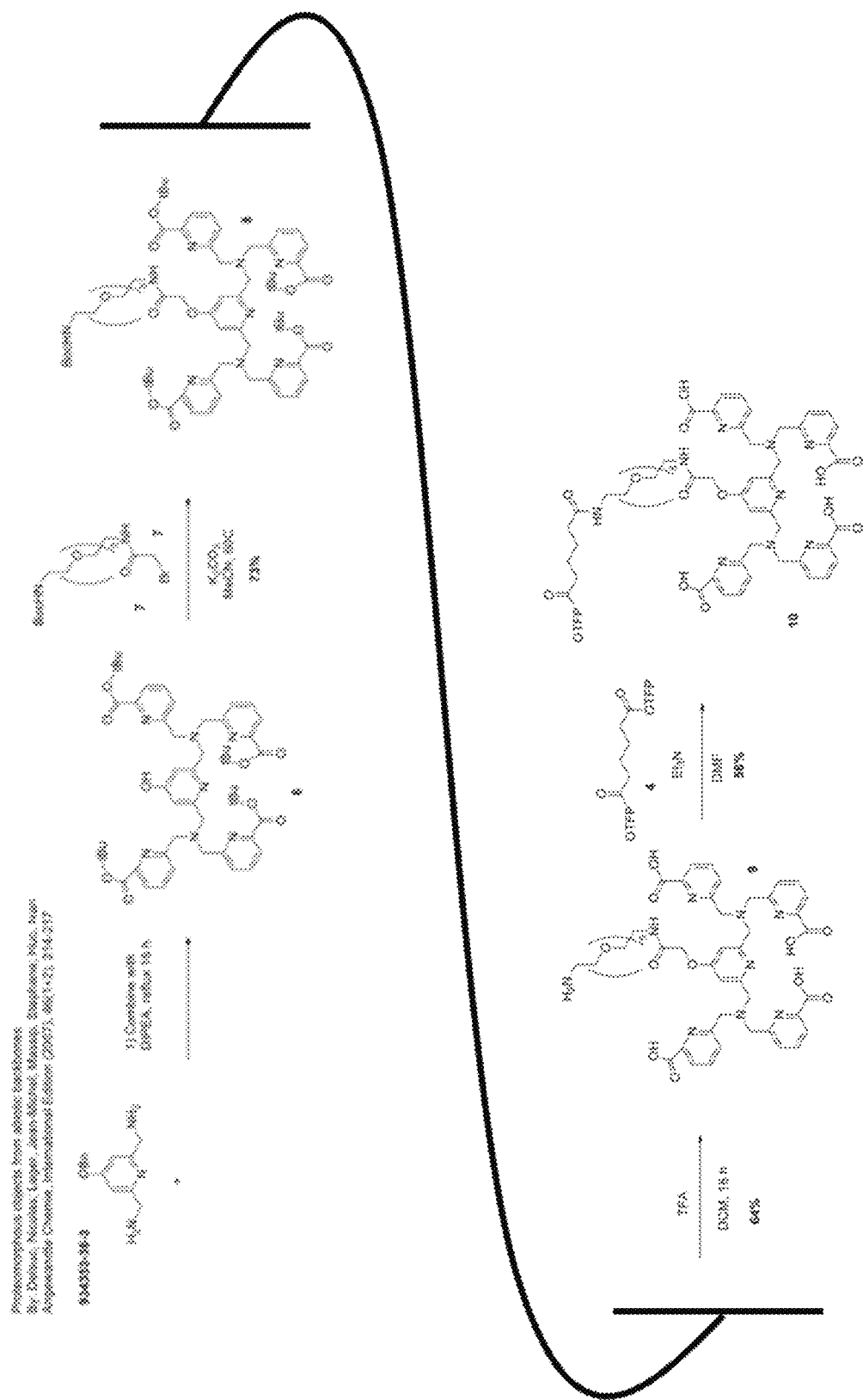
FIG. 6 shows a diagram for chemical synthesis of linker molecules.

FIG. 6 shows PEG5-Py4 Pa synthesis, including compounds numbered (6)-(10) as described below.

Synthesis of Compound (6) tert-butyl 6-[({[4-(benzyloxy)-6-{[bis({6-[(tert-butoxy)carbonyl]pyridin-2-yl}methyl)amino]methyl}pyridin-2-yl]methyl}({6-[(tert-butoxy)carbonyl]pyridin-2-yl}methyl)amino)methyl] pyridine-2-carboxylate. To a stirred solution of 1-[6-(aminomethyl)-4-(benzyloxy)pyridin-2-yl]methanamine (0.65 g, 2.67 mmol) (available from N. Delsuc, et al. *Angew Chem. Int. Ed.* 2007, 46, 214-217) in acetonitrile (50 mL) was added DIPEA (1.40 mL, 1.04 mg, 8.01 mmol) and tert-butyl 6-(bromomethyl)pyridine-2-carboxylate (4.36 g, 16.0 mmol) (available from P. Coomba, et al. *Inorg. Chem.* 2016, 55, 12531-12543) and the solution was heated to reflux. After 16 h, the reaction was allowed to cool and the solvent removed in vacuo. The crude was taken up in 200 mL DCM and washed 2×75 mL NaHCO$_3$(sat) and 2×75 mL saturated brine. The DCM layer was then dried over sodium sulfate, filtered, and concentrated in vacuo to yield a brown crude oil (950 mg) that could be used in the following step without further purification. The intermediate from above was dissolved in EtOH, ammonium formate (297 mg, 4.71 mmol) was added, and the flask was purged with N$_2$. 10% Pd/C (250 mg, 0.23 mmol) was added followed by another purge with N$_2$, then 30% Pd/C (50 mg, 0.14 mmol) was added. Following another purge with N$_2$, the reaction was heated to 50 C and stirred for 6 h where the reaction was complete by LCMS. The reaction mixture was filtered through celite, washed 3×50 mL MeOH, then concentrated in vacuo to a pale-yellow oil. The crude was purified by flash chromatography using a Biotage Sfar amino D cartridge and a gradient of 40-100% EtOAc/Hexanes followed by 0-20% MeOH/DCM to yield the title compound as a yellow solid (278 mg, 11%). $^1$H NMR (400 MHz, Methanol-d$_4$) δ 7.88 (dd, J=7.7, 1.3 Hz, 4H), 7.82 (t, J=7.7 Hz, 4H), 7.73 (dd, J=7.7, 1.2 Hz, 4H), 6.41 (s, 2H), 4.00 (s, 8H), 3.94 (s, 4H), 1.61 (s, 36H). m/z found=918.4 (M+H).

Synthesis of Compound (7) tert-butyl N-[17-(2-bromoacetamido)-3,6,9,12,15-pentaoxaheptadecan-1-yl]carbamate: A solution of tert-butyl N-(17-amino-3,6,9,12,15-pentaoxaheptadecan-1-yl)carbamate (200 mg, 0.53 mmol) and DIPEA (0.146 mL, 109 mg, 0.84 mmol) in 5 mL DCM was cooled to 0° C. A solution of 2-bromoacetyl bromide (0.069 mL, 159 mg, 0.79 mmol) in 5 mL DCM cooled to 0° C. was added dropwise over 2 min. The reaction was allowed to warm to rt, after 90 min HPLC showed full conversion to product. The reaction was concentrated, partitioned between Et$_2$O and water, NaHCO$_{3(sat)}$ was added, then the mixture was extracted 3×25 mL with Et$_2$O. The combined organics were washed with brine, dried over sodium sulfate, filtered and concentrated in vacuo. The crude residue was co-evaporated once with acetonitrile to remove water. The title compound was recovered as a brownish oil (261 mg, 99%). $^1$H NMR (400 MHz, Chloroform-d) δ 3.90 (s, 2H), 3.75-3.64 (m, 18H), 3.61 (d, J=4.5 Hz, 2H), 3.56 (t, J=5.1 Hz, 2H), 3.52 (t, J=5.2 Hz, 2H), 3.37-3.30 (m, 2H), 1.46 (s, 9H). m/z found=523.2 (M+Na).

Synthesis of Compound (8) tert-butyl 6-({[(6-{[bis({6-[(tert-butoxy) carbonyl]pyridin-2-yl}methyl)amino] methyl}-4-{[(17-{[(tert-butoxy)carbonyl]amino}-3,6,9,12, 15-pentaoxaheptadecan-1-yl)carbamoyl]methoxy}pyridin-2-yl)methyl]({6-[(tert-butoxy)carbonyl]pyridin-2-yl}methyl)amino}methyl)pyridine-2-carboxylate.

Compound 6 (100 mg, 0.11 mmol) and compound 7 (81.9 mg, 0.163 mmol) were taken up in acetonitirile (5 mL), then potassium carbonate (30.1 mg, 0.218 mmol) was added and the reaction was stirred at 60 C. After 24 h, no starting material remained by HPLC. The reaction was concentrated and purified by flash chromatography (Biotage amino D cartridge, gradient 0.2-15% MeOH/DCM) to yield the title compound as a yellow film (106 mg, 73%). $^1$H NMR (400 MHz, Methanol-$d_4$) δ 7.89 (d, J=7.8 Hz, 4H), 7.83 (t, J=7.7 Hz, 4H), 7.66 (d, J=7.6 Hz, 4H), 6.95 (s, 2H), 4.66 (s, 2H), 4.04 (s, 8H), 3.92 (s, 4H), 3.75-3.55 (m, 20H), 3.53-3.43 (m, 2H), 3.30-3.13 (m, 2H), 1.52 (s, 36H), 1.43 (s, 9H). m/z found=670.0 (M+2H/2).

Synthesis of Compound (9) 6-({[(4-{[(17-amino-3,6,9, 12,15-pentaoxaheptadecan-1-yl)carbamoyl]methoxy}-6-({bis[(6-carboxypyridin-2-yl)methyl]amino}methyl)pyridin-2-yl)methyl][(6-carboxypyridin-2-yl)methyl] amino}methyl)pyridine-2-carboxylic acid: Compound 8 (125 mg, 0.093 mmol) was taken up in DCM (5 mL) and TFA (5 mL) was added. After 18 h, HPLC showed no starting material or t-butyl intermediates remaining. The reaction was concentrated in vacuo and co-evaporated once with DCM. The crude oil was triturated 2× with $Et_2O$ with sonication and collected by filtration to yield 100 mg (64%, as a 5×TFA salt) of the title compound as a brownish solid. $^1$H NMR (400 MHz, Methanol-$d_4$) δ 8.04 (d, J=7.7 Hz, 4H), 7.96 (t, J=7.8 Hz, 4H), 7.66 (t, J=8.4 Hz, 4H), 7.45 (s, 2H), 4.84 (s, 2H), 4.74-4.49 (m, 12H), 3.74 (t, J=5.0 Hz, 2H), 3.71-3.63 (m, 14H), 3.60 (t, J=5.3 Hz, 2H), 3.48 (t, J=5.6 Hz, 2H), 3.20-3.12 (m, 2H). m/z found=1014.3 (M+H).

Synthesis of Compound (10) 6-[({[6-({bis[(6-carboxypyridin-2-yl)methyl]amino}methyl)-4-[({17-[6-oxo-6-(2,3, 5,6-tetrafluorophenoxy)hexanamido]-3,6,9,12,15-pentaoxaheptadecan-1-yl}carbamoyl)methoxy]pyridin-2-yl]methyl} [(6-carboxypyridin-2-yl)methyl]amino)methyl]pyridine-2-carboxylic acid. To a solution of compound 9 (80 mg, 0.079 mmol) in DMF (2.5 mL) was added bis(2,3,5,6-tetrafluorophenyl) hexanedioate (4) (140 mg, 0.32 mmol) and triethylamine (0.027 mL, 20 mg, 0.197 mmol). Full conversion to product was confirmed by HPLC. After stirring for 4 h, the reaction was diluted with DMSO (1.5 mL) and purified by direct injection onto prep-HPLC (Agilent, Hanover, CT) with a gradient of 25-60% MeCN/water+0.1% TFA to yield the title compound (57.5 mg, 56%) as a white powder (3×TFA salt). $^1$H NMR (400 MHz, Deuterium Oxide) δ7.85 (t, J=7.8 Hz, 4H), 7.78 (dd, J=7.8, 1.2 Hz, 4H), 7.50 (dd, J=7.8, 1.2 Hz, 4H), 7.11 (tt, J=10.4, 7.2 Hz, 1H), 6.99 (s, 2H), 4.59 (s, 2H), 4.49 (s, 8H), 4.45 (s, 4H), 3.60-3.45 (m, 18H), 3.46 (t, J=5.3 Hz, 2H), 3.36 (t, J=5.3 Hz, 2H), 3.22 (t, J=5.3 Hz, 2H), 2.59 (t, J=6.7 Hz, 2H), 2.14 (t, J=6.7 Hz, 2H), 1.61-1.46 (m, 4H). m/z found=1290.3 (M+H).

Synthesis of Compound (11) 6-[({[6-({bis[(6-carboxypyridin-2-yl)methyl]amino}methyl)-4-{2-[4-(cyanosulfanyl)phenyl]ethoxy}pyridin-2-yl]methyl][(6-carboxypyridin-2-yl)methyl]amino)methyl]pyridine-2-carboxylic acid; bis(tri-fluoroacetic acid): The title compound was prepared by following the conditions in L Li et al. Bioconjugate Chem. 2021, 32, 1348-1363. Spectral and LCMS data matched reported values.

Example 13. Conjugation of VHH-Fc Proteins with Chelator-Linkers

Conjugations can be carried out using many of the methods available for preparation of IgG radioconjugates and IgG antibody-drug conjugates. For information on the range of applicable methodologies, see PW Howard Antibody-Drug Conjugates (ADCs), *Protein Therapeutics*, First Edition, chapter 9, pp. 278-279 (2017).

For a typical lysine-based conjugation, a VHH-Fc was buffer-exchanged into 0.1 M $NaHCO_3$, pH 8.5-9.5 by either Microsep Advance Centrifugal Device (Pall 10K MWCO, Cat #: MCP010C41) or by Zeba column (ThermoFisher, Cat #: 87768), followed by sterilization with a Costar Spin-X Centrifuge Tube, 0.22 μm (Corning, Cat #: 8160). The buffer-exchanged antibody was quantified by BCA assay. An appropriate molar excess (5-20 eq) of chelator-linker (50 mM in DMSO) was added to the VHH-Fc (2 mg/mL final concentration) and the reaction was incubated at 25° C. either for 2 h or overnight in the Thermomixer. After the reaction was complete, the sample was passed through a Zeba column (ThermoFisher, Cat #: 87770) according to the manufacturer's protocol to remove unused chelator-linker and buffer-exchange into PBS (pH 7.4) (LifeTechnologies, Cat #: 10010-023). This VHH-Fc-chelator conjugate (VFCC) was stored at 4° C. until analysis and purification.

Example 14. VHH-Fc-Chelator Conjugate (VFCC) Purification with SEC

To remove high molecular weight species (HMWS) and low molecular weight species (LMWS), VHH-Fcs were purified by SEC using an AKTA Pure FPLC system with a Cytiva HiLoad 16/600 Superdex 200 μg column. TBS buffer (50 mM Tris, 150 mM NaCl, OmniTrace Ultra water [VWR, Cat #: CAWX0003-2]), pH 7.6 was used for the SEC buffer. The fractions containing intact VHH-Fcs were pooled together and concentrated using Microsep Advance Centrifugal Device (Pall 10k MWCO, Cat #: MCP010C41). The concentrated sample was transferred to an Ultrafree-MC GV Centrifugal Filter, 0.22 μm 0.5 mL (Millipore, Cat #: UFC30GV0S) and spun at 3,000×g for 3 minutes.

Example 15. Protein Quantification

VHH-Fc protein content was quantified with a Pierce BCA Protein Assay Kit (Thermo, Cat #: 23225) standardized by Cetuximab (LIST/E: 094822, DIN 02271249, 2 mg/mL).

Example 16. Chelator to VHH-Fc Ratio (CAR) Analysis

The chelator loading ratio, herein described as CAR, can be analyzed through methods applicable to practitioners of the art of antibody conjugates. For a review of these methods in the context of ADCs, see A Wakankar et al., *mAbs* 3:161 (2011). The CAR of each conjugate was analyzed by DG-SEC-MS.

Conjugates were analyzed through the deglycosylation and UPLC-Q-TOF procedure described in Example 11. In this case, a distribution of masses is obtained after spectrum deconvolution that allows calculation of the average CAR of the preparation.

Conjugates were analyzed through the deglycosylation and UPLC-Q-TOF procedure described in Example 11. In this case, a distribution of masses is obtained after spectrum deconvolution that allows calculation of the average CAR of the preparation.

Example 17. Binding of VHH-Fc Conjugates to Cells Expressing Target Protein

In some instances, conjugation can negatively impact binding of the VHH-Fc to the target protein. Binding of VHH-Fc conjugates was therefore tested, similar to as described above. Table 8 shows cell binding data of VHH-Fc chelator conjugates.

Example 19. Endotoxin Level Determination

Endotoxin test was performed using Wako's Limulus Amebocyte Lysate Pyrostar™ ES-F Single Test (Cat #: WPESK-0015) according to manufactural protocol. The QC cutoff was set based on the maximum injection dose projected for each animal in the study while following appropriate animal care and FDA guidelines.

Example 20. Radiolabeling with In-111

40 µg of each of the 4 test articles was diluted to 100 µL with 0.1 M ammonium acetate buffer in a 500 µL lo-bind Eppendorf tube and 18-25 µL (20-22 MBq) of $[^{111}In]InCl3$ was added and mixed with a pipette. The reaction mixtures were incubated at 37° C. in an incubator for 1 hour. The tubes were then transferred to a 4° C. fridge.

Incorporation of radionuclides was determined by spotting 0.5 µL of sample at the origin of a 1.5×10 cm iTLC strip. The strip was then placed in a 50 mL Falcon tube containing 2 mL of mobile phase (25 mM EDTA in pH 5 0.1 M sodium acetate buffer) until the solvent had reached the top of the strip. The strip was removed and exposed to a phosphor imaging plate which was then scanned in a Cyclone phosphor imager. Regions of interest were drawn over spots corresponding to the migration of protein-bound and unbound In-111 and the proportion in each calculated.

TABLE 8

| Cell binding data of VHH-Fc chelator conjugates EC50 (nM) | | | | | |
|---|---|---|---|---|---|
| Controls | Antibody | SHP-77 | HCT-116 | HEK-DLL3 | HEK-293 |
|  | Rovalpituzumab | 0.11 | — | 0.06 | — |
|  | Trastuzumab hIgG1 | — | 1.16 | 1.06 | 0.69 |
| Short Linker DOTA p-SCN-Bn-DOTA | H101 (CAR 0) | — | 2.21 | 1.62 | 1.14 |
|  | H101 (CAR 0.6) | — | 1.96 | 1.73 | 1.16 |
|  | H101 (CAR 1.1) | — | 2.46 | 1.39 | 1.42 |
|  | H101 (CAR 2.3) | — | 3.34 | 2.05 | 1.68 |
|  | H101 (CAR 2.7) | — | 2.96 | 1.88 | 1.58 |
|  | H101 (CAR 4.6) | — | 5.63 | 2.99 | 2.27 |
|  | H101 (CAR 8.3) | — | 5.32 | 4.43 | 3.52 |
|  | D102 (CAR 0) | 0.53 | >100 | 1.42 | >10 |
|  | D102 (CAR 0.9) | 0.41 | — | 0.48 | — |
|  | D102 (CAR 4.7) | 0.38 | — | 0.56 | — |
| Long Linker DOTA | H101 (CAR 0) | — | 2.21 | 1.62 | 1.14 |
|  | H101 (CAR 2.0) | — | 4.01 | 3.99 | 3.11 |
|  | H101 (CAR 8.9) | — | 40.11 | 28.37 | 28.89 |
| TFP-Ad-PEG5-DOTA | D102 (CAR 0) | 0.53 | >100 | 1.42 | >10 |
|  | D102 (CAR 2.7) | 0.50 | — | 0.58 | — |
|  | D102 (CAR 9.3) | 0.60 | — | 0.91 | — |

H101 = Her2 antigen binding;
D102 = DLL3 antigen binding;
CAR = Chelator to VHH ratio As observed in Table 8, binding was observed for both long and short DOTA linkers. As also shown in Table 8, binding was also observed across increasing chelator VHH-Fc ratios (CAR).

Example 18. Percent Intact Analysis

The percent intact immunoconjugate was established by HPLC-SEC. 12 µL of conjugate was added to a glass vial insert in a standard HPLC vial. 10 µL of sample was injected onto an Agilent HPLC-SEC with a Wyatt Technology WTC-050S5 SN:0429 BN WBD129 column column and eluted with 1×PBS (100%) for 40 min at a flow rate of 0.5 mL/min Radioconjugates were also analyzed by SEC-HPLC: A volume corresponding to 0.1-0.2 MBq of the sample was pipetted into a 500 µL lo-bind Eppendorf tube and the radioactivity measured in an ionization chamber. The sample was drawn up into a syringe and injected onto the HPLC system. Samples were eluted with PBS. The eluate from the system was collected and the radioactivity measured in order to determine the recovery from the column (corrected for activity remaining in the sample tube and the injection syringe).

TABLE 9

Indium-111 Radiolabeling Efficiency

| | | Labelling efficiency post-synthesis | |
|---|---|---|---|
| Chelator-Linker | Antibody | Attempt 1 | Attempt 2 |
| P-SCN-Bn-DOTA | H101 | 95.9% | 96.5% |
| TFP-Ad-PEG5-DOTAGA | | 97.5% | 97.7% |

TABLE 9-continued

Indium-111 Radiolabeling Efficiency

| | | Labelling efficiency post-synthesis | |
|---|---|---|---|
| Chelator-Linker | Antibody | Attempt 1 | Attempt 2 |
| P-SCN-Bn-DOTA | D102 | 97.5% | 97.0% |
| TFP-Ad-PEG5-DOTAGA | | 98.1% | 97.2% |

Example 21. Radiolabeling with Ac-225

800 μg of each of the 4 test articles was diluted to 200 μL with 0.2 M ammonium acetate buffer pH 6.5 in a 500 μL lo-bind Eppendorf tube and 2 μL (400 kBq) of 225-Actinium chloride was added and mixed with a pipette. The reaction mixtures were incubated at 37° C. in an incubator for 1 hour in the case of the Py4 Pa conjugates and 2 hours for the DOTA conjugates. The tubes were then transferred to a 4° C. fridge.

Incorporation was measured by spotting 0.5 μL of sample at the origin of a 1.5×10 cm iTLC strip and allowing it to dry for a few minutes. The strip was then placed in a 50 mL Falcon tube containing 2 mL of mobile phase (25 mM EDTA in pH 5 0.1 M sodium acetate buffer) until the solvent had reached the top of the strip. The strip was removed and allowed to equilibrate for at least 2 hours, after which it was exposed to a phosphor imaging plate which was then scanned in a Cyclone phosphor imager. Regions of interest were drawn over spots corresponding to the migration of protein-bound and un-bound Ac-225 and the proportion in each calculated.

Alternately, samples could be assayed by HPLC-SEC: HPLC of DOTA conjugates used a BioSEP SEC 5 μm s3000 3007.88 mm column with 20% acetonitrile in PBS elution. HPLC of Py4 Pa conjugates used a Wyatt 050S5 5 μm 500 Å 7.8×300 mm column with 20% acetonitrile in PBS elution).

50 μL of each sample was drawn up into a Hamilton syringe and injected onto the HPLC system. From 10-30 minutes post injection, 30 second fractions of the eluate (0.25 mL) were collected by hand into counting tubes. The fractions were allowed to reach secular equilibrium for 24 hours and then measured in a gamma counter. A 5 μL sample of each preparation was also counted to enable the recovery from the HPLC system to be calculated. Radiochemical purity was determined by determining the area under the peak for 18.5-22.5 mins and 19.5-23.5 mins for DOTA and Py4 Pa conjugates, respectively, as a percentage of total counts. As shown in Table 10 all chelator-linker combinations showed good labeling efficiency.

TABLE 10

Ac-225 Radiolabeling Efficiency

| Chelator-Linker | Antibody | iTLC Labelling efficiency immediately after preparation |
|---|---|---|
| p-SCN-Bn-DOTA | H101 | 92.0% |
| TFP-Ad-PEG5-DOTAGA | | 96.3% |
| TFP-Ad-PEG5-Py4Pa | | 93.1% |
| p-SCN-Ph-Et-Py4Pa | | 96.0% |
| p-SCN-Bn-DOTA | D102 | 98.5% |
| TFP-Ad-PEG5-DOTAGA | | 99.5% |
| TFP-Ad-PEG5-Py4Pa | | 98.0% |
| p-SCN-Ph-Et-Py4Pa | | 100% |

Example 22. Stability of VHH-Fc Radioconjugates

The stability of the radiolabeled immunoconjugates was tested, both for $^{225}$Ac and $^{111}$In. VHH-Fc chelator-conjugates were radiolabeled (either In-111 or Ac-225) as described above. For stability in PBS, 50 μL of each labelled test article was then added to either 200 μL of PBS (with In-111) or 200 uL PBS/ascorbate (with Ac-225) and stored at 4° C. For stability in serum, 50 μL of each labelled test article was added to 200 μL of mouse serum and incubated at 37° C. Aliquots of were taken at different time points and analyzed for radiochemical purity using iTLC and/or HPLC-SEC as described above. The results of these stability experiments are shown in Table 11 and Table 12 below and indicated that the radio conjugates were stable in both PBS and serum.

TABLE 11

Stability of Her2 and DLL3 conjugates labeled with In-111

| Radiochemical purity by HPLC (iTLC) | DLL3 (D102) | | HER2 (H101) | |
|---|---|---|---|---|
| | P-SCN-Bn-DOTA | TFP-Ad-PEG5-DOTAGA | P-SCN-Bn-DOTA | TFP-Ad-PEG5-DOTAGA |
| PBS 1 h | 97.5% | 98.1% | 97.5% | 98.4% |
| PBS 24 h | 89.1% | 95.2% | 96.5% | 98.4% |
| Serum 24 h | 94% (94%) | 98% (94%) | 97% | 94% |
| Serum 72 h | 92% (92%) | 96% (94%) | 100% (87%) | 100% (84%) |
| Serum 168 h | 92% (94%) | 95% | 95% (91%) | 92% |

TLC radiochemical incorporation values presented in parentheses.

iTLC incorporation >95% except where shown

TABLE 12

Stability of Her2 and DLL3 conjugates labeled with Ac-225

| Radiochemical purity by HPLC (iTLC) | DLL3 (D102) | | | | HER2 (H101) | | | |
|---|---|---|---|---|---|---|---|---|
| | P-SCN-Bn-DOTA | TFP-Ad-PEG5-DOTAGA | TFP-Ad-PEG5-Py4Pa | P-SCN-Ph-Et-Py4Pa | P-SCN-Bn-DOTA | TFP-Ad-PEG5-DOTAGA | TFP-Ad-PEG5-Py4Pa | P-SCN-Ph-Et-Py4Pa |
| PBS 1 h | 91% | 92% | 83% | 82% | 93% | 93% | 84% | N/D |
| PBS 24 h | 92% | 92% | 83% | 83% | 93% | 91% | 82% | 82% |
| Serum 24 h | 88% (94%) | 91% | 78% | 69% | 91% | 90% | 75% | 68% |
| Serum 72 h | 89% (90%) | 90% (94%) | 73% | 65% | 89% (87%) | 85% (94%) | 74% | 61% |
| Serum 168 h | 81% (91%) | 86% | 71% | 59% | 85% (89%) | 80% | 70% | 56% |

TLC radiochemical incorporation values presented in parentheses. iTLC incorporation >95% except where shown

Example 23. Immunoreactivity of VHH-Fc Radioconjugates

Figure 7A:
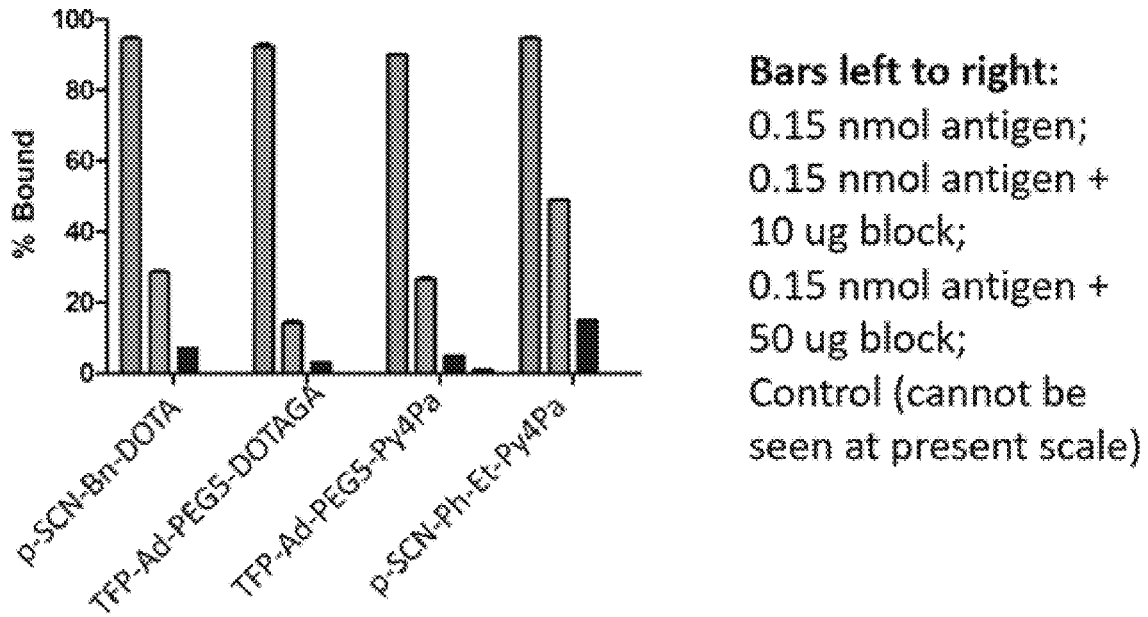
FIGS. 7A, 7B, and 7C shows the immunoreactive fraction of different VHH-Fc constructs.
Figure 7B:
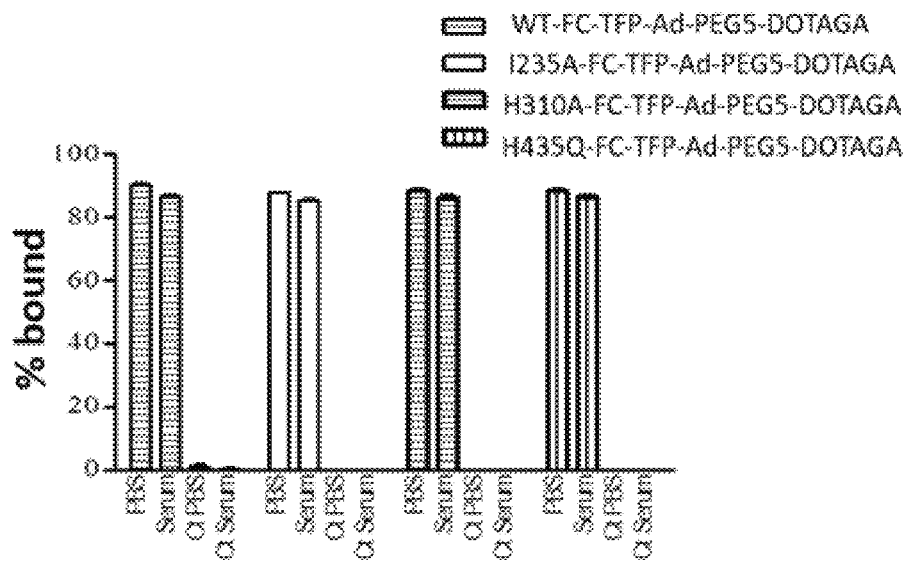
Figure 7C:
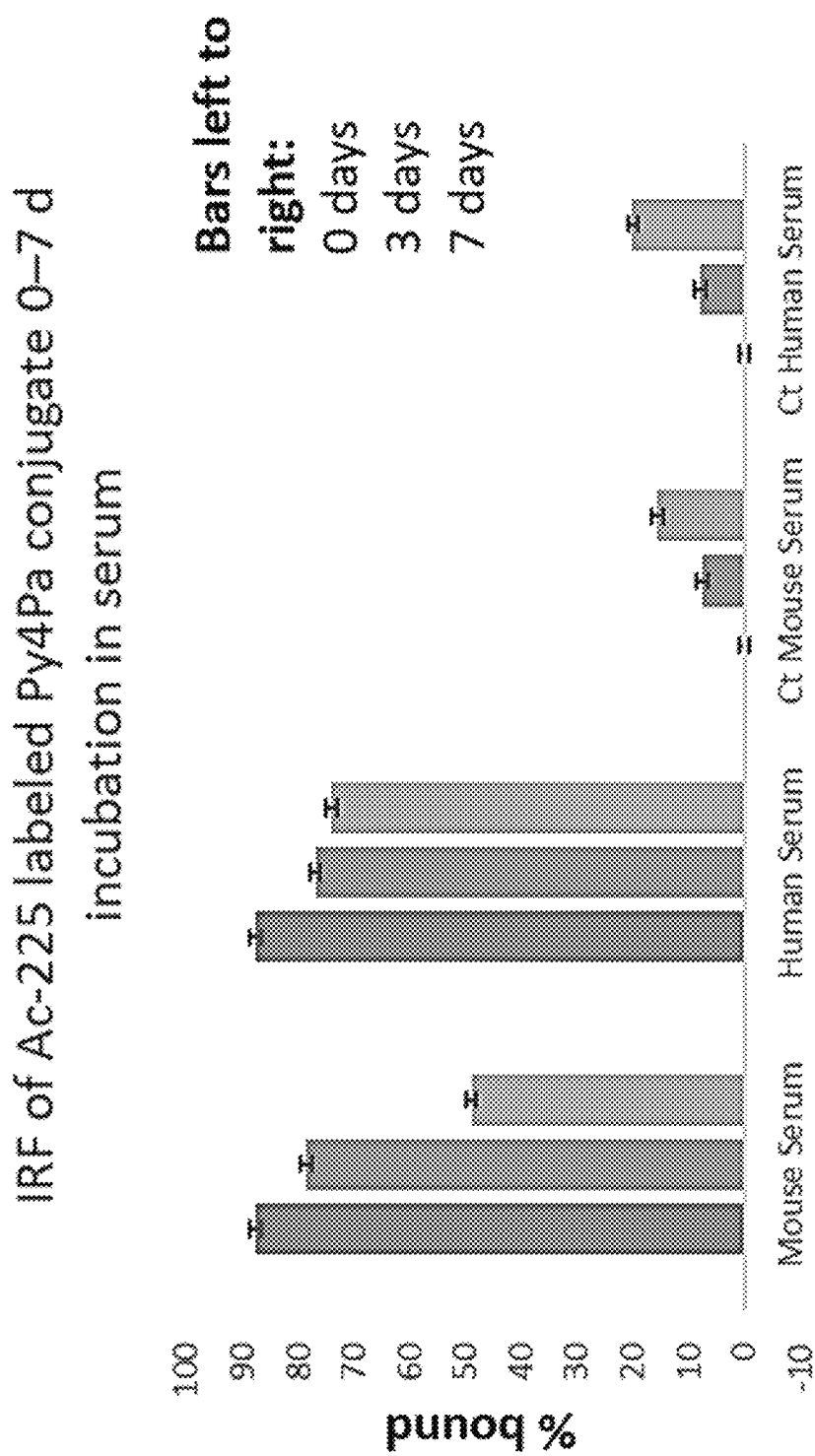

The immunoreactive fraction (IRF) was determined though a method described by SK Sharma et al. in *Nucl. Med. Biol.* 2019, 71, 32-38. Samples were incubated overnight in PBS at 4° C. for analysis and before in vivo experiments, while some samples were incubated in serum at 37° C. for 3 and 7 days as an alternate measure of stability.
Bead Coating
Dynabeads and antigen (0.15 nmol per 0.125 ug beads) were incubated in B/W buffer (25 uL/0.125 ug beads) at room temperature on a tube rotator for 30 minutes. The Eppendorfs were spun at 100×g for 15 seconds and placed on a magnetic rack for 3 minutes. The supernatant was removed and the beads washed with PBSF. 1 mg of beads was then resuspended in 200 µL of B/W buffer and 2 mg in 400 µL of B/W buffer. Control beads were prepared the same way, except with no antigen added to the tubes.
Immunoreactive Fraction (IRF) Assay
The appropriate volume of beads (25 uL/0.125 mg beads) generated above was added to microcentrifuge tubes, prewashed with 1 mL PBSF. Radiolabeled VHH-Fc-conjugate (10 ng), block (10 or 50 ug unconjugated antibody; if required), and PBSF were added to each reaction to achieve a final volume of 350 µL. The samples were incubated at room temperature on a rotor for 30 minutes. After this the tubes were centrifuged at 100×g for 15 seconds and placed on a magnetic rack for 3 minutes. The supernatant was collected in a gamma counter tube. The beads were washed twice with 400 µL PBSF and collected in a separate gamma counter tube. The beads were finally resuspended in 500 µL PBSF and transferred to a gamma counter tube. The reaction tube was washed with 500 µL PBSF and this was added to the gamma counter tube containing the beads.
As shown in FIG. 7A for DLL3 all linker chelator combinations showed a similar immunoreactive fraction indicating no bias in labeling based upon the specific linker chelator combination, FIG. 7B shows that there was no effect due to Fc region mutations in immunoreactive fraction after 24 hours in PBS or serum, and FIG. 7C shows the immunoreactive fraction of $^{225}$AC labeled anti-DLL3 VHH-Fc (D102) and stability in serum and plasma.

Example 24. Biodistribution of VHH-Fc Radioimmunoconjugates

Biodistribution and Tissue Accumulation Over Time in HER2+BT474 Tumors
Imaging (e.g., using Indium-111 ($^{111}$In)) provides for the ability to collect pharmacokinetic and biodistribution data that can be used to perform dosimetry calculations for treatment planning. (See, e.g., Sgouros G, Hobbs R F. "Dosimetry for radiopharmaceutical therapy." *Semin Nucl Med.* 2014 May; 44(3):172-8).). Without being bound by theory, a quantitative demonstration of targeting observed with an imaging label is indicative of the ability to target with a radiolabel (e.g., an alpha emitter) capable of causing targeted cell death. Such phenomena is illustrated by FIG. 8, which illustrates that mice labeled with the imaging isotope $^{111}$In (top), exhibit accumulation of the therapeutic isotope $^{225}$Ac in tumors that express low amounts of antigen and high amounts of antigen, in this example DLL3 expressing SHP77 tumors and HER2 expressing BT474 tumors respectively.

Figure 9A:
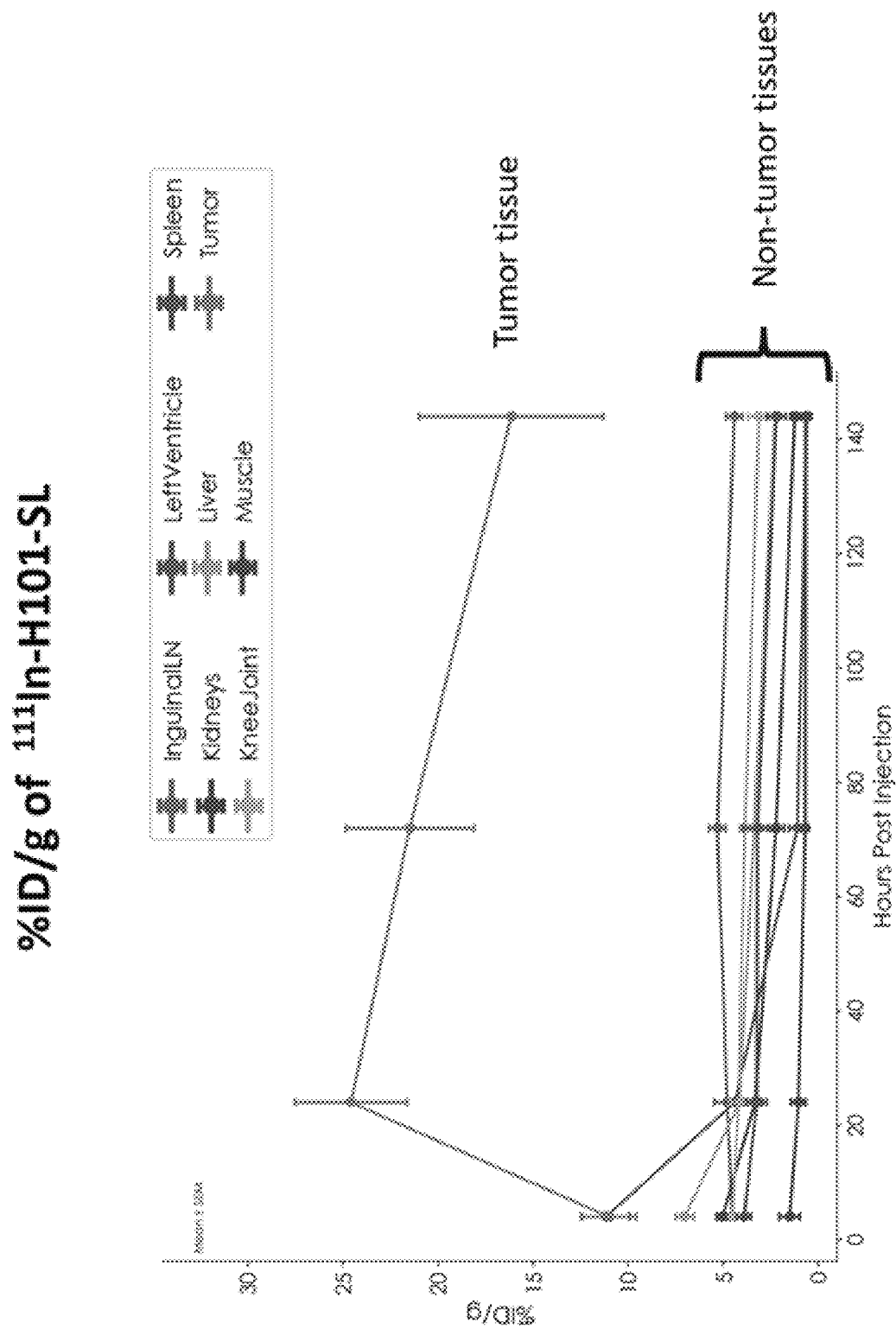
FIGS. 9A, 9B, 9C, and 9D show biodistribution over time for labeled anti-HER2 VHH-Fc constructs.
Figure 9B:
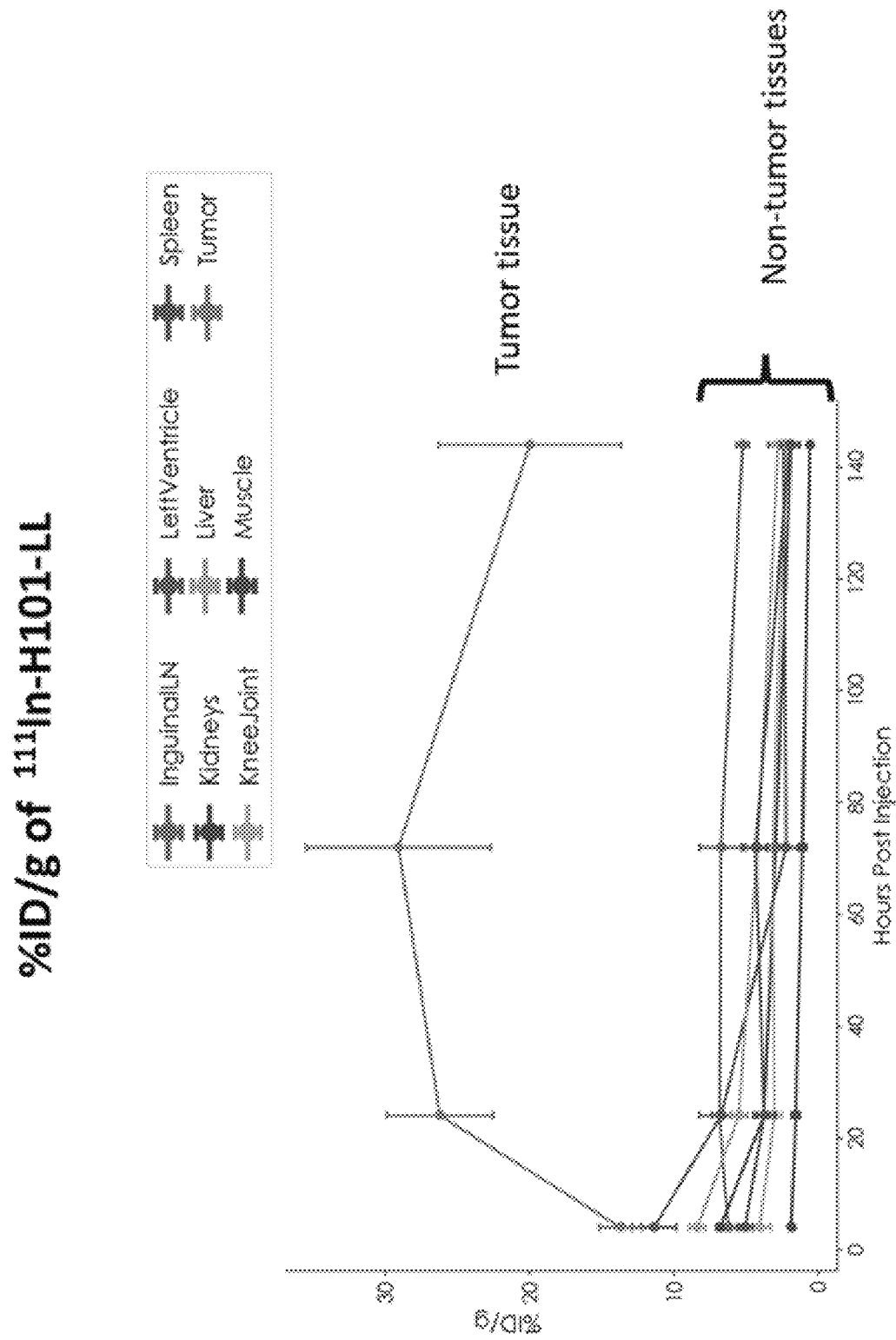
Figure 9C:
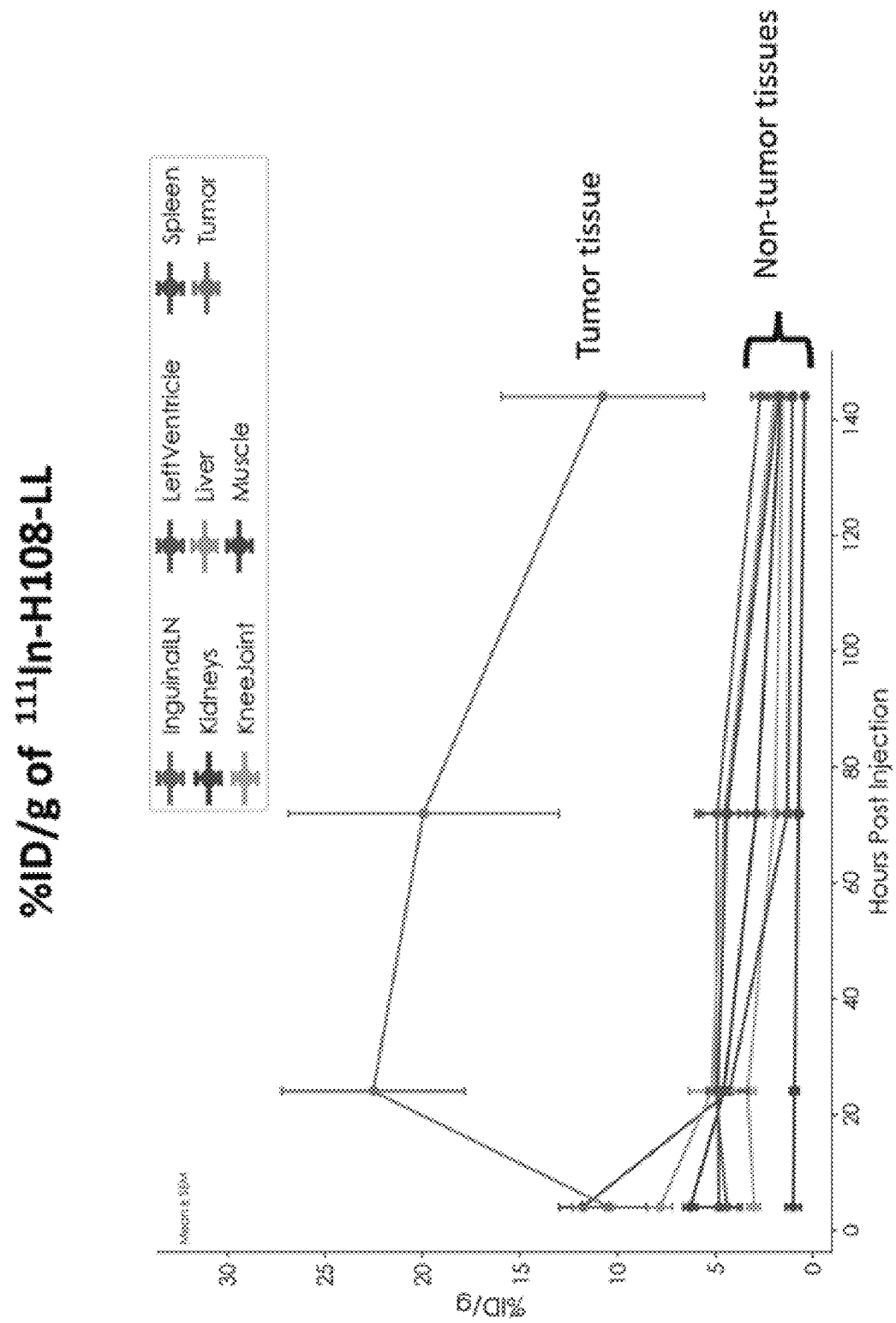
Figure 9D:
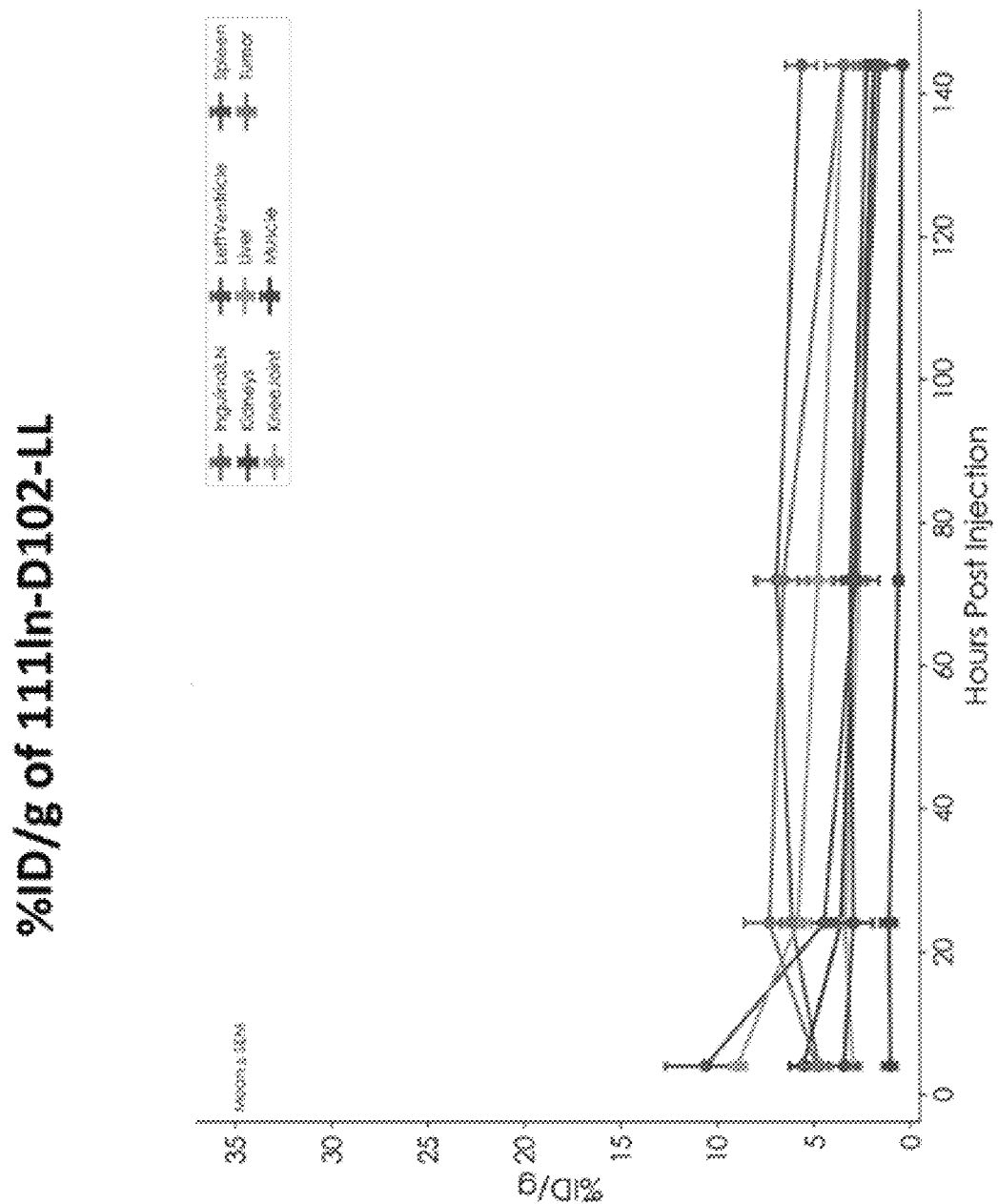
Figure 10A:
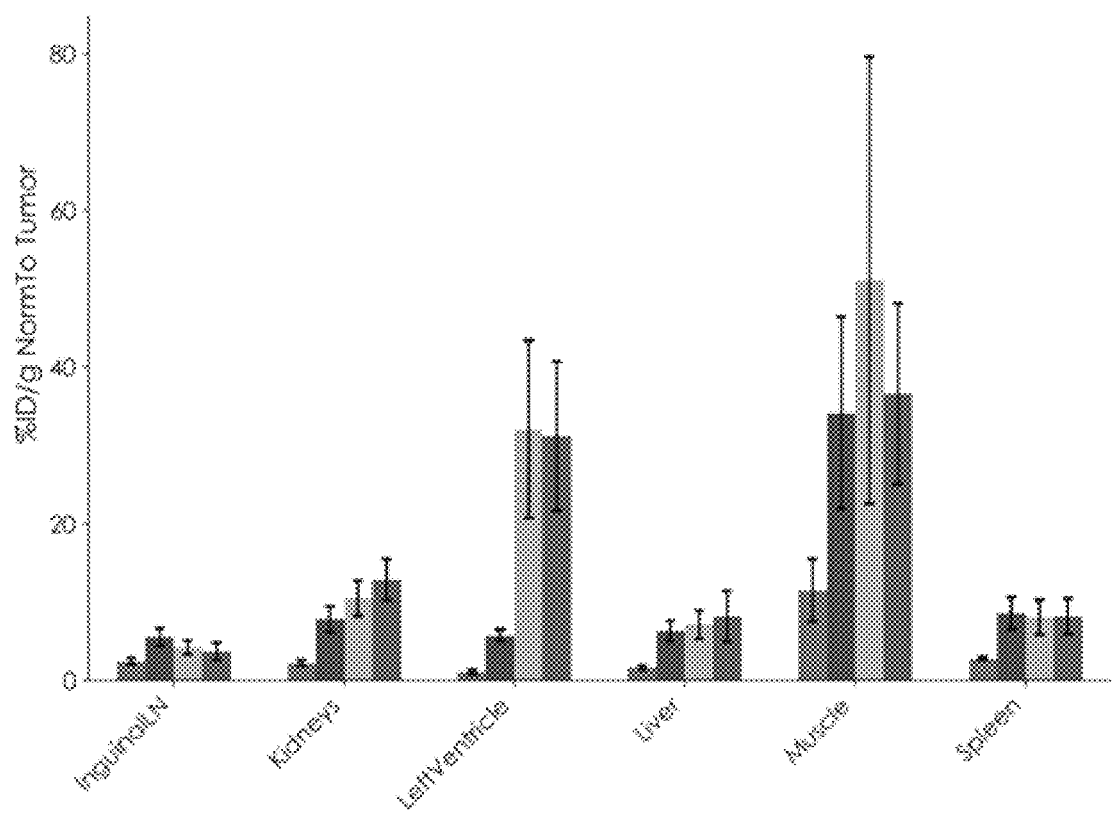
FIGS. 10A, 10B and 10C show tumor:non-tumor tissue ratios for labeled anti-HER2 VHH-Fc constructs.
Figure 10B:
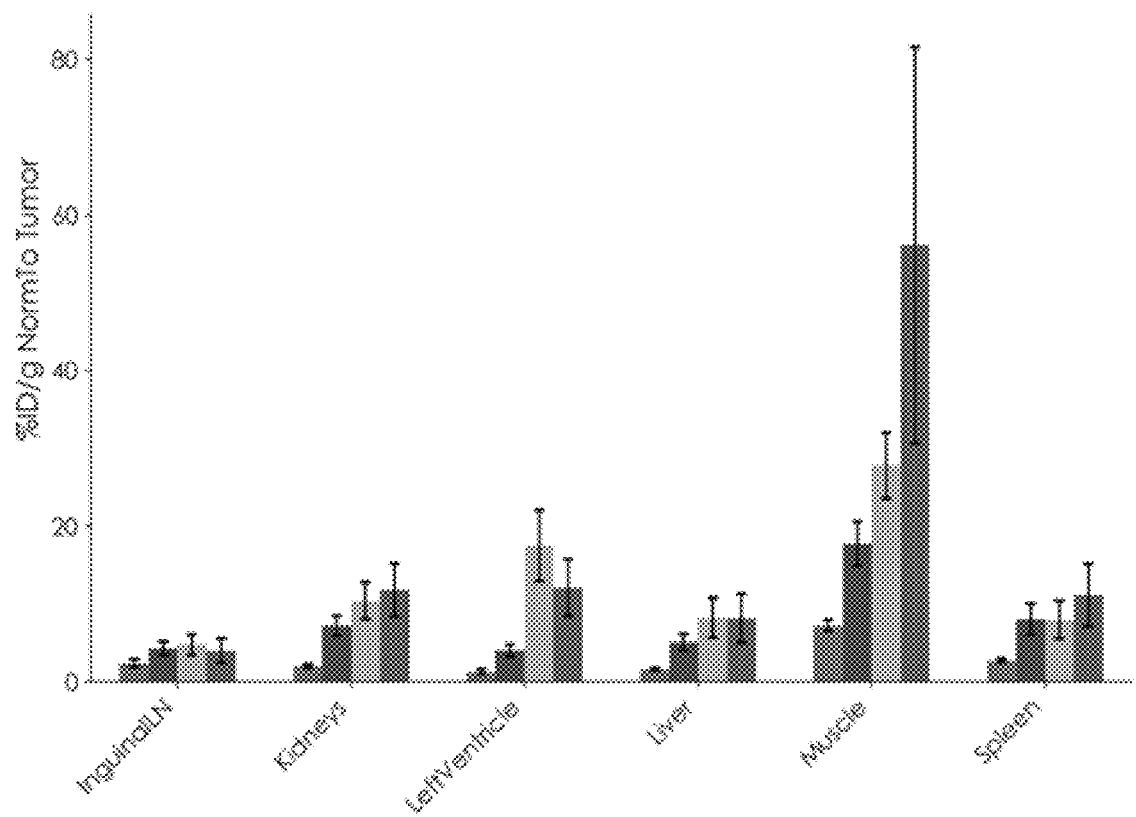
Figure 10C:
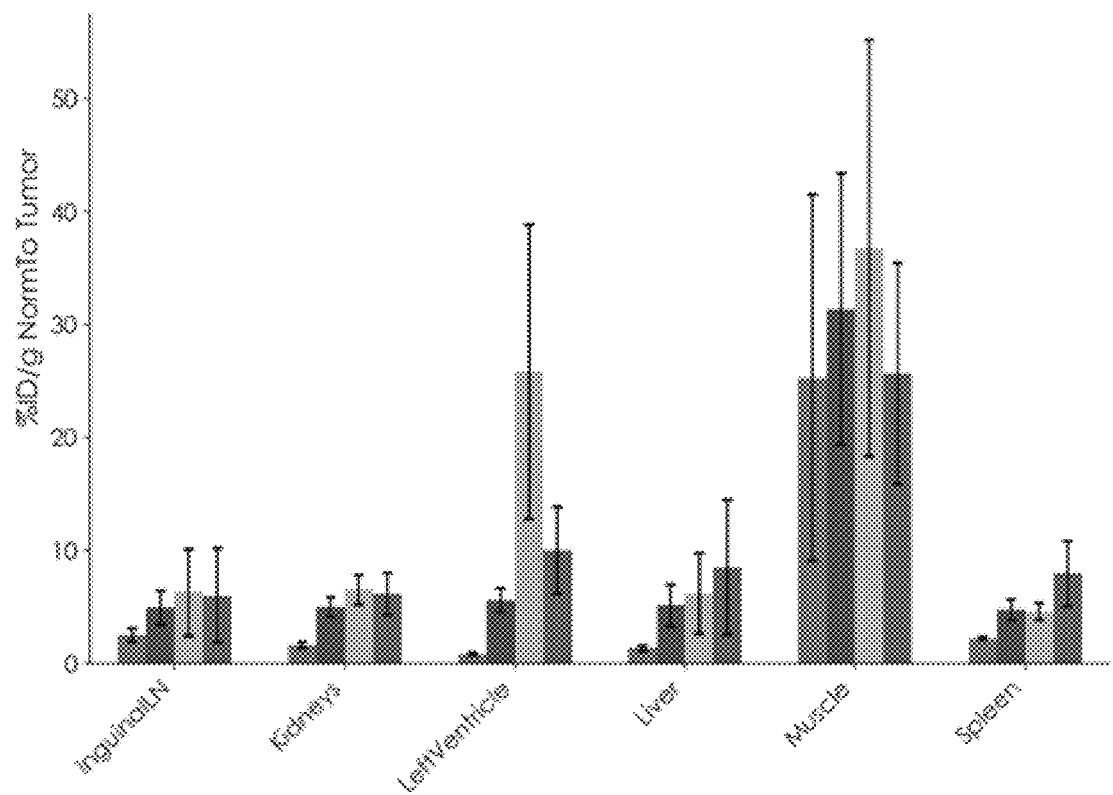
Figure 11:
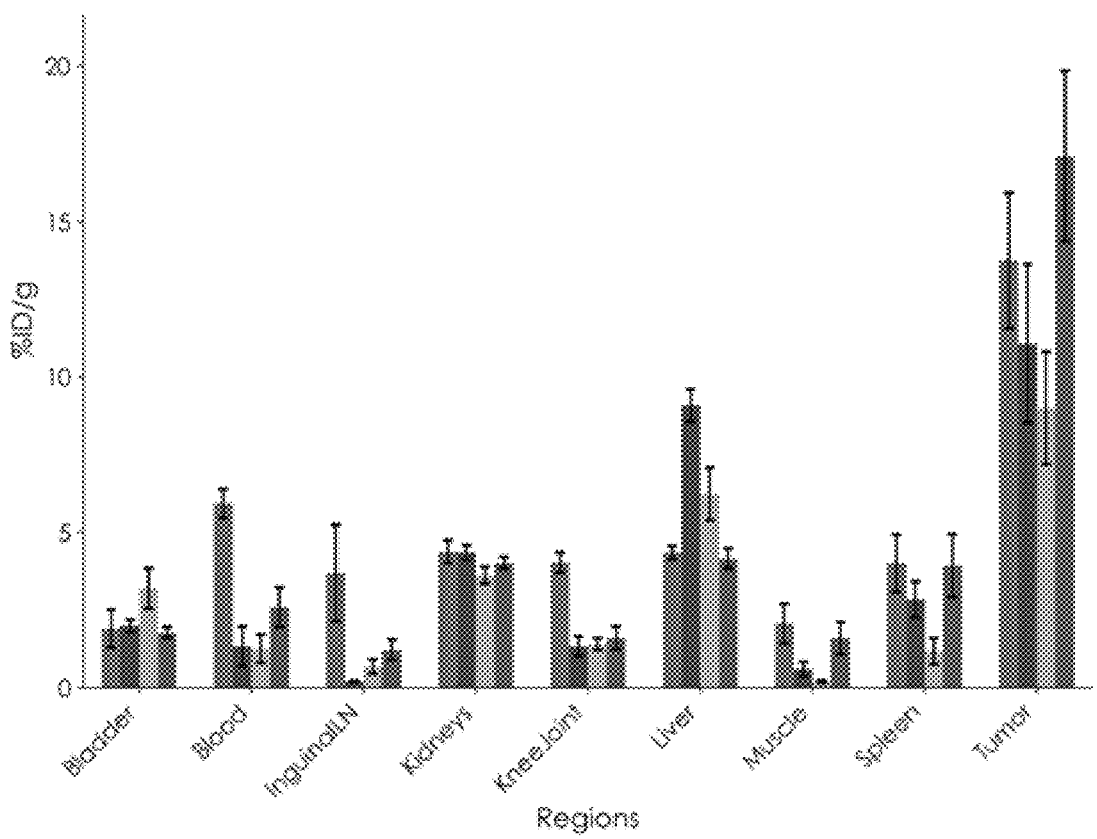
FIG. 11 shows biodistribution for labeled anti-HER2 VHH-Fc constructs.
Figure 12:
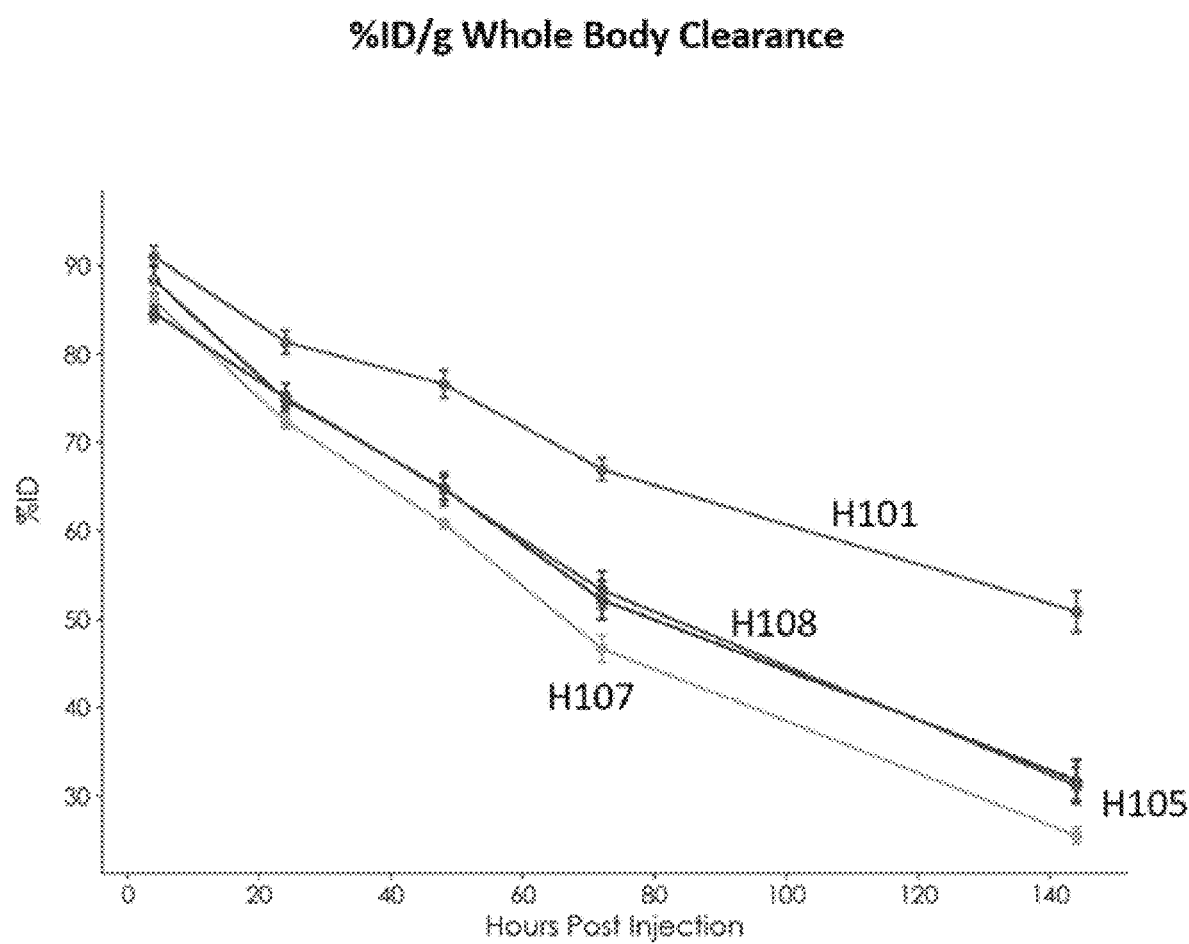

The objective of this study was to observe the biodistribution of $^{111}$In radiolabeled SPECT/CT imaging across select test articles in BT-474 tumor (breast cancer cells) bearing nude mice. The following articles were tested at a CAR of about 4: $^{111}$In-H101-short DOTA linker (p-SCN-Bn-DOTA, SL), $^{111}$In-H101-long DOTA linker (TFP-Ad-PEG5-DOTAGA, LL), $^{111}$In-H105-LL, $^{111}$In-H107-LL, and $^{111}$In-H108-LL. FIGS. 9A, 9B, and 9C show tissue accumulation over time for $^{111}$In-H101-SL, $^{111}$In-H101-LL, and $^{111}$In-H108-LL. FIG. 9D shows minimal tumor accumulation with DLL3 targeting VHH-Fc in HER2+ tumor model, further demonstrating specificity of the HER2 targeting VHH-Fcs. FIGS. 10A, 10B, and 10C show tumor:tissue ratios. In each case, the tumor:tissue ratios were greater than 5, indicating increased tumor accumulation and better profiles used for determining safety (e.g., as compared lower tumor:tissue ratios). FIG. 11 shows % ID/g at 144 hours for $^{111}$In-H101-LL, $^{111}$In-H105-LL, $^{111}$In-H107-LL, and $^{111}$In-H108-LL. In each case, the VHH-Fc variants show advantageous targeting of tumor tissue. FIG. 12 shows whole body clearance of VHH-Fc (H101) and VHH-Fc variants (H105, H107, and H108), wherein the VHH-Fc variants show increased clearance which can further be advantageous when considering safety and preventing unwanted tissue toxicity. In all cases, all test articles avoided significant kidney accumulation, further demonstrating favorable profiles for safety and avoiding unwanted tissue toxicity. Table 13 specifically shows the tumor accumulation for $^{111}$In-H101-LL, $^{111}$In-H105-LL, $^{111}$In-H107-LL, and $^{111}$In-H108-LL over time.

TABLE 13

Tumor accumulation of anti-HER2 VHH-Fc variants
(mean % ID/g; n = 4)

| | | 4 h | 24 h | 48 h | 72 h | 144 h |
|---|---|---|---|---|---|---|
| 111In-H108-LL | mean | 4.7 | 12.2 | 14.4 | 12.7 | 13.7 |
| | SEM | 0.6 | 1.8 | 2.1 | 0.9 | 2.2 |
| 111In-H101-LL | mean | 4.9 | 9.3 | 14.2 | 14.1 | 11.1 |
| | SEM | 0.5 | 1.1 | 2.0 | 2.6 | 2.6 |
| 111In-H105-LL | mean | 4.9 | 7.1 | 9.0 | 9.4 | 9.0 |
| | SEM | 1.1 | 2.0 | 1.9 | 2.2 | 1.8 |
| 111In-H107-LL | mean | 6.2 | 12.6 | 18.6 | 18.0 | 17.1 |
| | SEM | 1.1 | 1.9 | 2.3 | 2.6 | 2.8 |

Biodistribution and Tissue Accumulation Over Time in DLL3+ SHP-77 Tumors

Figure 13:
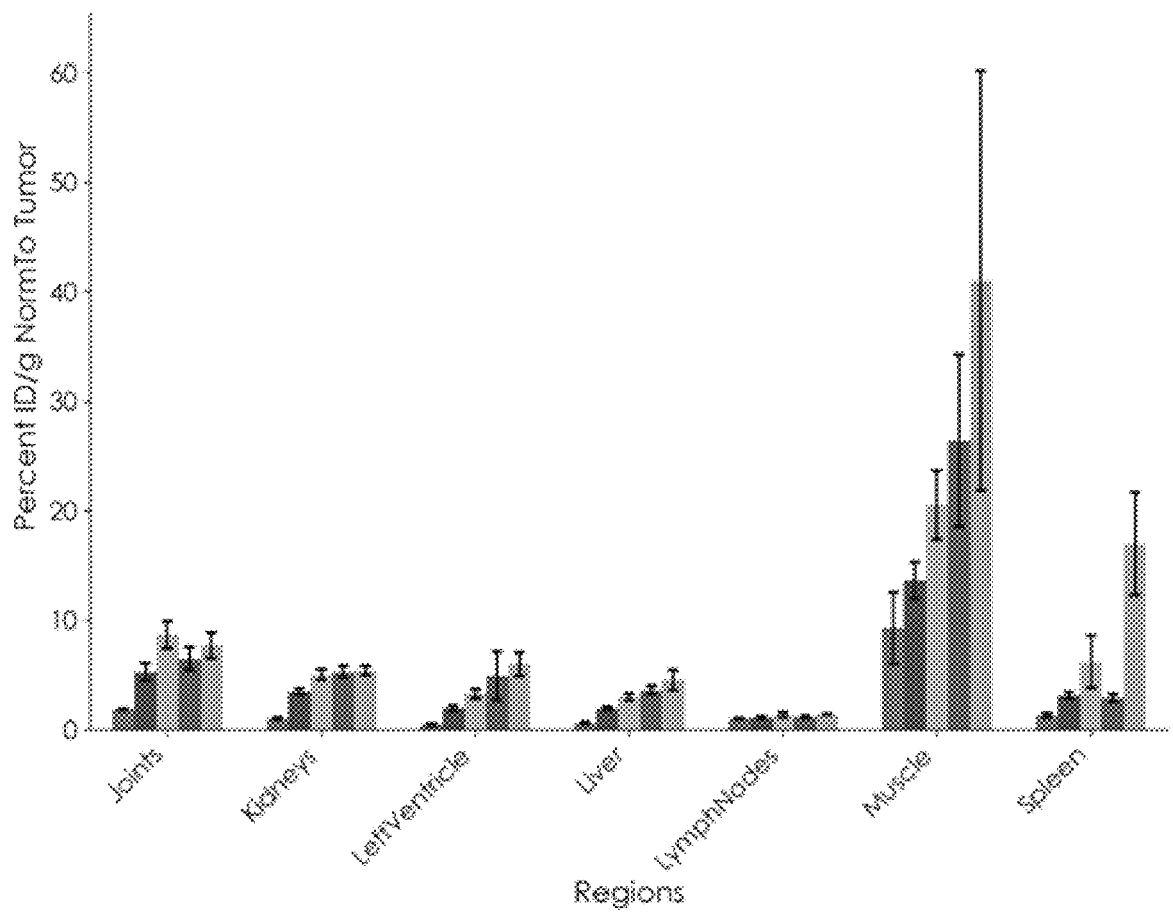
FIG. 13 shows biodistribution over time for labeled anti-DLL3 VHH-Fc constructs.
Figure 14:
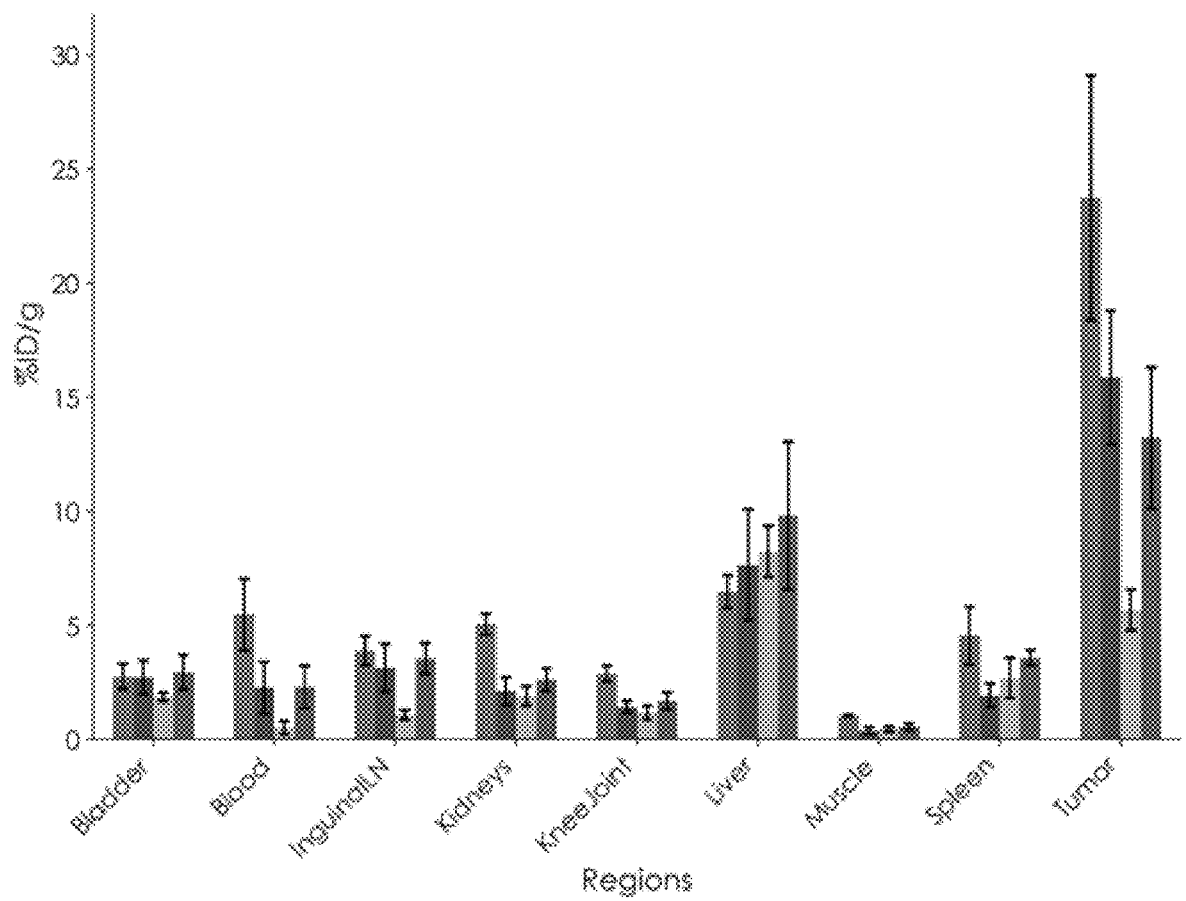
FIG. 14 shows biodistribution for labeled anti-DLL3 VHH-Fc constructs.

The objective of this study was to observe the biodistribution of $^{111}$In SPECT/CT across select test articles in SHP-77 tumor bearing nude mice. In contrast to HER2, DLL3 is generally present at lower copy numbers on the cell surface. Accordingly, the DLL3 represents the ability to target low copy number target proteins, whereas HER2 represents the ability to safely and effectively target high copy number target proteins. The following articles were tested: $^{111}$In-D102-long DOTA linker (LL), $^{111}$In-D111-LL, $^{111}$In-D113-LL, and $^{111}$In-D114-LL. Interestingly, similar targeting profiles and observations to the HER2 model were observed for the DLL3 model, demonstrating the ability to target high and low copy number targets. FIG. 13 shows $^{111}$In-D102-LL Tumor: Tissue ratios and FIG. 14 shows % ID/g at 144 hours for $^{111}$In-D102-LL, $^{111}$In-D111-LL, $^{111}$In-D113-LL, and $^{111}$In-D114-LL. As observed for HER2, anti-DLL3 VHH-Fc variants showed advantageous targeting of tumor tissue. Additionally, liver accumulation is indicative of increased clearance, which can further be advantageous when considering safety and preventing unwanted tissue toxicity. In all cases, all test articles avoided significant kidney accumulation, further demonstrating favorable profiles for safety and avoiding unwanted tissue toxicity. Table 14 specifically shows the tumor accumulation for $^{111}$In-D102-LL, $^{111}$In-D111-LL, $^{111}$In-D113-LL, and $^{111}$In-D114-LL over time.

TABLE 14

Tumor accumulation of anti-DLL3 VHH-Fc variants
(mean % ID/g; n = 4)

| | | 4 h | 24 h | 48 h | 72 h | 144 h |
|---|---|---|---|---|---|---|
| 111In-D102-LL | mean | 6.0 | 12.8 | 18.0 | 19.0 | 23.7 |
| | SEM | 0.7 | 1.7 | 2.1 | 2.1 | 5.4 |
| 111In-D111-LL | mean | 5.5 | 12.8 | 16.6 | 16.8 | 15.9 |
| | SEM | 1.4 | 1.1 | 2.0 | 2.3 | 2.9 |
| 111In-D113-LL | mean | 4.5 | 8.7 | 10.0 | 9.4 | 5.7 |
| | SEM | 0.6 | 1.2 | 1.4 | 1.2 | 0.9 |
| 111In-D114-LL | mean | 5.1 | 10.9 | 14.6 | 15.8 | 13.2 |
| | SEM | 0.5 | 0.9 | 1.6 | 2.4 | 3.1 |

Taken together, the $^{111}$In imaging results show that targeting of both high copy number and low copy number targets can be achieved with the radiolabeled VHH-Fcs and VHH-Fc variants. These results further indicate favorable safety and specificity profiles for targeting tumor tissue, avoiding non-tumor tissue, and in certain instances, effectively clearing radiolabeled VHH-Fcs (e.g., VHH-Fcs having mutations that reduced FcRn affinity).

Biodistribution and Tissue Accumulation of Ac-225 Radiolabeled VHH-Fcs

The objective of this study was to observe biodistribution of (i) Ac-225 radiolabeled HER2 VHH-Fcs in a BT-474 tumor mouse model, as described above, and (ii) Ac-225 radiolabeled DLL3 VHH-Fcs in a SHP-77 tumor mouse model, as described above. Ex vivo radioactive quantitation in tumor and normal tissues was achieved by gamma counting.

Figure 15A:
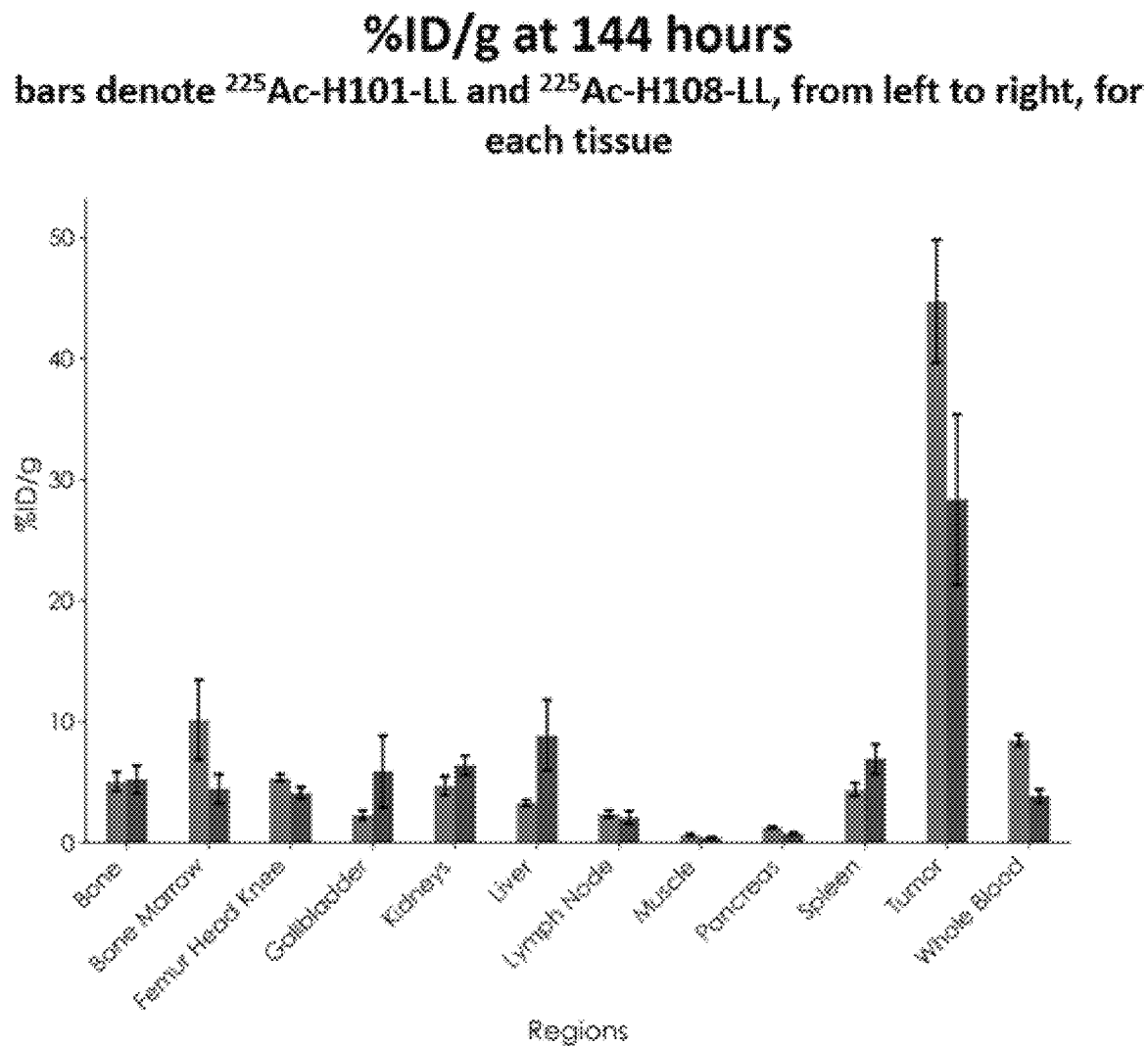
FIGS. 15A and 15B show biodistribution for $^{225}$Ac labeled anti-HER2 (15A) and anti-DLL3 (15B) VHH-Fc constructs.

As described herein, the HER2 model represents a target with high receptor density on cancer cells (e.g., ~300,000 copies/cell). FIG. 15A shows % ID/g at 144 hours for 225Ac-H101-LL and 225Ac-H108-LL. Both test articles showed advantageous targeting profiles, consistent with the $^{111}$In imaging data. Notably, specific targeting of tumor tissue was achieved with a favorable tumor:tissue ratio consistent with the imaging data. For the VHH-Fc variant 225Ac-H108-LL, lower radioactivity was detected in blood indicating more rapid clearance of the VHH-Fc variant (consistent with results in Example 10). 225Ac-H108-LL also demonstrated lesser kidney accumulation and greater liver accumulation indicating increased clearance through the hepatic route and avoidance of the kidneys which further supports an increase in the safety profile of VHH-Fcs with FcRn mutations. The lower tumor accumulation for 225Ac-H108-LL can be attributed to the decreased serum half-life (i.e., more rapid clearance). Table 15 further shows tumor volume through Day 6 post injection, wherein tumor volumes decreased after administration of 225Ac-H101-LL and 225Ac-H108-LL. Table 15 indicates that mice injected with VHH immunoconjugates with wild-type Fc or with FcRn mutations both saw tumor shrinkage by 6 days post injection.

TABLE 15

Tumor volumes before and after anti-HER2 VHH-Fc treatment
(mean mm$^3$; n = 5)

| Day | | −15 | −11 | −8 | −6 | −4 | −1 | 0 (dose) | 3 | 6 |
|---|---|---|---|---|---|---|---|---|---|---|
| 225AC-H101-LL | mean | 57.4 | 66.5 | 51.9 | 54.7 | 65.6 | 73.9 | 74.4 | 31.3 | 47.0 |
| | SD | 19 | 10 | 10 | 10 | 20 | 36 | 22 | 11 | 12 |
| 225AC-H108-LL | mean | 46.4 | 56.5 | 67.9 | 63.2 | 67.3 | 62.6 | 78.1 | 46.2 | 51.2 |
| | SD | 9 | 11 | 16 | 12 | 14 | 14 | 27 | 19 | 23 |

Figure 15B:
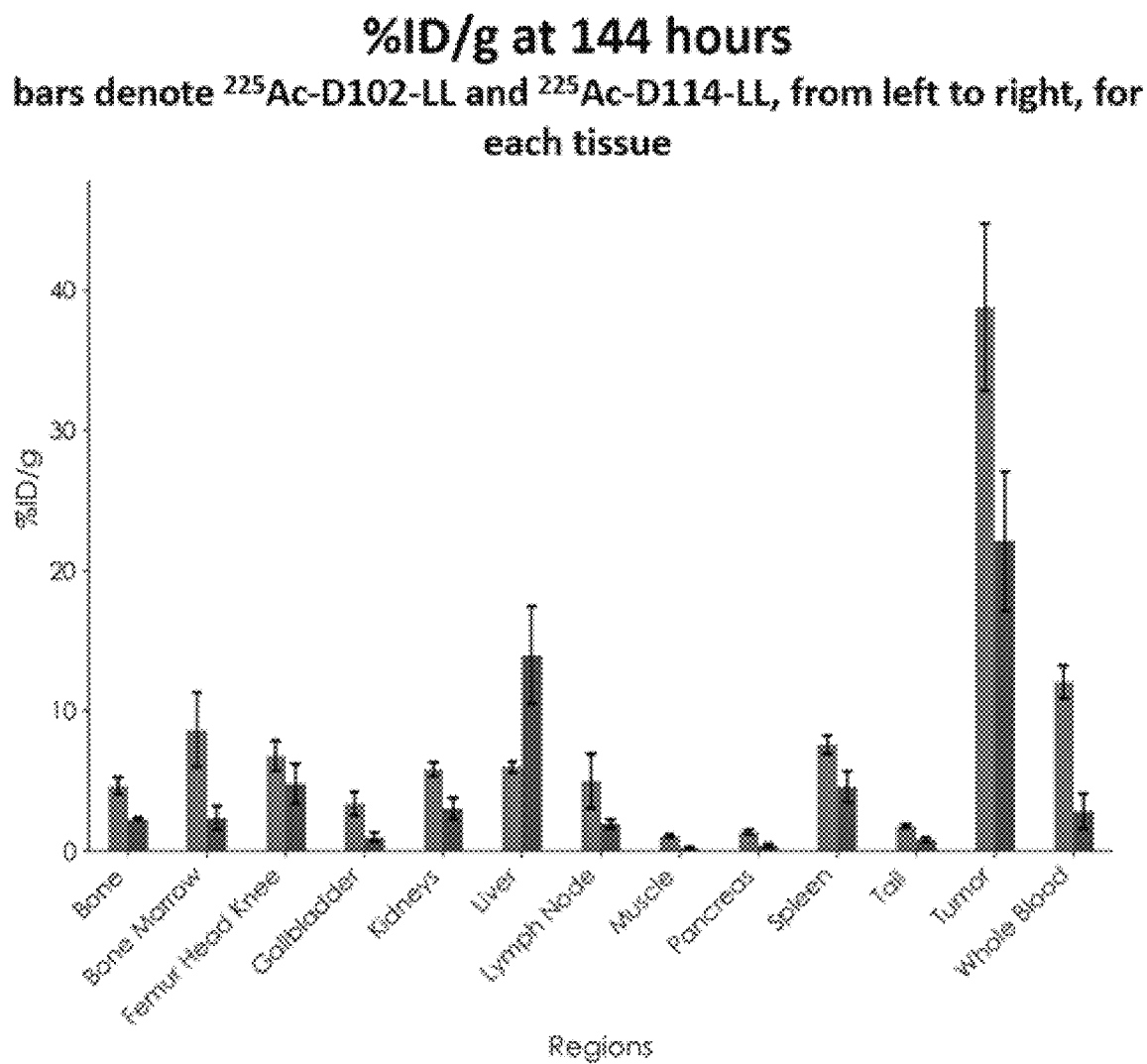

As also described herein, DLL3 represents a target with low target density on cancer cells (e.g., ~3,000 copies/cell). FIG. 15B shows % ID/g at 144 hours for 225Ac-D102-LL and 225Ac-D114-LL. Both test articles showed advantageous targeting profiles, consistent with the $^{111}$In imaging data. Additionally, specific targeting of tumor tissue was achieved with a favorable tumor:tissue ratio consistent with the imaging data. As observed with the anti-HER2 VHH-Fc variants, for the VHH-Fc variant 225Ac-D114-LL, the VHH-Fc variants show increased clearance and decreased kidney exposure which can further be advantageous when considering safety and preventing unwanted tissue toxicity. The lower tumor accumulation for 225Ac-D114-LL can be attributed to the decreased serum half-life (i.e., more rapid clearance).

Example 25. Low Toxicity Associated with VHH-Fc Radioimmunoconjugates

Figure 16A:
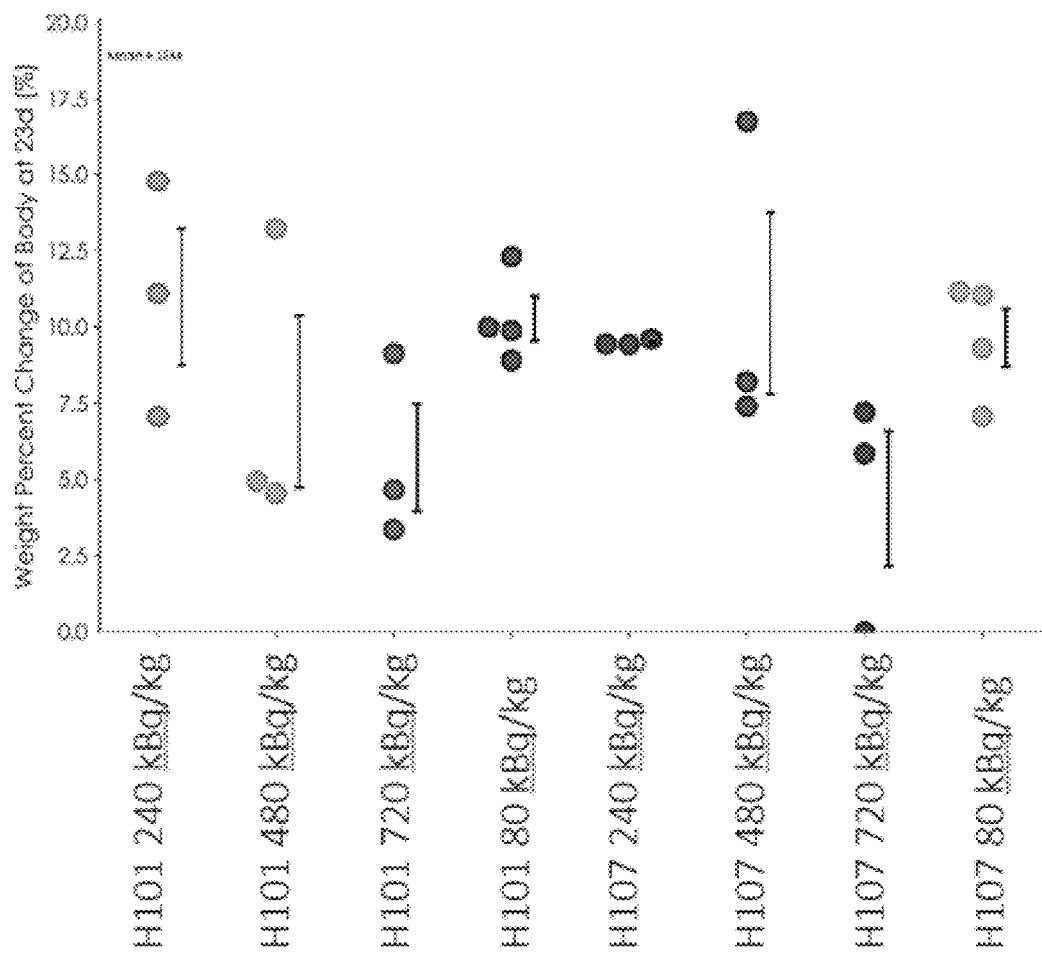
FIGS. 16A, 16B, and 16C show the results of a toxicity study carried out with $^{225}$Ac labeled anti-HER2 VHH-Fc constructs.
Figure 16B:
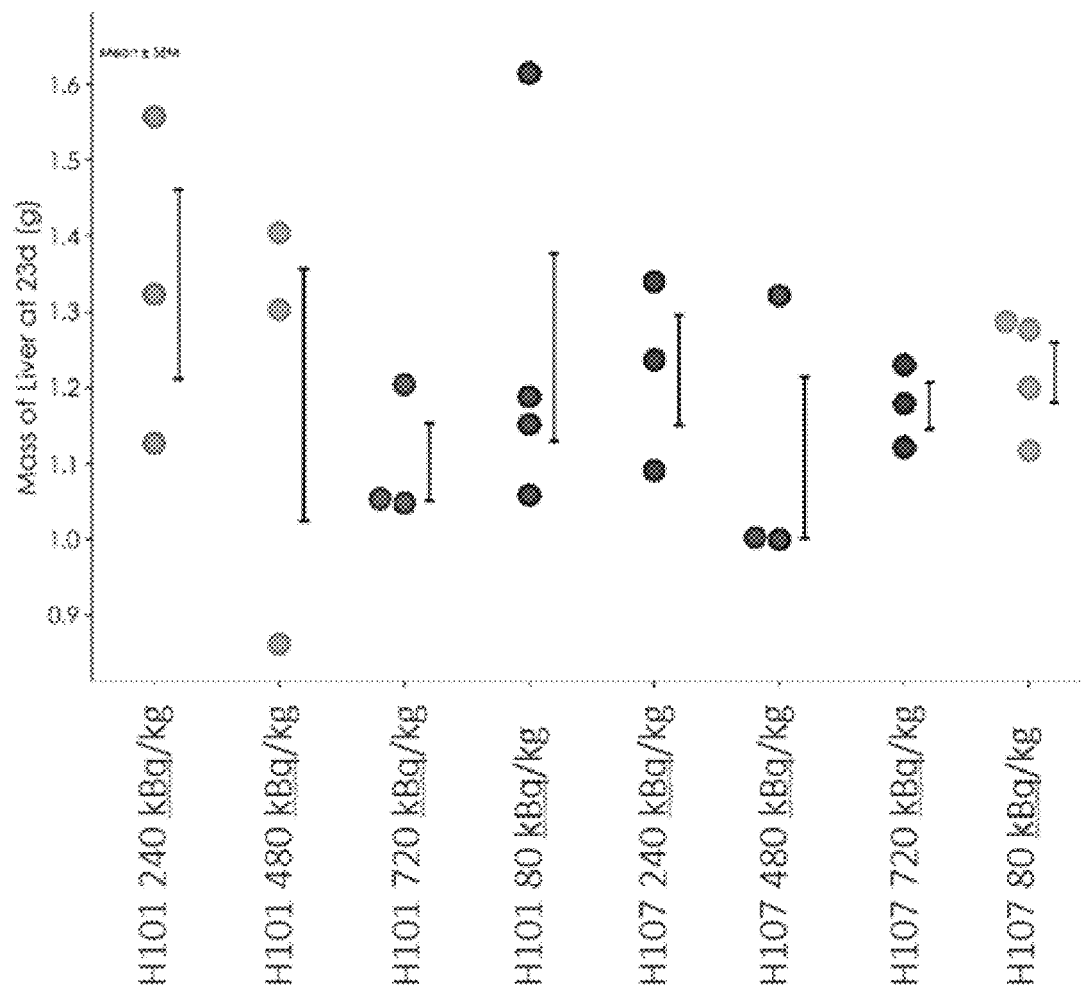
Figure 16C:
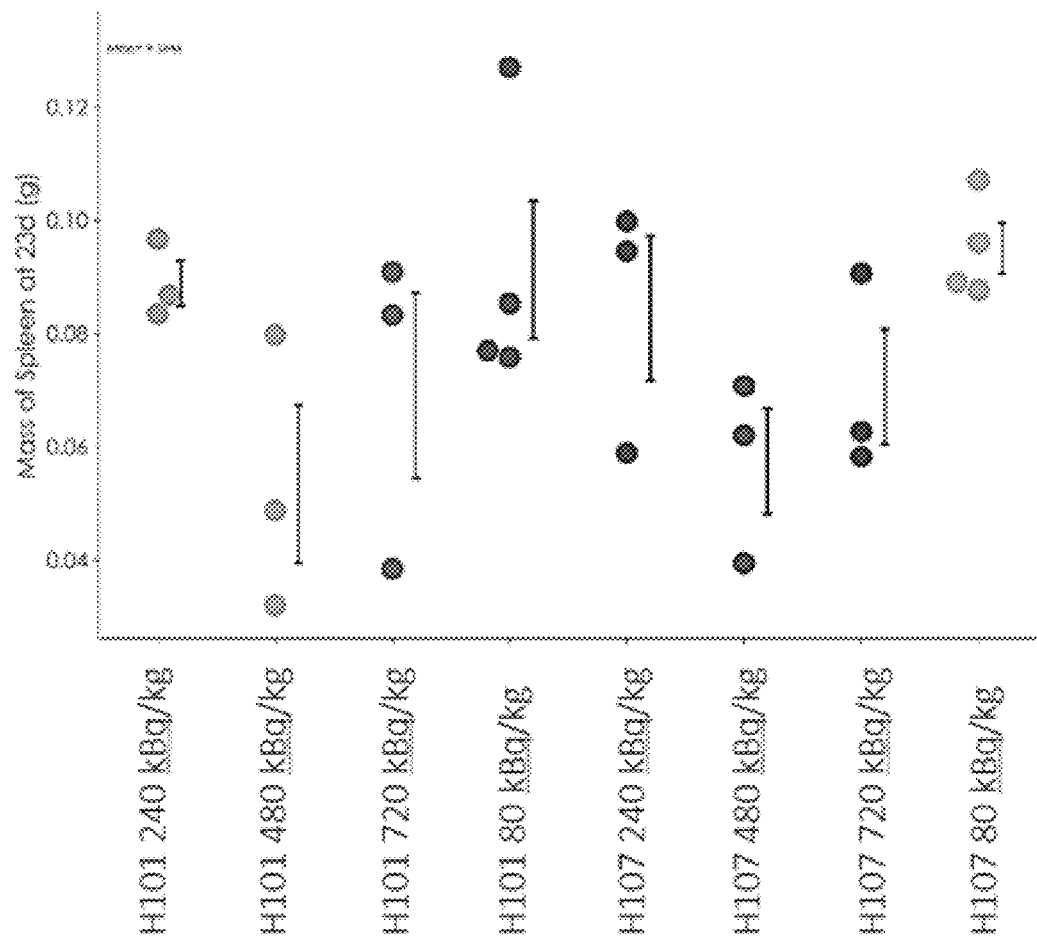

A study was undertaken to determine the tolerability of VHH-Fc loaded with $^{225}$AC. Naïve female athymic nude mice were injected intravenously (IV) into the tail vein with $^{225}$Ac-H101-447804 (anti-HER2 with wildtype Fc, TFP-Ad-PEG5-DOTAGA) or $^{225}$Ac-H107-447804 (anti-HER2 with H310A Fc, TFP-Ad-PEG5-DOTAGA) at four different activity dose levels (18.5 kBq, 12 kBq, 6 kBq, 2 kBq). Activity dose volume was adjusted for body weights measured on the injection day. All animals were monitored for adverse effects daily. Body weights were recorded three (occasionally two or four) times a week for all animals until end of study at 23 days post-injection. 23 Days post-injection all animals were sacrificed. Carcasses underwent necropsy. Whole body, spleen, and liver weights were recorded. FIGS. 16A, 16B, and 16C show that, as measured by percent weight change (16A), liver mass (16B), and spleen mass (16C) All doses of $^{225}$Ac-labeled antibodies of up to 740 kBq/kg were well tolerated and no indications of radiation sickness were observed.

Example 26. Efficacy Testing in a SHP77 Xenograft Mice

An efficacy study of anti-DLL3 VHH-Fc (WT and different variants) using the SHP77 lung cancer cell line is conducted. Eighty (80) animals with similar sized tumors will be selected for test article injection. Animals on study will be assigned to the following groups and will be injected with a single bolus intravenous injection (IV) in the tail vein with the labeled test article. Target injection volume 150 μL per mouse, a) Group 1: IV injection of vehicle (PBS), n=8; b); Group 2: IV injection of V002 (no radiolabel), n=8; Group 3: IV injection of $^{225}$Ac-V002-447804-4, low dose, n=8; Group 4: IV injection of $^{225}$Ac-V002-447804-4, high dose, n=8; Group 5: IV injection of $^{225}$Ac-V014-447804-4, low dose, n=8; Group 6: IV injection of $^{225}$Ac-V014-447804-4, high dose, n=8; Group 7: IV injection of $^{177}$Lu-V002-447804-4, low dose, n=8; Group 8: IV injection of $^{177}$Lu-V002-447804-4, high dose, n=8; Group 9: IV injection of $^{177}$Lu-V014-447804-4, low dose, n=8; Group 10: IV injection of $^{177}$Lu-V014-447804-4, high dose, n=8.

Activity dose levels for both test articles are: a) Ac-225: 6 kBq/mouse (low), 18.5 kBq/mouse (high); b) Lu-177: 350 kBq (low), 700 kBq (high).

Mass dose levels for both test articles: based on activity dose and specific activity, a) for Ac-225 groups: 10 ug/mouse (low), 31 ug/mouse (high); b) for Lu-177 groups: 10 ug (low), 20 ug (high).

Animals will be weighed and tumors measured on day of dosing or on the day before (reference data). All animals will be monitored for adverse effects daily. For any animal with adverse effects, scoring will commence for the affected animal on the welfare scoring sheet (Appendix). After dosing, mice will be inspected daily, weighed twice per week, and tumor measurements taken with calipers three times per week for up to 12 weeks (but expecting only ~4 weeks for control groups 1 and 2). Frequency of weight measurements will be increased when reaching a body weight loss of 10% or more. Actions will be taken such as providing mashed food or gel food. License limit is weight loss of 15%. Animals will be euthanized before planned end of study if tumors exceed the limit (length×width=144 mm$^2$). While the foregoing invention has been described in some detail for purposes of clarity and understanding, it will be clear to the skilled worker from a reading of this disclosure that various changes in form and detail can be made without departing from the true scope of this disclosure. For example, all the techniques and apparatus described above can be used in various combinations. All publications, patents, patent applications, and/or other documents cited in this application are each incorporated by reference in their entirety for all purposes to the same extent as if each individual publication, patent, patent application, and/or other document were individually indicated to be incorporated by reference for all purposes.

Example 27. Radiolabeling with Lu-177

50 μg of test article (D102) was diluted to 100 μL with 0.1 M ammonium acetate buffer pH 5.5 in a 500 μL lo-bind Eppendorf tube and 51 MBq in 3.2 μL-3.5 μL of 177-Lutetium chloride was added and mixed with a pipette. The reaction mixtures were incubated at 37° C. in an incubator for 3 hours and samples taken at 30 min, and 1, 2, and 3 h for iTLC analysis. Results of the labeling are shown in Table 16 below, and indicate efficient labeling with 177-Lutetium.

TABLE 16

| Test article | Incubation time at 37 deg C. | | | |
|---|---|---|---|---|
| D102 | 30 min | 60 min | 2 hr | 3 hr |
| TFP-Ad-PEG5-DOTAGA | 99.0% | 99.2% | 99.2% | 99.3% |

After dilution in PBS/ascorbate and storage at 4° C. the purity as assessed by iTLC analysis as in Example 22.

To analyze stability, 50 μL of test article was added to 200 μL of PBS/ascorbate and stored at 4° C. The samples were analyzed by iTLC and SEC-HPLC after 1-4 h and 18-24 h. Results are shown in Table 17 below, and indicate stability of the construct.

TABLE 17

| Test article | Incubation time | |
|---|---|---|
| D102 | 1 hr | 1 d |
| TFP-Ad-PEG5-DOTAGA | 98.8% | 98.6% |

Figure 17:
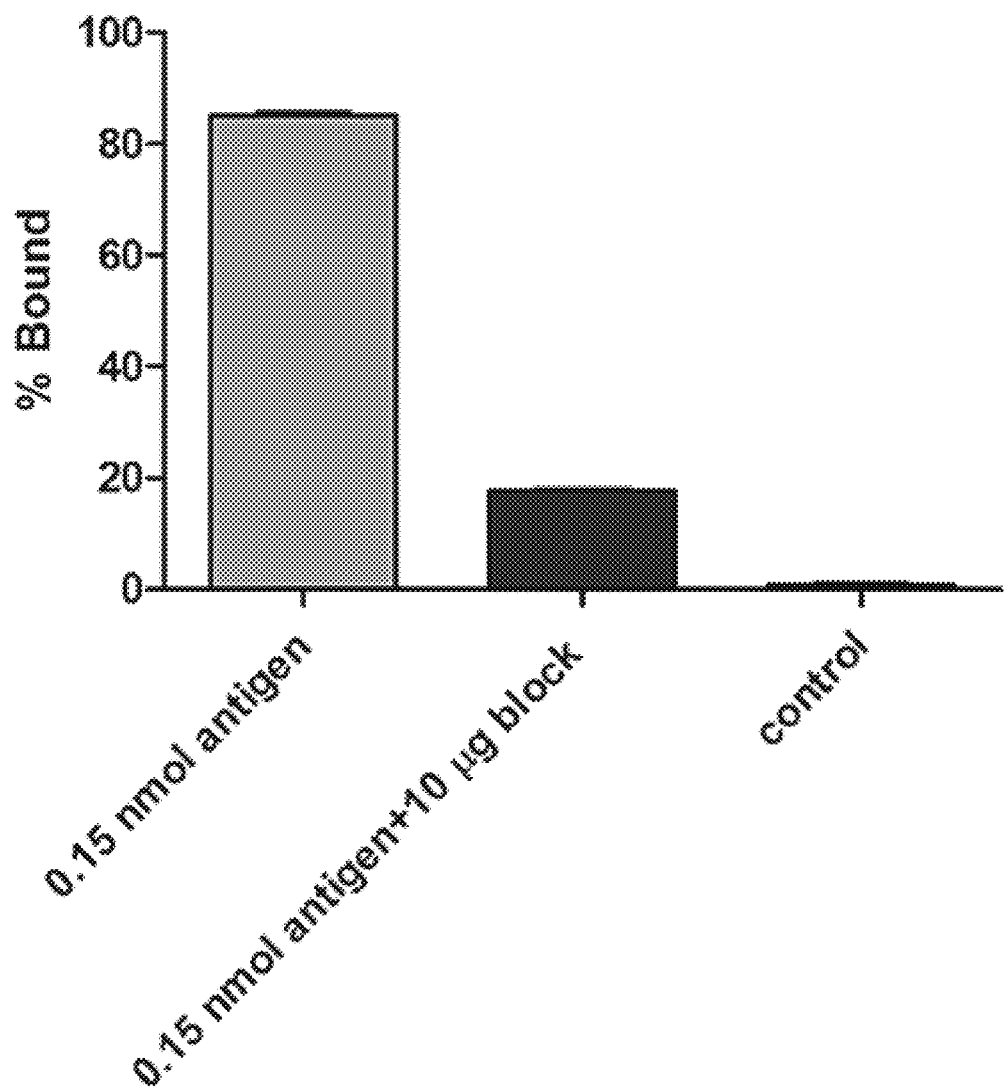
FIG. 17 shows the immunoreactive fraction of different anti-DDL3 VHH-Fc constructs loaded with $^{177}$Lu.

The Lu-177 conjugate was analyzed by the IRF assay described above in Example 23 and the results are shown in FIG. 17. In this example, the control is beads with no antigen loaded.

Example 28. Generation and Characterization of DLL3 Binding Regions

Camelids (llamas and alpacas) were immunized subcutaneously (SC) with recombinant human DLL3 in complete Freud's adjuvant (CFA) or incomplete Freud's adjuvant (IFA) at 2-4 week intervals. Serum titer response was assessed using dilution series of serum. Sera samples were incubated with multiplexed beads differentially optically encoded to various DLL3 antigens (human, mouse, cynomolgus monkey). Binding of antigen-specific antibodies in the serum to the beads was then detected using a fluorescently labelled secondary antibody via high-throughput, plate-based flow cytometry. Samples were selected for screening and peripheral blood mononuclear cells were collected.

Single-Cell Screening and Recovery

Peripheral blood mononuclear cells were thawed, activated in culture to generate memory B cells, and enriched for heavy chain-only antibody-secreting B cells before screening. Single B cells secreting target-specific antibodies were identified and isolated using a multi-step assay assessing both internalization in cells and binding to DLL3 immobilized on beads. Cross-reactivity to species homologs was assessed using a multiplexed bead assay using differentially optically encoded beads, each conjugated to different species of DLL3 antigens (human, mouse, cynomolgus monkey) and binding was detected using a fluorescently labelled secondary antibody specific to alpaca IgG subclasses 2 and 3. Internalization was assessed by flowing in HEK293T cells expressing human DLL3 and internalizing antibodies were detected using a pH-sensitive fluorescent reagent.

Single-Cell Sequencing and Bioinformatic Analysis

Single-cell polymerase chain reaction (PCR) and custom molecular biology protocols generated NGS sequencing libraries (MiSeq, Illumina) using automated workstations (Bravo, Agilent). Sequencing data were analyzed using a custom bioinformatics pipeline to yield heavy chain sequences for recovered antibody-secreting cells. Each sequence was annotated with the closest germline (V(D)J) genes and degree of somatic hypermutation. Antibodies were considered members of the same clonal family if they shared the same inferred heavy V and J genes and had the same CDR3 length.

VHH-Fc plasmids were generated by cloning the VHH sequence, with a hinge and Fc portion (human IgG1 CH2-CH3) into a mammalian expression vector. In some instances, mutations were introduced into the Fc portion. To produce recombinant VHH-Fc and variants thereof, plasmid was transfected into HEK293.SUS cells (ATUM, or similar). After 3-5 days of secretion, the antibody-containing supernatant was cleared of cells by centrifugation and sterile filtration. Antibodies were purified using Mab Select SuRe PCC column (GE, Cat #: 11003495) and buffer exchanged into PBS, pH 7.0. Proteins were quantified using A280 or BCA. The purity of the antibodies were tested by SDS-PAGE, capillary electrophoresis, HPLC-SEC and LC-MS using standard protocols.

A total of 209 VHH clones were tested for properties important for the development of immunoconjugates useful for the delivery of toxic payloads. These criteria included binding to murine DLL3, binding to cynoDLL3, binding to human DLL3, the ability to be internalized by target expressing cells, the absence of lysine residues in CDR regions, high sequence redundancy and absence of known sequence liabilities for developability.

Of these 209 clones, 46 were selected for expression and purification as VHH-Fc (with wildtype Fc and modified hinge region, SEQ ID: 42) for further analysis. A summary of the data generated on these 46 VHH.Fcs is shown in Tables 18 to 20.

High-Throughput Antibody Expression and Purification

The variable [V(D)J] region of each antibody heavy chain was synthesized and inserted into expression plasmids. Plasmids were verified by Sanger sequencing. Chimeric human Fc, camelid VHH (VHH-Fc) antibodies were recombinantly produced by transient transfection. Antibody-encoding plasmid DNA was transfected into Expi293F cells (Thermo Fisher Scientific). Antibody titers were measured by biolayer interferometry on an Octet HTX instrument (FortéBio). Antibodies were purified using protein A-based purification and quantified by UV/Vis Spectroscopy at 280 nm absorbance.

Antibody Bead Binding and Cell Internalization Validation

Recombinant VHH-Fc antibodies were confirmed to bind targets and induce internalization via high-throughput flow cytometry using fluorescently labelled anti-human IgG. In a multiplexed bead-based assay, optically encoded beads were conjugated to one of the following antigens: human DLL3, mouse DLL3, or cynomolgus monkey DLL3. Purified VHH-Fc antibodies were incubated with target-conjugated beads at 25 nM antibody concentration for 30 minutes at 4° C. Beads were washed and binding was detected using a fluorescently labelled secondary antibody. In a live cell-based internalization assay, purified VHH-Fc antibodies were incubated with HEK293T cells expressing human DLL3, parental HEK293T cells or SHP-77 cells at 5 nM antibody concentration and a pH-sensitive fluorescent reagent for two hours at 37° C. Fluorescence was measured using high-throughput, plate-based flow cytometry. An irrelevant antibody, chimeric human Fc camelid VHH specific to HER2 (VHH-Fc anti-HER2) was used as a negative control. Median fluorescence intensity of each antibody was normalized over median fluorescence intensity of the negative control.

SPR Binding Experiments

All SPR binding experiments were performed on a Carterra LSA instrument equipped with an HC-30M chip type (Carterra-bio) using a 384-ligand array format as described herein. The HC-30M chip was prepared by immobilizing a goat anti-human IgG Fc antibody (Southern Biotech #2014-01) via direct coupling: The chip surface was first activated by flowing a freshly prepared 1:1:1 activation mix of 100 mM MES (pH 5.5), 100 mM sulfo-N-hydroxysuccinimide, and 400 mM 1-ethyl-3-(3-dimethylaminopropyl)carbodiimide for 7 minutes, and goat anti-human IgG Fc antibody diluted to 50 µg/ml in 10 mM NaOAc (pH 4.25) buffer+0.01% Tween was injected onto the chip surface for 10 minutes. The chip surface was quenched by flowing 1 M ethanolamine for 7 minutes, followed by two wash steps of 15 seconds each in 25 mM MES (pH 5.5) buffer. The test antibodies diluted to 5 µg/ml in HEPES-buffered saline containing 0.05% Tween 20 and 3 mM EDTA (HBSTE)+0.1% BSA running buffer were captured on the chip surface for 5 minutes. Relevant benchmarks and negative control antibodies (VHH-Fc anti-HER2, VHH-Fc anti-DLL3, Rovalpituzumab) were also captured on the chip surface.

For binding kinetics and affinity measurements, a three-fold dilution series of the antigen of interest (human DLL3), starting at 300 nM in HEPES-buffered saline containing 0.05% Tween 20 and 3 mM EDTA (HBSTE)+0.1% BSA running buffer, was sequentially injected onto the chip surface. For each concentration, the antigen was injected for 10 min (association phase), followed by running buffer injection for 15 min (dissociation phase). The data were analyzed using the Carterra Kinetics analysis software using a 1:1 Langmuir binding model to determine apparent association (ka) and dissociation (kd) kinetic rate constants and binding affinity constants ($K_D$).

Capillary Electrophoresis Sodium Dodecyl Sulfate (CE-SDS)

The purity of the expressed and purified VHH-Fc antibodies was analyzed by denaturing CE-SDS using the LabChip GXII Touch instrument (Perkin Elmer, Protein Express LabChip #760528) according to the manufacturer's protocol. Two (2) uL of VHH-Fc solution at a concentration of 0.35 mg/mL in PBS was mixed with a non-reducing denaturing buffer solution (Perkin Elmer Reagent Kit #CLS960008) and incubated at 70° C. for 10 min. Separation was performed using the HT Antibody Analysis 200 assay setting on the LabChipGXII Touch instrument (Perkin Elmer). The data was analyzed using the LabChip GX Reviewer Software (Perkin Elmer).

Dynamic Light Scattering (DLS)

Percent aggregation and polydispersity of VHH-Fc antibodies was assessed by DLS on a DynaPro® Plate Reader III instrument (Wyatt Technology). Seven (7) L of each sample at 0.35 mg/mL in PBS were dispensed into glass-bottom 1536 well Sensoplates (Greiner Bio-One, #783892) and covered with silicon oil. DLS of individual samples was then acquired at 20° C. with 5×5 seconds acquisitions per sample. Data was analyzed in the Dynamics software (Wyatt Technology, v 7.10.1.21) using the regularization algorithm and replicate measurements with less than 60% of acquisitions unmarked were omitted from the analysis. Replicates were then averaged using an in-house developed Python script. Filter settings were a maximum sum of squares deviation of 50 between autocorrelation function and data fit, a minimum and maximum autocorrelation function amplitude of 0.05 and 1, respectively, and a baseline limit of 1±0.005. Percent polydispersity and percent mass of soluble mAbs were calculated for the size range of 1-10 nm.

Nanoscale Differential Scanning Fluorimetry (nDSF)

All nano-DSF studies were performed using the Nanotemper Prometheus NT.Plex instrument equipped with a Backreflection Optics and an NT.Robotic Autosampler for automated sample loading and measurement.

Samples at 350 μg/mL were loaded by capillarity into premium grade nDSF capillaries (NanoTemper, Cat #PR-AC006). Capillaries were then placed on the Prometheus thermal element and subjected to a temperature ramping of 1° C./minute from 20° C. to 95° C. The melting point (Tm, in ° C.) was obtained by monitoring the intrinsic tryptophan and tyrosine fluorescence at the emission wavelengths of 330 nm and 350 nm. To generate an unfolding curve, the ratio of the fluorescence intensities (F350 nm/F330 nm) was plotted versus the temperature. The Tm corresponds to the inflection point of the unfolding curve and was determined via the derivative of the curve using the NanoTemper PR.Stability Analysis software (version 1.1). The onset of aggregation (Tagg, in ° C.) was obtained by monitoring the light backreflection of protein aggregates and determined using the NanoTemper's PR.Stability Analysis software (version 1.1).

Analytical Size-Exclusion Chromatography (aSEC)

The relative percentage of monomer, high molecular weight (HMW), and low molecular weight (LMW) species in purified VHH-Fc antibodies was assessed using aSEC. Using a Vanquish Duo UHPLC System for Dual LC (Thermo Fisher Scientific), 5 μL of each sample at 0.35 mg/mL was injected onto a size exclusion column (ACQUITY UPLC Protein BEH SEC Column, 200 Å, 1.7 μm, 4.6 mm×150 mm, Waters #186005226). The mobile phase (100 mM sodium phosphate pH 6.8, 250 mM NaCl; Fisher Scientific #S468-500, #S373-500, and #S271-500) was applied to the column for 10 minutes per injection at a flow rate of 0.3 mL/min to separate species based on their size. Chromatograms monitoring absorbance at 280 nm were acquired and analyzed using Chromeleon software (Thermo Fisher Scientific, v7.3). The relative percentage of each species was determined based on the integrated area of each peak.

Analytical Hydrophobic Interaction Chromatography (aHIC)

Relative surface hydrophobicity of the purified VHH-Fc antibodies was assessed by aHIC. Using a Vanquish Duo UHPLC System for Dual LC (Thermo Fisher Scientific), 5 μL of each sample at 0.35 mg/mL was injected onto a hydrophobic interaction column (TSKgel Butyl-NPR, 2.5 μm, 4.6 mm ID×3.5 cm, TOSOH #0014947). A linear gradient method from 42% to 0% buffer A over 6 minutes with a flow rate of 0.5 mL/min was used to separate samples based on their surface hydrophobicity properties (buffer A: 25 mM sodium phosphate pH 7.0, 2.5 M ammonium sulfate; buffer B: 25 mM sodium phosphate pH 7.0; Fisher Scientific #S468-500, #S373-500, and #A702-3). Chromatograms monitoring absorbance at 280 nm were acquired and analyzed using Chromeleon software (Thermo Fisher Scientific, v7.3). Relative hydrophobicity of each sample was determined based on retention time of the largest peak by integrated area.

TABLE 18

Summary of initial screening VHH formatted on Wildtype Fc/modified hinge (SEQ ID NO: 42)

| Clone ID | hDLL3 Binding | mDLL3 binding | cDLL3 Binding | Internalisation HEK-DLL3 | Redundancy | [Liability] Status | CDR liability |
|---|---|---|---|---|---|---|---|
| 4 | Yes | Yes | Yes | Yes | 3 | 1 | 0 |
| 5 | Yes | Yes | Yes | Yes | 22 | 2 | 0 |
| 6 | Yes | Yes | Yes | Yes | 4 | 2 | 2 |
| 22 | Yes | Yes | Yes | Yes | 1 | 2 | 2 |
| 24 | Yes | Yes | Yes | Yes | 24 | 1 | 0 |
| 28 | Yes | Yes | Yes | Yes | 11 | 1 | 0 |
| 29 | Yes | Yes | Yes | Yes | 12 | 1 | 0 |
| 33 | Yes | Yes | Yes | Yes | 8 | 1 | 0 |
| 34 | Yes | Yes | Yes |  | 2 | 1 | 0 |
| 39 | Yes | Yes | Yes | Yes | 4 | 2 | 0 |
| 40 | Yes | Yes | Yes |  | 5 | 3 | 1 |
| 41 | Yes | Yes | Yes | Yes | 3 | 1 | 0 |
| 45 | Yes | Yes | Yes | Yes | 5 | 1 | 0 |

TABLE 18-continued

Summary of initial screening VHH formatted on Wildtype Fc/modified hinge (SEQ ID NO: 42)

| Clone ID | hDLL3 Binding | mDLL3 binding | cDLL3 Binding | Internalisation HEK-DLL3 | Redundancy | [Liability] Status | CDR liability |
|---|---|---|---|---|---|---|---|
| 49 | Yes | Yes | Yes | Yes | 1 | 2 | 1 |
| 51 | Yes | Yes | Yes | Yes | 1 | 2 | 2 |
| 53 | Yes | Yes | Yes | Yes | 7 | 0 | 0 |
| 54 | Yes | Yes | Yes | Yes | 3 | 1 | 0 |
| 60 | Yes | Yes | Yes | Yes | 1 | 2 | 0 |
| 87 | Yes | Yes | Yes | Yes | 4 | 2 | 1 |
| 88 | Yes | Yes | Yes | Yes | 4 | 2 | 1 |
| 90 | Yes | Yes | Yes | Yes | 2 | 2 | 1 |
| 91 | Yes | Yes | Yes | Yes | 3 | 1 | 0 |
| 97 | Yes | Yes | Yes | Yes | 13 | 1 | 0 |
| 100 | Yes | Yes | Yes | Yes | 7 | 2 | 2 |
| 104 | Yes | Yes | Yes | Yes | 8 | 1 | 0 |
| 105 | Yes | Yes | Yes | Yes | 66 | 2 | 0 |
| 106 | Yes | Yes | Yes | Yes | 12 | 0 | 0 |
| 107 | Yes | Yes | Yes |  | 11 | 2 | 1 |
| 109 | Yes | Yes | Yes |  | 7 | 2 | 1 |
| 112 | Yes | Yes | Yes | Yes | 4 | 2 | 1 |
| 113 | Yes | Yes | Yes |  | 2 | 2 | 0 |
| 118 | Yes |  | Yes | Yes | 2 | 0 | 0 |
| 119 | Yes | Yes | Yes | Yes | 2 | 1 | 0 |
| 123 | Yes | Yes | Yes | Yes | 1 | 2 | 1 |
| 126 | Yes |  | Yes | Yes | 14 | 2 | 1 |
| 130 | Yes | Yes | Yes |  | 4 | 2 | 2 |
| 162 | Yes | Yes | Yes | Yes | 24 | 2 | 2 |
| 163 | Yes |  | Yes | Yes | 18 | 2 | 1 |
| 166 | Yes | Yes | Yes |  | 12 | 2 | 1 |
| 167 | Yes |  | Yes | Yes | 11 | 2 | 1 |
| 168 | Yes | Yes | Yes | Yes | 1 | 2 | 1 |
| 179 | Yes |  | Yes | Yes | 12 | 2 | 1 |
| 186 | Yes |  | Yes | Yes | 2 | 2 | 0 |
| 187 | Yes | Yes | Yes | Yes | 4 | 2 | 1 |
| 189 | Yes | Yes | Yes | Yes | 2 | 2 | 0 |
| 191 | Yes |  | Yes | Yes | 2 | 2 | 1 | mDLL3 = mouse DLL3;
cDLL3 = cynoDLL3;
hDLL3 = human DLL3;
blank cells indicate no binding observed in initial screening assays

TABLE 19

Summary of initial screening, biophysical characteristics VHH formatted on Wildtype Fc/modified hinge (SEQ ID NO: 42)

| Clone ID | Purified Titer (mg/L) | % Purity analytical SEC | PI | PD | Hydrodynamic radius (nm) DLS | % Polydispersity DLS | % Aggregation DLS |
|---|---|---|---|---|---|---|---|
| 4 | 256.71 | 100 | 1.9 | 2.1 | 5.77 | 35.50 | 97.76 |
| 5 | 294.03 | 100 | 5.2 | 4 | 5.18 | 36.62 | 97.35 |
| 6 | 260.96 | 100 | 4.1 | 4.5 | 5.86 | 41.76 | 98.85 |
| 22 | 1.79 | 0 |  |  | nan | nan | 0.00 |
| 24 | 272.8 | 100 | 2.1 | 2.5 | 4.80 | 27.34 | 97.40 |
| 28 | 279.45 | 100 | 1.9 | 1.8 | 5.32 | 30.27 | 97.42 |
| 29 | 199.76 | 100 | 2.5 | 2.3 | 4.73 | 24.27 | 97.97 |
| 33 | 119.52 | 98.38 | 2 | 1.8 | 5.56 | 31.19 | 97.38 |
| 34 | 277.31 | 100 | 2 | 2 | 4.94 | 23.29 | 93.74 |
| 39 | 270.79 | 100 | 5.1 | 10.3 | 4.86 | 26.35 | 98.94 |
| 40 | 265.95 | 100 | 2.6 | 4.2 | 4.44 | 18.93 | 99.55 |
| 41 | 229.8 | 100 | 2.8 | 2.1 | 5.28 | 30.13 | 96.07 |
| 45 | 305.46 | 100 | 1.2 | 1.5 | 5.84 | 39.01 | 97.81 |
| 49 | 182.91 | 94.79 | 4 | 5.9 | 5.32 | 30.54 | 45.44 |
| 51 | 238.05 | 100 | 1 | 1.2 | 4.51 | 19.91 | 99.98 |
| 53 | 288.51 | 100 | 1.9 | 2.5 | 5.05 | 34.15 | 98.00 |
| 54 | 281.75 | 100 | 1.9 | 2.9 | 5.07 | 28.53 | 98.36 |
| 60 | 273.37 | 100 | 1.1 | 1.2 | 5.58 | 25.80 | 98.47 |
| 87 | 202.48 | 98.71 | 1.1 | 1.4 | 5.31 | 34.60 | 99.27 |
| 88 | 137.34 | 99.34 | 4.8 | 2.9 | 4.05 | 24.06 | 91.57 |
| 90 | 284.07 | 100 | 3.6 | 2.3 | 4.86 | 25.24 | 98.64 |
| 91 | 303 | 100 | 3.5 | 3.1 | 5.57 | 30.95 | 96.90 |
| 97 | 289.44 | 100 | 1.6 | 1.3 | 5.24 | 28.87 | 99.31 |
| 100 | 228.26 | 100 | 1.6 | 1.3 | 4.87 | 29.93 | 96.76 |
| 104 | 268.28 | 100 | 3.9 | 2.4 | 6.28 | 23.39 | 90.13 |

TABLE 19-continued

Summary of initial screening, biophysical characteristics VHH formatted on Wildtype Fc/modified hinge (SEQ ID NO: 42)

| Clone ID | Purified Titer (mg/L) | % Purity analytical SEC | PI | PD | Hydrodynamic radius (nm) DLS | % Polydispersity DLS | % Aggregation DLS |
|---|---|---|---|---|---|---|---|
| 105 | 1.08 | 0 | | | 8.87 | 14.17 | 18.60 |
| 106 | 254.7 | 95.29 | 1.1 | 1 | 6.74 | 29.62 | 99.94 |
| 107 | 282.08 | 100 | 1.6 | 2 | 5.22 | 31.31 | 98.30 |
| 109 | 289.91 | 100 | 1.1 | 1 | 7.76 | 32.73 | 46.68 |
| 112 | 311.61 | 100 | 2.4 | 2 | 5.33 | 34.08 | 98.32 |
| 113 | 157.14 | 98.65 | 9.2 | 5.8 | 5.38 | 35.88 | 98.01 |
| 118 | 16.42 | 0 | | | 8.17 | 10.84 | 18.66 |
| 119 | 267.47 | 100 | 3.2 | 2.2 | 4.41 | 14.48 | 99.95 |
| 123 | 247.72 | 100 | 1.4 | 1.1 | 5.53 | 33.23 | 97.09 |
| 126 | 281.1 | 100 | 1.3 | 1 | 5.47 | 35.42 | 98.92 |
| 130 | 274.63 | 100 | 1.6 | 1.1 | 4.44 | 19.82 | 98.74 |
| 162 | 307.01 | 100 | 2.4 | 2 | nan | nan | nan |
| 163 | 292.7 | 100 | 2.9 | 2.2 | 4.81 | 24.32 | 99.01 |
| 166 | 257.03 | 100 | 1.3 | 1.1 | 5.55 | 39.27 | 99.47 |
| 167 | 289.82 | 100 | 5.1 | 3.7 | 4.48 | 20.00 | 99.90 |
| 168 | 286.42 | 97.95 | 1.1 | 1 | 4.81 | 23.57 | 99.32 |
| 179 | 275.83 | 100 | 7.5 | 4.2 | 4.51 | 14.77 | 99.50 |
| 186 | 234.22 | 100 | 1.4 | 1.2 | 5.04 | 29.79 | 99.31 |
| 187 | 3.12 | 0 | | | nan | nan | 0.00 |
| 189 | 193.27 | 42 | 3.6 | 3.8 | 5.57 | 34.51 | 96.50 |
| 191 | 271.89 | 100 | 4 | 12 | 5.07 | 28.36 | 95.72 |

PI = polyreactivity for insulin;
PD = polyreactivity for double-stranded DNA;
blank cells indicate no results acquired;
nan = data not available

TABLE 20

Summary of initial screening, binding properties VHH formatted on Wildtype Fc/modified hinge (SEQ ID NO: 42)

| Clone ID | HEK-DLL3 Internalization FOI | ka (1/Ms) hDLL3 | kd(1/S) hDLL3 | KD nM hDLL3 |
|---|---|---|---|---|
| 4 | 5.236 | 9.05e+04 | 1.24e−03 | 13.70 |
| 5 | 6.811 | 7.78e+04 | 3.38e−04 | 4.34 |
| 6 | 8.076 | 2.49e+05 | 1.31e−03 | 5.26 |
| 22 | 0.471 | | | |
| 24 | 6.668 | 1.69e+05 | 1.33e−03 | 7.83 |
| 28 | 8.704 | 1.55e+05 | 1.93e−03 | 12.50 |
| 29 | 6.305 | 1.53e+05 | 1.85e−03 | 12.10 |
| 33 | 5.885 | 7.73e+04 | 5.36e−04 | 6.93 |
| 34 | 0.817 | | | |
| 39 | 3.626 | | | |
| 40 | 3.482 | | | |
| 41 | 7.687 | 3.50e+04 | 1.98e−03 | 56.70 |
| 45 | 5.938 | 1.37e+05 | 2.08e−03 | 15.30 |
| 49 | 0.746 | | | |
| 51 | 0.596 | | | |
| 53 | 7.706 | 4.93e+04 | 2.39e−03 | 48.50 |
| 54 | 5.336 | 8.29e+04 | 1.02e−03 | 12.30 |
| 60 | 0.323 | | | |
| 87 | 4.934 | 6.99e+04 | 3.50e−03 | 50.00 |
| 88 | 7.556 | 1.32e+05 | 1.32e−03 | 9.96 |
| 90 | 6.382 | 1.85e+05 | 1.26e−04 | 0.68 |
| 91 | 6.721 | 1.39e+05 | 1.71e−04 | 1.23 |
| 97 | 6.737 | 1.40e+05 | 1.31e−03 | 9.35 |
| 100 | 8.776 | 1.62e+05 | 2.70e−04 | 1.67 |
| 104 | 7.746 | 9.44e+04 | 5.81e−04 | 6.16 |
| 105 | 0.370 | | | |
| 106 | 0.334 | | | |
| 107 | 8.136 | 9.15e+04 | 4.42e−04 | 4.83 |
| 109 | 0.749 | | | |
| 112 | 6.016 | 7.96e+04 | 2.63e−03 | 33.10 |
| 113 | 5.298 | 4.83e+04 | 3.16e−04 | 6.53 |
| 118 | 0.965 | | | |
| 119 | 4.125 | | | |
| 123 | 6.012 | 8.42e+04 | 6.58e−04 | 7.82 |
| 126 | 7.561 | 5.23e+05 | 2.21e−04 | 0.42 |

TABLE 20-continued

Summary of initial screening, binding properties VHH formatted on Wildtype Fc/modified hinge (SEQ ID NO: 42)

| Clone ID | HEK-DLL3 Internalization FOI | ka (1/Ms) hDLL3 | kd(1/S) hDLL3 | KD nM hDLL3 |
|---|---|---|---|---|
| 130 | 7.856 | 3.51e+05 | 2.91e−04 | 0.83 |
| 162 | 0.279 | | | |
| 163 | 5.902 | | | |
| 166 | 4.644 | 4.34e+04 | 1.71e−03 | 39.50 |
| 167 | 7.480 | | | |
| 168 | 0.272 | | | |
| 179 | 4.711 | 1.71e+05 | 9.72e−04 | 5.68 |
| 186 | 7.716 | 3.00e+05 | 3.79e−04 | 1.27 |
| 187 | 0.893 | | | |
| 189 | 0.296 | | | |
| 191 | 7.915 | | | |

Blank cells indicate experiments were not performed or data was out of normal range 11 clones of the 46 initially characterized were selected for further characterization. Clones were further characterized by epitope binning, binding affinity to cancer cell lines that naturally express DLL3, in silico immunogenicity analysis, sequence identity to human germline variable region sequences, and developability characteristics. Clones were formatted as VHH with WT-Fc or Fc with H435Q mutations or Fc with H435Q and AEASS Fc effector mutation. Results from these experiments are shown in Tables 21 and 22.

TABLE 21 in silico characteristics and epitope binning of selected clones
*VHH only or **VHH formatted on Wildtype Fc/modified hinge (SEQ ID NO: 42)

| Clone ID | Immunogenicity Risk* | Epivax score* | Treg-adjusted Epimatrix Score* | Identity to Human germline* | AC-SINS** | epitope bin** |
|---|---|---|---|---|---|---|
| 5 | None | 5.83 | −18.34 | 84.7 | 8.13 | 1 |
| 6 | Low | 15.56 | −4.32 | 77.2 | 7.27 | 1 |
| 24 | None | 3.05 | −35.61 | 86.1 | 1.58 | 1 |
| 91 | Med | 26.5 | 2.34 | 84.7 | 1.25 | 1 |
| 100 | None | 12.93 | −24.67 | 85.1 | 0.82 | 1 |
| 104 | None | −1.3 | −39.97 | 85.8 | 5.53 | 1 |
| 107 | Low | 5.22 | −3.99 | 84.1 | 7.08 | 3 |
| 119 | High | 65.26 | 65.26 | 77.9 | 2.95 | 1 |
| 123 | Med | 20.67 | −2.89 | 79.6 | 0.67 | 1 |
| 126 | Low | 19.44 | −18.86 | 84.4 | −0.11 | 2 |
| 186 | None | −7.16 | −7.16 | 81.5 | 1.73 | 2 |

TABLE 22 binding characteristics of selected clones

| Clone ID | WT-Fc SHP-77 Binding EC50 nM | H435Q-Fc SHP-77 Binding EC50 nM | H435Q-Fc SHP-77 Internalization FOI | H435Q Fc- KD (nM) hDLL3 |
|---|---|---|---|---|
| 5 | 2.371 | 4.05 | 1.21 | 0.39 |
| 6 | 0.3853 | 0.22 | 1.16 | 1.17 |
| 24 | 1.99 | 1.2 | 1.19 | 1.08 |
| 91 | 1.97 | 1.52 | 1.16 | <1 |
| 100 | 2.589 | 1.16 | 1.19 | 0.20 |
| 104 | 2.148 | 2.02 | 1.19 | 0.75 |
| 107 | Not done | 0.74 | 1.27 | 0.72 |
| 119 | 1.878 | 1.12 | 1.16 | 3.69 |
| 123 | 92.2 | 67.52 | 1.17 | 1.19 |
| 126 | 1.068 | 0.44 | 1.19 | <1 |
| 186 | 0.4753 | 0.47 | 1.18 | 0.55 |

Several clones were excluded at this stage. For example, clone 123 bound to cancer cells with endogenous DLL3 expression with a binding EC50 that was too high, clones 119 and 91 had a poor immunogenicity score in silico, clones 5 and 6 had unfavorable (e.g., high ACSINS) score. Based on the data generated in in the further characterization screens 5 clones representing 3 epitope bins were selected for further analysis. Notably, these epitope bins do not overlap with DLL3 antibody Rovalpituzumab.

VHH-Fcs were tested for internalization by target-expressing cells or target-negative cells. The VHH-Fcs show higher fluorescence signals than the negative control (isotype, expressed as fold over isotype FOI) on target-positive cells, in a dose dependent manner. No internalisation is observed on target negative cells (data not shown). The FOI for 200 nM VHHFc on target positive cells SHP77 is shown in Table 22.

Clones selected for further analysis were: 24 (SEQ ID NO: 101); 100 (SEQ ID NO: 201); 107 (SEQ ID NO: 301); 126 (SEQ ID NO: 401); and 186 (SEQ ID NO: 501); were selected for further analysis and characterization. These 5 clones were humanized and were tested for binding and developability characteristics after humanization. Humanized variable regions were formatted on an Fc with H435Q, L234A, L235E, G237A, A330S, P331S mutations (Eu numbering).

Figure 19:
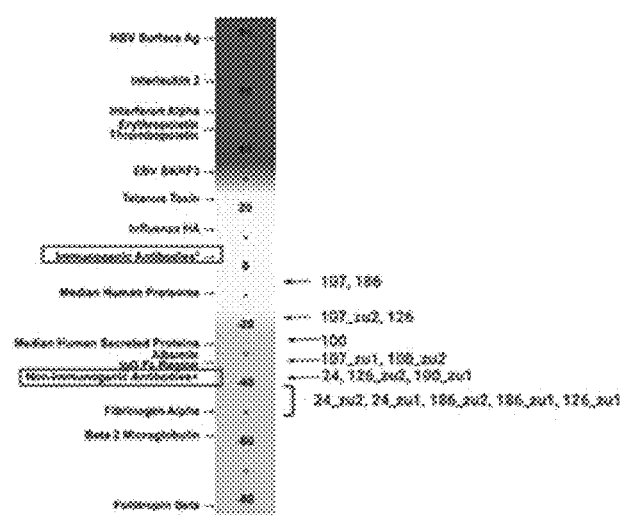
FIG. 19 shows immunogenicity scores for selected clones described herein.

Humanization was performed to increase identity to human germline sequences and reduce the immunogenic potential of the camelid-derived antibodies. Sequences were modified by grafting the CDRs of a non-human antibody variable region (donor) onto a suitable human framework sequence (acceptor), and selecting a minimal number of key framework residues (back-mutations) from the donor sequence to be incorporated into the acceptor framework sequence to maintain CDR conformation and desired biophysical properties, while minimizing the camelid content of the humanized sequence. Such humanization methods are known in the art, and include those described in Vincke et al., J Biol Chem (2009) (14); Sang et al., Structure (2021) (15) and Moutel et al., Elife (2016) (16). Following in silico design, humanized antibodies were expressed and characterized in vitro to assess retention of functional and biophysical properties As shown in FIG. 19 humanization of these clones further reduced immunogenicity scores of these clones.

In silico immunogenicity analysis was carried out using the EpiVax algorithm tool called EpiMatrix to predict T cell epitopes presented by human MHC molecules (also known as HLA), which is a prerequisite for immunogenicity. EpiVax tests for binding potential to 9 common human MHC alleles, representative of >95% of human populations worldwide (reference (Jawa et et al Clin Immunol 2013 December; 149(3):534-55.). The platform considers the contribution of regulatory T cell epitopes (Tregitopes) to immunogenic potential also. A protein candidate is ranked against other known immunogenic and non-immunogenic protein sequences. EpiVax suggests proteins with T-regitope-adjusted scores of <−10 at most, and <−20 ideally, should be considered 'safe', based on scores from an average of 10 antibodies known to induce anti-therapeutic responses in >5% of patients, and an average of 10 antibodies known to induce anti-therapeutic responses in <5% of patients.

Immunogenicity scores were determined for all humanized clones and are shown in

TABLE 23

| Clone | VHH SEQ ID NO | EpiMatrix Score | tReg Adjusted Epx Score |
|---|---|---|---|
| 24-H | 101 | 3.05 | −35.61 |
| 100-H | 201 | 12.93 | −24.67 |
| 107-H | 301 | 5.22 | −3.99 |
| 126-H | 401 | 19.44 | −18.86 |
| 186-H | 501 | −7.16 | −7.16 |
| 24_ZU1 | 102 | 43.99 | −43.93 |
| 24_ZU2 | 103 | 47.61 | −40.31 |
| 24_ZU3 | 104 | 49.96 | −37.96 |
| 24_ZU4 | 105 | 44.25 | −43.66 |
| 24_ZU5 | 106 | 31.06 | −56.86 |
| 100_ZU1 | 202 | 42.57 | −37.09 |
| 100_ZU2 | 203 | 46.12 | −33.55 |
| 100_ZU3 | 204 | 45.65 | −34.02 |
| 100_ZU4 | 205 | 34.31 | −45.36 |
| 100_ZU5 | 206 | 35.97 | −43.69 |
| 107_ZU1 | 302 | 26.65 | −32.37 |
| 107_ZU2 | 303 | 40.93 | −18.09 |
| 107_ZU3 | 304 | 35.05 | −23.97 |
| 107_ZU4 | 305 | 29.09 | −29.93 |
| 107_ZU5 | 306 | 27.69 | −31.33 |
| 126_ZU1 | 402 | 36.93 | −50.17 |
| 126_ZU2 | 403 | 50.7 | −36.4 |
| 126_ZU3 | 404 | 51.93 | −35.16 |
| 126_ZU4 | 405 | 45.59 | −41.51 |
| 126_ZU5 | 406 | 40.54 | −46.56 |
| 186_ZU1 | 502 | 32.63 | −49.38 |
| 186_ZU2 | 503 | 32.84 | −49.17 |
| 186_ZU3 | 504 | 32.08 | −49.92 |
| 186_ZU4 | 505 | 12.83 | −69.18 |
| 186_ZU5 | 506 | 13.28 | −68.72 |

Epitope Binning

Antibodies were assessed for binding and competition with each other to determine which epitope bin they belonged to, using Octet. The in-tandem assay was set up using Ni-NTA biosensors, and his-tagged antigens as the ligand, and antibody as the analyte. Ni-NTA biosensors (Cat #: 18-5101) were pre-wet for 10 mins in kinetics buffer (PBS+1% BSA+0.02% Tween 20) at RT. Ni-NTA biosensors were activated with 10 mM NiCl2 for 600 s. DLL3.his antigens were captured as ligand for 600 s at 10 ug/mL diluted in kinetics buffer. Saturating antibody (Ab1) was allowed to associate for 900 s at 250 nM diluted in kinetics buffer. Immediately, competing antibody (Ab2) was allowed to associate for 600 s at 250 nM diluted in kinetics buffer. Ni-NTA biosensors were regenerated using 3× cycles of 5 s regeneration buffer (10 mM glycine pH 1.5)+5 s neutralization (kinetics buffer). Data was analyzed using Octet Data Analysis Software HT 11.1 Epitope Bin operation. Values for Ab pairing were normalized to blank (Ab2 only). Values for Ab pairing were clustered using "Pearson" similarity metric and "Mean" linkage criteria.

Example 29. Biodistribution and Tumor Targeting of VHH-Fc Comprising Anti-DLL3 Binding Regions VHH-Fc with variable region sequences from parental clones 24, 100, 107 and 126 and comprising a H435Q FcRn binding mutation in the Fc region were tested for their ability to target tumors in mice. Clone hz10D9v7.251 comprising a H435Q FcRn binding mutation was used as a comparator. The beta emitting isotope $^{111}$In was coupled to the VHH-Fc using a DOTA chelator and used as an imaging agent to visualize tumor uptake of the VHH-Fc. Human small cell lung cancer xenografts of NCI-H82 cells or SHP-77 cells were established in 10 week-old athymic nude mice. Mice were dosed with between 11 and 12 MBq of activity. Results for these experiments are shown in Table 24 and Table 25 below. All clones tested showed increased tumor uptake compared to the comparator clone hz10D9v7.251.

TABLE 24

Biosdistribution in NCI-H82 xenografts

| Group | N | Time (h) | Blood (% ID/g) mean | SEM | Kidneys (% ID/g) mean | SEM | Liver (% ID/g) mean | SEM | Tumor (% ID/g) mean | SEM |
|---|---|---|---|---|---|---|---|---|---|---|
| Clone hz10D9v7.251 | 4 | 24 | 6.2 | 1.1 | 6.8 | 0.4 | 16.2 | 2.8 | 8.5 | 0.5 |
|  | 4 | 72 | 2.2 | 0.6 | 5.7 | 0.7 | 13.4 | 2.3 | 11.6 | 1.0 |
|  | 4 | 168 | 0.8 | 0.3 | 2.5 | 0.6 | 8.9 | 1.7 | 8.3 | 2.0 |
| Clone 24 | 4 | 24 | 6.3 | 0.8 | 9.0 | 0.6 | 13.6 | 2.9 | 7.8 | 0.3 |
|  | 4 | 72 | 3.2 | 0.8 | 9.4 | 1.0 | 11.3 | 2.5 | 10.5 | 0.7 |
|  | 4 | 168 | 1.2 | 0.4 | 5.2 | 1.1 | 7.2 | 2.0 | 9.6 | 1.4 |
| Clone 107 | 4 | 24 | 6.4 | 0.6 | 8.8 | 0.8 | 10.2 | 0.3 | 7.5 | 0.1 |
|  | 4 | 72 | 3.5 | 0.4 | 8.8 | 0.9 | 8.2 | 0.5 | 10.4 | 1.0 |
|  | 4 | 168 | 1.2 | 0.2 | 5.3 | 1.0 | 4.7 | 0.4 | 10.9 | 0.9 |
| Clone 126 | 4 | 24 | 7.5 | 1.0 | 8.2 | 0.6 | 14.5 | 2.2 | 9.2 | 0.4 |
|  | 4 | 72 | 3.7 | 0.4 | 7.3 | 0.6 | 12.6 | 2.3 | 13.8 | 0.8 |
|  | 3 | 168 | 1.2 | 0.5 | 3.7 | 0.8 | 9.3 | 1.3 | 12.7 | 1.4 |

TABLE 25

Biosdistribution in SHP77 xenografts

| Group | N | Time (h) | Blood (% ID/g) mean | SEM | Kidneys (% ID/g) mean | SEM | Liver (% ID/g) mean | SEM | Tumor (% ID/g) mean | SEM |
|---|---|---|---|---|---|---|---|---|---|---|
| Clone hz10D9v7.251 | 3 | 24 | 3.6 | 1.0 | 4.8 | 1.3 | 13.4 | 5.5 | 9.6 | 3.8 |
|  | 3 | 72 | 2.0 | 0.6 | 3.9 | 1.3 | 11.6 | 4.6 | 12.1 | 5.0 |
|  | 3 | 144 | 0.6 | 0.3 | 2.4 | 0.5 | 8.7 | 3.7 | 9.3 | 4.4 |
| Clone 24 | 4 | 24 | 5.3 | 1.1 | 8.3 | 0.6 | 12.4 | 1.9 | 14.7 | 0.8 |
|  | 4 | 72 | 2.5 | 0.5 | 8.0 | 1.1 | 10.7 | 2.1 | 19.0 | 2.3 |
|  | 4 | 144 | 0.9 | 0.4 | 6.1 | 0.8 | 6.9 | 1.5 | 14.9 | 3.0 |
| Clone 100 | 4 | 24 | 5.1 | 0.6 | 8.2 | 0.4 | 13.3 | 1.4 | 13.1 | 1.0 |
|  | 4 | 72 | 2.7 | 0.6 | 8.0 | 0.4 | 10.8 | 1.5 | 19.2 | 1.6 |
|  | 4 | 144 | 0.6 | 0.1 | 5.1 | 0.5 | 8.3 | 0.9 | 16.2 | 1.8 |
| Clone 107 | 4 | 24 | 5.7 | 0.6 | 7.9 | 0.5 | 12.7 | 1.7 | 10.2 | 1.3 |
|  | 4 | 72 | 3.1 | 0.4 | 7.4 | 0.9 | 11.5 | 2.3 | 13.9 | 2.0 |
|  | 4 | 168 | 1.5 | 0.7 | 5.1 | 0.5 | 8.4 | 1.9 | 11.2 | 1.7 |
| Clone 126 | 3 | 24 | 7.1 | 0.8 | 8.2 | 0.6 | 11.5 | 1.8 | 17.9 | 0.3 |
|  | 3 | 72 | 3.2 | 0.5 | 7.2 | 0.6 | 9.4 | 2.2 | 26.9 | 2.1 |
|  | 3 | 144 | 1.3 | 0.3 | 4.8 | 0.4 | 6.6 | 1.6 | 25.7 | 3.0 |

Example 30. Expression and Purification of Humanized DLL3-Fc Variants

Humanized variants were expressed and purified as described above. All constructs were designed incorporating an Fc with mutations for FcRn binding and FcgR binding, and mutated hinge. (SEQ ID NO: 43 (435Q/AEASS-Fc/C220S IgG1-hinge). A number of variants were highly aggregated or lost binding to target due to FW mutations made during humanization (Table 26).

TABLE 26

Characterization of humanized variant aggregation and target binding.
nb = no binding observed

| ID | % purity aSEC | hDLL3 binding (ELISA) | mDLL3 binding (ELISA) | ID | % purity aSEC | hDLL3 binding (ELISA) | mDLL3 binding (ELISA) |
|---|---|---|---|---|---|---|---|
| 24 | 100 | +++ | +++ | 100 | 100 | +++ | +++ |
| 24_zu1 | 31 | ++ | ++ | 100_zu1 | 98 | nb | nb |
| 24_zu2 | 42 | nb | nb | 100_zu2 | 75 | nb | nb |
| 24_zu3 | 71 | nb | nb | 100_zu3 | 100 | nb | nb |
| 24_zu4 | 97 | nb | nb | 100_zu4 | 100 | nb | nb |
| 24_zu5 | 94 | nb | nb | 100_zu5 | 100 | nb | nb |
| 107 | 100 | +++ | +++ | 126 | 100 | ++ | nb |
| 107_zu1 | 17 | ++ | ++ | 126_zu1 | 95 | ++ | nb |
| 107_zu2 | 100 | +++ | +++ | 126_zu2 | 97 | ++ | nb |
| 107_zu3 | 100 | +++ | +++ | 126_zu3 | 100 | ++ | nb |
| 107_zu4 | 100 | +++ | +++ | 126_zu4 | 100 | ++ | nb |
| 107_zu5 | 100 | +++ | +++ | 126_zu5 | 100 | ++ | nb |
| 186 | 100 | ++ | nb | | | | |
| 186_zu1 | 100 | ++ | nb | | | | |
| 186_zu2 | 100 | ++ | nb | | | | |
| 186_zu3 | 100 | ++ | nb | | | | |
| 186_zu4 | 100 | ++ | nb | | | | |
| 186_zu5 | 100 | ++ | nb | | | | |

Example 31. Humanized DLL3 In Vitro Characterization

Humanized VHHFcs were tested for binding to DLL3 expressing SHP-77 cells (FIG. 20A). 126_zu1 showed lower binding to cells compared to all other clones. VHHFcs were tested for internalization on SHP-77 cells, and whilst all levels were low as seen previously, the 107 set of variants showed higher internalization signals (FIG. 20B).

Figure 21:
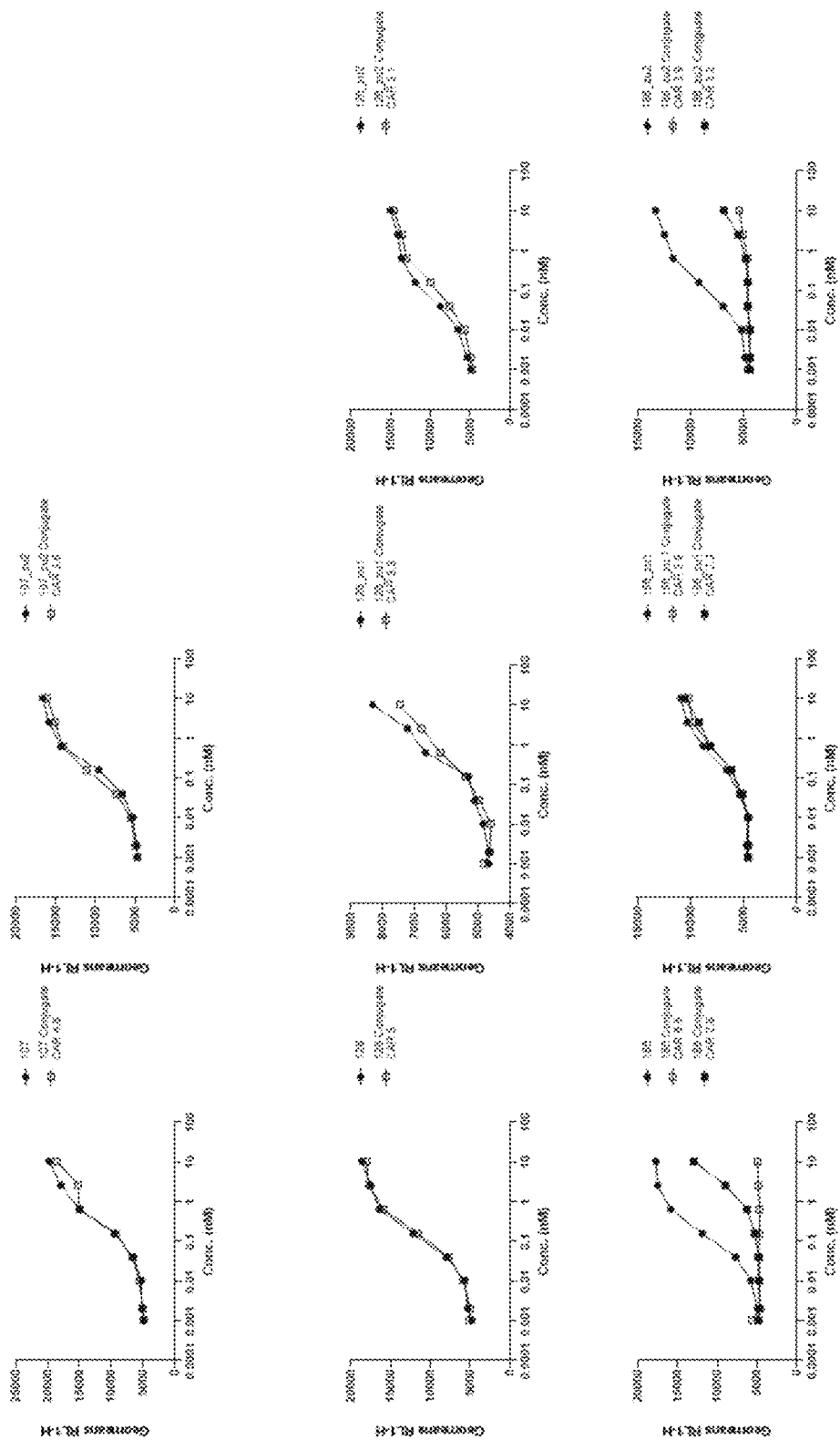
FIG. 21 shows humanized VHHFc conjugates SHP-77 cell binding.

VHHFcs were conjugated to p-SCN-Bn-DOTA (Macrocyclics, Cat #: B-205), with chelator-antibody ratio of 3-5, as described above, and assessed for retained binding to DLL3 expressing cells. For clone 186, and humanized variant 186_zu2, conjugation resulted in reduction of binding to cells, with increased reduction observed at higher CAR level. (FIG. 21). Both clones have a lysine residue at position 52 in FW2. This position is one of the camelid hallmark residue sites for VHHs, known to influence binding due to its interaction with CDR3. In 186_zu1, this lysine was substituted K48A during the humanization design process, and cell binding was maintained upon conjugation. All other parental and humanized sequences that were conjugated did not have a lysine at this FW2 position, and showed similar target binding to the unconjugated VHHFc.

Figure 22:
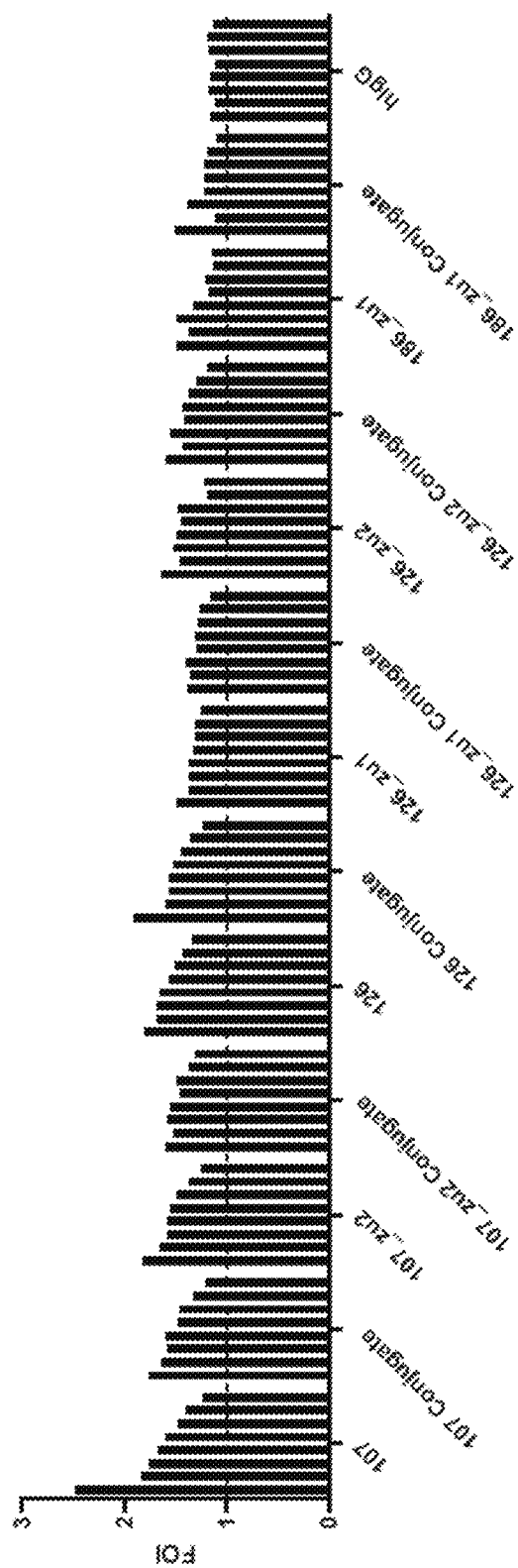
FIG. 22 shows humanized VHHFc Conjugate SHP-77 cell internalization.

Conjugates were tested for internalization on DLL3 expressing SHP-77 cells and conjugation appeared to have little or no impact on internalization levels (FIG. 22).

Example 32. Biophysical Analysis of Humanized Leads and Conjugates

Humanized leads were assessed for biophysical properties to aid selection of a developable candidate, following methods described above. In the polyreactivity assay, which measures non-specific charge-based interactions, 107 and variants 107_zu2 and 107_zu3 had higher polyreactivity scores than 107_zu4, 126 and its variant 126_zu1, 126-zu2, 186 and variant 186_zu1. (Table 27). In the ACSINs assay which measures self-interaction, 107, 107_zu2 and 107_zu3 had higher scores than 107_zu4, 126 and 126-zu2, 186 and variant 186_zu1. VHHFc conjugates resulted in slightly reduced scores for both assays, but follow the same ranking. Thermostability measurements (Tm1) for VHHFcs and conjugates by DSF were similar.

TABLE 27

Biophysical Analysis of Humanized Leads and Conjugates

| Clone ID | Polyreactivity Score Insulin | Polyreactivity Score dsDNA | ACSINS $\Delta\gamma$max (nM) | Tm1° C. |
|---|---|---|---|---|
| 107 | 6.24 | 14.9 | 10.13 | 60.1 |
| 107_zu2 | 4.34 | 11.88 | 18.04 | 59.8 |
| 107_zu3 | 8.95 | 14.3 | 13.53 | 60.0 |
| 107_zu4 | 7.59 | 7.67 | 7.54 | 60.6 |
| 126 | 1.64 | 3.77 | 6.69 | 59.8 |
| 126_zu1 | 3.04 | 5.42 | 8.77 | 58.5 |
| 126_zu2 | 2.33 | 4.4 | 7.83 | 59.9 |
| 186_zu1 | 2.57 | 3.9 | 8.13 | 58.6 |
| 107 Conjugate | 3.49 | 5.69 | 5.67 | 60.4 |
| 107_zu2 Conjugate | 3.71 | 8.13 | 11.04 | 60.6 |
| 126 Conjugate | 0.97 | 1.19 | 3.18 | 58.9 |
| 126_zu1 Conjugate | 0.93 | 0.85 | 8.22 | 58.5 |
| 126_zu2 Conjugate | 0.96 | 0.83 | 7.68 | 59.3 |
| 186_zu1 Conjugate | 1.00 | 0.83 | 6.45 | 58.6 |

Example 33. Antibody Specificity Measured by Protein Array

Membrane Proteome Array (MPA) screening was conducted. The MPA is a protein library composed of 6,000 distinct human membrane protein clones, each overexpressed in live cells from expression plasmids. Each clone was individually transfected in separate wells of a 384-well plate followed by a 24 h incubation (Tucker et al., 2018). Cells expressing each individual MPA protein clone were arrayed in duplicate in a matrix format for high-throughput screening. Before screening on the MPA, the test ligand concentration for screening was determined on cells expressing positive (membrane-tethered Protein A) and negative (mock-transfected) binding controls, followed by detection by flow cytometry using a fluorescently-labeled secondary antibody. Each test ligand was added to the MPA at the predetermined concentration, and binding across the protein library was measured on an Intellicyt iQue using a fluorescently labeled secondary antibody. Each array plate contains both positive (Fc-binding) and negative (empty vector) controls to ensure plate-by-plate reproducibility. Test ligand interactions with any targets identified by MPA screening were confirmed in a second flow cytometry experiment using serial dilutions of the test antibody, and the target identity was re-verified by sequencing. 107_zu2 and 126_zu2 were screened on the array at 20 µg/ml by flow cytometry. Targets are screened in duplicate, and hits demonstrating binding signal >3 standard deviations above background in both wells were selected for downstream validation experiments. Non-specific fluorescence was determined to be any value below 3 standard deviations of the mean background value. Targets validated in the secondary screen are indicated in FIG. 23. Both 107_zu2 and 126_zu2 bound DLL3 as expected. 126_zu2 had 1 off-target hit to an ion-channel protein which was shown to be an assay artifact due to absence of binding to several different forms of that target including protein, endogenous cell expression and stable cell line expression, (data not shown).

Figure 24:
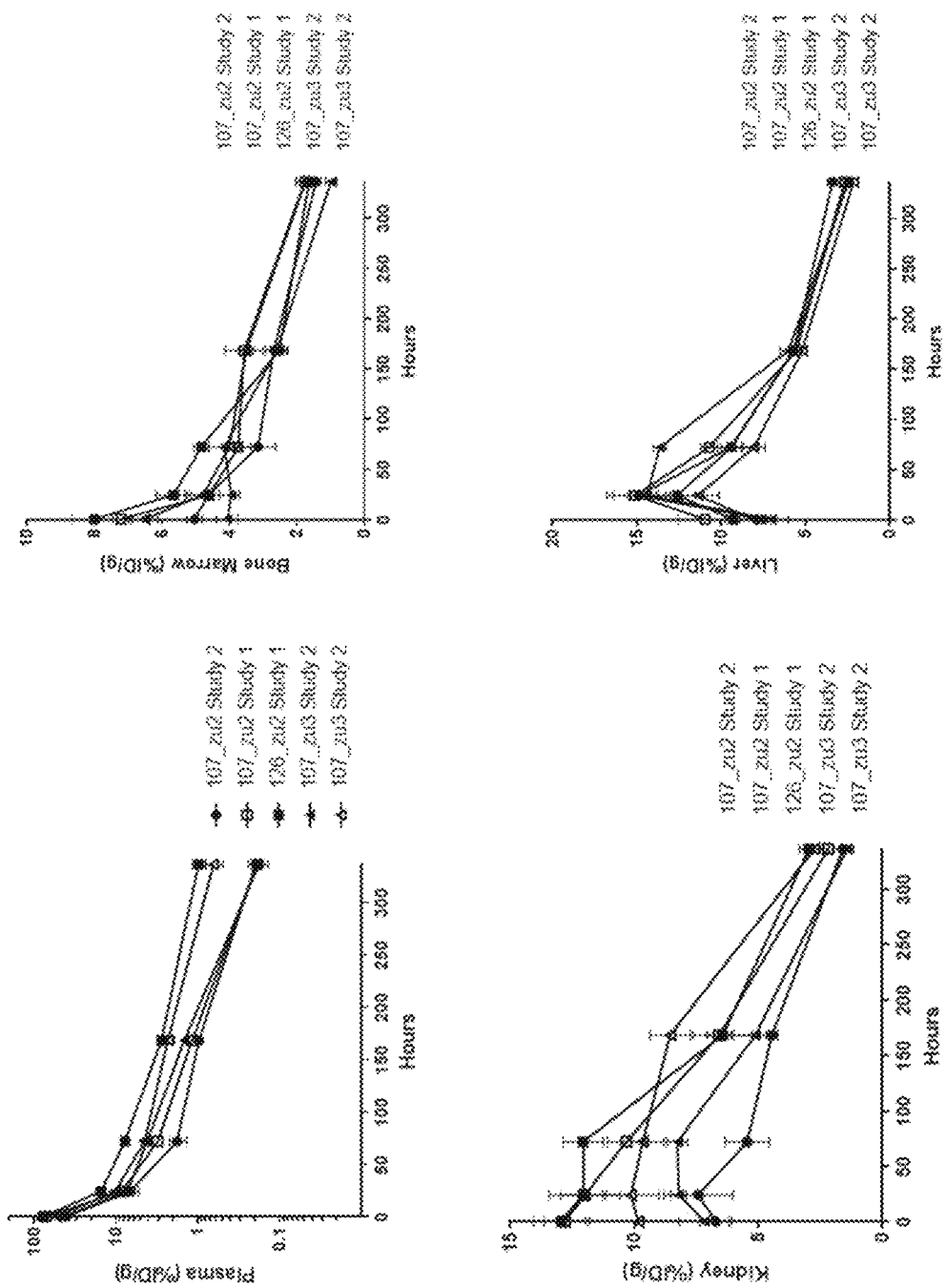
FIG. 24 shows biodistribution of In-111 radiolabeled humanized VHHFcs in non-tumor-bearing mice.

Example 34. Single-Dose Pharmacokinetics and Normal Tissue Biodistribution of In-111-Radiolabeled Humanized VHHFcs in Non-Tumor-Bearing Mice Normal tissue biodistribution of In-111-radiolabeled conjugates was evaluated following intravenous administration in CD1 mice. The biodistribution was determined by ex vivo gamma counting of tissues resected 96 hours post-injection and analyzed to obtain tissue activity concentration (% ID/g). Time-course ex vivo biodistribution (3 MBq In-111, 0.3 mg/kg antibody, n=3 mice/group/time point, 0.5 MBq/ug specific activity) FIG. 24 shows conjugates are rapidly cleared from the blood compartment and normal tissues. 126_zu2 and 107_zu4 show slower blood clearance than 107_zu2 or 107_zu3, with 107_zu4 also showing slower kidney clearance. Half-life was determined for each test article (Table 28).

TABLE 28

Half-life of Indium 111 radiolabeled
VHHFcs in non-tumor bearing mice

| VHHFc Conjugate | t1/2 days |
|---|---|
| 107_zu2 | 2.8 |
| 107_zu3 | 2.5 |
| 107_zu4 | 3.5 |
| 126_zu2 | 3.4 |

Figure 25:
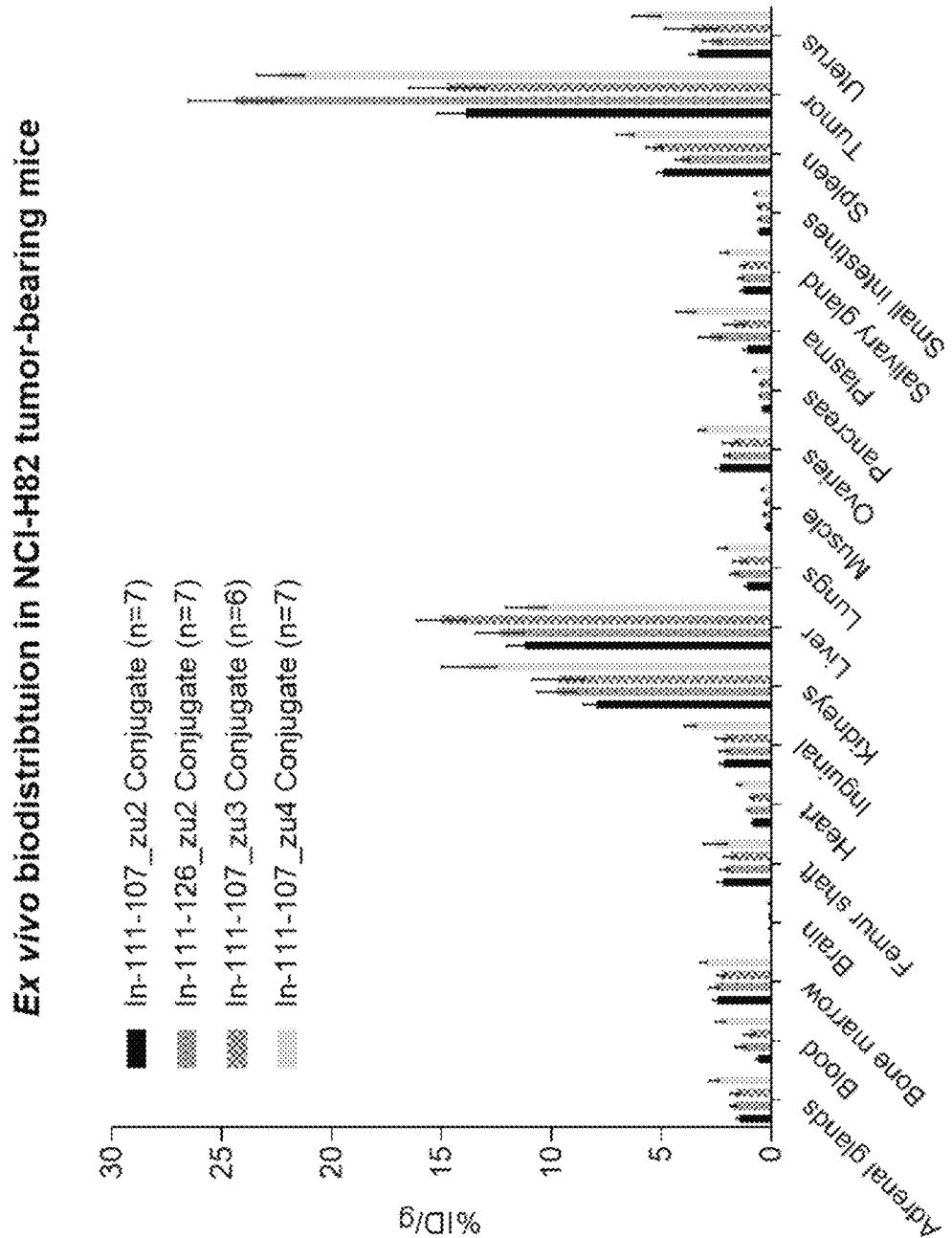
FIG. 25 shows biodistribution of In-111 radiolabeled humanized VHHFcs in NCI-H82 tumor bearing mice
Figure 26:
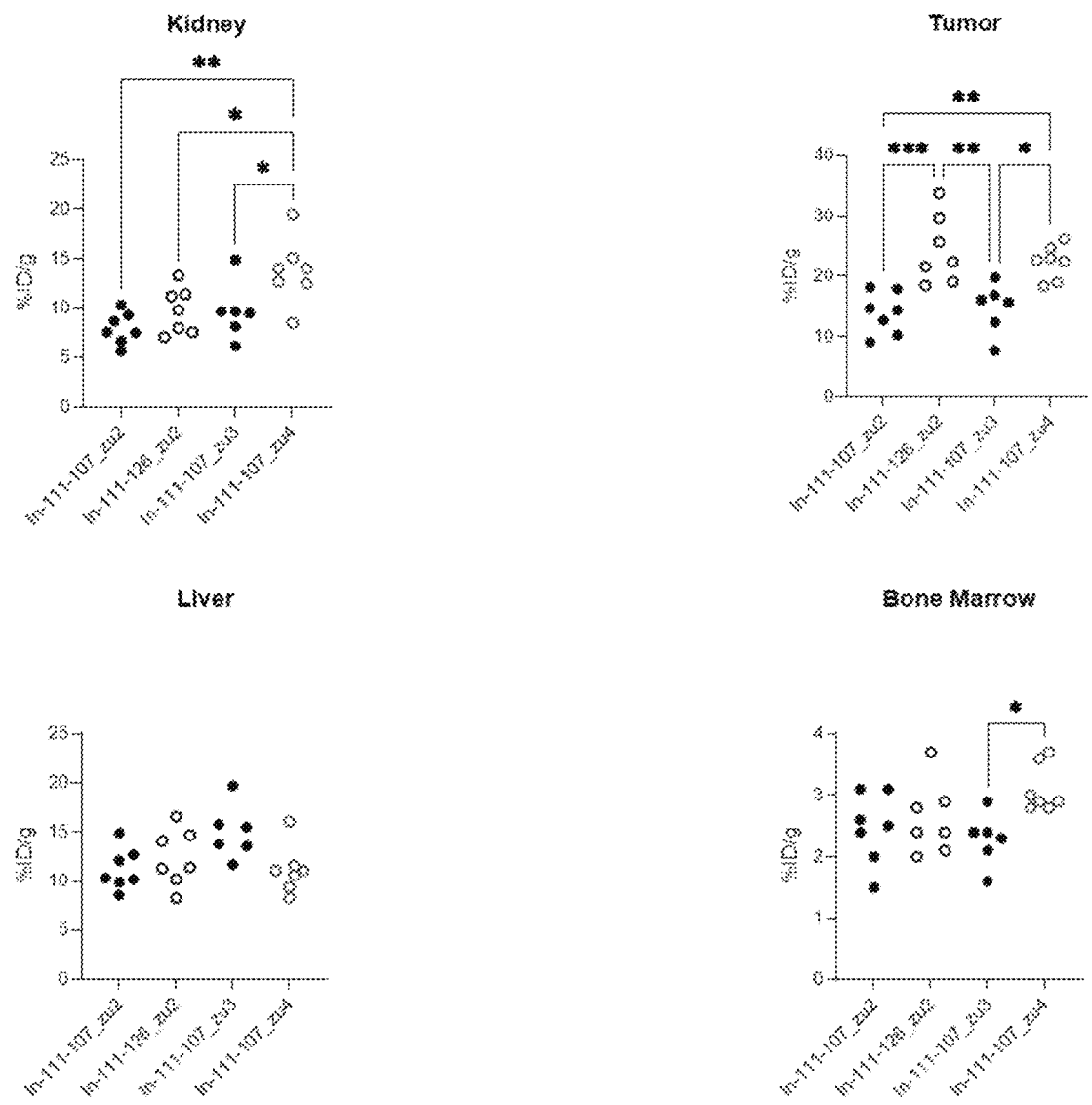
FIG. 26 shows a comparison of In-111 radiolabeled humanized VHHFcs tissue activity concentration in NCI-H82 tumor bearing mice.

Example 35. Single-Dose Biodistribution of In-111-Radiolabeled Humanized VHHFcs in NCI-H82 SCLC Tumor-Bearing Mice Athymic nude mice with xenografted NCI-H82 tumors (DLL3 receptor density of approximately 800 epitopes/cell) were treated with In-111 radiolabeled VHHFcs (n=6-7 mice/group, 3 MBq, 0.3 mg/kg, 0.5 MBq/g specific activity). Ex vivo biodistribution was evaluated 4 days after single-dose administration (FIG. 25 and FIG. 26). 126_zu2 and 107_zu4 show high tumor accumulation. However, 107_zu4 also shows higher kidney biodistribution, consistent with the longer kidney retention in the non-tumor bearing mice study.

Figure 27:
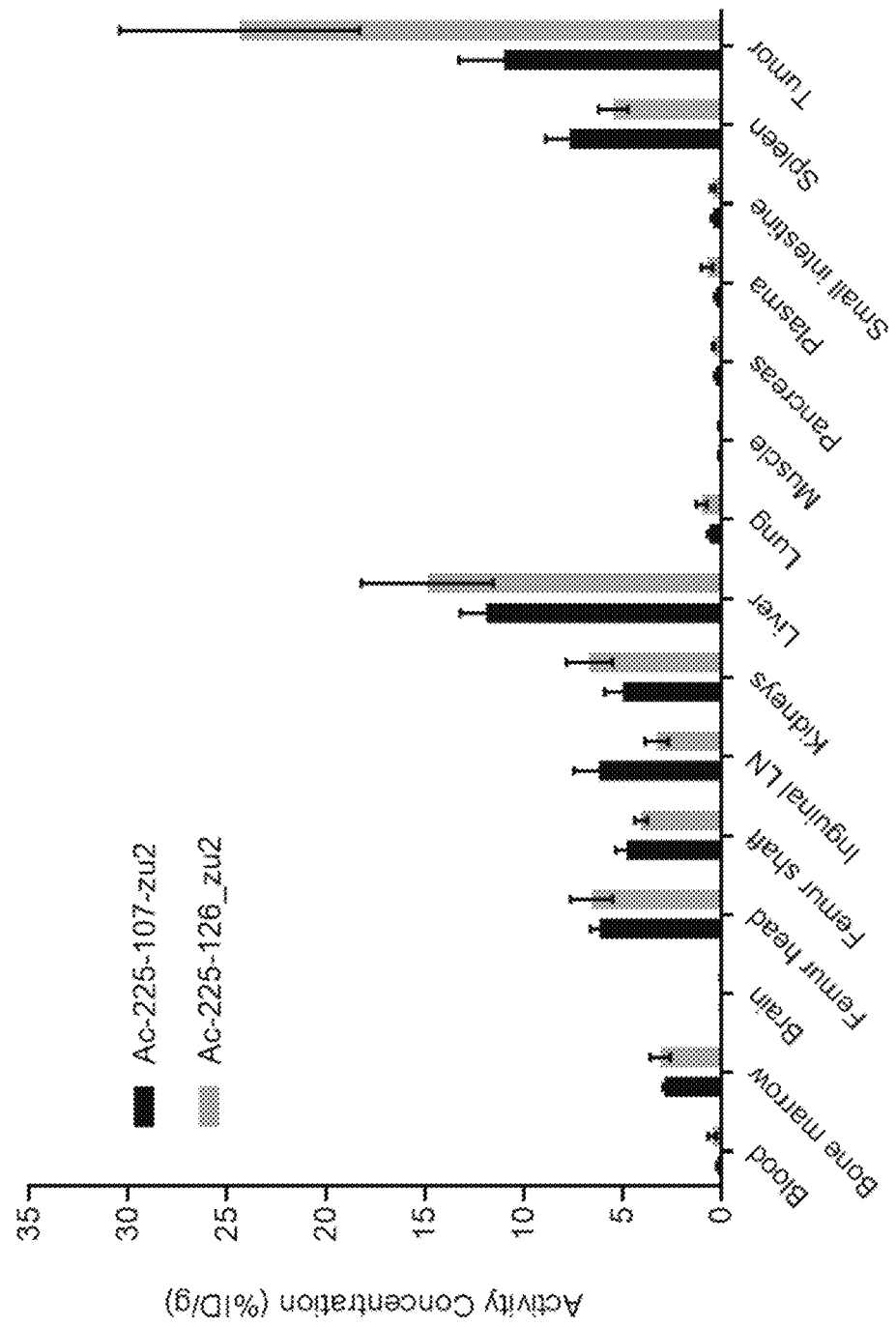
FIG. 27 shows biodistribution of Acc-225 radiolabeled humanized VHHFcs in NCI-H82 tumor bearing nude mice.

Example 36. Single-Dose Biodistribution of Acc-225 Radiolabeled Humanized VHHFcs in NCI-H82 SCLC Tumor Bearing Nude Mice Ex vivo biodistribution of Ac-225 radiolabeled conjugates (n=5 mice/group, 12.5 kBq, 1 mg/kg protein, 0.5 kBq/g specific activity) was evaluated using athymic nude mice with xenografted NCI-H82 tumors 7 days following single-dose intravenous administration. 126_zu2 shows favorable tumor-to-tissue biodistribution in NCI-H82 SCLC tumors. (FIG. 27).

Figure 28:
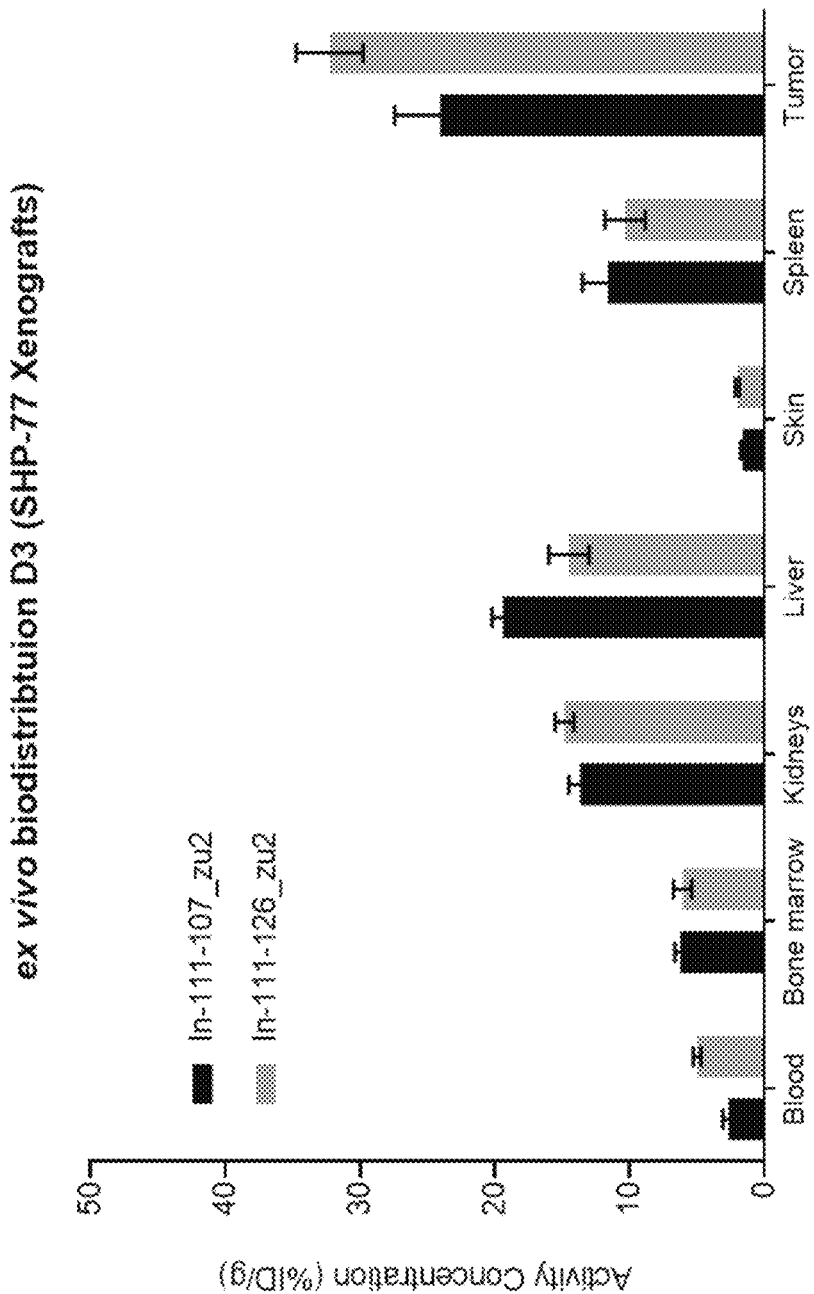
FIG. 28 shows biodistribution of Ind-111 labelled VHHFcs in SHP-77 tumor bearing SCID Beige mice.

Example 37. Single-Dose Biodistribution of Ind-111 Labelled Humanized Leads in SHP-77 Tumor Bearing SCID Beige Mice Ex vivo tissue biodistribution of In-111 radiolabeled 107_zu2 versus 126_zu2 (3 MBq In-111, 0.3 mg/kg antibody, n=4 mice, specific activity 0.5 MBq/ug) was evaluated 72 hours following single-dose intravenous administration in SCID beige mice bearing SHP-77 SCLC xenografts (DLL3 receptor density of approximately 900 epitopes/cell). Higher tumor uptake was confirmed for 126_zu2 versus 107_zu2 in an alternate SCLC xenograft model (FIG. 28).

Figure 29:
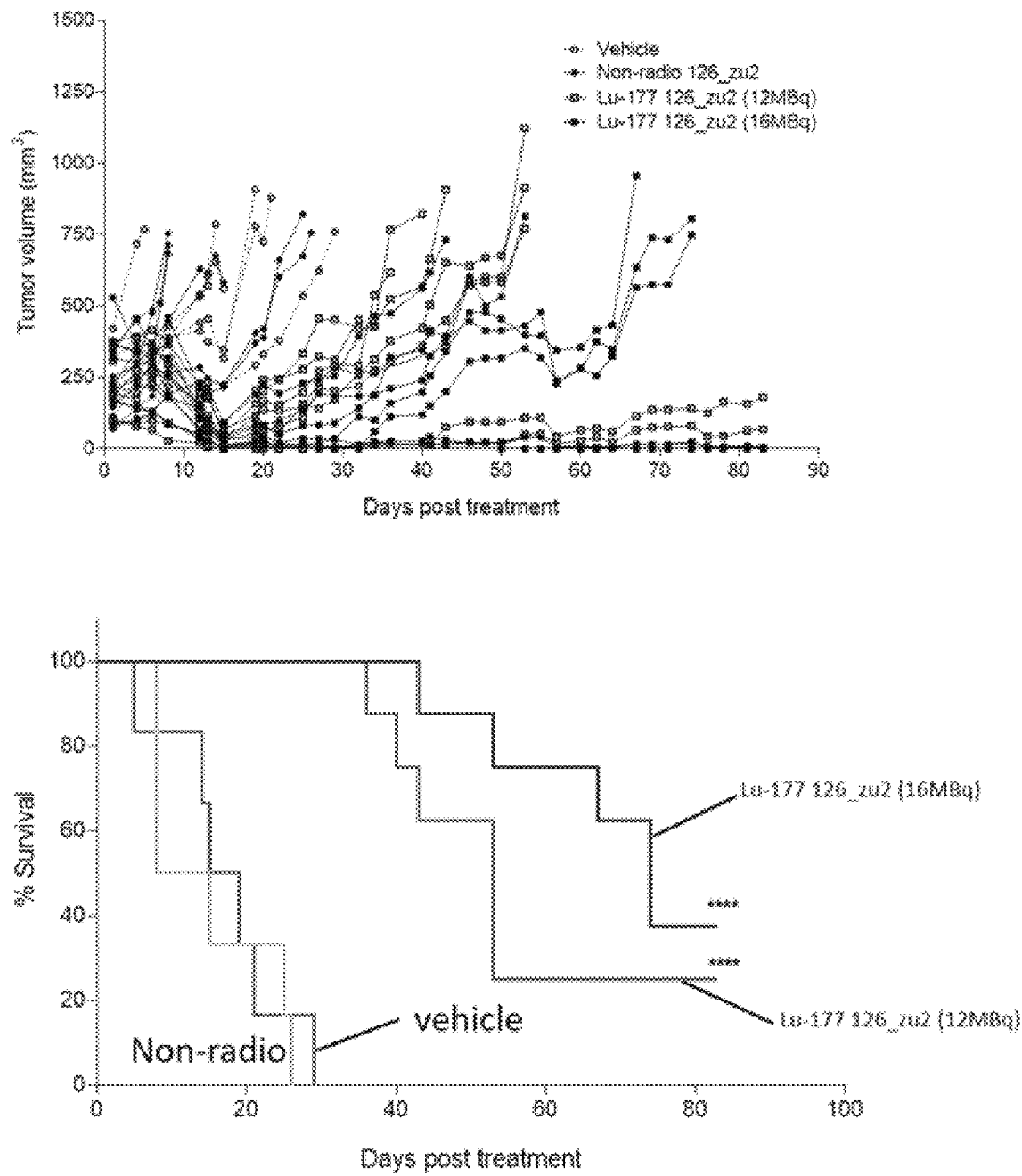
FIG. 29 shows tumor growth and survival with single-dose Lu-177 labeled 126_zu2 in NCI-H82 SCLC tumor-bearing mice.

Example 38. Single Dose Efficacy of a Lu-177 Labeled 126_Zu2 Conjugate in NCI-H82 SCLC Tumor-Bearing Mice Anti-tumor activity and extension of survival of Lu-177 radiolabeled 126_zu2 was assessed in female athymic nude mice implanted with subcutaneous NCI-H82 tumors. Animals were administered a single IV dose of vehicle (PBS with 50 mM sodium ascorbate and 5 mM DTPA; n=6), non-radiolabeled 126_zu2 (n=6) or Lu-177 labeled 126_zu2 (1 MBq/ug specific activity, n=8/group) at 12 MBq Lu-177 (0.6 mg/kg) or 16 MBq Lu-177 (0.8 mg/kg) on Day 0. Body weight and tumor size were measured 3 times weekly throughout the study, and mice were sacrificed due to tumor burden or when they reached the study endpoint on Day 83. The Lu-177 labeled 126_zu2 shows anti-tumor efficacy with initial regression followed by regrowth (FIG. 29). Complete response/sustained regression was achieved in 38% (⅜) of animals in the 16 MBq Lu-177 dose group and 25% (⅖) of the animals in the 12 MBq Lu-177 dose group. The Lu-177 labeled 126_zu2 significantly extends the survival of mice in both dose groups compared to the vehicle (log-rank $p<0.0001$; median survival of 17 days for vehicle-treated, 11.5 days for non-radiolabeled 126_zu2, 53 days for 12 MBq Lu-177 dose group and 74 days for the 16 MBq Lu-177 dose group. The non-radiolabeled 126_zu2 showed no pharmacological activity.

Figure 30:
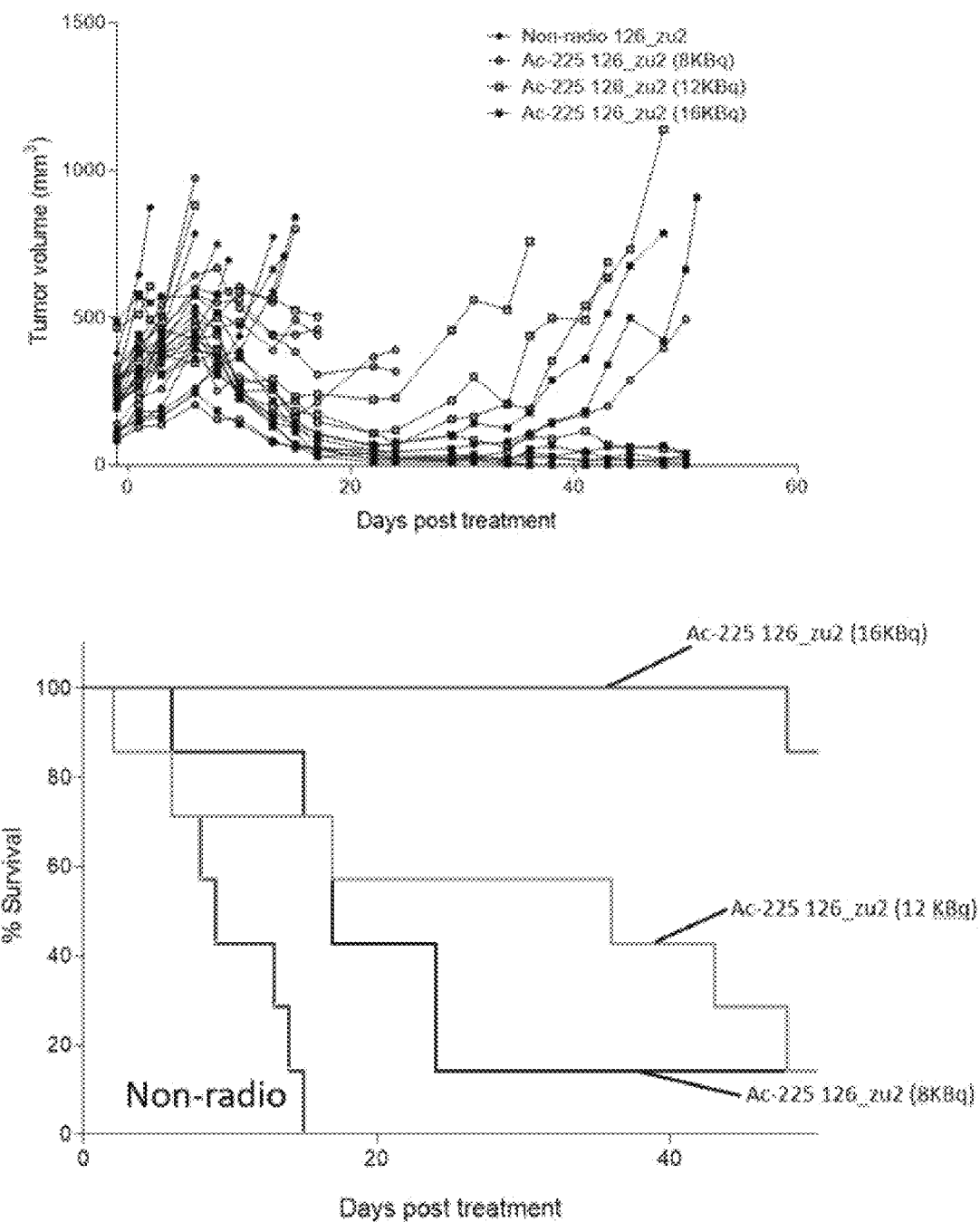
FIG. 30 shows tumor growth and Survival with single-dose Ac-225 labeled 126_zu2 in SHP-77 SCLC tumor-bearing mice.

Example 39. Single Dose Efficacy of a Ac-225 Labeled 126_Zu2 in SHP-77 SCLC Tumor-Bearing Mice Female athymic nude mice were implanted with subcutaneous SHP-77 tumors. Animals (n=7/group) were administered a single IV dose of non-radiolabeled 126_zu2, or Ac-225 labeled 126_zu2 (0.5 kBq/ug specific activity) at a low dose (8 kBq Ac-225 and a 0.8 mg/kg), mid dose (12 kBq Ac-225 and a 1.2 mg/kg) or high dose (16 kBq Ac-225 and 1.6 mg/kg) on Day 0. Ac-225 labeled 126_zu2 shows dose-dependent anti-tumor efficacy and extension of survival up to Day 51 (FIG. 30). Tumors grew rapidly in the non-radiolabeled 126_zu2 group, and all animals were euthanized due to tumor burden within 15 days post-treatment. The Ac-225 126_zu2 treated mice showed tumor regression, which extended for longer periods before regrowth in the higher dose groups. Tumor ablation or sustained regression was achieved in 71% (5/7) of the animal in the high dose group and 14% (1/7) of animals in the low dose group at day 51. Median survival at day 51; 9 days for non-radio 126_zu2, 17 days for Ac-225 low dose, 36 days for Ac-225 mid dose and 51 days for Ac-225 high dose.

Example 40. In Vitro Immunogenicity

T cell activation is an important part of the immune response to therapeutic proteins. In vitro T cell assays allow an assessment of the capacity of a therapeutic protein to induce a T cell response in a human target population. Test products are added to human PBMC (peripheral blood mononuclear cells) and lymphocyte activation can be detected by various assays to determine the number of donors eliciting a significant T cell response, and also the magnitude of the T cell response over the test population in vitro. T cell assays are often used during lead selection or lead optimization where test proteins can be ranked by their relative immunogenicity risk and enable the lowest risk candidates to be selected.

An in vitro immunogenicity risk assessment was carried out using Lonza's in vitro DC:CD4 re-stimulation assay for the assessment of T cell activation, using PBMC from 31 healthy human donors, qualified suitable for the assay, according to standard protocol. The DC:CD4 restimulation assay to determine CD4+ T cell response induced by each antibody was assessed by IFNγ and IL-5 FluoroSpot. Analysis uses a non-parametric statistical test that compares each test condition and reference condition for each donor, and indicates if the difference is statistically significant, utilizing permutation resampling (DFR(eq)).

KLH positive control is a potent stimulator of CD4+ T cells, and behaved as expected, inducing strong IFNγ (100.0%) and IL-5 (87.1%) responses in the majority of the donors.

126_zu2 ranked as a low risk product (<10% individual response rate) in both IFNγ (6.5%) and IL-5 (6.5%) responses, whilst 107_zu2 produced data suggesting the capacity to activate T cells (>10% individual response rate), with a moderate risk for IFNγ response (16.1%) and low risk for IL-5 response (12.9%). The data suggests 126_zu2 to be associated with low risk of sequence-related immunogenicity for T cell response.

Example 41. Epitope Mapping of Humanized VHH Clones

The epitope binning assay described above, confirmed humanized antibodies 107_zu2 and 126—do not compete with each other for binding to hDLL3, indicating they are in different epitope bins.

To further map regions of binding for these two antibodies, a truncated form of DLL3 was designed. FIG. 31 shows the structure of hDLL3. The N-terminal domain is presented by aa 27-175 (in italics), the DSL domain is aa 176-215 (bold underline), and EGF1-6 is aa 216-492 (normal text). A mIgG2a CH2-CH3 Fc fused to aa 216-492 of hDLL3 was expressed in HEK cells and purified using Protein G by FPLC. (SEQ ID NO: 532). An antibody previously described and shown to recognize the EGF domain was expressed and purified for use as an assay control, DL301 hIgG1 (Chugai patent US 2015/0368355A1 SEQ ID NO: 11 (Heavy chain) SEQ ID NO: 17 (Light chain).

An antibody previously described and shown to recognize the N-terminal domain was expressed and purified for use as an assay control, Sc16.23 (Abbvie Patent WO2017031458A2 SEQ ID NO: 78/79 (VH) SEQ ID NO: 76/77 (VL).

Rovalpituzumab, an anti-DLL3 antibody previously characterized as a DSL domain binder was expressed and purified for use as an assay control (KEGG Drug Database D1117).

An antibody previously described as a DSL binder was used as an assay control (MAB4315, R&D).

Binding to full length DLL3 ECD (which incorporates aa 27-492, Cat #ab255797, Abcam) was compared with binding to the hDLL3 EGF domain construct. Medium binding plates (Corning, Cat #3368) were incubated with 50 ul of antigen in PBS pH7.4 at 2 ug/ml, overnight at 4 C. Plates were washed 3 times with dH2O, and blocked with 100 ul 5% skim milk for 1 h, RT. Test VHHFcs and control antibodies were diluted in block in a 1:4 serial titration from 100 nM to 0.01 nM, and incubated for 1 h, RT. Plates were washed 3 times with H20, and incubated with 50 ul 0.2 ug/ml Gt-anti-hIgG-Fc-HRP (Jackson Immunoresearch Labs, Cat #109-035-098) for 1 h RT. Plate was washed 3 times with H2O, and wells incubated with 50 ul TMB substrate for 4-5 min at RT. The reaction was quenched with 50 ul/well iN HCl. The plate was read on a Synergy Neo2 at absorbance 450 nm.

Figure 32:
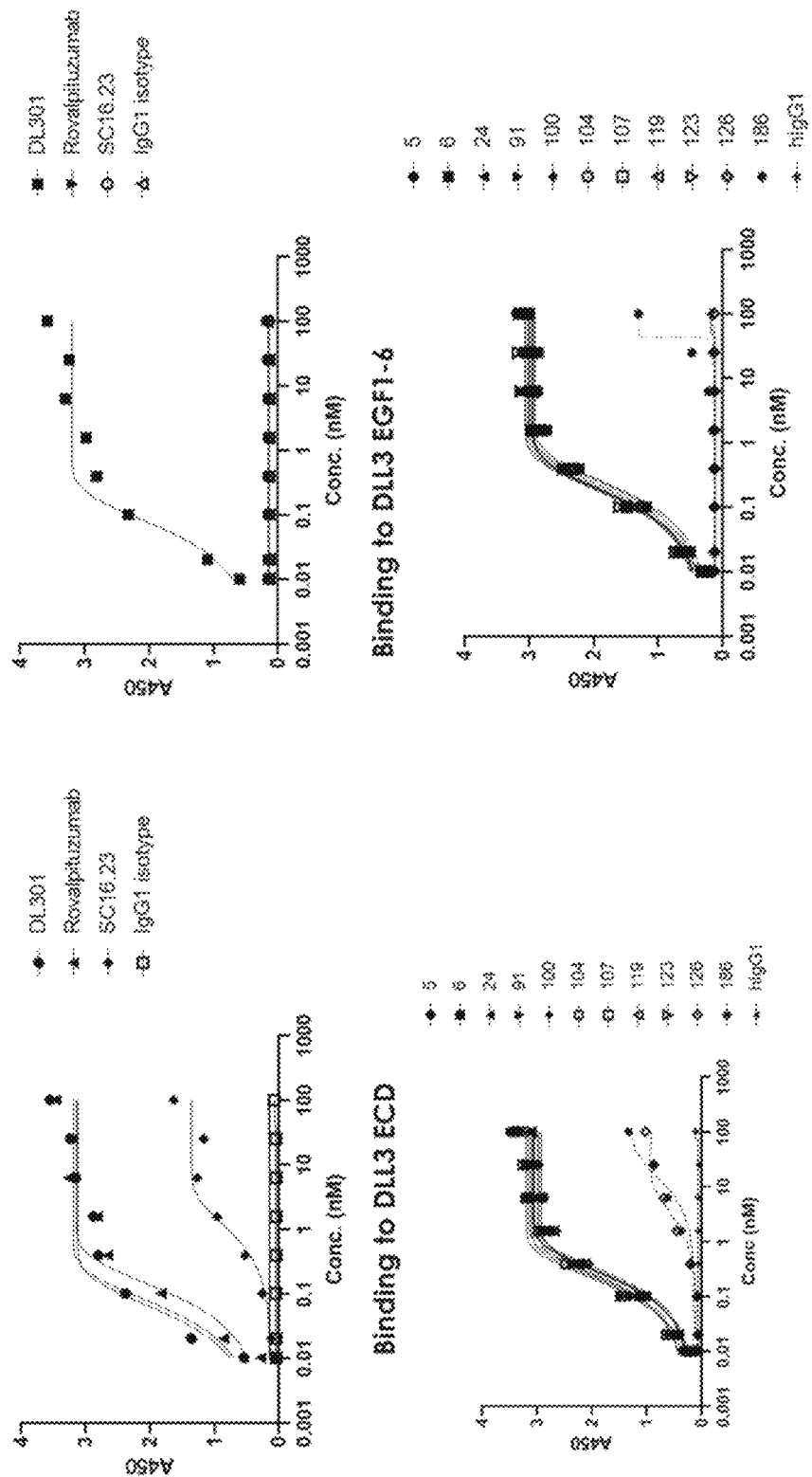
FIG. 32 shows epitope mapping of different VHH binding clones.

DL301 bound to the EGF domain, whilst Rovalpituzumab and SC16.23 did not bind to the EGF domain, as expected (FIG. 32, upper panels). A panel of parental VHHFcs were assessed for binding to the EGF domain. All showed binding to the EGF domain apart from 126 and 186. This correlates with previous data showing 126 and 186 are in a different epitope bin to all other VHHFcs (FIG. 32, lower panels).

Analysis of EGF binding for humanized lead variants 126_zu2 and 107_zu2 was characterized using an Octet based assay. Anti-human capture sensors (Fortebio AHC, Cat #18-5063) were dipped into 20 nM VHHFc or hIgG controls, followed by DLL3 EGF1-6 (mIgG2aCH2-CH3) titration. Sensors were regenerated with Glycine pH 1.7 and sample buffer was PBS/0.02% Tween-20/0.1% BSA, pH 7.4. Data was analyzed using Octet Analysis software. 107_zu2 and DL301 bound the DLL3 EGF domain, whilst 126-zu2 and Rovalpituzumab did not bind the DLL3 EGF1-6 domain. (Table 29).

TABLE 29

| Sample | KDnM | Ka (1/Ms) | Kd (1/s) | X^2 | R^2 |
| --- | --- | --- | --- | --- | --- |
| 107_zu2 | 5.037 | 1.018E+05 | 5.129E−04 | 1.2077 | 0.9982 |
| 126_zu2 | | | No binding | | |
| DL301 | 0.108 | 5.99E+05 | 6.455E−05 | 0.6616 | 0.9975 |
| Rovalpituzumab | | | No binding | | |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Sequences Described Herein

```
Fc1 (SEQ ID NO: 1)
I253A
APELLGGPSVFLFPPKPKDTLMASRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPPSREEM
TKNQVSLTCLVKGFYPSDIAVEWESNGQPENNYKTTPPVLDSDGSFFLYSKLTVDKSRWQQGNV
FSCSVMHEALHNHYTQKSLSLSPG

Fc2 (SEQ ID NO: 2)
S254A
APELLGGPSVFLFPPKPKDTLMIARTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPPSREEM
TKNQVSLTCLVKGFYPSDIAVEWESNGQPENNYKTTPPVLDSDGSFFLYSKLTVDKSRWQQGNV
FSCSVMHEALHNHYTQKSLSLSPG

Fc3 (SEQ ID NO: 3)
H310A
APELLGGPSVFLFPPKPKDTLMISRTPEVTCVVVDVSHEDPEVKFNWYVDGVEVHNAKTKPREE
QYNSTYRVVSVLTVLAQDWLNGKEYKCKVSNKALPAPIEKTISKAKGQPREPQVYTLPPSREEM
TKNQVSLTCLVKGFYPSDIAVEWESNGQPENNYKTTPPVLDSDGSFFLYSKLTVDKSRWQQGNV
FSCSVMHEALHNHYTQKSLSLSPG

Fc4 (SEQ ID NO: 4)
H435Q
APELLGGPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPPSREEM
TKNQVSLTCLVKGFYPSDIAVEWESNGQPENNYKTTPPVLDSDGSFFLYSKLTVDKSRWQQGNV
FSCSVMHEALHNQYTQKSLSLSPG

Fc5 (SEQ ID NO: 5)
Y436A
APELLGGPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPPSREEM
TKNQVSLTCLVKGFYPSDIAVEWESNGQPENNYKTTPPVLDSDGSFFLYSKLTVDKSRWQQGNV
FSCSVMHEALHNHATQKSLSLSPG

Fc6 (SEQ ID NO: 6)
H310A/H435Q
APELLGGPSVFLFPPKPKDTLMISRTPEVTCVVVDVSHEDPEVKFNWYVDGVEVHNAKTKPREE
QYNSTYRVVSVLTVLAQDWLNGKEYKCKVSNKALPAPIEKTISKAKGQPREPQVYTLPPSREEM
TKNQVSLTCLVKGFYPSDIAVEWESNGQPENNYKTTPPVLDSDGSFFLYSKLTVDKSRWQQGNV
FSCSVMHEALHNQYTQKSLSLSPG

Fc7 (SEQ ID NO: 7)
AEASS
APEAEGAPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPSSIEKTISKAKGQPREPQVYTLPPSREEM
TKNQVSLTCLVKGFYPSDIAVEWESNGQPENNYKTTPPVLDSDGSFFLYSKLTVDKSRWQQGNV
FSCSVMHEALHNHYTQKSLSLSPG

Fc8 (SEQ ID NO: 8)
AEASS/H310A
APEAEGAPSVFLFPPKPKDTLMISRTPEVTCVVVDVSHEDPEVKFNWYVDGVEVHNAKTKPREE
QYNSTYRVVSVLTVLAQDWLNGKEYKCKVSNKALPSSIEKTISKAKGQPREPQVYTLPPSREEM
TKNQVSLTCLVKGFYPSDIAVEWESNGQPENNYKTTPPVLDSDGSFFLYSKLTVDKSRWQQGNV
FSCSVMHEALHNHYTQKSLSLSPG

Fc9 (SEQ ID NO: 9)
AEASS/H435Q
APEAEGAPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPSSIEKTISKAKGQPREPQVYTLPPSREEM
TKNQVSLTCLVKGFYPSDIAVEWESNGQPENNYKTTPPVLDSDGSFFLYSKLTVDKSRWQQGNV
FSCSVMHEALHNQYTQKSLSLSPG

Fc wild type (SEQ ID NO: 10)
APELLGGPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPPSREEM
TKNQVSLTCLVKGFYPSDIAVEWESNGQPENNYKTTPPVLDSDGSFFLYSKLTVDKSRWQQGNV
FSCSVMHEALHNHYTQKSLSLSPG 2RS15d (SEQ ID NO: 20)
QVQLQESGGGSVQAGGSLKLTCAASGYIFNSCGMGWYRQSPGRERELVSRISGDGDTWHKESVK
GRFTISQDNVKKTLYLQMNSLKPEDTAVYFCAVCYNLETY WGQGTQVTVSS 2RS15d CDR1 GYIFNSCG (SEQ ID NO: 21)

2RS15d CDR2 ISGDGDT (SEQ ID NO: 22)

2RS15d CDR3 AVCYNLETY (SEQ ID NO: 23)
``` hz10D9v7.251 (SEQ ID NO: 30)
EVQLVESGGGEVQPGGSLRLSCAASGSIFSINAMGWYRQAPGKQRELVAG
FTGDTNTIYAESVKGRFTISRDNAKNTVYLQMSSLRAEDTAVYYCAADVQLFSRDYEFYWGQGT
LVTVKP hz10D9v7.251 CDR1 GSIFSINA (SEQ ID NO: 31)

hz10D9v7.251 CDR2 FTGDINT (SEQ ID NO: 32)

hz10D9v7.251 CDR3 AADVQLFSRDYEFY (SEQ ID NO: 33)

SEQ ID NO: 40 (Wild-type human IgG1-hinge)
EPKSCDKTHTCPPCP

SEQ ID NO: 41 (C220S IgG1-hinge)
EPKSSDKTHTCPPCP

SEQ ID NO: 42 (WT-Fc/C220S IgG1-hinge)
EPKSSDKTHTCPPCPAPELLGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKALPAPIEKTISKAKGQP
REPQVYTLPPSREEMTKNQVSLTCLVKGFYPSDIAVEWESNGQPENNYKTTPPVLDSDGSFFLY
SKLTVDKSRWQQGNVFSCSVMHEALHNHYTQKSLSLSPG SEQ ID NO: 43 (435Q/AEASS-Fc/C220S IgG1-hinge)
EPKSSDKTHTCPPCPAPEAEGAPSVFLFPPKPKDTLMISRTPEVTCVVVDVSHEDPEVKFNWYV
DGVEVHNAKTKPREEQYNSTYRVVSVLTVLHQDWLNGKEYKCKVSNKALPSSIEKTISKAKGQP
REPQVYTLPPSREEMTKNQVSLTCLVKGFYPSDIAVEWESNGQPENNYKTTPPVLDSDGSFFLY
SKLTVDKSRWQQGNVFSCSVMHEALHNQYTQKSLSLSPG

| SEQ ID | Sequence |
|---|---|
| 101 | QVQYVESGGGLVQPGGSLRLSCAASGFTFSSYRINWYRQPPGKGRELVGSITDTGSTNY<br>ADSVKGRFTISRDNAKNTVYLQMSSLKPEDTAVYYCRAPTIAAYWGQGTQVTVSS |
| 102 | QVQLVESGGGLVQPGGSLRLSCAASGFTFSSYRINWFRQAPGQGLEAVASITDTGSTNY<br>ADSVKGRFTISRDNSKNTLYLQMNSLRAEDTAVYYCAAPTIAAYWGQGTLVTVSS |
| 103 | QVQLVESGGGLVQPGGSLRLSCAASGFTFSSYRINWFRQAPGQGLELVASITDTGSTNY<br>ADSVKGRFTISRDNSKNTLYLQMNSLRAEDTAVYYCAAPTIAAYWGQGTLVTVSS |
| 104 | QVQLVESGGGLVQPGGSLRLSCAASGFTFSSYRINWYRQAPGQGLELVASITDTGSTNY<br>ADSVKGRFTISRDNSKNTLYLQMNSLRAEDTAVYYCAAPTIAAYWGQGTLVTVSS |
| 105 | QVQLVESGGGLVQPGGSLRLSCAASGFTFSSYRINWYRQAPGQGRELVASITDTGSTNY<br>ADSVKGRFTISRDNSKNTLYLQMNSLRAEDTAVYYCAAPTIAAYWGQGTLVTVSS |
| 106 | QVQLVESGGGLVQPGGSLRLSCAASGFTFSSYRINWYRQPPGKGRELVGSITDTGSTNY<br>ADSVKGRFTISRDNSKNTLYLQMNSLRAEDTAVYYCAAPTIAAYWGQGTLVTVSS |
| 107 | GFTFSSYR |
| 108 | SYRIN |
| 109 | GFTFSSY |
| 110 | ITDTGST |
| 111 | SITDTGSTNYADSVKG |
| 112 | TDTGS |
| 113 | AAPTIAAY |
| 114 | PTIAAY |
| 115 | PTIAAY |
| 116 | QVQLVESGGGLVQPGGSLRLSCAASGFTFSSYRINWFRQAPGQGLEAVASITDTGSTNY<br>ADSVKGRFTISRDNSKNTLYLQMNSLRAEDTAVYYCAAPTIAAYWGQGTLVTVSSEPKS<br>SDKTHTCPPCPAPEAEGAPSVFLFPPKPKDTLMISRTPEVTCVVVDVSHEDPEVKFNWY<br>VDGVEVHNAKTKPREEQYNSTYRVVSVLTVLHQDWLNGKEYKCKVSNKALPSSIEKTIS<br>KAKGQPREPQVYTLPPSREEMTKNQVSLTCLVKGFYPSDIAVEWESNGQPENNYKTTPP<br>VLDSDGSFFLYSKLTVDKSRWQQGNVFSCSVMHEALHNQYTQKSLSLSPG |
| 117 | QVQLVESGGGLVQPGGSLRLSCAASGFTFSSYRINWFRQAPGQGLELVASITDTGSTNY<br>ADSVKGRFTISRDNSKNTLYLQMNSLRAEDTAVYYCAAPTIAAYWGQGTLVTVSSEPKS<br>SDKTHTCPPCPAPEAEGAPSVFLFPPKPKDTLMISRTPEVTCVVVDVSHEDPEVKFNWY<br>VDGVEVHNAKTKPREEQYNSTYRVVSVLTVLHQDWLNGKEYKCKVSNKALPSSIEKTIS |

-continued

| | |
|---|---|
| | KAKGQPREPQVYTLPPSREEMTKNQVSLTCLVKGFYPSDIAVEWESNGQPENNYKTTPP<br>VLDSDGSFFLYSKLTVDKSRWQQGNVFSCSVMHEALHNQYTQKSLSLSPG |
| 118 | QVQLVESGGGLVQPGGSLRLSCAASGFTFSSYRINWYRQAPGQGLELVASITDTGSTNY<br>ADSVKGRFTISRDNSKNTLYLQMNSLRAEDTAVYYCAAPTIAAYWGQGTLVTVSSEPKS<br>SDKTHTCPPCPAPEAEGAPSVFLFPPKPKDTLMISRTPEVTCVVVDVSHEDPEVKFNWY<br>VDGVEVHNAKTKPREEQYNSTYRVVSVLTVLHQDWLNGKEYKCKVSNKALPSSIEKTIS<br>KAKGQPREPQVYTLPPSREEMTKNQVSLTCLVKGFYPSDIAVEWESNGQPENNYKTTPP<br>VLDSDGSFFLYSKLTVDKSRWQQGNVFSCSVMHEALHNQYTQKSLSLSPG |
| 119 | QVQLVESGGGLVQPGGSLRLSCAASGFTFSSYRINWYRQAPGQGRELVASITDTGSTNY<br>ADSVKGRFTISRDNSKNTLYLQMNSLRAEDTAVYYCAAPTIAAYWGQGTLVTVSSEPKS<br>SDKTHTCPPCPAPEAEGAPSVFLFPPKPKDTLMISRTPEVTCVVVDVSHEDPEVKFNWY<br>VDGVEVHNAKTKPREEQYNSTYRVVSVLTVLHQDWLNGKEYKCKVSNKALPSSIEKTIS<br>KAKGQPREPQVYTLPPSREEMTKNQVSLTCLVKGFYPSDIAVEWESNGQPENNYKTTPP<br>VLDSDGSFFLYSKLTVDKSRWQQGNVFSCSVMHEALHNQYTQKSLSLSPG |
| 120 | QVQLVESGGGLVQPGGSLRLSCAASGFTFSSYRINWYRQPPGKGRELVGSITDTGSTNY<br>ADSVKGRFTISRDNSKNTLYLQMNSLRAEDTAVYYCAAPTIAAYWGQGTLVTVSSEPKS<br>SDKTHTCPPCPAPEAEGAPSVFLFPPKPKDTLMISRTPEVTCVVVDVSHEDPEVKFNWY<br>VDGVEVHNAKTKPREEQYNSTYRVVSVLTVLHQDWLNGKEYKCKVSNKALPSSIEKTIS<br>KAKGQPREPQVYTLPPSREEMTKNQVSLTCLVKGFYPSDIAVEWESNGQPENNYKTTPP<br>VLDSDGSFFLYSKLTVDKSRWQQGNVFSCSVMHEALHNQYTQKSLSLSPG |
| 131 | RAPTIAAY |
| 201 | QVQLVESGGGSVQPGGSLRLSCAASGIVFNSDVMGWYRQVPGKPRELVATITGGGSTNY<br>ATSVKGRFTISRDNAKNTVYLQMNSLRPEDTAVYYCNGRRGDSMLAFWAQGTQVTVSS |
| 202 | QVQLVESGGGLVQPGGSLRLSCAASGIVFNSDVMGWFRQAPGQGLEAVATITGGGSTNY<br>ATSVKGRFTISRDNSKNTLYLQMNSLRAEDTAVYYCAARRGDSMLAFWGQGTLVTVSS |
| 203 | QVQLVESGGGLVQPGGSLRLSCAASGIVFNSDVMGWFRQAPGQGLELVATITGGGSTNY<br>ATSVKGRFTISRDNSKNTLYLQMNSLRAEDTAVYYCAARRGDSMLAFWGQGTLVTVSS |
| 204 | QVQLVESGGGLVQPGGSLRLSCAASGIVFNSDVMGWYRQAPGQGLELVATITGGGSTNY<br>ATSVKGRFTISRDNSKNTLYLQMNSLRAEDTAVYYCAARRGDSMLAFWGQGTLVTVSS |
| 205 | QVQLVESGGGLVQPGGSLRLSCAASGIVFNSDVMGWYRQAPGQPRELVATITGGGSTNY<br>ATSVKGRFTISRDNSKNTLYLQMNSLRAEDTAVYYCAARRGDSMLAFWGQGTLVTVSS |
| 206 | QVQLVESGGGLVQPGGSLRLSCAASGIVFNSDVMGWYRQVPGKPRELVATITGGGSTNY<br>ATSVKGRFTISRDNSKNTLYLQMNSLRAEDTAVYYCAARRGDSMLAFWGQGTLVTVSS |
| 207 | GIVFNSDV |
| 208 | SDVMG |
| 209 | GIVFNSD |
| 210 | ITGGGST |
| 211 | TITGGGSTNYATSVKG |
| 212 | TGGGS |
| 213 | AARRGDSMLAF |
| 214 | RRGDSMLAF |
| 215 | RRGDSMLAF |
| 216 | QVQLVESGGGLVQPGGSLRLSCAASGIVFNSDVMGWFRQAPGQGLEAVATITGGGSTNY<br>ATSVKGRFTISRDNSKNTLYLQMNSLRAEDTAVYYCAARRGDSMLAFWGQGTLVTVSSE<br>PKSSDKTHTCPPCPAPEAEGAPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALPSSIEK<br>TISKAKGQPREPQVYTLPPSREEMTKNQVSLTCLVKGFYPSDIAVEWESNGQPENNYKT<br>TPPVLDSDGSFFLYSKLTVDKSRWQQGNVFSCSVMHEALHNQYTQKSLSLSPG |
| 217 | QVQLVESGGGLVQPGGSLRLSCAASGIVFNSDVMGWFRQAPGQGLELVATITGGGSTNY<br>ATSVKGRFTISRDNSKNTLYLQMNSLRAEDTAVYYCAARRGDSMLAFWGQGTLVTVSSE<br>PKSSDKTHTCPPCPAPEAEGAPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALPSSIEK<br>TISKAKGQPREPQVYTLPPSREEMTKNQVSLTCLVKGFYPSDIAVEWESNGQPENNYKT<br>TPPVLDSDGSFFLYSKLTVDKSRWQQGNVFSCSVMHEALHNQYTQKSLSLSPG |
| 218 | QVQLVESGGGLVQPGGSLRLSCAASGIVFNSDVMGWYRQAPGQGLELVATITGGGSTNY<br>ATSVKGRFTISRDNSKNTLYLQMNSLRAEDTAVYYCAARRGDSMLAFWGQGTLVTVSSE<br>PKSSDKTHTCPPCPAPEAEGAPSVFLFPPKPKDTLMISRTPEVTCVVVDVSHEDPEVKF |

| | |
|---|---|
| | NWYVDGVEVHNAKTKPREEQYNSTYRVVSVLTVLHQDWLNGKEYKCKVSNKALPSSIEK<br>TISKAKGQPREPQVYTLPPSREEMTKNQVSLTCLVKGFYPSDIAVEWESNGQPENNYKT<br>TPPVLDSDGSFFLYSKLTVDKSRWQQGNVFSCSVMHEALHNQYTQKSLSLSPG |
| 219 | QVQLVESGGGLVQPGGSLRLSCAASGIVFNSDVMGWYRQAPGQPRELVATITGGGSTNY<br>ATSVKGRFTISRDNSKNTLYLQMNSLRAEDTAVYYCAARRGDSMLAFWGQGTLVTVSSE<br>PKSSDKTHTCPPCPAPEAEGAPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALPSSIEK<br>TISKAKGQPREPQVYTLPPSREEMTKNQVSLTCLVKGFYPSDIAVEWESNGQPENNYKT<br>TPPVLDSDGSFFLYSKLTVDKSRWQQGNVFSCSVMHEALHNQYTQKSLSLSPG |
| 220 | QVQLVESGGGLVQPGGSLRLSCAASGIVFNSDVMGWYRQVPGKPRELVATITGGGSTNY<br>ATSVKGRFTISRDNSKNTLYLQMNSLRAEDTAVYYCAARRGDSMLAFWGQGTLVTVSSE<br>PKSSDKTHTCPPCPAPEAEGAPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALPSSIEK<br>TISKAKGQPREPQVYTLPPSREEMTKNQVSLTCLVKGFYPSDIAVEWESNGQPENNYKT<br>TPPVLDSDGSFFLYSKLTVDKSRWQQGNVFSCSVMHEALHNQYTQKSLSLSPG |
| 231 | NGRRGDSMLAF |
| 301 | QVQLVESGGGLVQAGDSLRLSCVASDRTFSSYAVGWERQAPGKEREFVAAISWNGGRTL<br>YTDSVTGRFTISRDNAKSTVYLQMNGLKPEDTAVYYCAARPAAPTRRLEYDYWGQGTQV<br>TVSS |
| 302 | QVQLVESGGGLVQPGGSLRLSCAASDRTFSSYAVGWFRQAPGQGLEAVAAISWNGGRTL<br>YTDSVTGRFTISRDNSKNTLYLQMNSLRAEDTAVYYCAARPAAPTRRLEYDYWGQGTLV<br>TVSS |
| 303 | QVQLVESGGGLVQPGGSLRLSCAASDRTFSSYAVGWFRQAPGQGLEFVAAISWNGGRTL<br>YTDSVTGRFTISRDNSKNTLYLQMNSLRAEDTAVYYCAARPAAPTRRLEYDYWGQGTLV<br>TVSS |
| 304 | QVQLVESGGGLVQPGGSLRLSCAASDRTFSSYAVGWFRQAPGQGREFVAAISWNGGRTL<br>YTDSVTGRFTISRDNSKNTLYLQMNSLRAEDTAVYYCAARPAAPTRRLEYDYWGQGTLV<br>TVSS |
| 305 | QVQLVESGGGLVQPGGSLRLSCAASDRTFSSYAVGWFRQAPGQEREFVAAISWNGGRTL<br>YTDSVTGRFTISRDNSKNTLYLQMNSLRAEDTAVYYCAARPAAPTRRLEYDYWGQGTLV<br>TVSS |
| 306 | QVQLVESGGGLVQPGGSLRLSCAASDRTFSSYAVGWFRQAPGKEREFVAAISWNGGRTL<br>YTDSVTGRFTISRDNSKNTLYLQMNSLRAEDTAVYYCAARPAAPTRRLEYDYWGQGTLV<br>TVSS |
| 307 | DRTESSYA |
| 308 | SYAVG |
| 309 | DRTFSSY |
| 310 | ISWNGGRT |
| 311 | AISWNGGRTLYTDSVTG |
| 312 | SWNGGR |
| 313 | AARPAAPTRRLEYDY |
| 314 | RPAAPTRRLEYDY |
| 315 | RPAAPTRRLEYDY |
| 316 | QVQLVESGGGLVQPGGSLRLSCAASDRTFSSYAVGWFRQAPGQGLEAVAAISWNGGRTL<br>YTDSVTGRFTISRDNSKNTLYLQMNSLRAEDTAVYYCAARPAAPTRRLEYDYWGQGTLV<br>TVSSEPKSSDKTHTCPPCPAPEAEGAPSVFLFPPKPKDTLMISRTPEVTCVVVDVSHED<br>PEVKFNWYVDGVEVHNAKTKPREEQYNSTYRVVSVLTVLHQDWLNGKEYKCKVSNKALP<br>SSIEKTISKAKGQPREPQVYTLPPSREEMTKNQVSLTCLVKGFYPSDIAVEWESNGQPE<br>NNYKTTPPVLDSDGSFFLYSKLTVDKSRWQQGNVFSCSVMHEALHNQYTQKSLSLSPG |
| 317 | QVQLVESGGGLVQPGGSLRLSCAASDRTFSSYAVGWFRQAPGQGLEFVAAISWNGGRTL<br>YTDSVTGRFTISRDNSKNTLYLQMNSLRAEDTAVYYCAARPAAPTRRLEYDYWGQGTLV<br>TVSSEPKSSDKTHTCPPCPAPEAEGAPSVFLFPPKPKDTLMISRTPEVTCVVVDVSHED<br>PEVKFNWYVDGVEVHNAKTKPREEQYNSTYRVVSVLTVLHQDWLNGKEYKCKVSNKALP<br>SSIEKTISKAKGQPREPQVYTLPPSREEMTKNQVSLTCLVKGFYPSDIAVEWESNGQPE<br>NNYKTTPPVLDSDGSFFLYSKLTVDKSRWQQGNVFSCSVMHEALHNQYTQKSLSLSPG |
| 318 | QVQLVESGGGLVQPGGSLRLSCAASDRTFSSYAVGWFRQAPGQGREFVAAISWNGGRTL<br>YTDSVTGRFTISRDNSKNTLYLQMNSLRAEDTAVYYCAARPAAPTRRLEYDYWGQGTLV<br>TVSSEPKSSDKTHTCPPCPAPEAEGAPSVFLFPPKPKDTLMISRTPEVTCVVVDVSHED |

-continued

|     | |
|---|---|
| | PEVKFNWYVDGVEVHNAKTKPREEQYNSTYRVVSVLTVLHQDWLNGKEYKCKVSNKALP SSIEKTISKAKGQPREPQVYTLPPSREEMTKNQVSLTCLVKGFYPSDIAVEWESNGQPE NNYKTTPPVLDSDGSFFLYSKLTVDKSRWQQGNVFSCSVMHEALHNQYTQKSLSLSPG |
| 319 | QVQLVESGGGLVQPGGSLRLSCAASDRTFSSYAVGWERQAPGQEREFVAAISWNGGRTL YTDSVTGRFTISRDNSKNTLYLQMNSLRAEDTAVYYCAARPAAPTRRLEYDYWGQGTLV TVSSEPKSSDKTHTCPPCPAPEAEGAPSVFLFPPKPKDTLMISRTPEVTCVVVDVSHED PEVKFNWYVDGVEVHNAKTKPREEQYNSTYRVVSVLTVLHQDWLNGKEYKCKVSNKALP SSIEKTISKAKGQPREPQVYTLPPSREEMTKNQVSLTCLVKGFYPSDIAVEWESNGQPE NNYKTTPPVLDSDGSFFLYSKLTVDKSRWQQGNVFSCSVMHEALHNQYTQKSLSLSPG |
| 320 | QVQLVESGGGLVQPGGSLRLSCAASDRTFSSYAVGWFRQAPGKEREFVAAISWNGGRTL YTDSVTGRFTISRDNSKNTLYLQMNSLRAEDTAVYYCAARPAAPTRRLEYDYWGQGTLV TVSSEPKSSDKTHTCPPCPAPEAEGAPSVFLFPPKPKDTLMISRTPEVTCVVVDVSHED PEVKFNWYVDGVEVHNAKTKPREEQYNSTYRVVSVLTVLHQDWLNGKEYKCKVSNKALP SSIEKTISKAKGQPREPQVYTLPPSREEMTKNQVSLTCLVKGFYPSDIAVEWESNGQPE NNYKTTPPVLDSDGSFFLYSKLTVDKSRWQQGNVFSCSVMHEALHNQYTQKSLSLSPG |
| 401 | QVQLVESGGGMVQPGGSLRLSCAASGITFSMYSMSWYRQPPGKQRELVAATTTFGSTNY ADSVKGRFTISRDNAKNTVYLQMNSLKPEDTAVYLCNARFTSEEYWGQGTQVTVSS |
| 402 | QVQLVESGGGLVQPGGSLRLSCAASGITFSMYSMSWFRQAPGQGLEAVAATTTFGSTNY ADSVKGRFTISRDNSKNTLYLQMNSLRAEDTAVYYCAARFTSEEYWGQGTLVTVSS |
| 403 | QVQLVESGGGLVQPGGSLRLSCAASGITFSMYSMSWFRQAPGQGLELVAATTTFGSTNY ADSVKGRFTISRDNSKNTLYLQMNSLRAEDTAVYYCAARFTSEEYWGQGTLVTVSS |
| 404 | QVQLVESGGGLVQPGGSLRLSCAASGITFSMYSMSWYRQAPGQGLELVAATTTFGSTNY ADSVKGRFTISRDNSKNTLYLQMNSLRAEDTAVYYCAARFTSEEYWGQGTLVTVSS |
| 405 | QVQLVESGGGLVQPGGSLRLSCAASGITFSMYSMSWYRQAPGQQRELVAATTTFGSTNY ADSVKGRFTISRDNSKNTLYLQMNSLRAEDTAVYYCAARFTSEEYWGQGTLVTVSS |
| 406 | QVQLVESGGGLVQPGGSLRLSCAASGITFSMYSMSWYRQPPGKQRELVAATTTFGSTNY ADSVKGRFTISRDNSKNTLYLQMNSLRAEDTAVYYCAARFTSEEYWGQGTLVTVSS |
| 407 | GITFSMYS |
| 408 | MYSMS |
| 409 | GITFSMY |
| 410 | TTTFGST |
| 411 | ATTTFGSTNYADSVKG |
| 412 | TTFGS |
| 413 | AARFTSEEY |
| 414 | RFTSEEY |
| 415 | RFTSEEY |
| 416 | QVQLVESGGGLVQPGGSLRLSCAASGITFSMYSMSWFRQAPGQGLEAVAATTTFGSTNY ADSVKGRFTISRDNSKNTLYLQMNSLRAEDTAVYYCAARFTSEEYWGQGTLVTVSSEPK SSDKTHTCPPCPAPEAEGAPSVFLFPPKPKDTLMISRTPEVTCVVVDVSHEDPEVKFNW YVDGVEVHNAKTKPREEQYNSTYRVVSVLTVLHQDWLNGKEYKCKVSNKALPSSIEKTI SKAKGQPREPQVYTLPPSREEMTKNQVSLTCLVKGFYPSDIAVEWESNGQPENNYKTTP PVLDSDGSFFLYSKLTVDKSRWQQGNVFSCSVMHEALHNQYTQKSLSLSPG |
| 417 | QVQLVESGGGLVQPGGSLRLSCAASGITFSMYSMSWFRQAPGQGLELVAATTTFGSTNY ADSVKGRFTISRDNSKNTLYLQMNSLRAEDTAVYYCAARFTSEEYWGQGTLVTVSSEPK SSDKTHTCPPCPAPEAEGAPSVFLFPPKPKDTLMISRTPEVTCVVVDVSHEDPEVKFNW YVDGVEVHNAKTKPREEQYNSTYRVVSVLTVLHQDWLNGKEYKCKVSNKALPSSIEKTI SKAKGQPREPQVYTLPPSREEMTKNQVSLTCLVKGFYPSDIAVEWESNGQPENNYKTTP PVLDSDGSFFLYSKLTVDKSRWQQGNVFSCSVMHEALHNQYTQKSLSLSPG |
| 418 | QVQLVESGGGLVQPGGSLRLSCAASGITFSMYSMSWYRQAPGQGLELVAATTTFGSTNY ADSVKGRFTISRDNSKNTLYLQMNSLRAEDTAVYYCAARFTSEEYWGQGTLVTVSSEPK SSDKTHTCPPCPAPEAEGAPSVFLFPPKPKDTLMISRTPEVTCVVVDVSHEDPEVKFNW YVDGVEVHNAKTKPREEQYNSTYRVVSVLTVLHQDWLNGKEYKCKVSNKALPSSIEKTI SKAKGQPREPQVYTLPPSREEMTKNQVSLTCLVKGFYPSDIAVEWESNGQPENNYKTTP PVLDSDGSFFLYSKLTVDKSRWQQGNVFSCSVMHEALHNQYTQKSLSLSPG |
| 419 | QVQLVESGGGLVQPGGSLRLSCAASGITFSMYSMSWYRQAPGQQRELVAATTTFGSTNY ADSVKGRFTISRDNSKNTLYLQMNSLRAEDTAVYYCAARFTSEEYWGQGTLVTVSSEPK SSDKTHTCPPCPAPEAEGAPSVFLFPPKPKDTLMISRTPEVTCVVVDVSHEDPEVKFNW YVDGVEVHNAKTKPREEQYNSTYRVVSVLTVLHQDWLNGKEYKCKVSNKALPSSIEKTI |

-continued

```
    SKAKGQPREPQVYTLPPSREEMTKNQVSLTCLVKGFYPSDIAVEWESNGQPENNYKTTP
    PVLDSDGSFFLYSKLTVDKSRWQQGNVFSCSVMHEALHNQYTQKSLSLSPG

420 QVQLVESGGGLVQPGGSLRLSCAASGITFSMYSMSWYRQPPGKQRELVAATTTFGSTNY
    ADSVKGRFTISRDNSKNTLYLQMNSLRAEDTAVYYCAARFTSEEYWGQGTLVTVSSEPK
    SSDKTHTCPPCPAPEAEGAPSVFLFPPKPKDTLMISRTPEVTCVVVDVSHEDPEVKFNW
    YVDGVEVHNAKTKPREEQYNSTYRVVSVLTVLHQDWLNGKEYKCKVSNKALPSSIEKTI
    SKAKGQPREPQVYTLPPSREEMTKNQVSLTCLVKGFYPSDIAVEWESNGQPENNYKTTP
    PVLDSDGSFFLYSKLTVDKSRWQQGNVFSCSVMHEALHNQYTQKSLSLSPG

431 NARFTSEEY

501 QVQVVESGGGLVQPGGSLTLSCAASGFDFSTYTVNWYRQAPGKEREKVARISSTGTTTN
    YANSAKGRFTLSRDNAKNRVYLQMNNLKPEDTAVYFCNFERFDSNYWGQGTQVTVSS

502 QVQLVESGGGLVQPGGSLRLSCAASGFDFSTYTVNWFRQAPGQGLEAVARISSTGTTTN
    YANSAKGRFTISRDNSKNTLYLQMNSLRAEDTAVYYCAAERFDSNYWGQGTLVTVSS

503 QVQLVESGGGLVQPGGSLRLSCAASGFDFSTYTVNWERQAPGQGLEKVARISSTGTTTN
    YANSAKGRFTISRDNSKNTLYLQMNSLRAEDTAVYYCAAERFDSNYWGQGTLVTVSS

504 QVQLVESGGGLVQPGGSLRLSCAASGFDFSTYTVNWYRQAPGQGLEKVARISSTGTTTN
    YANSAKGRFTISRDNSKNTLYLQMNSLRAEDTAVYYCAAERFDSNYWGQGTLVTVSS

505 QVQLVESGGGLVQPGGSLRLSCAASGFDFSTYTVNWYRQAPGQEREKVARISSTGTTTN
    YANSAKGRFTISRDNSKNTLYLQMNSLRAEDTAVYYCAAERFDSNYWGQGTLVTVSS

506 QVQLVESGGGLVQPGGSLRLSCAASGFDFSTYTVNWYRQAPGKEREKVARISSTGTTTN
    YANSAKGRFTISRDNSKNTLYLQMNSLRAEDTAVYYCAAERFDSNYWGQGTLVTVSS

507 GFDFSTYT

508 TYTVN

509 GFDFSTY

510 ISSTGTTT

511 RISSTGTTTNYANSAKG

512 SSTGTT

513 AAERFDSNY

514 ERFDSNY

515 ERFDSNY

516 QVQLVESGGGLVQPGGSLRLSCAASGFDFSTYTVNWFRQAPGQGLEAVARISSTGTTTN
    YANSAKGRFTISRDNSKNTLYLQMNSLRAEDTAVYYCAAERFDSNYWGQGTLVTVSSEP
    KSSDKTHTCPPCPAPEAEGAPSVFLFPPKPKDTLMISRTPEVTCVVVDVSHEDPEVKFN
    WYVDGVEVHNAKTKPREEQYNSTYRVVSVLTVLHQDWLNGKEYKCKVSNKALPSSIEKT
    ISKAKGQPREPQVYTLPPSREEMTKNQVSLTCLVKGFYPSDIAVEWESNGQPENNYKTT
    PPVLDSDGSFFLYSKLTVDKSRWQQGNVFSCSVMHEALHNQYTQKSLSLSPG

517 QVQLVESGGGLVQPGGSLRLSCAASGFDFSTYTVNWFRQAPGQGLEKVARISSTGTTTN
    YANSAKGRFTISRDNSKNTLYLQMNSLRAEDTAVYYCAAERFDSNYWGQGTLVTVSSEP
    KSSDKTHTCPPCPAPEAEGAPSVFLFPPKPKDTLMISRTPEVTCVVVDVSHEDPEVKFN
    WYVDGVEVHNAKTKPREEQYNSTYRVVSVLTVLHQDWLNGKEYKCKVSNKALPSSIEKT
    ISKAKGQPREPQVYTLPPSREEMTKNQVSLTCLVKGFYPSDIAVEWESNGQPENNYKTT
    PPVLDSDGSFFLYSKLTVDKSRWQQGNVFSCSVMHEALHNQYTQKSLSLSPG

518 QVQLVESGGGLVQPGGSLRLSCAASGFDFSTYTVNWYRQAPGQGLEKVARISSTGTTTN
    YANSAKGRFTISRDNSKNTLYLQMNSLRAEDTAVYYCAAEREDSNYWGQGTLVTVSSEP
    KSSDKTHTCPPCPAPEAEGAPSVFLFPPKPKDTLMISRTPEVTCVVVDVSHEDPEVKFN
    WYVDGVEVHNAKTKPREEQYNSTYRVVSVLTVLHQDWLNGKEYKCKVSNKALPSSIEKT
    ISKAKGQPREPQVYTLPPSREEMTKNQVSLTCLVKGFYPSDIAVEWESNGQPENNYKTT
    PPVLDSDGSFFLYSKLTVDKSRWQQGNVFSCSVMHEALHNQYTQKSLSLSPG

519 QVQLVESGGGLVQPGGSLRLSCAASGFDFSTYTVNWYRQAPGQEREKVARISSTGTTTN
    YANSAKGRFTISRDNSKNTLYLQMNSLRAEDTAVYYCAAERFDSNYWGQGTLVTVSSEP
    KSSDKTHTCPPCPAPEAEGAPSVFLFPPKPKDTLMISRTPEVTCVVVDVSHEDPEVKFN
    WYVDGVEVHNAKTKPREEQYNSTYRVVSVLTVLHQDWLNGKEYKCKVSNKALPSSIEKT
    ISKAKGQPREPQVYTLPPSREEMTKNQVSLTCLVKGFYPSDIAVEWESNGQPENNYKTT
    PPVLDSDGSFFLYSKLTVDKSRWQQGNVFSCSVMHEALHNQYTQKSLSLSPG

520 QVQLVESGGGLVQPGGSLRLSCAASGFDFSTYTVNWYRQAPGKEREKVARISSTGTTTN
    YANSAKGRFTISRDNSKNTLYLQMNSLRAEDTAVYYCAAERFDSNYWGQGTLVTVSSEP
    KSSDKTHTCPPCPAPEAEGAPSVFLFPPKPKDTLMISRTPEVTCVVVDVSHEDPEVKFN
```

-continued

```
          WYVDGVEVHNAKTKPREEQYNSTYRVVSVLTVLHQDWLNGKEYKCKVSNKALPSSIEKT
          ISKAKGQPREPQVYTLPPSREEMTKNQVSLTCLVKGFYPSDIAVEWESNGQPENNYKTT
          PPVLDSDGSFFLYSKLTVDKSRWQQGNVFSCSVMHEALHNQYTQKSLSLSPG

531       NFERFDSNY

532       APLVCRAGCSPEHGFCEQPGECRCLEGWTGPLCTVPVSTSSCLSPRGPSSATTGCLVPG
          PGPCDGNPCANGGSCSETPRSFECTCPRGFYGLRCEVSGVTCADGPCFNGGLCVGGADP
          DSAYICHCPPGFQGSNCEKRVDRCSLQPCRNGGLCLDLGHALRCRCRAGFAGPRCEHDL
          DDCAGRACANGGTCVEGGGAHRCSCALGFGGRDCRERADPCAARPCAHGGRCYAHFSGL
          VCACAPGYMGARCEFPVHPDGASALPAAPPGLRPGDPQRYLARGPTIKPCPPCKCPAPN
          LLGGPSVFIFPPPKIKDVLMISLSPIVTCVVVDVSEDDPDVQISWFVNNVEVHTAQTQTH
          REDYNSTLRVVSALPIQHQDWMSGKEFKCKVNNKDLPAPIERTISKPKGSVRAPQVYVL
          PPPEEEMTKKQVTLTCMVTDEMPEDIYVEWTNNGKTELNYKNTEPVLDSDGSYFMYSKL
          RVEKKNWVERNSYSCSVVHEGLHNHHTTKSFSRTPGK
```

The invention claimed is:
1. A polypeptide comprising a single-domain antibody variable region that binds DLL3, wherein the single-domain antibody variable region comprises:
   a heavy chain complementarity determining region 1 (CDRH1) comprising the amino acid sequence of SEQ ID NO: 407, a heavy chain complementarity determining region 2 (CDRH2) comprising the amino acid sequence of SEQ ID NO: 410, and a heavy chain complementarity determining region 3 (CDRH3) comprising the amino acid sequence of SEQ ID NO: 413.
2. The polypeptide of claim 1, wherein the single-domain antibody variable region comprises at least 90% sequence identity to any one of SEQ ID NOs: 401-406.
3. The polypeptide of claim 1, wherein the single-domain antibody variable region comprises the sequence of any one of SEQ ID NOs: 401-406.
4. The polypeptide of claim 1, wherein the single-domain antibody variable region binds to DLL3 with an affinity dissociation constant ($K_D$) of 0.1 nanomolar to 10 nanomolar.
5. The polypeptide of claim 1, wherein the polypeptide comprises an immunoglobulin heavy chain constant region comprising an immunoglobulin $C_H2$ domain and an immunoglobulin $C_H3$ domain.
6. The polypeptide of claim 5, wherein the immunoglobulin heavy chain constant region is an IgG1 isotype or an IgG4 isotype.
7. The polypeptide of claim 5, wherein the immunoglobulin heavy chain constant region comprises an alteration to one or more amino acid residues relative to wild-type IgG1, and wherein the alteration reduces binding of the immunoglobulin heavy chain constant region to a neonatal Fc receptor (FcRn) relative to wild-type IgG1.
8. The polypeptide of claim 5, wherein the immunoglobulin heavy chain constant region comprises an alteration to one or more amino acid residues relative to wild-type IgG1, and wherein the alteration reduces complement dependent cytotoxicity (CDC), antibody-dependent cell-cytotoxicity (ADCC), antibody-dependent cell-phagocytosis (ADCP), or a combination thereof relative to wild-type IgG1.
9. The polypeptide of claim 5, wherein the immunoglobulin heavy chain constant region comprises a hinge region, and wherein the hinge region comprises a C220S alteration per EU numbering relative to wild-type IgG1.
10. An immunoconjugate comprising a polypeptide that binds to DLL3, wherein the polypeptide that binds to DLL3 is covalently linked to a linker-chelator moiety, or a radionuclide complex thereof, wherein:
   the polypeptide comprises a single-domain antibody variable region comprising a heavy chain complementarity determining region 1 (CDRH1) comprising the amino acid sequence of SEQ ID NO: 407, a heavy chain complementarity determining region 2 (CDRH2) comprising the amino acid sequence of SEQ ID NO: 410, and a heavy chain complementarity determining region 3 (CDRH3) comprising the amino acid sequence of SEQ ID NO: 413; and
   the linker-chelator moiety or the radionuclide complex thereof is conjugated to the polypeptide.
11. The immunoconjugate of claim 10, or the radionuclide complex thereof, wherein the linker-chelator moiety comprises:
   1,4,7,10-tetraazacyclododecane-1,4,7,10-tetraacetic acid (DOTA),
   1,4,7-Tris(carboxymethyl)-1,4,7,10-tetraazacyclododecane (DO3A),
   α-(2-Carboxyethyl)-1,4,7,10-tetraazacyclododecane-1,4,7,10-tetraacetic acid (DOTAGA),
   6,6',6'',6'''-(((pyridine-2,6-diylbis(methylene))bis(azanetriyl))tetrakis(methylene))-tetrapicolinic acid (Py4Pa),
   2,2',2'',2'''-(1,10-dioxa-4,7,13,16-tetraazacyclooctadecane-4,7,13,16-tetrayl)-tetraacetic acid (Crown),
   6,6'-((1,4,10,13-tetraoxa-7,16-diazacyclooctadecane-7,16-diyl)bis(methylene))-dipicolinic acid,
   1,4,7,10,13,16-hexaazacyclohexadecane-1,4,7,10,13,16-hexaacetic acid (HEHA),
   6,6'-[(1R,2R)-1,2-Cyclohexanediylbis[[(carboxymethyl)imino]methylene]]bis[2-pyridinecarboxylic acid] (CHXoctapa),
   3,7-Diazabicyclo[3.3.1]nonane-1,5-dicarboxylic acid (Bispa), or
   6,6'-(((oxybis(ethane-2,1-diyl))bis((carboxymethyl)azanediyl))-bis(methylene))-dipicolinic acid (Noneunpa).
12. The immunoconjugate of claim 10, or the radionuclide complex thereof, wherein the linker-chelator moiety is:

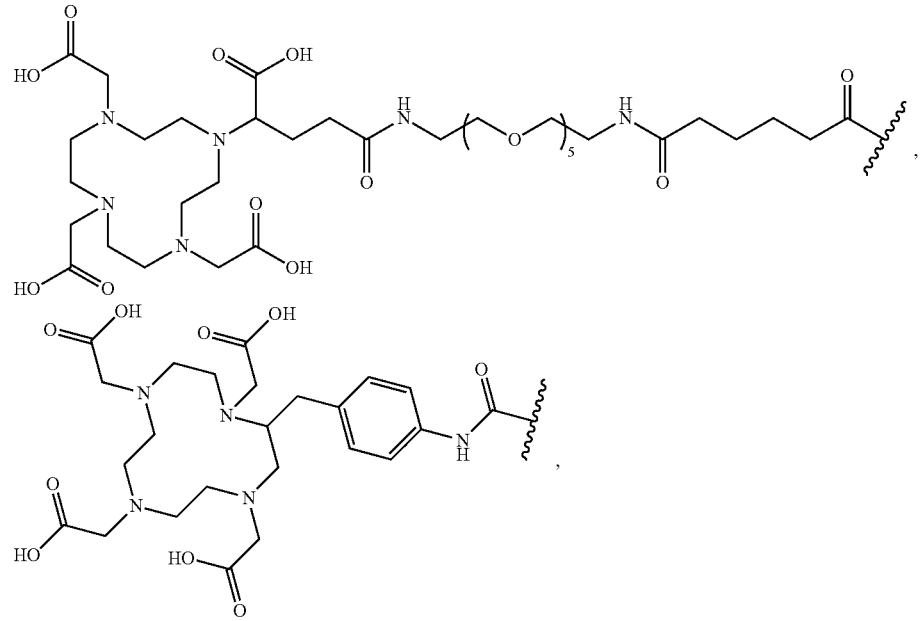

-continued

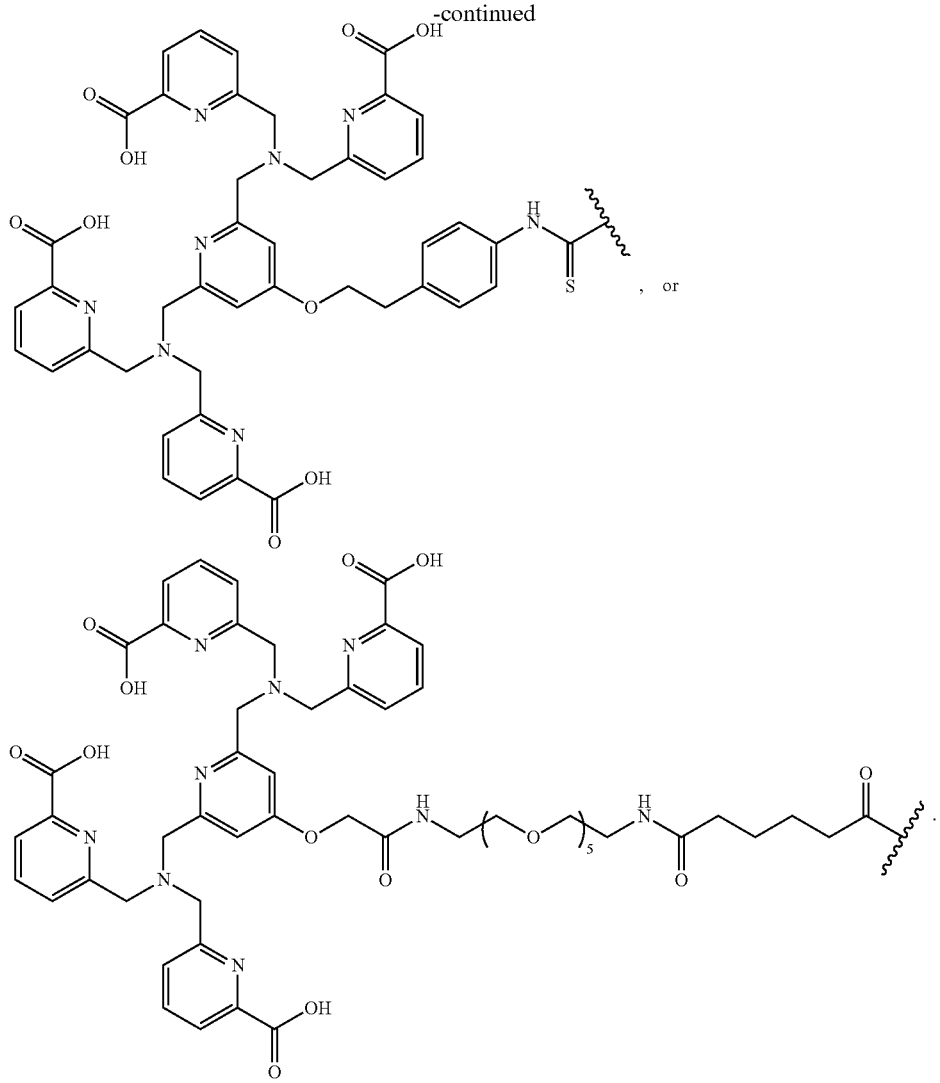

13. The immunoconjugate of claim 12, or the radionuclide complex thereof, wherein the linker-chelator moiety is

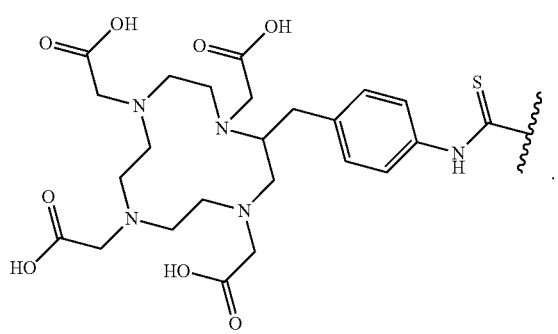 [SMILES: *C(=S)Nc1ccc(CC2CN(CC(=O)O)CCN(CC(=O)O)CCN(CC(=O)O)CCN2CC(=O)O)cc1]

14. The immunoconjugate of claim 10, or the radionuclide complex thereof, wherein the single-domain antibody variable region comprises at least 90% sequence identity to any one of SEQ ID NOs: 401-406.

15. The immunoconjugate of claim 10, wherein the antibody variable region comprises the sequence of any one of SEQ ID NOs: 401-406.

16. The immunoconjugate of claim 10, or the radionuclide complex thereof, wherein the single-domain antibody variable region binds to DLL3 with an affinity dissociation constant ($K_D$) of 0.1 nanomolar to 10 nanomolar.

17. The immunoconjugate of claim 10, or the radionuclide complex thereof, wherein the polypeptide comprises an immunoglobulin heavy chain constant region comprising an immunoglobulin $C_H2$ domain and an immunoglobulin $C_H3$ domain.

18. The immunoconjugate of claim 17, or the radionuclide complex thereof, wherein the immunoglobulin heavy chain constant region is an IgG1 isotype or an IgG4 isotype.

19. The immunoconjugate of claim 17, or the radionuclide complex thereof, wherein the immunoglobulin heavy chain constant region comprises A310, Q435, or both A310 and A435 per EU numbering.

20. The immunoconjugate of claim 19, or the radionuclide complex thereof, wherein the immunoglobulin heavy chain constant region comprises A234, E235, A237, S330, and S331 per EU numbering.

21. The immunoconjugate of claim 17, or the radionuclide complex thereof, wherein the immunoglobulin heavy chain constant region comprises a hinge region, and wherein the hinge region comprises S220 per EU numbering.

22. The immunoconjugate of claim 10, or the radionuclide complex thereof, wherein a lysine residue of the polypeptide is covalently linked via a thiourea to the para position of the benzyl of -p-Bn-DOTA formed from the isothiocyanate of -p-SCN-Bn-DOTA:

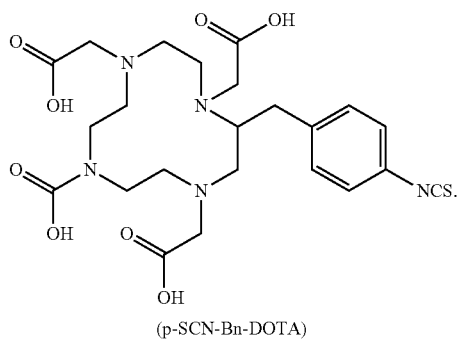
(p-SCN-Bn-DOTA)

23. The immunoconjugate of claim 10, or the radionuclide complex thereof, wherein the immunoconjugate has the following structure:

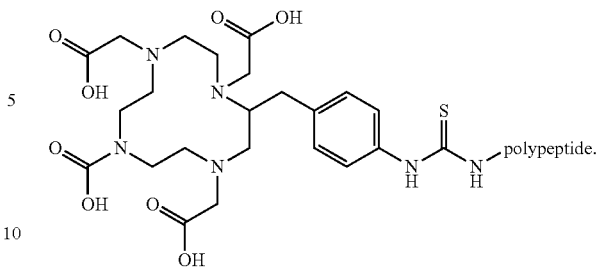

24. The immunoconjugate of claim 10, or the radionuclide complex thereof, wherein the immunoconjugate has a chelator to polypeptide ratio of 3:1 to 5:1.

25. The immunoconjugate of claim 10, or the radionuclide complex thereof, wherein the immunoconjugate comprises a linker-chelator radionuclide complex, and wherein the radionuclide is an alpha emitter, a beta emitter, or a gamma emitter.

26. The immunoconjugate of claim 25, wherein the alpha emitter is 225-Ac.

27. A method of making a radionuclide complex of the immunoconjugate of claim 10, the method comprising complexing the linker-chelator moiety of the immunoconjugate of claim 10 a radionuclide, thereby obtaining a radionuclide complex of the immunoconjugate.

28. The immunoconjugate of claim 10, or the radionuclide complex thereof, wherein a lysine residue of the polypeptide is conjugated with one of the following linker-chelator moieties:

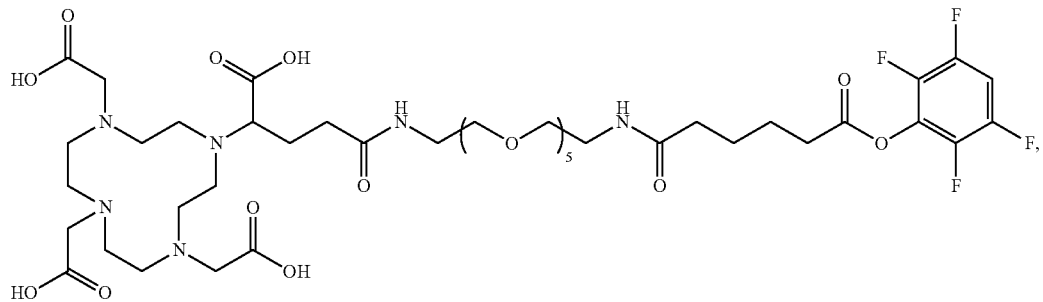

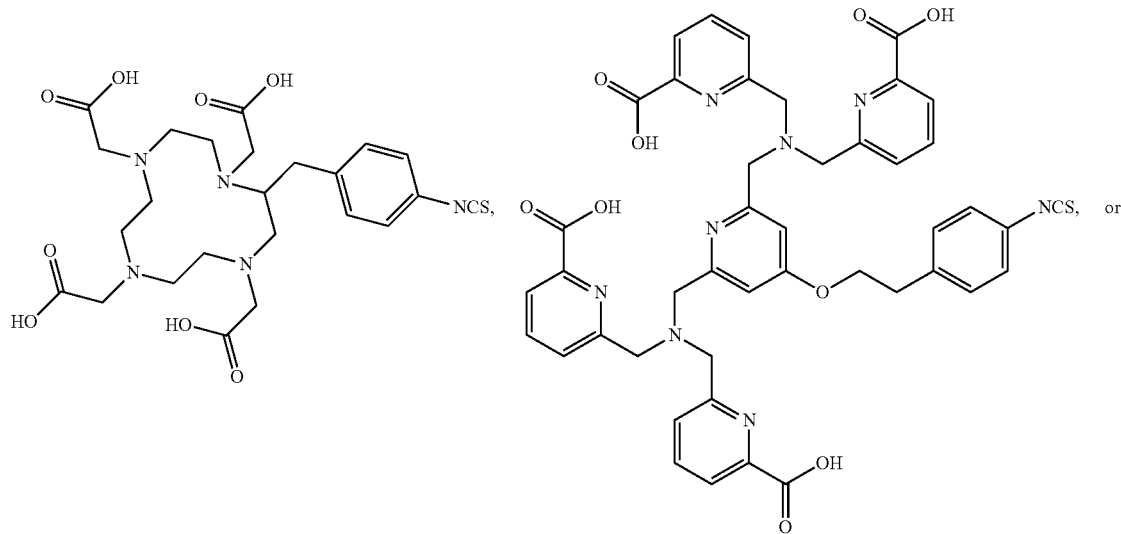

-continued
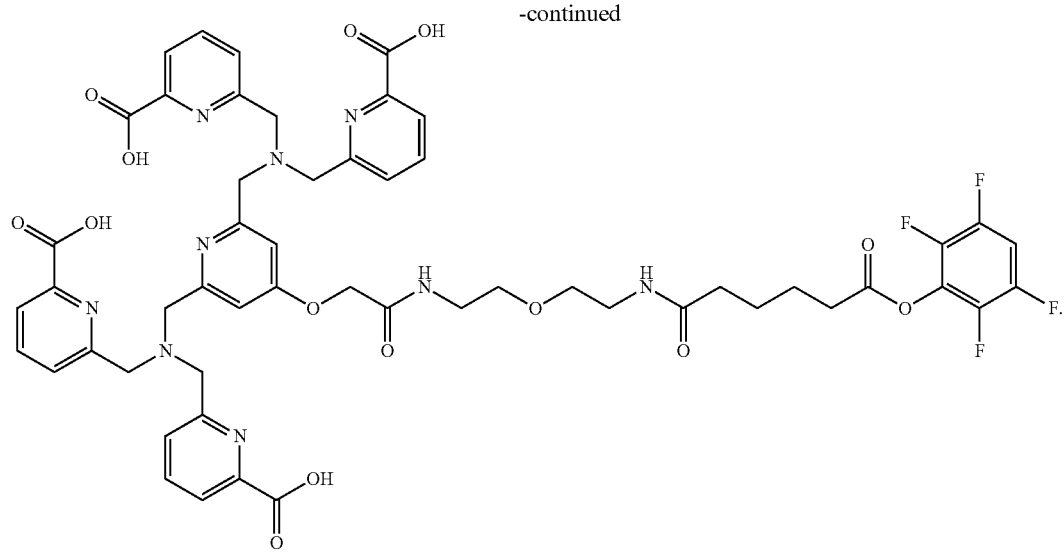
29. The immunoconjugate of claim 10, or the radionuclide complex thereof, wherein the immunoconjugate has one of the following structures:
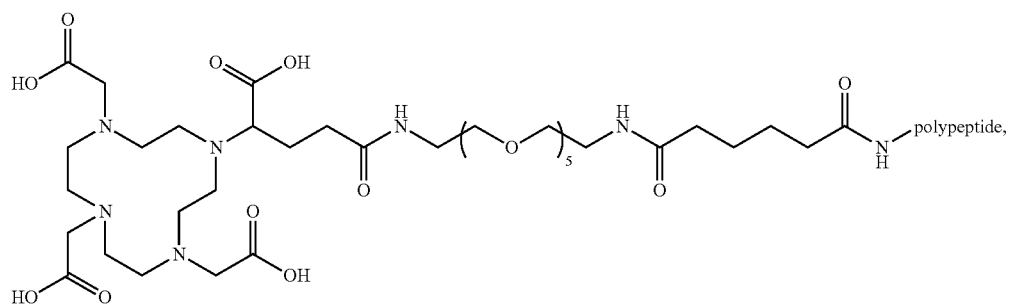
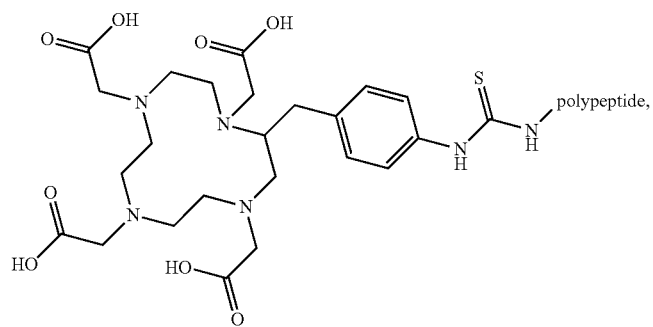

-continued
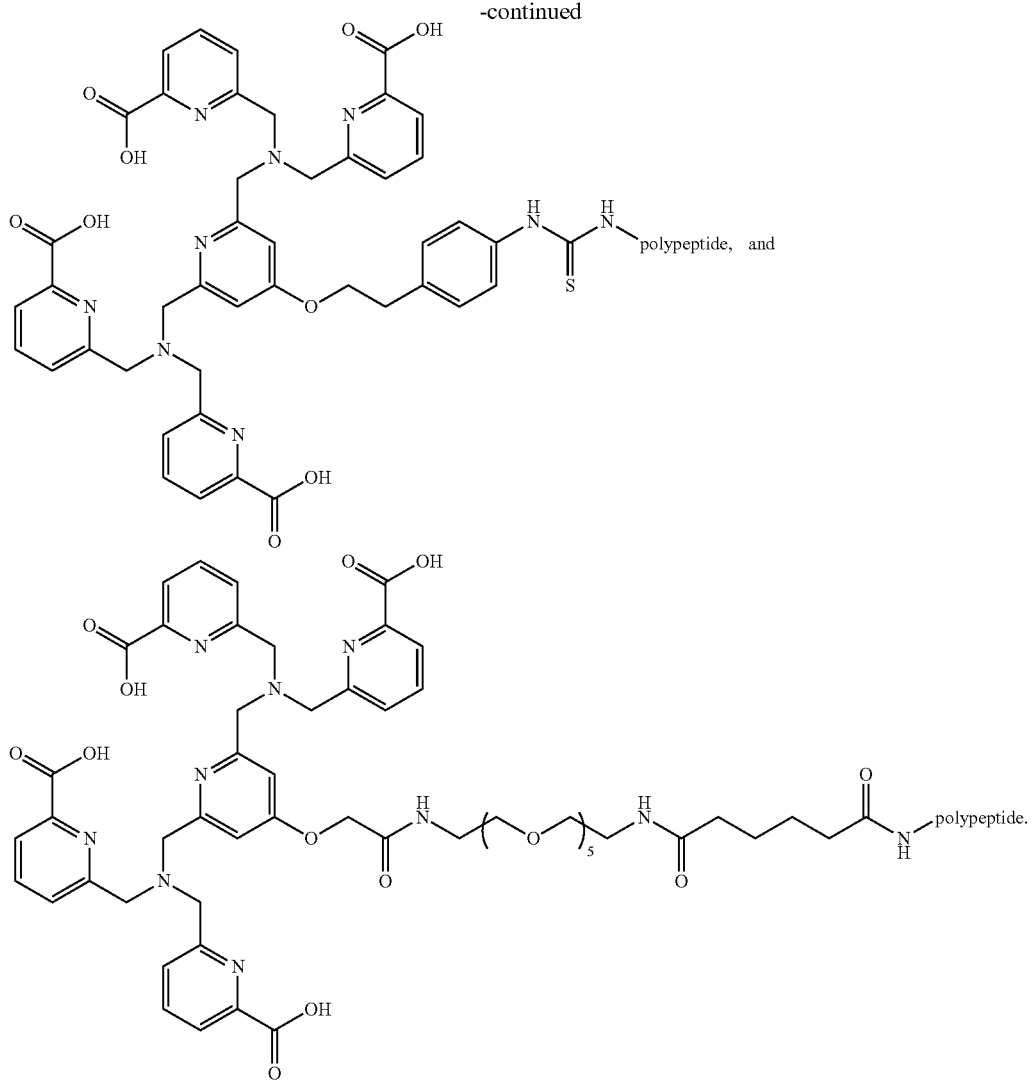
30. The method of claim 27, wherein the radionuclide comprises 225-Ac.

UNITED STATES PATENT AND TRADEMARK OFFICE
CERTIFICATE OF CORRECTION

PATENT NO. : 12,344,675 B2
APPLICATION NO. : 18/927497
DATED : July 1, 2025
INVENTOR(S) : Michael J. Abrams et al.

Page 1 of 1

It is certified that error appears in the above-identified patent and that said Letters Patent is hereby corrected as shown below:

On the Title Page

Item (71):
(71) Applicant: ABDERA THERAPEUTICS INC.,
Vancouver (CA)

Should read:
(71) Applicant: ABDERA THERAPEUTICS INC.,
South San Francisco, CA (US)

Signed and Sealed this
Nineteenth Day of August, 2025

Coke Morgan Stewart
*Acting Director of the United States Patent and Trademark Office*